(12) United States Patent
Arbit et al.

(10) Patent No.: US 8,962,554 B2
(45) Date of Patent: Feb. 24, 2015

(54) ORAL INSULIN THERAPIES AND PROTOCOL

(71) Applicant: Emisphere Technologies, Inc., Roseland, NJ (US)

(72) Inventors: Ehud Arbit, Englewood, NJ (US); Michael Goldberg, Englewood, NJ (US); Shingai Majuru, Brewster, NY (US)

(73) Assignee: Emisphere Technologies, Inc., Roseland, NJ (US)

( * ) Notice: Subject to any disclaimer, the term of this patent is extended or adjusted under 35 U.S.C. 154(b) by 0 days.

(21) Appl. No.: 14/222,272

(22) Filed: Mar. 21, 2014

(65) Prior Publication Data

US 2014/0206612 A1    Jul. 24, 2014

Related U.S. Application Data

(63) Continuation of application No. 12/485,521, filed on Jun. 16, 2009, now Pat. No. 8,729,016, which is a continuation of application No. 11/072,941, filed on Mar. 4, 2005, now abandoned, which is a continuation-in-part of application No. PCT/US2004/006943, filed on Mar. 5, 2004.

(60) Provisional application No. 60/576,912, filed on Jun. 4, 2004, provisional application No. 60/574,096, filed on May 24, 2004, provisional application No. 60/561,102, filed on Apr. 9, 2004, provisional application No. 60/550,401, filed on Mar. 5, 2004, provisional application No. 60/540,462, filed on Jan. 29, 2004, provisional application No. 60/535,091, filed on Jan. 4, 2004, provisional application No. 60/497,296, filed on Aug. 22, 2003.

(51) Int. Cl.
*A61K 38/28* (2006.01)
*A61B 5/145* (2006.01)
*A61K 31/192* (2006.01)
*A61K 38/00* (2006.01)

(52) U.S. Cl.
CPC ............ *A61K 38/28* (2013.01); *A61B 5/14532* (2013.01); *A61K 31/192* (2013.01); *A61K 38/00* (2013.01)
USPC ...................................................... 514/5.9

(58) Field of Classification Search
None
See application file for complete search history.

(56) References Cited

U.S. PATENT DOCUMENTS

| 5,698,515 | A  | 12/1997 | Plate et al. |
| 6,610,649 | B2 | 8/2003  | Wahren et al. |
| 7,060,675 | B2 | 6/2006  | Ekwuribe et al. |
| 7,084,114 | B2 | 8/2006  | Ekwuribe et al. |
| 7,115,663 | B2 | 10/2006 | Moye-Sherman et al. |
| 7,118,762 | B2 | 10/2006 | Byrd |
| 7,137,951 | B2 | 11/2006 | Pilarski |
| 7,208,178 | B2 | 4/2007  | Bhandarkar et al. |
| 7,227,033 | B2 | 6/2007  | Bhandarkar et al. |
| 2002/0147135 | A1 | 10/2002 | Schnell |
| 2003/0198666 | A1 | 10/2003 | Abbas et al. |

FOREIGN PATENT DOCUMENTS

| WO | WO-89/06540 | 7/1989 |
| WO | WO-02/02509 | 1/2002 |
| WO | WO-2004/062587 | 7/2004 |
| WO | WO-2005/112633 | 12/2005 |

OTHER PUBLICATIONS

Kidron et al., "A novel per-oral insulin formulation: proof of concept study in non-diabetic subjects", Diabetic Medicine, 21, 354-357.*
Gerich, M.D., John E., "Novel Insulins: expanding options in diabetes management", American Journal of Medicine, vol. 113, No. 4, pp. 308-316, Sep. 2002.
Canadian Office Action for Canadian Application No. 2,518,216, dated Jun. 2, 2009.
Miller J. L., "Bedtime Insulin Added to Daytime Sulfonylureas Improves Glycemic Control in Uncontrolled Type II Diabetes", Clinical Pharmacology and Therapeutics, vol. 53, No. 3., pp. 380-384, Mar. 1993.
Mesiha Mounir S., "Oral Absorption of Insulin Encapsulated in Artificial Chyles of Bile Salt, Palmitic Acid and α-Tocopherol Dispersions", International Journal of Pharmaceutics, vol. 249, No. 1-2, pp. 1-5,2002.
Hosny Ehab A., "Oral Delivery of Insulin from Enteric-coated Capsules Containing Sodium Salicylate: Effect on Relative Hypoglycemia of Diabetic Beagle Dogs", International Journal of Pharmaceutics, vol. 237, No. 1-2, pp. 71-76, 2002.
Yki-Jarvinen H., "Comparison of Bedtime Insulin Regimens in Patients with Type II Diabetes Mellitus. A randomized, controlled triaL", Annals of Internal Medicine, vol. 130, No. 5, pp. 389-396, Mar. 2, 1999.
Clement Stephen, "Oral Insulin Product Hexyl-Insulin Monoconjugate 2 (HIM2) in Type 1 Diabetes Mellitus: The Glucose Stabilization Effects of HIM2", Diabetes Technology & Therapeutics, V. 4, No. 4, pp. 459-466, Aug. 2002.

(Continued)

*Primary Examiner* — Suzanne M Noakes
(74) *Attorney, Agent, or Firm* — Blank Rome LLP

(57) ABSTRACT

Methods for treating impaired glucose tolerance and early and late stage diabetes in mammals, for prophylactically sparing β-cell function, aiding in preventing β-cell death, preventing the onset of overt diabetes in a mammal with type 2 diabetes, treating the current level of glycemic control dysfunction of a mammal with impaired glucose tolerance or diabetes, comprising orally administering insulin and a delivery agent that facilitates insulin absorption from the gastrointestinal tract at the time of or shortly before mealtime, e.g., within about 10 minutes prior to ingestion of a meal, on a chronic basis. The methods also comprise, in addition to administering a rapid-acting insulin to provide a first insulin peak, administering a slow acting insulin to provide a second insulin peak occurring at a later time but of a longer duration. These methods achieve improved glycemic control without the risks of hypoglycemia, hyperinsulinemia and weight gain and the need for frequent blood glucose monitoring that are normally associated with insulin therapy.

22 Claims, 42 Drawing Sheets

(56) References Cited

OTHER PUBLICATIONS

Frequently Asked Questions on Drug Development and Investigational New Drug Applications: www.fda.gov/cder/about/smallbiz/faq.htm—pp. 1-8, 2008.

Drugs Approved by the FDA: Avandia—www.centerwatch.com/patient/drugs/dru528.html—pp. 1-3, 1999.

Taton et al., Medical Science Monitor, vol. 7, No. 4, pp. 848-859, 2001.

Gavin et al., Clinical Cornerstone, vol. 1, No. 3, pp. 1-12, 1998.

\* cited by examiner

Mean +/- SD (N=8) % Change in Blood Glucose Following Oral Administration of Insulin/DA Tablets to T2DM Patients with a Mixed Meal (175A-C-11)

PRELIMINARY Mean +/- SD (N=8) Percent Change from Baseline Blood (SuperGL) Glucose Following a Single Oral Administration of Insulin/4-CNAB Tablets to Fed or Fasted T2DM Patients Mean (N=8) +/- SD Plasma Glucose Change (%) Following Oral Tablet Administration of Insulin/4-CNAB to T2DM Patients with or without a Meal (I75A-C-11)

Mean (n=8) +/- SD Serum Insulin Concentration Following a Single Oral Administration of Insulin/4-CNAB Tablets to Fasted or Fed T2DM Patients (175A-C-11)

Serum Insulin Concentration Following a Single Oral Administration of
Insulin/4-CNAB Tablets to Fasted T2DM Patients (175A-C-11)
Subject 105

Serum Insulin Concentration Following a Single Oral Administration of
Insulin/4-CNAB Tablets to Fasted T2DM Patients (175A-C-11)
Subject 106

Serum Insulin Concentration Following a Single Oral Administration of
Insulin/4-CNAB Tablets to Fasted T2DM Patients (175A-C-11)
Subject 107

Serum Insulin Concentration Following a Single Oral Administration of
Insulin/4-CNAB Tablets to Fasted T2DM Patients (175A-C-11)
Subject 108

Mean (n=8) +/- SD Plasma C-Peptide Concentration Following a Single Oral Administration of Insulin/4-CNAB Tablets to Fasted or Fed T2DM Patients (175A-C-11)

ORAL INSULIN THERAPIES AND PROTOCOL

CROSS REFERENCE TO RELATED APPLICATIONS

This application is a continuation of U.S. patent application Ser. No. 12/485,521, filed Jun. 16, 2009, which is a continuation of U.S. patent application Ser. No. 11/072,941, filed Mar. 4, 2005, which claims the benefit of U.S. Provisional Patent Applications No. 60/550,401, filed Mar. 5, 2004, No. 60/561,102, filed Apr. 9, 2004, No. 60/574,096, filed May 24, 2004, and No. 60/576,912, filed Jun. 4, 2004, and is a continuation-in-part of International Application No. PCT/US04/06943, filed Mar. 5, 2004, which claimed the benefit of U.S. Provisional Patent Applications No. 60/535,091, filed Jan. 7, 2004, No. 60/540,462, filed Jan. 29, 2004, and No. 60/497,296 filed Aug. 22, 2003, which are all hereby incorporated by reference.

FIELD OF THE INVENTION

This invention relates to the oral delivery of insulin in a therapeutically effective amount to the bloodstream as part of a therapeutic regimen for the treatment of diabetes. This invention also relates to oral administration of compositions of insulin and a delivery agent that facilitates insulin transport in a therapeutically effective amount to the bloodstream for the treatment of diabetes. The present invention is also directed to therapies and protocols for administration of oral pharmaceutical dosage forms of insulin on a chronic basis to pre-diabetics, including those with impaired glucose tolerance and/or insulin resistance, to early stage diabetics, and to late stage diabetics. The present invention further relates to methods for reducing adverse effects and the incidence of diseases that are associated with systemic hyperinsulinemia and hyperglycemia, especially to the β-cells of the pancreas.

BACKGROUND OF THE INVENTION

Proteins, peptides and other biological molecules ("biological macromolecules", namely biological polymers such as proteins and polypeptides) are increasingly being use in many diverse areas of science and technology. For example, proteins are employed as active agents in the fields of pharmaceuticals, vaccines and veterinary products. Unfortunately, the use of biological macromolecules as active agents in pharmaceutical compositions is often severely limited by the presence of natural barriers of passage to the location where the active agent is required. Such barriers include the skin, lipid bi-layers, mucosal membranes, severe pH conditions and digestive enzymes.

There are many obstacles to successful oral delivery of biological macromolecules. For example, biological macromolecules are large and are amphipathic in nature. More importantly, the active conformation of many biological macromolecules may be sensitive to a variety of environmental factors, such as temperature, oxidizing agents, pH, freezing, shaking and shear stress. In planning oral delivery systems comprising biological macromolecules as an active agent for drug development, these complex structural and stability factors must be considered. In addition, in general, for medical and therapeutic applications, where a biological macromolecule is being administered to a patient and is expected to perform its physiologic action, delivery vehicles can be used to facilitate absorption through the gastro-intestinal tract. These delivery vehicles must be able to release active molecules at a rate that is consistent with the needs of the particular patient or the disease process.

One specific biological macromolecule, the hormone insulin, contributes to the normal regulation of blood glucose levels through its release by the pancreas, more specifically by the β-cells of a major type of pancreatic tissue (the islets of Langerhans), so that the glucose can be used as a source of energy. Insulin secretion is a regulated process that, in normal subjects, provides stable concentrations of glucose in blood during both fasting and feeding. In healthy humans, insulin is secreted from the pancreas into the portal vein, which carries the insulin to the liver. The liver utilizes and/or metabolizes a large portion of the insulin that it receives from the portal circulation. In very basic terms, the liver plays a key role in the metabolism of glucose as follows: in the presence of excess insulin, excess glucose, or both, the liver modulates the production of glucose released into the blood; and, in the absence of insulin or when the blood glucose concentration falls very low, the liver manufactures glucose from glycogen and releases it into the blood. The liver acts as a key blood glucose buffer mechanism by keeping blood glucose concentrations from rising too high or from falling too low.

Blood glucose concentration is the principal stimulus to insulin secretion in healthy humans. The exact mechanism by which insulin release from the pancreas is stimulated by increased glucose levels is not fully understood, but the entry of glucose into the β-cells of the pancreas is required. Glucose enters the pancreatic β-cells by facilitated transport and is then phosphorylated by glucokinase. Expression of glucokinase is primarily limited to cells and tissues involved in the regulation of glucose metabolism, such as the liver and the pancreatic β-cells. The capacity of sugars to undergo phosphorylation and subsequent glycolysis correlates closely with their ability to stimulate insulin release. It is noted that not all tissues are dependent on insulin for glucose uptake. For example, the brain, kidneys and red blood cells are insulin independent tissues, while the liver, adipose and muscle are insulin dependent tissues.

When evoked by the presence of glucose (e.g., after a solid meal is ingested) in a non-diabetic individual, insulin secretion is biphasic: shortly after ingesting food, the pancreas releases the stored insulin in a burst, called a first phase insulin response, and then approximately 15-20 minutes later outputs further insulin to control the glycemic level from the food. The first phase insulin response reaches a peak after 1 to 2 minutes and is short-lived, whereas a second phase of secretion has a delayed onset but a longer duration. Thus, secretion of insulin rises rapidly in normal human subjects as the concentration of blood glucose rises above base levels (e.g., 100 mg/100 ml of blood), and the turn-off of insulin secretion is also rapid, occurring within minutes after reduction in blood glucose concentrations back to the fasting level.

In healthy human subjects, insulin secretion is a tightly regulated process that maintains blood concentrations of glucose within an acceptable range regardless of whether or not the subject has ingested a meal (i.e., fasting and fed states). Insulin facilitates (and increases the rate of) glucose transport through the membranes of many cells of the body, particularly skeletal muscle and adipose tissue. Insulin has three basic effects: the enhanced rate of glucose metabolism, the promotion of increased glycogen stores in muscle and adipose tissue, and decreased circulating blood glucose concentration.

Diabetes Mellitus ("diabetes") is a disease state in which the pancreas does not release insulin at levels capable of controlling blood glucose and/or in which muscle, fat and liver cells respond poorly to normal insulin levels because of insulin resistance. Diabetes thus can result from a dual defect of insulin resistance and "burn out" of the β-cells of the pancreas. Diabetes is classified into two types: Type 1 and Type 2. Approximately 5 to 10% of diagnosed cases of diabetes are attributed to Type 1, and approximately 90% to 95% are attributed to Type 2.

Type 1 diabetes is diabetes that is insulin dependent and usually first appears in young people. In Type 1 diabetes, the islet cells of the pancreas stop producing insulin mainly due to autoimmune destruction, and the patient must self-inject the missing hormone. For type 1 diabetics, insulin therapy is essential and is intended to replace the absent endogenous insulin with an exogenous insulin supply.

Type 2 diabetes is commonly referred to as adult-onset diabetes or non-insulin dependent diabetes and may be caused by a combination of insulin resistance (or decreased insulin sensitivity) and, in later stages, insufficient insulin secretion. This is the most common type of diabetes in the Western world. Close to 6% of the adult population of various countries around the world, including the United States, have Type 2 diabetes, and about 30% of these patients will need exogenous insulin at some point during their lifespans due to secondary pancreatic exhaustion and the eventual cessation of insulin production. For type 2 diabetics, therapy has consisted first of oral antidiabetic agents, which increase insulin sensitivity and/or insulin secretion, and only then insulin if, and when, the oral agents fail.

Diabetes is the sixth leading cause of death in the United States and accounted for more than 193,000 deaths in 1997. However, this figure is an underestimate because complications resulting from diabetes are a major cause of morbidity in the population. Diabetes is associated with considerable morbidity and mortality in the form of cardiovascular disease, stroke, digestive diseases, infection, metabolic complications, ophthalmic disorders, neuropathy, kidney disease and failure, peripheral vascular disease, ulcerations and amputations, oral complications, and depression. Thus, diabetes contributes to many deaths that are ultimately ascribed to other causes.

The main cause of mortality with Diabetes Mellitus is long term micro- and macrovascular disease. Cardiovascular disease is responsible for up to 80% of the deaths of type 2 diabetic patients, and diabetics have a two- to four-fold increase in the risk of coronary artery disease, equal that of patients who have survived a stroke or myocardial infarction. In other words, heart disease, high blood pressure, heart attacks and strokes occur two to four times more frequently in adult diabetics than in adult non-diabetics. This increased risk of coronary artery disease combined with an increase in hypertensive cardiomyopathy manifests itself in an increase in the risk of congestive heart failure. These vascular complications lead to neuropathies, retinopathies and peripheral vascular disease. Diabetic retinopathy (lesions in the small blood vessels and capillaries supplying the retina of the eye, i.e., the breakdown of the lining at the back of the eye) is the leading cause of blindness in adults aged 20 through 74 years, and diabetic kidney disease, e.g., nephropathy (lesions in the small blood vessels and capillaries supplying the kidney, which may lead to kidney disease, and the inability of the kidney to properly filter body toxins), accounts for 40% of all new cases of end-stage renal disease (kidney failure). Furthermore, diabetes is also the leading cause for amputation of limbs in the United States. Diabetes causes special problems during pregnancy, and the rate of congenital malformations can be five times higher in the children of women with diabetes.

Poor glycemic control contributes to the high incidence of these complications, and the beneficial effects of tight glycemic control on the chronic complications of diabetes are widely accepted in clinical practice. However, only recently has it been firmly established that elevated blood glucose levels are a direct cause of long-term complications of diabetes. The Diabetes Control and Complications Trial and the United Kingdom Prospective Diabetes Study both showed that control of blood glucose at levels as close to normal as possible prevents and retards development of diabetic retinopathy, nephropathy, neuropathy and microvascular disease.

Insulin resistance (or decreased insulin sensitivity) is also prevalent in the population, especially in overweight individuals, in those with risk of diabetes (i.e., pre-diabetic, wherein blood glucose levels are higher than normal but not yet high enough to be diagnosed as diabetes) and in individuals with type 2 diabetes who produce enough insulin but whose tissues have a diminished ability to adequately respond to the action of insulin. When the liver becomes insulin-resistant, the mechanism by which insulin affects the liver to suppress its glucose production breaks down, and the liver continues to produce glucose, even under hyperinsulinemic conditions (elevated plasma insulin levels). This lack of suppression can lead to a hyperglycemia (elevated blood glucose levels), even in a fasting state.

In order to compensate and to overcome the insulin resistance, the pancreatic β-cells initially increase their insulin production such that insulin resistant individuals often have high plasma insulin levels. This insulin is released into the portal vein and presented to the liver constantly or almost constantly. It is believed that the liver's constant exposure to high levels of insulin plays a role in increased insulin resistance and impaired glucose tolerance. After a period of high demand placed on the pancreatic β-cells, the cells start to decompensate and exhaust, and insulin secretion, or insulin secretory capacity, is reduced at later stages of diabetes. It is estimated that, by the time an individual is diagnosed with type 2 diabetes, roughly 50% of the β-cells have already died due to increased demand for insulin production.

Insulin resistance plays an important role in the pathogenesis of hyperglycemia in type 2 diabetes, eventually inducing the development of diabetic complications. Furthermore, insulin resistance ostensibly plays a role in the pathogenesis of macrovascular disease, cardiovascular diseases and microvascular disease. See, for example, Shinohara K. et al., Insulin Resistance as an Independent Predictor of Cardiovascular Mortality in Patients With End-Stage Renal Disease, *J. Am. Soc. Nephrol.*, Vol. 13, No. 7, July 2002, pp. 1894-1900. Research currently shows that insulin resistance reaches a maximum and then plateaus. Once the insulin resistance plateaus, it is believed to not get appreciably worse, but can improve.

Diabetes or insulin resistance can be diagnosed in many ways, as is known to those in the art. For example, the initial diagnose may be made from a glucose tolerance test (GTT), where a patient is given a bolus of glucose, usually orally, and then the patient's blood glucose levels are measured at regular time intervals for approximately 2 hours, or as many as 6 hours in the case of an extended GTT. Another method of testing for diabetes or insulin resistance is a test of the patients fasting or postprandial glucose. Other tests, such as Glycosolated Hemoglobin, often reported as Hemoglobin $A_{1c}$ ($HbA_{1c}$) can be used to assess blood glucose over 2-3 months.

Several methods to assess insulin resistance are currently available, including the euglycemic-hyperinsulinemic clamp, fasting plasma insulin, homeostasis model assessment (HOMA) of insulin resistance (HOMA-IR), the fasting glucose-to-insulin ratio method and quantitative insulin sensitivity check index (QUICKI). Except for the euglycemic-hyperinsulinemic clamp method, the others are surrogate indices and are indirect methods of assessing insulin resistance. For example, the HOMA-IR is calculated from fasting plasma glucose (FPG) and fasting immunoreactive insulin (FIRI) with the formula HOMA-IR=FIRI in mU/l×FPG in mg/dl/405. In addition, the reciprocal index of homeostasis model assessment (1/HOMA-IR) is also calculated. Similarly, QUICKI is derived from logarithmic-transformed FPG and insulin levels as calculated from FPG and FIRI levels with the formula QUICKI=1/(log [FIRI in mU/l]+log [FPG in mg/dl]).

Several oral hypoglycemic agents have been developed for specifically improving a patient's insulin resistance, such as thiazolidinediones, which make the patient more sensitive to insulin, and biguanides, which decrease the amount of glucose made by the liver, and these are currently available clinically for patients with diabetes and insulin resistance. In addition, sulfonylureas stimulate the pancreas to make more insulin, alpha-glucosidase inhibitors slow the absorption of the starches eaten by an individual, meglitinides stimulate the pancreas to make more insulin, and D-phenylalanine derivatives help the pancreas make more insulin quickly. Present treatment of insulin resistance involves sensible lifestyle changes, including weight loss to attain healthy body weight, 30 minutes of accumulated moderate-intensity physical activity per day and diet control, including increased dietary fiber intake and regulation of blood sugar levels and of caloric intake. In addition, Metformin, which has been used successfully for some time to treat diabetes because it increases insulin sensitivity, is also being studied as a treatment.

The aim of insulin treatment of diabetics is typically to administer enough insulin such that the patient will have normal carbohydrate metabolism throughout the day. Because the pancreas of a diabetic individual does not secrete sufficient insulin throughout the day, in order to effectively control diabetes through insulin therapy, a long-lasting insulin treatment, known as basal insulin, must be administered to provide the slow and steady release of insulin that is needed to control blood glucose concentrations and to keep cells supplied with energy when no food is being digested. Basal insulin is necessary to suppress glucose production between meals and overnight, and preferably mimics the patient's normal pancreatic basal insulin secretion over a 24-hour period. Thus, a diabetic patient may administer a single dose of a long-acting insulin each day subcutaneously, with an action lasting about 24 hours.

Furthermore, in order to effectively control diabetes through insulin therapy by dealing with post-prandial rises in glucose levels, a bolus, fast-acting treatment must also be administered. The bolus insulin, which has generally been administered subcutaneously, provides a rise in plasma insulin levels at approximately 1 hour after administration, thereby limiting hyperglycemia after meals. Thus, these additional quantities of regular insulin, with a duration of action of, e.g., 5-6 hours, may be subcutaneously administered at those times of the day when the patient's blood glucose level tends to rise too high, such as at meal times. Alternative to administering basal insulin in combination with bolus insulin, repeated and regular lower doses of bolus insulin may be administered in place of the long-acting basal insulin, and bolus insulin may be administered postprandially as needed.

The problem of providing bioavailable unmodified human insulin, in a useful form, to an ever-increasing population of diabetics has occupied physicians and scientists for almost 100 years. Many attempts have been made to solve some of the problems of stability and biological delivery of this peptide. Because insulin is a peptide drug (MW approx. 6000 Da) that is not absorbed intact in the gastrointestinal tract, it ordinarily requires parenteral administration such as by subcutaneous injection. Thus, most diabetic patients self-administer insulin by subcutaneous injections, often multiple times per day. However, the limitations of multiple daily injections, such as pain, inconvenience, frequent blood glucose monitoring, poor patient acceptability, compliance and the difficulty of matching postprandial insulin availability to postprandial glucose-control requirements, are some of the shortcomings of insulin therapy.

Currently, regular subcutaneously injected insulin is recommended to be dosed at 30 to 45 minutes prior to mealtime. As a result, diabetic patients and other insulin users must engage in considerable planning of their meals and of their insulin administrations relative to their meals. Unfortunately, intervening events that may take place between administration of insulin and ingestion of the meal may affect the anticipated glucose excursion. Furthermore, there is also the potential for hypoglycemia if the administered insulin provides a therapeutic effect over too great a time, e.g., after the rise in glucose levels that occur as a result of ingestion of the meal has already been lowered.

Despite studies demonstrating the beneficial effects of tight glycemic control on chronic complications of diabetes, clinicians do not often recommend aggressive insulin therapy, particularly in the early stages of the disease, and this is widely accepted in clinical practice. The unmet challenge of achieving tight glycemic control is due, in part, to the shortcomings of frequent blood glucose monitoring, the available subcutaneous route of insulin administration and the fear of hypoglycemia. In addition to the practical limitations of multiple daily injections discussed above, the shortcomings of the commonly available subcutaneous route of insulin administration have resulted in the generally inadequate glycemic control believed to be associated with many of the chronic complications (comorbidities) associated with diabetes. Thus, while intensive insulin therapy may reduce many of the complications of diabetes, the treatment also increases the risk of hypoglycemia and often results in weight gain, as reported in *Diabetes Care*, Volume 24, pp. 1711-21 (2001).

In addition, hyperinsulinemia (elevated blood concentrations of insulin) can also occur, such as by the administration of insulin in a location (and manner) that is not consistent with the normal physiological route of delivery. Insulin circulates in blood as the free monomer, and its volume of distribution approximates the volume of extracellular fluid. Under fasting conditions, the concentration of insulin in portal blood is, e.g., about 2-4 ng/mL, whereas the systemic (peripheral) concentration of insulin is, e.g., about 0.5 ng/mL, in normal healthy humans, translating into, e.g., a 5:1 ratio. In human diabetics who receive insulin via subcutaneous injection, the portal vein to periphery ratio is changed to about 0.75:1. Thus, in such diabetic patients, the liver does not receive the necessary concentrations of insulin to adequately control blood glucose, while the peripheral circulation is subjected to higher concentrations of insulin than are found in healthy subjects. Elevated systemic levels of insulin may lead to increased glucose uptake, glycogen synthesis, glycolysis, fatty acid synthesis, cortisol synthesis and triacylglycerol synthesis, leading to the expression of key genes that result in greater utilization of glucose.

One aspect of the physiological response to the presence of insulin is the stimulation of glucose transport into muscle and adipose tissue. It has been reported that hyperglycemia and/or hyperinsulinemia is related to vascular diseases associated with diabetes. Impairment to the vascular system is believed to be the reason behind conditions such as microvascular complications or diseases, such as retinopathy, neuropathy (impairment of the function of the autonomic nerves, leading to abnormalities in the function of the gastrointestinal tract and bladder and loss of feeling in lower extremities) and nephropathy, or macrovascular complications or diseases, such as cardiovascular disease, etc.

In the field of insulin delivery, where multiple repeated administrations are required on a daily basis throughout the patient's life, it is desirable to create compositions of insulin that do not alter physiological clinical activity and that do not require injections. Oral delivery of insulin is a particularly desirable route of administration, for safety and convenience considerations, because it can minimize or eliminate the discomfort that often attends repeated hypodermic injections. It has been a significant unmet goal in the art to imitate normal insulin levels in the portal and systemic circulation via oral administration of insulin.

Oral delivery of insulin may have advantages beyond convenience, acceptance and compliance issues. Insulin absorbed in the gastrointestinal tract is thought to mimic the physiologic route of insulin secreted by the pancreas because both are released into the portal vein and carried directly to the liver before being delivered into the peripheral circulation. Absorption into the portal vein maintains a peripheral-portal insulin gradient that regulates insulin secretion. In its first passage through the liver, roughly 60% of the insulin is retained and metabolized, thereby reducing the incidence of peripheral hyperinsulinemia, a factor linked to complications in diabetes.

However, insulin exemplifies the problems confronted in the art in designing an effective oral drug delivery system for biological macromolecules. Insulin absorption in the gastrointestinal tract is prevented presumably by its molecular size and its susceptibility for enzymatic degradation. The physicochemical properties of insulin and its susceptibility to enzymatic digestion have precluded the design of a commercially viable oral or alternate delivery system.

Emisphere Technologies, Inc. has developed compositions of insulin that are orally administrable, e.g., absorbed from the gastrointestinal tract in adequate concentrations, such that the insulin is bioavailable and bioactive following oral administration and provide sufficient absorption and pharmacokinetic/pharmacodynamic properties to provide the desired therapeutic effect, i.e., cause a reduction of blood glucose, as disclosed in U.S. patent application Ser. Nos. 10/237,138, 60/346,746, 60/347,312, 60/368,617, 60/374,979, 60/389, 364, 60/438,195, 60/438,451, 60/578,967, 60/452,660, 60/488,465, 60/518,168, 60/535,091 and 60/540,462, as well as in International Patent Application Publications Nos. WO 03/057170, WO 03/057650 and WO 02/02509 and International Patent Application No. PCT/US04/00273, all assigned to Emisphere Technologies, Inc., all of which are incorporated herein by reference.

The novel drug delivery technology of Emisphere Technologies, Inc. is based upon the design and synthesis of low molecular weight compounds called "delivery agents." When formulated with insulin, the delivery agent, which is in a preferred embodiment sodium N-[4-(4-chloro-2 hydroxybenzoyl)amino]butyrate (4-CNAB), enables the gastrointestinal absorption of insulin. It is believed that the mechanism of this process is that 4-CNAB interacts with insulin non-covalently, creating more favorable physical-chemical properties for absorption. Once across the gastrointestinal wall, insulin disassociates rapidly from 4-CNAB and reverts to its normal, pharmacologically active state. 4-CNAB is not intended to possess any inherent pharmacological activity and serves only to increase the oral bioavailability of insulin by facilitating the transport of insulin across the gastrointestinal wall. The pharmacology of insulin is the desired therapeutic effect and is well characterized.

Insulin/4-CNAB capsules were evaluated by Emisphere Technologies, Inc. in a nonclinical program that included pharmacological screening, pharmacokinetic and metabolic profiles, and toxicity assessments in rats and monkeys. These studies in rats and monkeys showed that 4-CNAB is absorbed rapidly following oral administration and that, over the range tested, insulin absorption increased with increasing doses of 4-CNAB. Similarly, for a fixed oral dose of 4-CNAB, insulin absorption increased with increasing doses of insulin. Preclinical pharmacokinetic studies in rats and monkeys showed that both insulin and 4-CNAB were absorbed and eliminated rapidly following oral administration. Receptor binding screening assays revealed that 4-CNAB possessed no inherent pharmacological activity and serves only to facilitate the oral bioavailability of insulin.

Toxicology studies were also conducted in rats and monkeys to assess the potential toxicity of 4-CNAB, alone or in combination with insulin. Based on the 14-day oral repeated dose toxicity studies, the NOAEL (No-Adverse Effect Level) was estimated to be 500 mg/kg in Sprague-Dawley rats, and 400 mg/kg in rhesus monkeys. In the 90-day oral repeated dose toxicity studies, NOAELs of 250 mg/kg and 600 mg/kg were observed in rats and monkeys, respectively. Four genotoxicity studies have also been conducted with 4-CNAB, with no positive findings. Developmental and reproductive toxicology studies have not yet been conducted.

Oral insulin/4-CNAB capsules were also evaluated by Emisphere Technologies, Inc. in clinical human studies for safety, pharmacokinetics, pharmacodynamics, and the effect of food on the absorption of insulin/4-CNAB. In these studies, 4-CNAB was shown to enhance the gastrointestinal absorption of insulin following oral administration in diabetic patients and healthy subjects. Oral administration of Insulin/4-CNAB capsules resulted in rapid absorption ($t_{max}$~20-30 minutes) of both insulin and 4-CNAB, and the insulin absorbed orally in combination with 4-CNAB was pharmacologically active, as demonstrated by a reduction of blood glucose in healthy and diabetic subjects and by a blunting of postprandial glucose excursion in diabetic patients. These studies suggest that oral administration of a formulation of insulin/4-CNAB is well-tolerated and reduces blood glucose concentrations in both healthy subjects and diabetic patients.

Whereas traditional subcutaneous insulin dosing shifts the point of entry of insulin into the systemic circulation from the natural site (the portal vein), the oral dosing method developed by Emisphere Technologies, Inc. is thought to mimic natural physiology, namely, the ratio of concentration of insulin in the portal circulation to that in the systemic circulation approaches the normal physiological ratio, e.g., from about 2:1 to about 6:1. The effect of this route of dosing is two fold. First, by targeting the liver directly, a greater control of glucose may be achieved. Various studies have shown that intraportal delivery of insulin can yield a comparable control of glucose at infusion rates lower than those required by peripheral administration. Because the orally-administered insulin will undergo substantial (~50%) first-pass metabolism prior to entering the systemic circulation, a lower plasma concentration and total exposure is achieved compared to an subcutaneous equivalent dose. This may, in turn, alleviate any detrimental effects of insulin on non-target tissues.

Thus, the oral insulin formulations of Emisphere Technologies, Inc. provide an advantage over subcutaneously administered insulin that is currently the state of the art, beyond the benefit of ease of administration, pain-free administration, and the potential for improved patient compliance. Because subcutaneously administered insulin is delivered peripheral to the GI tract and portal vein, and absorption of large biomolecules from the subcutaneous space is generally more prolonged, the first-phase insulin response is not well-replicated by subcutaneous insulin administration. By administration of the oral insulin formulations of the present invention, the plasma levels of insulin that occur upon the first (acute) phase of insulin secretion by the pancreas can be simulated by rapid, direct absorption from the GI tract.

In normal physiology, first-phase insulin secretion takes place 5 to 20 minutes after the start of a meal, and this effect has a well-known impact on prandial glucose homeostasis. The first phase of insulin secretion, while of short duration, has an important role in priming the liver to the metabolic events ahead (meal). The loss of first-phase insulin secretion is a characteristic feature of Type 2 diabetic patients in the early stages of the disease, and it is also observed in prediabetic states, namely individuals with impaired glucose tolerance. In the absence of first-phase insulin secretion, the stimulatory effect of glucagon on gluconeogenesis is not suppressed and may contribute to the development of prandial hyperglycemia. In the basal state as well as in the prandial phase, plasma glucose concentrations are correlated with hepatic glucose output. Therefore, restoration of first-phase insulin secretion at the time of meal ingestion should suppress prandial hepatic glucose output and subsequently improve the blood glucose profile.

Several approaches have been undertaken to prove this hypothesis. However, the therapeutic regimens were either too dangerous for a long-term treatment (such as intravenous administration of regular human insulin) or pharmacologically unsuitable (fast-acting insulin analogues). In addition, restoration of first phase insulin response appears to be difficult in patients with a long-standing history of diabetes who have lost most or all of their endogenous insulin secretion capacity. Furthermore, certain short acting insulin formulations, because of the speed with which the insulin provides a blood glucose lowering effect, may, between the time of administration of insulin and the time of ingestion of the meal, contribute to a lowering of blood glucose to a level that could range from subclinical hypoglycemia to more undesirable effects.

The rapid onset and the short duration of action of oral Insulin/4-CNAB following single dose administration in humans suggests that oral Insulin/4-CNAB may be well-suited for supplementation of first phase insulin secretion in subjects with type 2 diabetes. In a previous study, as set forth in International Patent Application No. PCT/US04/00273, patients with type 2 diabetes were administered a single doses of Insulin (300 U)/4-CNAB (400 mg) at or shortly before bedtime. Substantial decrease in insulin, C-peptide, and fasting blood glucose levels were observed. Insulin sensitivity, as assessed with the HOMA-model, was also significantly improved. This suggests that even a short-term treatment with pre-prandial Insulin/4-CNAB may be able to improve insulin sensitivity and, thereby, metabolic control.

It is, therefore, desirable to provide a pharmaceutical compositions of insulin that can be administered closer to as meal than previously known and to provide a protocol for insulin treatment for patients with impaired glucose tolerance or with early stage or late stage diabetes, which treatment can be administered orally multiple times daily, such as at or shortly prior to mealtime and/or at or shortly prior to bedtime, has a short duration of action, and has positive and long lasting effects on the patient's glucose tolerance, glycemic control, insulin secretory capacity and insulin sensitivity, but does not increase the risk of hypoglycemia, hyperinsulinemia and weight gain that are normally associated with insulin therapy treatments.

SUMMARY OF THE INVENTION

It is an object of the present invention to provide a therapeutic insulin treatment for patients with impaired glucose tolerance or with early stage or late stage diabetes to provide therapeutic effects to the patient greater than or unseen in current parenteral insulin therapy.

It is another object of the present invention to provide a therapeutic insulin treatment for patients with impaired glucose tolerance or with early stage or late stage diabetes to provide positive therapeutic effects on the patient's glucose tolerance and glycemic control.

It is an object of the present invention to provide a therapeutic insulin treatment for patients with impaired glucose tolerance or with early stage or late stage diabetes to provide long lasting therapeutic effects on the patient's glucose tolerance and glycemic control.

It is another object of the present invention to provide a therapeutic insulin treatment for patients with impaired glucose tolerance or with early stage or late stage diabetes to improve the patient's endogenous capacity to handle sugar load.

It is additionally an object of the present invention to provide a therapeutic insulin treatment for patients with impaired glucose tolerance or with early or late stage diabetes to provide for the patient an improved glucose profile, a decrease in glucose excursion or a decreased AUC of blood glucose, measured following a glucose load such as a meal or oral glucose tolerance test.

It is a further object of the present invention to provide a therapeutic insulin treatment for patients with impaired glucose tolerance or with early stage or late stage diabetes to provide for the patient a decreased fasting blood glucose concentration when compared with the patient's own baseline level prior to starting the treatment.

It is still another object of the present invention to provide a therapeutic insulin treatment for patients with impaired glucose tolerance or with early stage or late stage diabetes to provide for the patient a decreased serum fructosamine level.

It is yet another object of the present invention to provide a therapeutic insulin treatment for patients with impaired glucose tolerance or with early stage or late stage diabetes to improve the insulin utilization of the patient's body.

It is yet another object of the present invention to provide a therapeutic insulin treatment for patients with impaired glucose tolerance or with early stage or late stage diabetes to improve the insulin sensitivity of the patient's body.

It is still a further object of the present invention to provide a therapeutic insulin treatment for patients with impaired glucose tolerance or with early stage or late stage diabetes to improve the insulin secretion capacity of the patient's body.

It is yet a further object of the present invention to provide a therapeutic insulin treatment for patients with impaired glucose tolerance or with early stage or late stage diabetes without the negative side effects currently seen in parenteral insulin therapy.

It is another object of the present invention to provide a therapeutic insulin treatment for patients with impaired glucose tolerance or with early stage or late stage diabetes without inducing hypoglycemia.

It is a further object of the present invention to provide a therapeutic insulin treatment for patients with impaired glucose tolerance or with early stage or late stage diabetes without inducing hyperinsulinemia.

In yet another object of the present invention to provide a therapeutic insulin treatment for patients with impaired glucose tolerance or with early stage or late stage diabetes without the weight gain commonly associated with parenteral insulin therapy.

It is yet a further object of the present invention to provide a therapeutic insulin treatment for patients with impaired glucose tolerance or with early stage or late stage diabetes that reduces the need for frequent monitoring of blood sugar levels currently needed with current insulin therapy regimens.

It is another object of the present invention to provide a therapeutic insulin treatment for patients with impaired glucose tolerance or with diabetes from its earliest stages to its latest stages.

It is a further object of the present invention to provide a method of reversing impaired glucose tolerance or diabetes by administration of a therapeutic insulin treatment.

It is another object of the present invention to provide a therapeutic insulin treatment for patients who are failing dual or multiple therapy with sulfonureas and insulin sensitizers.

It is an object of the present invention to provide pharmaceutical compositions for oral administration comprising insulin and a delivery agent that facilitates insulin transport in a therapeutically effective amount to the bloodstream, which compositions are therapeutically and quickly effective.

It is another object of the present invention to provide therapeutically effective pharmaceutical compositions comprising insulin and a delivery agent for oral administration to patients with impaired glucose tolerance or with early stage or late stage diabetes to provide longer lasting therapeutic effects on the patient's glucose tolerance and glycemic control without the risks of hypoglycemia, hyperinsulinemia and weight gain that are normally associated with insulin therapy treatments.

It is a further object of the present invention to provide compositions for oral administration of insulin and a delivery agent that facilitates insulin transport in a therapeutically effective amount to the bloodstream for the treatment of diabetes, for the treatment of impaired glucose tolerance, for the purpose of achieving glucose homeostasis, for the treatment of early stage diabetes, for the treatment of late stage diabetes, and/or to serve as replacement therapy for type I diabetic patients to provide longer lasting effects on the patient's glucose tolerance and glycemic control without the risks of hypoglycemia, hyperinsulinemia and weight gain that are normally associated with insulin therapy treatments.

It is still a further object of the present invention to provide methods of treating mammals with impaired glucose tolerance, early stage diabetes or late stage diabetes, for achieving glucose homeostasis in mammals, for prophylactically sparing pancreatic β-cell function, for preventing β-cell death or dysfunction, for long term protection of a mammal from developing overt or insulin dependent diabetes, for delaying the onset of overt or insulin dependent diabetes in a mammal that has impaired glucose tolerance or early stage diabetes, and for reducing the incidence and/or severity of systemic hyperinsulinemia associated with chronic dosing of insulin or of one or more disease states associated with chronic dosing of insulin.

In accordance with these and other objects, the invention provides a method for treating a mammal with impaired glucose tolerance or with early or late stage diabetes, and of achieving glucose homeostasis in mammals, comprising orally administering to a mammal a therapeutically effective dose of a pharmaceutical formulation comprising insulin such that the mammal achieves improved glucose tolerance and glycemic control as compared with baseline levels prior to treatment.

The invention also provides a method for treating a mammal with impaired glucose tolerance or with early or late stage diabetes, comprising orally administering to a mammal a therapeutically effective dose of a pharmaceutical formulation comprising insulin such that the mammal achieves improved glucose tolerance and glycemic control as compared with baseline levels prior to treatment without any statistically significant weight gain by the mammal over the treatment period.

The invention also provides a method for treating a mammal with impaired glucose tolerance or with early or late stage diabetes, comprising orally administering to a mammal a therapeutically effective dose of a pharmaceutical formulation comprising insulin such that the mammal achieves improved glucose tolerance and glycemic control as compared with baseline levels prior to treatment without any statistically significant risk of hypoglycemia in the mammal over the treatment period.

The invention also provides a method for treating a mammal with impaired glucose tolerance or with early or late stage diabetes, comprising orally administering to a mammal a therapeutically effective dose of a pharmaceutical formulation comprising insulin such that the mammal achieves improved glucose tolerance and glycemic control as compared with baseline levels prior to treatment without any statistically significant risk of hyperinsulinemia in the mammal over the treatment period.

In certain preferred embodiments, the improved glucose tolerance is demonstrated by better endogenous capacity of the mammal to handle sugar load as measured by blood glucose concentration, following a sugar load, that is reduced by a statistically significant amount as compared with baseline blood glucose concentration, following a glucose load, prior to treatment. Preferably, the statistically significant amount is a mean of about 10-20%, preferably about 15%.

In certain preferred embodiments, the improved glucose tolerance is demonstrated by better endogenous capacity of the mammal to handle sugar load as measured by an AUC of blood glucose excursion, following a glucose load, that is reduced by a statistically significant amount as compared with AUC of blood glucose excursion, following a glucose load, prior to treatment. Preferably, the statistically significant amount is a mean of about 10-30%, preferably about 20%.

In certain preferred embodiments, the improved glycemic control is demonstrated by decreased fasting blood glucose levels as measured by fasting blood glucose concentration that is reduced by a statistically significant amount as compared with baseline fasting blood glucose concentration prior to treatment. Preferably, the statistically significant amount is a mean of about 10-30%, preferably about 19%.

In certain preferred embodiments, the improved glycemic control is demonstrated by decreased serum fructosamine levels, as measured by serum fructosamine assay, that is reduced by a statistically significant amount as compared with baseline serum fructosamine levels prior to treatment. Preferably, the statistically significant amount is a mean of about 5-20%, preferably about 9%.

In certain preferred embodiments, the improved glycemic control is demonstrated by improved HbA1c levels after treatment compared with baseline levels prior to treatment. Preferably, the improved HbA1c levels are measured by a statistically significant decline in HbA1c levels. More preferably, administration of the pharmaceutical formulation of the present invention can preferably be made to a mammal with impaired glucose tolerance or with early or late stage diabetes having an $HbA_{1c}$ level ranging from normal to elevated prior to treatment. In one embodiment, the mammal may have an $HbA_{1c}$ level preferably of less than about 8.0 prior to treatment.

In certain further preferred embodiments, the improved glucose tolerance and glycemic control are achieved without the need for monitoring the mammal's blood glucose concentrations or $HbA_{1c}$ levels over the treatment period.

In certain preferred embodiments, the mammal achieves improved insulin utilization and insulin sensitivity after the treatment as compared with baseline levels prior to treatment. Preferably, the improved insulin utilization and insulin sensitivity are measured by a statistically significant decline in HOMA (Homeostasis Model Assessment).

In certain preferred embodiments, the mammal achieves improved insulin secretion capacity after the treatment as compared with baseline levels prior to treatment. Preferably, the improved insulin secretion capacity is measured by a statistically significant decline in Stumvoll first-phase insulin secretion capacity index.

The invention is also directed in part to an oral solid dosage form comprising a dose of insulin that achieves a therapeutically effective reduction in blood glucose after oral administration to a human diabetic patient, and which maintains a physiological (portal/peripheral) gradient, and in certain embodiments provides a ratio of portal vein insulin concentration to peripheral blood insulin concentration from about 2.5:1 to about 6:1, and preferably from about 4:1 to about 5:1.

The invention is further directed in part to an oral dosage form comprising a therapeutically effective amount of insulin, said dosage form upon pre-prandial oral administration to diabetic patients causing the post prandial blood glucose concentration in said patients to be reduced for the first hour after oral administration relative to a post-prandial blood glucose concentration without treatment or following subcutaneous insulin administration or other standard treatment regimen.

The invention is further directed in part to an oral dosage form comprising a therapeutically effective amount of insulin, said oral dosage form upon pre-prandial oral administration provides a mean plasma glucose concentration which does not vary by more than about 40% (and more preferably not more than 30%) for the first hour after oral administration, relative to a mean baseline (fasted) plasma glucose concentration in said patients, where a meal is eaten by said patients within about one half hour of oral administration of said dosage form.

In certain preferred embodiments, the administration of the oral insulin formulation of the present invention achieves a reduction in blood glucose concentration in human diabetic patients comparable to a subcutaneous insulin injection in those patients, while providing a lower (e.g., 20% or greater) total exposure of insulin to the peripheral blood circulation under acute, sub-acute and chronic conditions as compared to the peripheral blood insulin exposure achieved via subcutaneous injection.

The present invention provides methods of treating mammals with impaired glucose tolerance, early stage diabetes and late stage diabetes; for achieving glucose homeostasis; for reducing the incidence and/or severity of systemic hyperinsulinemia associated with chronic dosing of insulin. It is believed that the present invention also provides methods for reducing the incidence and/or severity of one or more disease states associated with chronic dosing of insulin; for prophylactically sparing β-cell function or for preventing β-cell death or dysfunction, in a mammal which has impaired glucose tolerance or early stage diabetes mellitus; and for long-term protection from developing overt or insulin dependent diabetes, or for delaying the onset of overt or insulin dependent diabetes, in a mammal which has impaired glucose tolerance or early stage diabetes.

In a preferred embodiment of the invention, such methods comprise orally administering a therapeutically effective dose of a pharmaceutical formulation comprising insulin and a delivery agent that facilitates the absorption of the insulin from the gastrointestinal tract, to provide a therapeutically effective reduction in blood glucose and a plasma insulin concentration, to provide a therapeutically effective reduction and/or control in blood glucose concentration and a plasma insulin concentration that is reduced relative to the plasma insulin concentration provided by a therapeutically equivalent dose of subcutaneously injected insulin. The determination of insulin concentration obtained in patients who have been administered subcutaneous insulin are well known to those skilled in the art.

In a preferred embodiment, administration of the pharmaceutical formulation takes place multiple times daily, preferably at bedtime and preprandially during the day time, e.g., preprandially for breakfast, lunch and dinner. More preferably, administration of the pharmaceutical formulation is at or shortly prior to bedtime and concurrently with or shortly prior to ingestion of a meal, i.e., within about 15 minutes or less of ingestion of the meal.

In another preferred embodiment of the invention, the oral pharmaceutical formulation will be administered about once daily to about four times daily, preprandially and/or at bedtime, depending upon the extent of the patient's impaired glucose tolerance and need for exogenous glycemic control. If the patient has a need for fasting glycemic control, the oral pharmaceutical formulation will be administered only at or shortly prior to bedtime. If the patient has a need for postprandial glycemic control, the oral pharmaceutical formulation will be administered preprandially for all meals. If the patient has a need for comprehensive glycemic control, the oral pharmaceutical formulation will be administered preprandially for all meals and at or shortly prior to bedtime.

Preferably, the dosage form of the present invention will be administered for at least one day, more preferably on a chronic basis, and can be administered for the life of the patient. Most preferably, the dosage form of the present invention will be administered on a chronic basis, e.g., for at least about two weeks.

Preferably, the therapeutic insulin treatment of the present invention will be administered to patients having some form of impaired glucose tolerance. This can range from insulin resistance seen in pre-diabetics and early stage Type 2 diabetics to failure of insulin production by the pancreas seen in Type 1 diabetes and late stage Type 2 Diabetes. In certain embodiments, the resulting improved insulin utilization or insulin sensitivity of the patient's body is measured by HOMA (Homeostasis Model Assessment). In certain embodiments, the resulting improved insulin secretion capacity of the patient's body is measured by Stumvoll first-phase insulin secretion capacity index.

Further, the therapeutic insulin treatment of the present invention can be administered to a mammal with an $HbA_1c$ ranging from normal to elevated levels. More particularly, the treatment can be administered to anyone in the range of normal glycemic control to impaired glycemic control to late stage type 2 diabetes or type 1 diabetes. In certain embodiments, the resulting improved glycemic control in the patient's body is measured by a reduced serum fructos amine concentration. Preferably the average decline will be about 8.8% after at least two weeks of treatment with the present invention.

In preferred embodiments of the oral dosage forms of the invention described above, the oral dosage form is solid, and is preferably provided incorporated within a gelatin capsule or is contained in a tablet.

In certain preferred embodiments, the dose of unmodified insulin contained in one or more dosage forms is from about 50 Units to about 600 Units (from about 2 to about 23 mg), preferably from about 100 Units (3.8 mg) to about 450 Units (15.3 mg) insulin, more preferably from about 200 Units (7.66 mg) to about 350 Units (13.4 mg), and still more preferably about 300 Units (11.5 mg), based on the accepted conversion of factor of 26.11 Units per mg.

In certain preferred embodiments of the invention, the dosage forms begin delivering insulin into the systemic circulation via the portal vein (via absorption through the mucosa of the gastrointestinal tract) to achieve peak levels within about 30 minutes or less.

In certain preferred embodiments, the dosage forms of the invention provide a $t_{max}$ for insulin at from about 5 minutes to about 30 minutes, and more preferably at from about 10 minutes to about 25 minutes after oral administration to diabetic patients. In certain preferred embodiments of the invention, the dosage forms begin delivering insulin into the systemic circulation to produce a peak plasma insulin concentration at about 10 to about 20 minutes post oral administration and in further preferred embodiments, a peak plasma insulin concentration at about 10 minutes to about 15 minutes post oral administration to patients who ingested the dosage at about 0 or about 10 minutes prior to ingestion of a meal.

The invention is also directed in part to an oral dosage form comprising a dose of unmodified insulin that achieves a therapeutically effective control of post prandial blood glucose after oral administration to human diabetic patients in tablet form at or shortly before mealtime, the oral solid dosage form providing an insulin $t_{max}$ at a time point from about 10 minutes to about 15 minutes after oral administration to said patients, at least about 30% of the blood glucose concentration reduction caused by said dose of insulin occurring within about less than 1 hour after oral administration of said dosage form. In preferred embodiments of this invention, the oral dosage form is a tablet.

In certain preferred embodiments, the composition provides a $t_{max}$ for maximum control of glucose excursion at about 0.25 to about 1.5 hours, more preferably at about 0.75 to about 1.25 hours, after oral administration. In certain preferred embodiments, the $t_{max}$ for post-prandial glucose control occurs preferably at less than about 120 minutes, more preferably at less than about 80 minutes, and still more preferably at about 45 minutes to about 60 minutes, after oral administration of the composition.

In certain preferred embodiments, the pharmaceutical composition contained in one or more dosage forms comprises from about 5 mg to about 800 mg of delivery agent, preferably about 20 mg to about 600 mg, more preferably from about 30 mg to about 400 mg, even more preferably from about 40 mg to about 200 mg, most preferably about 40 mg, 80 mg or 160 mg. In certain embodiments, the composition provides a peak plasma delivery agent concentration $C_{max}$ from about 3,000 to about 15,000 ng/mL, and a $t_{max}$ at about 10 minutes to about 35 minutes. More preferably, the composition provides a peak plasma delivery agent concentration within about 15 minutes to about 35 minutes after oral administration and more preferably within about 20 minutes after oral administration to fed diabetic patients.

For purposes of the present invention, a preferred delivery agent is identified via chemical nomenclature as 4-[(4-chloro, 2-hydroxybenzoyl)amino]butanoic acid. In certain preferred embodiments, the delivery agent is a sodium salt, preferably monosodium salt. Alternatively, the same compound is identified by the alternative nomenclature monosodium N-(4-chlorosalicyloyl)-4-aminobutyrate, or by the short name "4-CNAB".

The following terms will be used throughout the application as defined below:

Patient—refers to any mammal in whom there is determined to be.

Diabetic patient—refers to a mammal with a form of pre-diabetes or diabetes, either diagnosed or undiagnosed, and/or with a condition that would respond to an anti-diabetic and/or insulin treatment.

Mammal—includes but is not limited to rodents, aquatic mammals, domestic animals such as dogs and cats, farm animals such as sheep, pigs, cows and horses, and preferably humans.

Diabetes or Diabetes Mellitus—is deemed to encompass type 1 and type 2 diabetes mellitus, unless specifically specified otherwise.

Overt Diabetes—is deemed to encompass type 1 and type 2 diabetes mellitus that is insulin dependent.

Early stage diabetes—refers to a condition of impaired glycemic control, absent treatment, wherein the function of the islet cells of the pancreas still exist, although in an impaired state, also including impaired glucose tolerance (IGT) and impaired fasting blood glucose (IFG), e.g., the patient's endogenous insulin production is insufficient to provide a first phase insulin response following ingestion of a meal but is sufficient to provide a second phase insulin response following ingestion of a meal.

Late stage diabetes—refers to a condition of impaired glycemic control, absent treatment, wherein the islet cells of the pancreas are approaching or have reached total failure, e.g., the patient's endogenous insulin production is insufficient to provide a first or a second phase insulin response following ingestion of a meal.

Treatment—when used herein with respect to diabetes is deemed to include prevention of diabetes, delay of the onset of diabetes, delay of worsening of diabetic conditions and delay of progression from an earlier stage of diabetes to a later stage of diabetes, unless specifically specified otherwise.

Delivery agent—refers to carrier compounds or carrier molecules that are effective in the oral delivery of therapeutic agents, and may be used interchangeably with "carrier".

Therapeutically effective amount of insulin—refers to an amount of insulin included in the dosage forms of the invention which is sufficient to achieve a clinically relevant control of blood glucose concentrations in a human diabetic patient either in the fasting state or in the fed state effective, during the dosing interval.

Effective amount of delivery agent—refers to an amount of the delivery agent that has been shown to deliver the drug following oral administration by measurement of pharmacokinetic and/or pharmacodynamic endpoints.

Organic solvents—refers to any solvent of non-aqueous origin, including liquid polymers and mixtures thereof. Organic solvents suitable for the present invention include:

acetone, methyl alcohol, methyl isobutyl ketone, chloroform, 1-propanol, isopropanol, 2-propanol, acetonitrile, 1-butanol, 2-butanol, ethyl alcohol, cyclohexane, dioxane, ethyl acetate, dimethylformamide, dichloroethane, hexane, isooctane, methylene chloride, tert-butyl alcohol, toluene, carbon tetrachloride, or combinations thereof.

Peptide—refers to a polypeptide of small to intermediate molecular weight, usually 2 or more amino acid residues and frequently but not necessarily representing a fragment of a larger protein.

Protein—refers to a complex high polymer containing carbon, hydrogen, oxygen, nitrogen and usually sulfur and composed of chains of amino acids connected by peptide linkages. Proteins in this application refer to glycoproteins, antibodies, non-enzyme proteins, enzymes, hormones and sub-units of proteins, such as peptides. The molecular weight range for proteins includes peptides of 1000 Daltons to glycoproteins of 600 to 1000 kiloDaltons.

Reconstitution—refers to dissolution of compositions or compositions in an appropriate buffer or pharmaceutical composition.

Unit-Dose Forms—refers to physically discrete units suitable for human and animal subjects and packaged individually as is known in the art. It is contemplated for purposes of the present invention that dosage forms of the present invention comprising therapeutically effective amounts of insulin may include one or more unit doses (e.g., tablets, capsules, powders, semisolids (e.g. gelcaps or films), liquids for oral administration, ampoules or vials for injection, loaded syringes) to achieve the therapeutic effect. It is further contemplated for the purposes of the present invention that a preferred embodiment of the dosage form is an oral dosage form.

The term "multiple dose" means that the patient has received at least two doses of the drug composition in accordance with the dosing interval for that composition.

The term "single dose" means that the patient has received a single dose of the drug composition or that the repeated single doses have been administered with washout periods in between.

Unless specifically designated as "single dose" or at "steady-state" the pharmacokinetic parameters disclosed and claimed herein encompass both single dose and multiple-dose conditions.

Unmodified insulin—refers to insulin prepared in any pharmaceutically acceptable manner or from any pharmaceutically acceptable source which is not conjugated with an oligomer such as that described in U.S. Pat. No. 6,309,633 and/or which not has been subjected to amphiphilic modification such as that described in U.S. Pat. Nos. 5,359,030; 5,438,040; and/or 5,681,811, which patents are hereby incorporated by reference in their entireties.

The phrase "equivalent therapeutically effective reduction" as used herein means that a maximal reduction of blood glucose concentration achieved by a first method of insulin administration (e.g. via oral administration of insulin in a patient(s)) is not more than 20%, and preferably not more than 10% and even more preferably not more than 5% different from a maximal reduction of blood glucose concentration after administration by a second method (e.g., subcutaneous injection) in the same patient(s) or a different patient requiring the same reduction in blood glucose level. The phrase may also mean the dose required to approximate normoglycemia by any method of administration, normoglycemia being defined as variability from a subject's baseline blood glucose of not more than 20%, preferably 10%, more preferably 5%, in the fasted state.

The term "meal" as used herein means a standard, ADA and/or a mixed meal.

The term "mean", when preceding a pharmacokinetic value (e.g., mean $t_{max}$), represents the arithmetic mean value of the pharmacokinetic value unless otherwise specified.

The term "mean baseline level" as used herein means the measurement, calculation or level of a certain value that is used as a basis for comparison, which is the mean value over a statistically significant number of subjects, e.g., across a single clinical study or a combination of more than one clinical study.

The term "$C_{max}$" as used herein is the highest plasma concentration of the drug or delivery agent observed within the sampling interval.

The term "$t_{max}$" as used herein is the time post-dose at which $C_{max}$ is observed.

The term "AUC" as used herein means area under the plasma concentration-time curve, as calculated by the trapezoidal rule over the complete sample collection interval.

The term "$AUC_{(0-last)}$" as used herein means the area under the plasma concentration-time curve using linear trapezoidal summation from time zero (dosing) to the time of the last quantifiable concentration post-dose.

The term "$AUC_{(0-t)}$" as used herein means the area under the plasma concentration-time curve using linear trapezoidal summation from time zero (dosing) to time t post-dose, where t is any quantifiable time point.

The term "$AUC_{(0-inf)}$" as used herein means an estimate of the area under the plasma concentration-time curve from time zero (dosing) to infinity.

The term "CL/F" as used herein means the apparent total body clearance calculated as $Dose/AUC_{(0-inf)}$, uncorrected for absolute bioavailability.

The term "$V_d/F$" as used herein means the apparent volume of distribution calculated as $(CL/F)/K_{el}$, uncorrected for absolute bioavailability.

The term "$E^b$" as used herein means the maximum observed effect (baseline subtracted) prior to intervention for hypoglycemia.

The term "$E_{max}$" as used herein means the maximum observed effect (baseline subtracted).

$K_{el}$ is the terminal elimination rate constant calculated by linear regression of the terminal linear portion of the log concentration vs. time curve The term "$t_{1/2}$" as used herein means the terminal half-life calculated as $\ln(2)/K_{el}$.

The term "BMI" as used herein means the body mass index, calculated as weight in kg divided by the squared height in m.

The term "Bioavailability" as used herein means the degree or ratio (%) to which a drug or agent is absorbed or otherwise available to the treatment site in the body relative to a parenteral route. This is calculated by the formula $$\text{Relative Bioavailability}(\%) = \frac{\text{Dose } SC}{\text{Dose Oral}} \times \frac{AUC \text{ Oral}}{AUC \, SC} \times 100$$

The term "Biopotency" as used herein means the degree or ratio (%) to which a drug or agent is effective relative to a parenteral route. This is calculated by the formula $$\text{Relative Biopotency}(\%) = \frac{\text{Dose } SC}{\text{Dose Oral}} \times \frac{AUC \text{ Oral}}{AUC \, SC} \times 100$$

The term "nighttime" or "bedtime" as used herein means a time before the patient goes to sleep and is not limited to clock time or cycles of light and dark, and alternately refers to a time during a day or night of longest fast, a period without external glucose source.

For the purposes of the present specification, as used herein, the phrase administered "at nighttime" or "at or shortly before (prior to) bedtime" means administered less than about 3 hours, preferably less than about 2 hours and more preferably less than about 1 hour prior to a prolonged period of sleep, or relative physical and/or mental inactivity, and fast, e.g., overnight. Whereas overnight typically means from the late night (p.m.) hours to the early morning (a.m.) hours, it could mean any period of a sleep-wake cycle during which a person obtains his/her necessary period of sleep. For the purposes of the present specification, administration should also occur at least about one hour, preferably at least about 1.5 hours, more preferably at least about 2 hours and still more preferably at least about 2 to about 3 hours after the last meal of the day.

For the purposes of the present specification, as used herein, the phrase administered "at mealtime" or "at or shortly before (prior to) ingestion of a meal" means administered within about 30 minutes prior to the meal. For the purposes of the present specification, the administration is preferably within about 25 minutes, more preferably within about 20 minutes, even more preferably within about 15 minutes, still more preferably within about 10 minutes, further more preferably within about 5 minutes of ingestion of the meal, and most preferably administered concurrently with ingestion of the meal (within about 0 minutes).

As used herein and in the appended claims, the singular forms "a," "an," and "the," include plural referents unless the context clearly indicates otherwise. Thus, for example, reference to "a molecule" includes one or more of such molecules, "a reagent" includes one or more of such different reagents, reference to "an antibody" includes one or more of such different antibodies, and reference to "the method" includes reference to equivalent steps and methods known to those of ordinary skill in the art that could be modified or substituted for the methods described herein.

Unless defined otherwise, all technical and scientific terms used herein have the same meaning as commonly understood by one of ordinary skill in the art to which the invention belongs. Although any methods, compositions, reagents, cells, similar or equivalent to those described herein can be used in the practice or testing of the invention, the preferred methods and materials are described herein. All publications mentioned herein are incorporated herein, including all figures, graphs, equations, illustrations, and drawings, to describe and disclose specific information for which the reference was cited in connection with.

The publications discussed above are provided solely for their disclosure before the filing date of the present application. Nothing herein is to be construed as an admission that the invention is not entitled to antedate such disclosure by virtue of prior invention. Throughout this description, the preferred embodiment and examples shown should be considered as exemplars, rather than as limitations on the present invention.

DETAILED DESCRIPTION OF THE INVENTION

Figure 1:
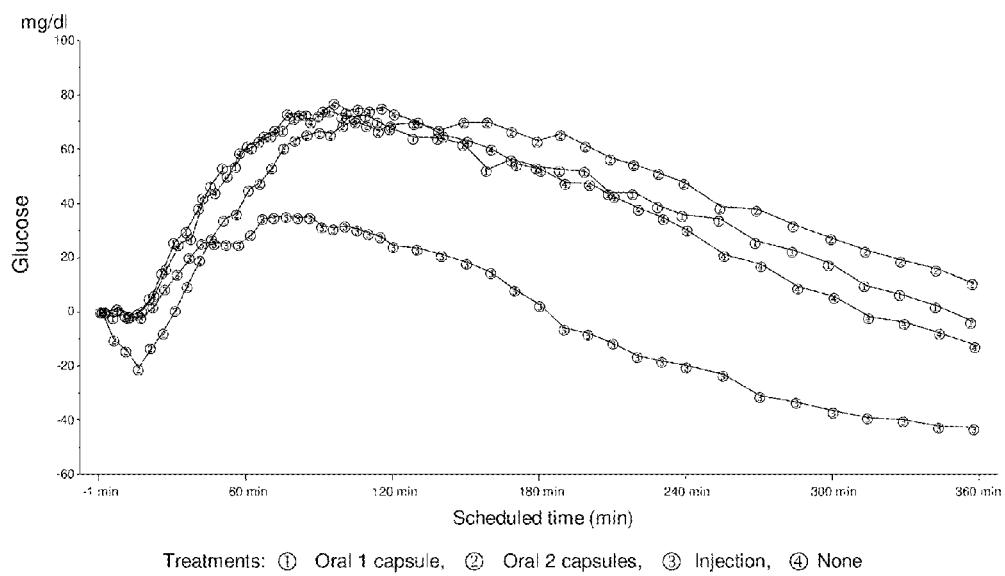
FIG. 1 shows a plot of the arithmetic means of postprandial blood glucose excursions for all subjects.

Because insulin entry into the bloodstream produces a decrease in blood glucose levels, oral absorption of insulin may be verified by observing the effect on a subject's blood glucose following oral administration of the composition. In a preferred embodiment of the invention, the oral dosage forms of the invention facilitate the oral delivery of insulin, and after insulin is absorbed into the bloodstream, the composition produces a maximal decrease in blood glucose in treated type 2 diabetic patients from about 5 to about 60 minutes after oral administration. In another embodiment of the present invention, the pharmaceutical composition produces a maximal decrease in blood glucose in treated type 2 diabetic patients from about 10 to about 50 minutes post oral administration. More particularly, the pharmaceutical composition produces a maximal decrease in blood glucose in treated type 2 diabetic patients within about 20 to about 40 minutes after oral administration.

The magnitude of the decrease in blood glucose produced by insulin absorbed into the bloodstream following entry into the gastrointestinal tract varies with the dose of insulin. In certain embodiments of the invention, type 2 diabetic patients show a maximal decrease in blood glucose by at least 10% within one hour post oral administration. In another embodiment, type 2 diabetic patients show a maximal decrease in blood glucose by at least 20% within one hour post oral administration, alternatively, at least 30% within one hour post oral administration.

Normal levels of blood glucose vary throughout the day and in relation to the time since the last meal. One goal of the present invention is to provide oral compositions of insulin that facilitate achieving close to normal levels of blood glucose throughout the 24-hour daily cycle. In a preferred embodiment of the invention, the pharmaceutical composition includes insulin or an insulin analog as the active agent and a delivery agent in an amount effective to achieve a fasting blood glucose concentration from about 90 to about 115 mg/dl. In another preferred embodiment of the invention, the pharmaceutical composition includes insulin or an insulin analog as the active agent and a delivery agent in an amount effective to achieve a fasting blood glucose concentration from about 95 to about 110 mg/dl, more preferably, the subject manifests fasting blood glucose concentrations at about 100 mg/dl.

In the time after a meal is consumed, blood glucose concentration rises in response to digestion and absorption into the bloodstream of carbohydrates derived from the food eaten. The present invention provides oral compositions of insulin that prevent or control very high levels of blood glucose from being reached and/or sustained. More particularly, the present invention provides compositions which facilitate achieving normal levels of blood glucose after a meal has been consumed, i.e., post-prandial. In a preferred embodiment of the invention, the pharmaceutical composition includes insulin as the active agent and a delivery agent in an amount effective to achieve a post-prandial blood glucose concentration from about 130 to about 190 mg/dl. In another preferred embodiment of the invention, the pharmaceutical composition includes insulin or an insulin analog as the active agent and a delivery agent in an amount effective to achieve a post-prandial blood glucose concentration from about 150 to about 180 mg/dl, more preferably, the subject manifests fasting blood glucose concentrations at less than about 175 mg/dl.

The present invention provides pharmaceutical compositions for oral administration which includes insulin or an insulin analog as the active agent and a delivery agent in an amount effective to achieve pre-prandial (before a meal is consumed) blood glucose concentration from about 90 to about 125 mg/dl. In a preferred embodiment, the present invention provides pharmaceutical compositions for oral administration which includes insulin or an insulin analog as the active agent and a delivery agent in an amount effective to achieve pre-prandial blood glucose concentration from about 100 to about 115 mg/dl.

The present invention provides pharmaceutical compositions for oral administration which include insulin as the active agent and a delivery agent in an amount effective to achieve blood glucose concentrations within the normal range during the evening period from about 70 to about 120 mg/dl. In a preferred embodiment, the present invention provides pharmaceutical compositions for oral administration which include insulin or an insulin analog as the active agent and a delivery agent in an amount effective to achieve blood glucose concentrations at about 4 hours after bed time from about 80 to about 120 mg/dl.

In general, the present invention provides a method of administering insulin and pharmaceutical compositions useful for administering insulin such that the insulin is bioavailable and biopotent. The delivery agent enables insulin to be orally absorbable through the mucosa of the stomach and facilitates the absorption of insulin administered therewith (either in the same dosage form, or simultaneously therewith), or sequentially (in either order, as long as both the delivery agent and insulin are administered within a time period which provides both in the same location, e.g., the stomach, at the same time). Following oral administration of the pharmaceutical compositions of the present invention, the delivery agent passes though the mucosal barriers of the gastrointestinal tract and is absorbed into the blood stream where it can be detected in the plasma and/or blood of subjects. The level of delivery agent in the bloodstream as measured in the plasma and/or blood is dose-dependent.

By virtue of the present invention, the ratio of portal (unmodified) insulin concentration to systemic (unmodified) insulin concentration approaches in human diabetic patients approaches that which is obtained in normal healthy humans. The chronic administration of oral dosage forms of the present invention result in a higher portal insulin concentration and lower systemic insulin concentration over time than that obtained with an equi-effective dose of insulin administered subcutaneously (i.e., which provide similar control of blood glucose levels). Transient peaks in insulin levels that may occur by virtue of the oral administration of insulin in accordance with the present invention is not believed to be associated with vascular diseases.

By virtue of the chronic administration of oral dosage forms of the present invention instead of equi-effective subcutaneous doses of insulin, lower levels of hyperinsulinemia are obtained, e.g., systemic insulin concentrations are at least about 20% lower when compared to a comparably effective subcutaneous dose of insulin. Therefore, the present invention provides a method for reducing the incidence and/or severity of systemic hyperinsulinemia associated with chronic dosing of insulin, and it is believed that the present invention also provides a method for reducing the incidence and/or severity of one or more disease states associated with chronic dosing of insulin.

By virtue of the chronic administration of oral dosage forms of the present invention, the patient achieves improved glucose tolerance and glycemic control as compared with baseline levels prior to treatment, even without any statistically significant increase in weight, risk of hypoglycemia or risk of hyperinsulinemia over the treatment period. Further, by virtue of the chronic administration of oral dosage forms of the present invention, the patient achieves improved insulin utilization, insulin sensitivity insulin secretion capacity and HbA1c levels as compared with baseline levels prior to treatment.

It is also believed that the chronic administration of oral dosage forms of the present invention to replace the endogenous insulin production in a mammal with impaired glucose tolerance or early stage diabetes mellitus will result in prophylactically sparing the function of the mammal's β-cells or will prevent death or dysfunction of the mammal's β-cells, and will thereby provide long-term protection to the mammal from developing overt or insulin dependent diabetes, or will delay the onset of overt or insulin dependent diabetes in the mammal.

The preferred pharmaceutical compositions of the invention comprise a combination of insulin and a delivery agent in a suitable pharmaceutical carrier or excipient as understood by practitioners in the art. The means of delivery of the pharmaceutical composition can be, for example, a capsule, compressed tablet, pill, solution, freeze-dried, powder ready for reconstitution or suspension suitable for administration to the subject.

Thus, in certain preferred embodiments of the present invention, the oral insulin formulations of the invention may be administered to a patient at meal time, and preferably slightly before (e.g., about 10-30 minutes before) ingestion of a meal, such that the peak plasma insulin concentrations are attained at or about the time of peak blood glucose concentrations resulting from the meal. As a further advantage in certain preferred embodiments, the administration of a relatively short-acting insulin (e.g., such as the insulin used to prepare the capsules administered in the clinical studies reported in the appended examples) will further result in plasma insulin levels returning to baseline levels within about 4 hours (and preferably within about 3 hours or less) after oral administration of the insulin formulations of the present invention.

As used herein, "insulin" refers to insulin from a variety of sources. Naturally occurring insulin and structurally similar bioactive equivalents (insulin analogues including short acting and analogues with protracted action) can be used. Insulin useful in the invention can be may be obtained by isolating it from natural source, such as different species of mammal. For example, animal insulin preparations extracted from bovine or porcine pancreas can be used. Insulin analogues, fragments, mimetics or polyethylene glycol (PEG)-modified derivatives of these compounds, derivatives and bioequivalents thereof can also be used with the invention.

The insulin used in the present invention may be obtained by chemically synthesizing it using protein chemistry techniques such as peptide synthesis, or by using the techniques of molecular biology to produce recombinant insulin in bacteria or eukaryotic cells. The physical form of insulin may include crystalline and/or amorphous solid forms. In addition, dissolved insulin may be used. Other suitable forms of insulin, including, but not limited to, synthetic forms of insulin, are described in U.S. Pat. Nos. 4,421,685, 5,474,978, and 5,534,488, the disclosure of each of which is hereby incorporated by reference in its entirety.

The most preferred insulin useful in the pharmaceutical compositions and methods of the present invention is human recombinant insulin optionally having counter ions including zinc, sodium, calcium and ammonium or any combination thereof. Human recombinant insulin can be prepared using genetic engineering techniques that are well known in the art. Recombinant insulin can be produced in bacteria or eukaryotic cells. Functional equivalents of human recombinant insulin are also useful in the invention. Recombinant human insulin can be obtained from a variety of commercial sources. For example, insulin (Zinc, human recombinant) can be purchased from Calbiochem (San Diego, Calif.). Alternatively, human recombinant Zinc-Insulin Crystals: Proinsulin Derived (Recombinant DNA Origin) USP Quality can be obtained from Eli Lilly and Company (Indianapolis, Ind.). All such forms of insulin, including insulin analogues (including but not limited to Insulin Lispro, Insulin Aspart, Insulin Glargine, and Insulin Detemir) are deemed for the purposes of this specification and the appended claims are considered to be encompassed by the term "insulin." The present invention also provides compositions of recombinant human zinc insulin and a delivery agent as a drug for oral administration of insulin in humans.

In other preferred embodiments of the invention, the insulin is a modified insulin, such as that conjugated with an oligomer such as that described in U.S. Pat. No. 6,309,633 and/or which not has been subjected to amphiphilic modification such as that described in U.S. Pat. Nos. 5,359,030; 5,438,040; and/or 5,681,811. The conjugated (modified) insulin may be incorporated into the oral formulations of the present invention in addition to or in the absence of any of the types of insulin described above, as well as with other insulin analogues. In such embodiments, the oral formulations include the modified insulin either with or without a pharmaceutically acceptable delivery agent that facilitates absorption of said insulin from the gastrointestinal tract.

The total amount of insulin to be used can be determined by those skilled in the art. It is preferable that the oral dosage form comprise a therapeutically effective amount of insulin, i.e., a pharmacologically or biologically effective amount, or an amount effective to accomplish the purpose of insulin. The dose of insulin administered should preferably be in such an amount that, upon oral administration, it results in a measurable and statistically significant reduction in blood glucose levels in normal healthy human subjects.

However, the amount can be less than a pharmacologically or biologically effective amount when the composition is used in a dosage unit form, such as a tablet, because the dosage unit form may contain a multiplicity of delivery agent/biologically or chemically active agent compositions or may contain a divided pharmacologically or biologically effective amount. The total effective amounts can then be administered in cumulative units containing, in total, pharmacologically, biologically or chemically active amounts of biologically or pharmacologically active agent.

It has been found that the use of the presently disclosed delivery agent provides extremely efficient delivery of insulin. Preferred insulin doses contained in one or more dosage forms, when dosed in combination with the delivery agents described herein, are about 50 to about 600 insulin Units USP (from about 2 to about 23 mg), preferably from about 100 Units (3.8 mg) to about 450 Units (15.3 mg), more preferably from about 200 Units (7.66 mg) to about 350 Units (13.4 mg), and still more preferably about 300 Units (11.5 mg), based on the accepted conversion of factor of 26.11 Units per mg.

Presently, different forms of typically subcutaneously-administered insulin preparations have been developed to provide different lengths of activity (activity profiles), often due to ingredients administered with insulin, ranging from short or rapid activity (e.g., solutions of regular, crystalline zinc insulin for injection; semilente insulin (prompt insulin zinc suspension); intermediate activity (e.g., NPH (isophane insulin suspension; lente (insulin zinc suspension; lente is a mixture of crystallized (ultralente) and amorphous (semilente) insulins in an acetate buffer); and slow activity (ultralente, which is extended insulin zinc suspension; protamine zinc). Short-acting insulin preparations that are commercially available in the U.S. include regular insulin and rapid-acting insulins. Regular insulin has an onset of action of 30-60 minutes, peak time of effect of 1.5 to 2 hours, and a duration of activity of 5 to 12 hours. Rapid acting insulins, such as aspart) (Humalog®/lispro) (Novolog®, have an onset of action of 10-30 minutes, peak time of effect of 30-60 minutes, and a duration of activity of 3 to 5 hours. Intermediate-acting insulins, such as NPH (neutral protamine Hagedorn) and Lente insulins (insulin zinc suspension), have an onset of action of 1-2 hours, peak time of effect of 4 to 8 hours, and a duration of activity of 10 to 20 hours. In the case of long-acting insulins, Ultralente insulin has an onset of action of 2-4 hrs, peak time of effect of 8-20 hours, and a duration of activity of 16 to 24 hours, while Glargine insulin has an onset of action of 1 to 2 hours, a duration of action of 24 hours but no peak effect.

There are over 180 individual insulin preparations available world-wide. Approximately 25% of these are soluble insulin (unmodified form); about 35% are basal insulins (mixed with NPH or Lente insulins, increased pI, or isoelectric point (insulin glargine), or acylation (insulin detemir); these forms have reduced solubility, slow subcutaneous absorption and long duration of action relative to soluble insulins); about 2% are rapid-acting insulins (e.g., which are engineered by amino-acid change, and have reduced self-association and increased subcutaneous absorption); and about 38% pre-mixed insulins (e.g., NPH/soluble/rapid-acting insulins; these preparations have the benefit, e.g., of reduced number of daily injections). In many cases, regimens that use insulin in the management of diabetes combine long-acting and short-acting insulin.

It is contemplated that the oral insulin formulations of the present invention, which include insulin preferably together with a pharmaceutically acceptable delivery agent that facilitates absorption of said insulin from the gastrointestinal tract, may be utilized in combination therapy to include an insulin that has rapid action, intermediate action, and/or slow action, as described above, in order to provide effective basal insulin levels in the diabetic patient. The rate of action of the insulin may be caused by virtue of its solubility, and/or by virtue of its half-life, etc. Thus, in alternative embodiments, the oral formulations of the present invention may be designed to provide the intermediate activity which is found with, e.g., a subcutaneously administered NPH insulin, or a slow action which is found with protamine zinc insulin. In each case, the oral formulations of the invention, which preferably include a pharmaceutically acceptable delivery agent which facilitates absorption of the insulin (as described herein) provide effective control of blood glucose levels, albeit for different time periods and with different plasma glucose time curves.

Intermediate-acting and long-acting insulin may be prepared using methodologies known to those skilled in the art to provide a continuous level of insulin, similar to the slow, steady (basal) secretion of insulin provided by the normal pancreas. For example, Lantus®, from Aventis Pharmaceuticals Inc., is a recombinant human insulin analog that is a long-acting, parenteral blood-glucose-lowering agent whose longer duration of action (up to 24 hours) is directly related to its slower rate of absorption. Lantus® is administered subcutaneously once a day, preferably at bedtime, and is said to provide a continuous level of insulin, similar to the slow, steady (basal) secretion of insulin provided by the normal pancreas. The activity of such a long-acting insulin results in a relatively constant concentration/time profile over 24 hours with no pronounced peak, thus allowing it to be administered once a day as a patient's basal insulin. Such long-acting insulin has a long-acting effect by virtue of its chemical composition, rather than by virtue of an addition to insulin when administered.

In a preferred embodiment, administration of the pharmaceutical formulation comprising long-acting insulin is once or twice a day. In a preferred embodiment, administration of the dosage form providing short-acting insulin effect can be once, twice, three times, four times or more than four times daily, and can be at nighttime, in the morning and/or preprandially. In a more preferred embodiment, administration of the dosage form is preferably at nighttime or morning and three times preprandially, and more preferably is at nighttime and preprandially for breakfast, lunch and dinner. Preferably, the insulin formulations are administered to such human patients on a chronic basis, e.g., for at least about 2 weeks.

In other embodiments of the invention, the oral formulations include an insulin conjugated with an oligomer such as that described in U.S. Pat. No. 6,309,633 and/or which not has been subjected to amphiphilic modification such as that described in U.S. Pat. Nos. 5,359,030; 5,438,040; and/or 5,681,811. The conjugated (modified) insulin may be incorporated into the oral formulations of the present invention in addition to or in the absence of any of the types of insulin described above, as well as with other insulin analogues. In such embodiments, the oral formulations preferably include the modified insulin together with a pharmaceutically acceptable delivery agent which facilitates absorption of said insulin from the gastrointestinal tract.

Oral administrable drugs currently available for management of type 2 diabetes fall into two general categories: those that increase insulin supply (sulfonylureas, other secretagogues and insulin itself) and those that decrease insulin resistance or improve its effectiveness (biguanides, thiazolidinediones). See The Medical Letter, Volume 1, Issue 1, September 2002, Treatment Guidelines, Drugs for Diabetes. Oral sulfonylurea secretagogues include the first and second generation insulin secretagogues which are believed to interact with ATP-sensitive potassium channels in the beta cell membrane to increase secretion of insulin. The more commonly used second-generation agents (glyburide, glipizide, and glimepiride), which are more potent than the first-generation drugs (acetohexamide, chlorpropamide, tolbutamide, and tolazamide), are similar to each other in efficacy, but differ in dosage and duration of action.

Typically, such secretagogues are useful for increasing insulin levels sufficiently to achieve desired basal insulin levels in patients with early stages of type II diabetes, who are still able to produce their own insulin. However, it is unlikely that such secretagogues would be useful for increasing insulin levels sufficiently to achieve desired basal insulin levels in patients with later stages of type II diabetes, who have very little pancreatic function left and produce very little insulin endogenously. In such patients, the basal insulin levels are achieved, e.g., via the use of subcutaneous injections of insulin (such as a long-acting insulin, for example Lantus®).

In certain embodiments of the present invention, the oral insulin formulations include one or more of the various types of secretagogues mentioned above in addition to a type of insulin as described above. For example, with respect to the first generation sulfonylureas, tolbutamide (Orinase®) has an onset of action of one (1) hour and a duration of action of 6-12 hours, and is usually given in a dose of 1000 mg to 2000 mg in divided daily doses (maximum daily dose, 3000 mg/day). Tolazamide (Tolinase®) has an onset of action of 4-6 hours and a duration of action of 10-14 hours, and is usually given in a dose of 250 mg to 500 mg either once or in divided daily doses (1000 mg/day). Acetohexamide (Dymelor®) has an onset of action of one (1) hour and a duration of action of 10-14 hours, and is usually given in a dose of 500 mg to 750 mg either once or in divided daily doses (maximum daily dose 1500 mg/day). Chlorpropamide (Diabinese®) has an onset of action of one hour and a duration of action of 72 hours, and is usually given in a dose of 250 mg to 375 mg once a day (maximum daily dose, 750 mg/day).

With respect to the second generation sulfonylureas, glyburide (DiaBeta®); Micronase®; Glynase®) has an onset of action of 1.5 hours and a duration of action of 18-24 hours. It is usually given in a dose of 5 to 20 mg either once or in divided daily doses (maximum daily dose, 20 mg/day). Glipizide (Glucotrol®) has an onset of action of one hour and a duration of action of 10-24 hours. It is usually given in a dose of 10 to 20 mg either once or in divided daily doses (maximum daily dose, 40 mg/day). Glimepiride (Amaryl®) has an onset of action of 2 hours and a duration of action of 18-28 hours. It is usually administered in a dose of 1 to 4 mg once a day (maximum daily dose, 8 mg/day). Lastly, gliclazide (Diamicron®) is usually administered in a dose of 40 to 80 mg per day (maximum daily dose, 320 mg).

Oral non-sulfonylurea secretagogues, such as repaglinide and nateglinide, although structurally different from the sulfonylureas, also bind to ATP-sensitive potassium channels on beta-cells and increase insulin release. See The Medical Letter, Volume 1, Issue 1, September 2002, Treatment Guidelines, Drugs for Diabetes. Both repaglinide and nateglinide are rapidly absorbed, resulting in plasma levels of insulin that peak within 30 to 60 minutes and return to baseline before the next meal. These drugs must be taken before each meal; if a meal is missed, the drug should be omitted. Repaglinide and nateglinide are much more expensive than sulfonylureas, but repaglinide may be a useful alternative to a sulfonylurea in patients with renal impairment (because it is cleared primarily by hepatic metabolism) or in patients who eat sporadically. Hypoglycemia may be slightly less frequent with nateglinide and repaglinide than with sulfonylureas, but data are limited. Nateglinide (Starlix®) stimulates pancreatic insulin secretion within 20 minutes of oral administration. Following oral administration immediately prior to a meal, nateglinide is rapidly absorbed with a mean peak plasma drug concentration ($C_{max}$) generally occurring within one hour ($t_{max}$) after dosing. When nateglinide is dosed three times daily before meals, there is a rapid rise in plasma insulin, with peak levels approximately one (1) hour after dosing and a fall to baseline by four (4) hours after dosing. Nateglinide is usually administered in a dose of 60 to 120 mg three times daily before meals (maximum daily dose, 360 mg/day). When given with or after meals, the extent of nateglinide absorption (AUC) remains unaffected. However, there is a delay in the rate of absorption characterized by a decrease in $C_{max}$ and a delay in time to peak plasma concentration ($t_{max}$). Similarly, repaglinide (Prandin®) is rapidly and completely absorbed from the gastrointestinal tract following oral administration. After single and multiple oral doses in healthy subjects or in patients, peak plasma drug levels ($C_{max}$) occur within 1 hour ($t_{max}$). Repaglinide is usually administered in a dose of 1 to 4 mg three times a day before meals (maximum daily dose, 16 mg/day). When repaglinide was given with food, the mean $t_{max}$ was not changed, but the mean $C_{max}$ and AUC (area under the time/plasma concentration curve) were decreased 20% and 12.4%, respectively.

In addition, long-term administration of specific inhibitors of dipeptidyl peptidase IV (DP IV), so as to enhance circulating active potent insulin secretagogues glucose-dependent insulinotropic polypeptide (GIP) and glucagon-like peptide-1 (GLP-1) levels, has been shown to improve glucose tolerance and beta-cell glucose responsiveness and to reduce hyperinsulinemia in the Vancouver diabetic fatty (VDF) rat model of type 2 diabetes. [Long-term treatment with dipeptidyl peptidase IV inhibitor improves hepatic and peripheral insulin sensitivity in the VDF Zucker rat: a euglycemic-hyperinsulinemic clamp study. Diabetes 2002 September; 51(9):2677-2683. Pospisilik J A, Stafford S G, Demuth H U, McIntosh C H, Pederson R A.] Upon release into the circulation, GIP and GLP-1 are rapidly cleaved and inactivated by the enzyme DP IV.

With respect to anti-diabetic drugs currently available for management of type 2 diabetes that decrease insulin resistance or improve its effectiveness, biguanides, which decrease the amount of glucose made by the liver, and thiazolidinediones, which make the patient more sensitive to insulin, are oral hypoglycemic agents that are currently used clinically for improving insulin resistance. Biguanides, such as Metformin (Glucophage® and Glucophage® XR by Bristol-Myers Squibb Company of Princeton, N.J.), which is the only biguanide available for therapeutic use, decreases hepatic glucose production (gluconeogenesis), decreases intestinal absorption of glucose and improves insulin sensitivity by increasing peripheral glucose uptake and utilization. There is no fixed dosage of Glucophage® for the management of hyperglycemia, and dosage must be individualized based upon effectiveness and tolerance, while not exceeding the maximum recommended daily dose of 2550 mg in adults and 2000 mg in pediatric patients, once or in divided doses. In general, clinically significant results are not seen at doses below 1500 mg per day. However, a lower recommended starting dose and gradually increased dosage is advised in order to minimize gastrointestinal symptoms.

Thiazolidinediones improve sensitivity to insulin in muscle and adipose tissue and inhibit hepatic gluconeogenesis, and thus depend on the presence of insulin for their action. The two currently approved thiazolidinedione compounds are pioglitazone (Actos® by Takeda Pharmaceuticals America, Inc. of Lincolnshire, Ill.) and rosiglitazone (Avandia® by GlaxoSmithKline of Research Triangle Park, N.C.). Actos® also improves hepatic sensitivity to insulin and improves dysfunctional glucose homeostasis. Actos® is first measurable in serum, following oral administration in the fasting state, within 30 minutes, with peak concentrations observed within 2 hours. Food slightly delays the time to peak serum concentration to 3 to 4 hours but does not alter the extent of absorption. Actos® is usually given once daily without regard to meals, and dosage must be individualized based upon $HbA_{1c}$ for a period of time adequate to evaluate changes in $HbA_{1c}$. Monotherapy dosage in patients not adequately controlled with diet and exercise may be initiated at 15 mg or 30 mg and can be increased incrementally up to 45 mg (maximum dose 45 mg per day). Avandia® reaches peak plasma concentrations within about 1 hour after dosing, and administration with food results in no change in overall exposure (AUC) but results in a 28% decrease in maximum plasma concentrations and a delay of the time to reach peak plasma concentrations to about 1.75 hours after dosing. Dosage of Avandia® must be individualized, and Avandia® may be administered either at a starting dose of 4 mg as a single daily dose or divided and administered twice a day with or without food. For patients who respond inadequately, as determined by reduction in fasting blood glucose, the dose may be increased to 8 mg daily (maximum dose 8 mg per day).

In certain preferred embodiments of the invention, the oral formulations of the invention provide two forms of insulin having different activity rates in order to simulate the biphasic release of insulin in non-diabetic humans. For example, such oral formulations may include a rapid-acting form of insulin together with a slow acting form of insulin so as to provide a first peak of insulin which occurs rapidly and is short-lived, followed by a second peak of insulin which occurs at a later time, but which preferably has a longer duration.

In further alternatively preferred embodiments of the invention, the oral formulations of the invention include a rapid-acting form of insulin together with a secretagogue that promotes the secretion of insulin from the beta-cells at a time and to an extent which mimics the second phase release of insulin in non-diabetic humans.

In alternatively preferred embodiments of the invention, the methods of insulin administration of the invention provide two separate forms of insulin having different activity rates in order for the regimen to simulate the biphasic release of insulin in non-diabetic humans. For example, the oral formulations may include a rapid-acting form of insulin so as to provide a first peak of insulin which occurs rapidly and is short-lived. Such fast-acting effect may be provided by the delivery agent that facilitates the absorption of insulin from the gastrointestinal tract. The slow acting form of insulin provides a second peak of insulin that occurs at a later time but that preferably has a longer duration. Such slower acting insulin may be provided by a separate dosage form, which may be administered orally or subcutaneously.

In further embodiments of the present invention, the oral dosage forms described herein are orally administered as described herein in combination with an additional therapy to treat diabetes, impaired glucose tolerance, or to achieve glucose homeostasis, said additional therapy comprising, for example, an additional drug such as a sulfonylurea, a biguanide (such as Metformin), an alpha-glucosidase, insulin delivered via a different pathway (e.g., parenteral insulin), and/or an insulin sensitizer such as thiazolidinedione.

In further embodiments of the invention, the oral dosage forms described herein reduce the likelihood of hypoglycemic events. Hypoglycemia usually results from a mismatch between insulin levels and degree of glycemia, e.g., when the administration of insulin and the ingestion of the meal are not timed such that the insulin peak occurs at peak glycemia, and administration of insulin shortly before a meal is more practical for a patient and is also safer, because glucose is ingested soon thereafter. The risk of hypoglycemia is lowered mainly due to the portal-physiologic route of administration of oral insulin. One cannot hyperinsulinize the liver, because, even under hyperinsulinemic condition, the uptake of glucose by the liver will be unchanged. Unlike the peripheral tissue, the pancreas will not sequester additional glucose but rather will only cease producing endogenous insulin. Second, the brief peak of insulin that results from the oral composition described herein shows that, even if insulin were to reach high peripheral levels, the peak quickly drops precipitously.

In addition, further embodiments of the oral dosage forms described herein avoid the risk of hypoglycemic events that may occur in certain short acting insulin formulations, which may, between the time of administration of insulin and the time of ingestion of the meal, contribute to a lowering of blood glucose to a level that could range from undesirable to clinically hypoglycemic. In the oral dosage forms disclosed herein, dosing closer to a meal eliminated the dip in blood glucose levels, which was precarious by itself. The effect seems to have also translated to lowering of the subsequent glucose excursion In preferred embodiments of the dosage forms described herein, in the absence of a delivery agent, the dose of insulin is not sufficiently absorbed when orally administered to a human patient to provide a desirable therapeutic effect but said dose provides a desirable therapeutic effect when administered to said patient by another route of administration. Previous disclosures by Emisphere Technologies, Inc. solved the problem of oral absorption of insulin by providing delivery agents that facilitate transport of insulin through the gut wall and into the bloodstream where the insulin can perform its biological function. As a result, effective oral drug delivery methods are provided to increase the oral bioavailability and absorption of insulin, which is currently administered parenterally.

The invention is thus directed to an methods involving oral administration of a dosage form comprising insulin together with a pharmaceutically acceptable delivery agent that serves to render the insulin orally absorbable through the gastrointestinal mucosa, the delivery agent being present in an amount effective to facilitate the absorption of said insulin, such that a therapeutically effective amount of said dose of insulin is absorbed from the gastrointestinal tract of human diabetic patients. This allows the oral dosage form to be dosed much closed to a meal than was previously taught.

In preferred embodiments, the oral dosage forms of the present invention comprise a mixture of insulin and a delivery agent, e.g., monosodium N-(4-chlorosalicyloyl)-4-aminobutyrate (4-CNAB), a novel compound discovered by Emisphere Technologies, Inc., or separately containing insulin and the delivery agent.

In other preferred embodiments, the delivery agents used in the invention have the following structure:

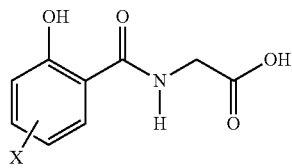

wherein X is one or more of hydrogen, halogen, hydroxyl or $C_1$-$C_3$ alkoxy, and R is substituted or unsubstituted $C_1$-$C_3$ alkylene, substituted or unsubstituted $C_1$-$C_3$ alkenylene.

In certain preferred embodiments, the delivery agents of the invention preferably have the following structure:

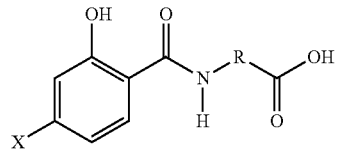

wherein X is halogen, and R is substituted or unsubstituted $C_1$-$C_3$ alkylene, substituted or unsubstituted $C_1$-$C_3$ alkenylene.

In a preferred embodiment of the present invention, the pharmaceutical composition includes a delivery agent wherein X is chlorine and R is $C_3$ alkylene. In another preferred embodiment of the present invention, the pharmaceutical composition includes the compound 4-[(4-chloro, 2-hydroxybenzoyl)amino]butanoic acid as a delivery agent for the oral delivery of insulin, preferably the monosodium salt thereof. In preferred embodiments, the oral dosage forms of the present invention comprise a mixture of insulin and a delivery agent, e.g., monosodium N-(4-chlorosalicyloyl)-4-aminobutyrate (4-CNAB), a novel compound discovered by Emisphere Technologies, Inc., or separately containing insulin and the delivery agent.

The delivery agents may be in the form of the carboxylic acid or salts thereof. Suitable salts include, but are not limited to, organic and inorganic salts, for example alkali-metal salts, such as sodium, potassium and lithium; alkaline-earth metal salts, such as magnesium, calcium or barium; ammonium salts; basic amino acids, such as lysine or arginine; and organic amines, such as dimethylamine or pyridine. Preferably, the salts are sodium salts. The salts may be mono- or multi-valent salts, such as monosodium salts and di-sodium salts. The salts may also be solvates, including ethanol solvates, and hydrates.

Other suitable delivery agents that can be used in the present invention include those delivery agents described U.S. Pat. Nos. 5,650,386, 5,773,647, 5,776,888, 5,804,688, 5,866,536, 5,876,710, 5,879,681, 5,939,381, 5,955,503, 5,965,121, 5,989,539, 5,990,166, 6,001,347, 6,051,561, 6,060,513, 6,090,958, 6,100,298, 5,766,633, 5,643,957, 5,863,944, 6,071,510 and 6,358,504, the disclosure of each of which is incorporated herein by reference. Additional suitable delivery agents are also described in International Publications Nos. WO 01/34114, WO 01/21073, WO 01/41985, WO 01/32130, WO 01/32596, WO 01/44199, WO 01/51454, WO 01/25704, WO 01/25679, WO 00/50386, WO 02/02509, WO 00/47188, WO 00/07979, WO 00/06534, WO 98/25589, WO 02/19969, WO 00/59863, WO 95/28838, WO 02/19969, WO 02/20466, WO 02/069937 and WO 02/070438, the disclosure of each of which is incorporated herein by reference.

Salts of the delivery agent compounds of the present invention may be prepared by methods known in the art. For example, sodium salts may be prepared by dissolving the delivery agent compound in ethanol and adding aqueous sodium hydroxide.

The compounds described herein may be derived from amino acids and can be readily prepared from amino acids by methods known by those with skill in the art based upon the present disclosure and the methods described in International Publications Nos. WO 96/30036, WO 97/36480, WO 98/34632 and WO 00/07979, and in U.S. Pat. Nos. 5,643,957 and 5,650,386, the disclosure of each of which is incorporated herein by reference. For example, the compounds may be prepared by reacting the single amino acid with the appropriate acylating or amine-modifying agent, which reacts with a free amino moiety present in the amino acid to form amides. Protecting groups may be used to avoid unwanted side reactions as would be known to those skilled in the art.

The delivery agents may also be prepared by the methods of International Patent Publications Nos. WO 02/02509 and WO 03/057170, the disclosure of each of which is incorporated herein by reference.

The delivery agents may also be prepared by alkylation of the appropriate salicylamide according to the methods of International Publication No. WO 00/46182, the disclosure of which is incorporated herein by reference. The salicylamide may be prepared from salicylic acid via the ester by reaction with sulfuric acid and ammonia.

In addition, polyamino acids and peptides comprising one or more of these compounds may be used. An amino acid is any carboxylic acid having at least one free amine group and includes naturally occurring and synthetic amino acids. Poly amino acids are either peptides (which are two or more amino acids joined by a peptide bond) or are two or more amino acids linked by a bond formed by other groups which can be linked by, e.g., an ester or an anhydride linkage. Peptides can vary in length from dipeptides with two amino acids to polypeptides with several hundred amino acids.

The delivery agent compound may be purified by recrystallization or by fractionation on one or more solid chromatographic supports, alone or linked in tandem. Suitable recrystallization solvent systems include, but are not limited to, ethanol, water, heptane, ethyl acetate, acetonitrile, methanol and tetrahydrofuran and mixtures thereof. Fractionation may be performed on a suitable chromatographic support such as alumina, using methanol/n-propanol mixtures as the mobile phase; reverse phase chromatography using trifluoroacetic acid/acetonitrile mixtures as the mobile phase; and ion exchange chromatography using water or an appropriate buffer as the mobile phase. When anion exchange chromatography is performed, preferably a 0-500 mM sodium chloride gradient is employed.

Following oral administration of the pharmaceutical compositions of the present invention, the delivery agent passes though the mucosal barriers of the GI tract and is absorbed into the blood stream where it can be detected in the plasma of subjects. The delivery agent facilitates the absorption of the drug (active agent) administered therewith (either in the same dosage form, or simultaneously therewith), or sequentially (in either order, as long as both the delivery agent and the drug are administered within a time period which provides both in the same location, e.g., the stomach, at the same time). The mechanism by which 4-CNAB facilitates the gastrointestinal absorption of insulin has not yet been fully elucidated. The current working hypothesis is that 4-CNAB interacts with insulin non-covalently, creating more favorable physicochemical properties for absorption. This working hypothesis is provided for explanation purposes only and is not intended to limit the present invention or the appended claims in any way.

The amount of delivery agent in the present composition is a delivery effective amount and can be determined for any particular delivery agent/insulin combination by methods known to those skilled in the art. The amount of delivery agent necessary to adequately deliver the therapeutic amount of insulin into the blood stream of a subject needing the therapeutic effect of insulin may vary depending on one or more of the following; the chemical nature of insulin; the chemical structure of the particular delivery agent; the nature and extent of interaction between insulin and delivery agent; the nature of the unit dose, i.e., solid, liquid, tablet, capsule or suspension; the concentration of delivery agent in the GI tract; the feeding state of the subject; the diet of the subject; the health of the subject and the ratio of delivery agent to insulin. In certain preferred embodiments of the invention, the amount of the delivery agent preferred for the pharmaceutical composition and contained in one or more dosage forms is from about 1 mg to about 2,000 mg, more preferably from about 5 mg to about 800 mg, more preferably about 20 mg to about 600 mg, even more preferably from about 30 mg to about 400 mg, still more preferably from about 40 mg to about 200 mg, most preferably about 40 mg, 80 mg or 160 mg.

The time it takes for the delivery agent to reach a peak in the bloodstream ($t_{max}$) may depend on many factors such as the following: the nature of the unit dose, i.e., solid, liquid, tablet, capsule, suspension; the concentration of delivery agent in the GI tract; the feeding state of the subject; the diet of the subject; the health of the subject and the ratio of delivery agent to the active agent. The delivery agents of the present invention are rapidly absorbed from the gastrointestinal tract when orally administered in an immediate release dosage form, preferably in tablet form, and preferably provide a peak plasma delivery agent concentration within about 5 minutes to about 40 minutes after oral administration, and preferably at about 10 minutes to about 35 minutes after oral administration. In a preferred embodiment of the invention, wherein the pharmaceutical composition includes the compound 4-CNAB as the delivery agent for insulin, the composition provides a peak plasma delivery agent concentration within about 25 minutes to about 35 minutes after oral administration to fasting diabetic patients and within about 15 minutes to about 25 minutes after oral administration to fed diabetic patients.

In certain preferred embodiments of the invention, a peak plasma concentration ($C_{max}$) of the delivery agent achieved after oral administration is preferably from about 10 to about 250,000 ng/ml, after oral administration, preferably from about 100 to about 125,000 ng/ml, and preferably the peak plasma concentration of the delivery agent is from about 1,000 to about 50,000 ng/ml, after oral administration. More preferably, the peak plasma concentration of the delivery agents of the present invention is from about 3,000 to about 15,000 ng/ml after oral administration.

In a preferred embodiment of the invention, wherein the pharmaceutical composition includes the compound 4-CNAB as the delivery agent and insulin as the active agent, the composition provides a peak plasma 4-CNAB concentration within about 0.1 to about 3 hours after oral administration. In certain preferred embodiments where the pharmaceutical composition includes the compound 4-CNAB as the delivery agent and insulin as the active agent, the peak plasma concentration of delivery agent attained is from about 8,000 to about 37,000 ng/ml.

Since the amount of delivery agent required to deliver a particular active agent is variable and the amount of active agent required to produce a desired therapeutic effect is also a variable, the ratio of active agent to delivery agent may vary for different active agent/delivery agent combinations. In certain preferred embodiments of the invention where the oral pharmaceutical composition includes insulin as the active agent and the delivery agent is the compound 4-CNAB, the amount of the delivery agent included in the pharmaceutical composition may be from about 20 mg to about 600 mg of said delivery agent.

The optimum ratio of insulin to delivery agent can vary depending on the delivery agent and the formulation. Optimizing the ratio of insulin to delivery agent is within the knowledge of one skilled in the art. In certain preferred embodiments of the invention, the pharmaceutical composition includes insulin as the active agent and the delivery agent is the monosodium salt of 4-CNAB, the ratio of insulin [Units] to delivery agent [mg] ranges from 10:1 [Units/mg] to 1:10 [Units/mg], preferably, the ratio of insulin [Units] to delivery agent [mg] ranges from 5:1 [Units/mg] to 0.5:1 [Units/mg].

Preferred insulin doses in a single administration are about 5 to about 1000 insulin units USP, preferably from about 50 to about 400, more preferably from about 150 to about 400, and still more preferably from about 150 to about 300 units.

Absorption of insulin can be detected in subjects treated with the pharmaceutical compositions of the present invention by monitoring the plasma levels of insulin after treatment. The time it takes for an active agent to reach a peak in the bloodstream ($t_{max}$) may depend on many factors such as the following: the nature of the unit dose, i.e., solid, liquid, tablet, capsule, suspension; the concentration of active agent and delivery agent in the GI tract; the feeding state of the subject; the diet of the subject; the health of the subject and the ratio of active agent to the delivery agent.

In a preferred embodiment of the invention, wherein the pharmaceutical composition includes the compound 4-CNAB as the delivery agent and insulin as the active agent, the composition provides a peak plasma insulin concentration from about 0.1 to about 1 hour after oral administration. In another embodiment, the composition provides a peak plasma insulin concentration from about 0.2 to about 0.6 hours after oral administration. In a preferred embodiment, the composition provides a peak plasma insulin concentration from about 0.3 to about 0.4 hours after oral administration. In another embodiment, the composition provides a peak plasma insulin concentration within about 1 hour after oral administration. In certain preferred embodiments, the pharmaceutical composition comprises insulin and the compound 4-CNAB as a delivery agent to facilitate the oral delivery of insulin, and after insulin is absorbed into the bloodstream, the plasma insulin levels in treated patients peak at about 20 minutes post oral administration with a second peak at about 105 minutes.

The effect of absorption of insulin is manifested in human patients treated with the pharmaceutical compositions of the present invention by observing reductions in C-peptide concentration following oral treatment. For example, in one embodiment of the invention, the pharmaceutical composition comprises insulin and the compound 4-CNAB as a delivery agent to facilitate the oral delivery of insulin, and, after insulin is absorbed into the bloodstream, the composition produces a maximal decrease in C-peptide concentration in treated patients from about 80 and about 120 minutes post oral administration. More particularly, the composition produces a maximal decrease in C-peptide concentration in treated patients from about 90 and about 110 minutes post oral administration.

In previous patent applications, such as those enumerated above that have been incorporated herein by reference, Emisphere Technologies, Inc. disclosed structures of various delivery agents, comparisons of their effectiveness of absorption and effectiveness of delivery, the preparation of the preferred delivery agent 4-CNAB, its preparation for human studies, and data regarding previous non-clinical and clinical studies involving the delivery agent 4-CNAB.

The delivery agent may be used directly by mixing with the unmodified insulin prior to administration, either in dry powder form or wet granulated together. To this mixture, other pharmaceutically acceptable excipients may be added. The mixture may be then tableted or placed into gelatin capsules containing a unit dose of the active agent and the delivery agent. Alternatively, the delivery agent/insulin mixture may be prepared as an oral solution or suspension. The delivery agent and insulin do not need to be mixed together prior to administration, such that, in certain embodiments, the unit dose of insulin (with or without other pharmaceutically acceptable excipients) is orally administered without the delivery agents of this invention, and the delivery agent is separately orally administered (with or without other pharmaceutically acceptable excipients) before, after, or simultaneously with the insulin.

In certain preferred embodiments, the oral dosage forms of the present invention are solid. The insulin in dry powder form is stable, and in certain preferred embodiments is simply mixed in a desirable ratio with the delivery agent. The dry powder mixture may then be filled into gelatin capsules, with or without optional pharmaceutical excipients. Alternatively, the insulin in dry powder form may be mixed with the delivery agent together with optional pharmaceutical excipients, and the mixture may be tableted in accordance with standard tableting procedures known to those having ordinary skill in the art.

The dosage forms of the present invention may be produced by first dissolving insulin and the delivery agent into one solution or separate solutions. The solvent will preferably be an aqueous solution, but organic solvents or aqueous organic solvent mixtures may be used when necessary to solubilize the delivery agent. If two solutions are used, the proportions of each necessary to provide the correct amount of either insulin or delivery agent are combined and the resulting solution may be dried, by lyophilization or equivalent means. In one embodiment of the invention, the oral dosage form may be dried and rehydrated prior to oral administration.

The administration mixtures may be prepared, e.g., by mixing an aqueous solution of the delivery agent with an aqueous solution of insulin just prior to administration. Alternatively, the delivery agent and insulin can be admixed during the manufacturing process. The solutions may optionally contain additives such as phosphate buffer salts, citric acid, acetic acid, gelatin, and gum acacia.

In preferred embodiments of the oral dosage forms of the invention described above, the oral dosage form is solid, and is preferably provided incorporated within a gelatin capsule or is contained in a tablet.

Stabilizing additives may be incorporated into the delivery agent solution. With some drugs, the presence of such additives promotes the stability and dispersibility of the agent in solution. The stabilizing additives may be employed at a concentration ranging from about 0.1 and 5% (W/V), preferably about 0.5% (W/V). Suitable, but non-limiting, examples of stabilizing additives include gum acacia, gelatin, methyl cellulose, polyethylene glycol, carboxylic acids and salts thereof, and polylysine. The preferred stabilizing additives are gum acacia, gelatin and methyl cellulose.

The oral dosage forms of the present invention, containing a mixture of the active agent, e.g., insulin and the delivery agent, e.g., 4-CNAB or separately containing the active agent and the delivery agent, may include additional materials known to those skilled in the art as pharmaceutical excipients. Any excipient or ingredient, including pharmaceutical ingredients or excipients. Such pharmaceutical excipients include, for example, the following: Acidifying agents (acetic acid, glacial acetic acid, citric acid, fumaric acid, hydrochloric acid, diluted hydrochloric acid, malic acid, nitric acid, phosphoric acid, diluted phosphoric acid, sulfuric acid, tartaric acid); Aerosol propellants (butane, dichlorodifluoro-methane, dichlorotetrafluoroethane, isobutane, propane, trichloromonofluoromethane); Air displacements (carbon dioxide, nitrogen); Alcohol denaturants (denatonium benzoate, methyl isobutyl ketone, sucrose octacetate); Alkalizing agents (strong ammonia solution, ammonium carbonate, diethanolamine, diisopropanolamine, potassium hydroxide, sodium bicarbonate, sodium borate, sodium carbonate, sodium hydroxide, trolamine); Anticaking agents (see glidant); Antifoaming agents (dimethicone, simethicone); Antimicrobial preservatives (benzalkonium chloride, benzalkonium chloride solution, benzelthonium chloride, benzoic acid, benzyl alcohol, butylparaben, cetylpyridinium chloride, chlorobutanol, chlorocresol, cresol, dehydroacetic acid, ethylparaben, methylparaben, methylparaben sodium, phenol, phenylethyl alcohol, phenylmercuric acetate, phenylmercuric nitrate, potassium benzoate, potassium sorbate, propylparaben, propylparaben sodium, sodium benzoate, sodium dehydroacetate, sodium propionate, sorbic acid, thimerosal, thymol); Antioxidants (ascorbic acid, acorbyl palmitate, butylated hydroxyanisole, butylated hydroxytoluene, hypophosphorous acid, monothioglycerol, propyl gallate, sodium formaldehyde sulfoxylate, sodium metabisulfite, sodium thiosulfate, sulfur dioxide, tocopherol, tocopherols excipient); Buffering agents (acetic acid, ammonium carbonate, ammonium phosphate, boric acid, citric acid, lactic acid, phosphoric acid, potassium citrate, potassium metaphosphate, potassium phosphate monobasic, sodium acetate, sodium citrate, sodium lactate solution, dibasic sodium phosphate, monobasic sodium phosphate); Capsule lubricants (see tablet and capsule lubricant); Chelating agents (edetate disodium, ethylenediaminetetraacetic acid and salts, edetic acid); Coating agents (sodium carboxymethylcellulose, cellulose acetate, cellulose acetate phthalate, ethylcellulose, gelatin, pharmaceutical glaze, hydroxypropyl cellulose, hydroxypropyl methylcellulose, hydroxypropyl methylcellulose phthalate, methacrylic acid copolymer, methylcellulose, polyethylene glycol, polyvinyl acetate phthalate, shellac, sucrose, titanium dioxide, carnauba wax, microcrystalline wax, zein); Colorants (caramel, red, yellow, black or blends, ferric oxide); Complexing agents (ethylenediaminetetraacetic acid and salts (EDTA), edetic acid, gentisic acid ethanolmaide, oxyquinoline sulfate); Desiccants (calcium chloride, calcium sulfate, silicon dioxide); Emulsifying and/or solubilizing agents (acacia, cholesterol, diethanolamine (adjunct), glyceryl monostearate, lanolin alcohols, lecithin, mono- and di-glycerides, monoethanolamine (adjunct), oleic acid (adjunct), oleyl alcohol (stabilizer), poloxamer, polyoxyethylene 50 stearate, polyoxyl 35 caster oil, polyoxyl 40 hydrogenated castor oil, polyoxyl 10 oleyl ether, polyoxyl 20 cetostearyl ether, polyoxyl 40 stearate, polysorbate 20, polysorbate 40, polysorbate 60, polysorbate 80, propylene glycol diacetate, propylene glycol monostearate, sodium lauryl sulfate, sodium stearate, sorbitan monolaurate, soritan monooleate, sorbitan monopalmitate, sorbitan monostearate, stearic acid, trolamine, emulsifying wax); Filtering aids (powdered cellulose, purified siliceous earth); Flavors and perfumes (anethole, benzaldehyde, ethyl vanillin, menthol, methyl salicylate, monosodium glutamate, orange flower oil, peppermint, peppermint oil, peppermint spirit, rose oil, stronger rose water, thymol, tolu balsam tincture, vanilla, vanilla tincture, vanillin); Glidants and/or anticaking agents (calcium silicate, magnesium silicate, colloidal silicon dioxide, talc); Humectants (glycerin, hexylene glycol, propylene glycol, sorbitol); Plasticizers (castor oil, diacetylated monoglycerides, diethyl phthalate, glycerin, mono- and di-acetylated monoglycerides, polyethylene glycol, propylene glycol, triacetin, triethyl citrate); Polymers (e.g., cellulose acetate, alkyl celloloses, hydroxyalkylcelloloses, acrylic polymers and copolymers); Solvents (acetone, alcohol, diluted alcohol, amylene hydrate, benzyl benzoate, butyl alcohol, carbon tetrachloride, chloroform, corn oil, cottonseed oil, ethyl acetate, glycerin, hexylene glycol, isopropyl alcohol, methyl alcohol, methylene chloride, methyl isobutyl ketone, mineral oil, peanut oil, polyethylene glycol, propylene carbonate, propylene glycol, sesame oil, water for injection, sterile water for injection, sterile water for irrigation, purified water); Sorbents (powdered cellulose, charcoal, purified siliceous earth); Carbon dioxide sorbents (barium hydroxide lime, soda lime); Stiffening agents (hydrogenated castor oil, cetostearyl alcohol, cetyl alcohol, cetyl esters wax, hard fat, paraffin, polyethylene excipient, stearyl alcohol, emulsifying wax, white wax, yellow wax); Suspending and/or viscosity-increasing agents (acacia, agar, alginic acid, aluminum monostearate, bentonite, purified bentonite, magma bentonite, carbomer 934p, carboxymethylcellulose calcium, carboxymethylcellulose sodium, carboxymethycellulose sodium 12, carrageenan, microcrystalline and carboxymethylcellulose sodium cellulose, dextrin, gelatin, guar gum, hydroxyethyl cellulose, hydroxypropyl cellulose, hydroxypropyl methylcellulose, magnesium aluminum silicate, methylcellulose, pectin, polyethylene oxide, polyvinyl alcohol, povidone, propylene glycol alginate, silicon dioxide, colloidal silicon dioxide, sodium alginate, tragacanth, xanthan gum); Sweetening agents (aspartame, dextrates, dextrose, excipient dextrose, fructose, mannitol, saccharin, calcium saccharin, sodium saccharin, sorbitol, solution sorbitol, sucrose, compressible sugar, confectioner's sugar, syrup); Tablet binders (acacia, alginic acid, sodium carboxymethylcellulose, microcrystalline cellulose, dextrin, ethylcellulose, gelatin, liquid glucose, guar gum, hydroxypropyl methylcellulose, methycellulose, polyethylene oxide, povidone, pregelatinized starch, syrup); Tablet and/or capsule diluents (calcium carbonate, dibasic calcium phosphate, tribasic calcium phosphate, calcium sulfate, microcrystalline cellulose, powdered cellulose, dextrates, dextrin, dextrose excipient, fructose, kaolin, lactose, mannitol, sorbitol, starch, pregelatinized starch, sucrose, compressible sugar, confectioner=s sugar); Tablet disintegrants (alginic acid, microcrystalline cellulose, croscarmellose sodium, corspovidone, polacrilin potassium, sodium starch glycolate, starch, pregelatinized starch); Tablet and/or capsule lubricants (calcium stearate, glyceryl behenate, magnesium stearate, light mineral oil, polyethylene glycol, sodium stearyl fumarate, stearic acid, purified stearic acid, talc, hydrogenated vegetable oil, zinc stearate); Tonicity agent (dextrose, glycerin, mannitol, potassium chloride, sodium chloride); Vehicle: flavored and/or sweetened (aromatic elixir, compound benzaldehyde elixir, iso-alcoholic elixir, peppermint water, sorbitol solution, syrup, tolu balsam syrup); Vehicle: oleaginous (almond oil, corn oil, cottonseed oil, ethyl oleate, isopropyl myristate, isopropyl palmitate, mineral oil, light mineral oil, myristyl alcohol, octyldodecanol, olive oil, peanut oil, persic oil, seame oil, soybean oil, squalane); Vehicle: solid carrier (sugar spheres); Vehicle: sterile (bacteriostatic water for injection, bacteriostatic sodium chloride injection); Viscosity-increasing (see suspending agent); Water repelling agent (cyclomethicone, dimethicone, simethicone); and Wetting and/or solubilizing agent (benzalkonium chloride, benzethonium chloride, cetylpyridinium chloride, docusate sodium, nonoxynol 9, nonoxynol 10, octoxynol 9, poloxamer, polyoxyl 35 castor oil, polyoxyl 40, hydrogenated castor oil, polyoxyl 50 stearate, polyoxyl 10 oleyl ether, polyoxyl 20, cetostearyl ether, polyoxyl 40 stearate, polysorbate 20, polysorbate 40, polysorbate 60, polysorbate 80, sodium lauryl sulfate, sorbitan monolaureate, sorbitan monooleate, sorbitan monopalmitate, sorbitan monostearate, tyloxapol). This list is not meant to be exclusive, but instead merely representative of the classes of excipients and the particular excipients which may be used in oral dosage forms of the present invention.

The stability of insulin has been well documented, and temperature, pH and moisture are some of the factors that affect the stability of insulin formulations. Likewise, the influence of pharmaceutical excipients on the stability of insulin has been well documented. The present specification discloses oral pharmaceutical formulations in tablet form that exhibit evidence of sufficient stability to warrant long term storage at room temperature, as demonstrated by a stability-indicating High Performance Liquid Chromatography (HPLC) assay methodology. Some of the factors that are believed to contribute to insulin stability in this formulation are:

- reduced surface area exposure to atmospheric conditions (only the outside surface of the tablet is exposed, while the inner tablet core is not);
- formulation of the tablet to provide an "insulin-friendly" local pH, perhaps in part due to the presence of dicalcium phosphate; and
- low moisture content (anhydrous excipients were used whenever possible, and 4-CNAB is not hygroscopic(residual moisture content <0.5%) below 75% RH and has moisture content below 0.5% w/w).

There are several ways to assess the stability of insulin. One way is an HPLC stability-indicating assay: This method determines the amount of intact insulin molecules present in a sample, but does not determine whether these molecules are in a bioactive conformation, which is necessary in order to have an effective product. Other methods are measurement of related substances (impurities) by HPLC and assessing the bioactivity of the product, which could be an in vivo assay or an in vitro predictor of in vivo performance.

Following administration, the insulin present in the dosage unit form is absorbed into the circulation. The circulating levels of the insulin itself can be measured directly. Similarly, levels of 4-CNAB delivery agent in the blood can be measured. The bioavailability of the insulin is readily assessed by measuring a known pharmacological activity in blood, e.g., decreased blood glucose. Further physiologic effects of the insulin can be measured using tests, for example, measurement of plasma C-peptide concentration as a measure of endogenous insulin production.

In addition, a fructosamine assay can be performed to determine the measure of the diabetic patient's glycemic control over the previous period of two to three weeks. Fructosamine is formed by a non-enzymatic reaction between glucose and amino acid residues of proteins, and serum fructosamine levels are elevated in diabetic patients with elevated blood glucose concentration. Whereas blood glucose concentration is a short-term indicator of diabetes control, fructosamine is a short- to medium-term indicator of diabetes control that correlates well with both fasting and mean blood glucose over a 2-week period.

In the present invention, the methods for treating a mammal with impaired glucose tolerance or with early or late stage diabetes comprise orally administering to the mammal a pharmaceutical formulation that includes a therapeutically effective amount of insulin or an insulin analog and a delivery agent in an amount effective to facilitate the absorption of the insulin from the gastrointestinal tract. It is preferred that the administration be on a chronic basis, e.g., for at least two weeks, and be preprandially and at bedtime such that, after two weeks of treatment, the mammal achieves improved glucose tolerance and glycemic control, as well as improved insulin utilization, insulin sensitivity, insulin secretion capacity and HbA$_1$c levels, as compared with baseline levels prior to treatment.

Improved glucose tolerance can be demonstrated by better endogenous capacity of the mammal to handle sugar load as measured by blood glucose concentration, following a sugar load, that is reduced by a statistically significant amount as compared with baseline blood glucose concentration, following a glucose load, prior to treatment. Preferably, the statistically significant reduction in blood glucose concentration is a mean of about 10-20%, preferably about 15%.

Improved glucose tolerance and better endogenous capacity of the mammal to handle sugar load can also be measured by an AUC of blood glucose excursion, following a glucose load, that is reduced by a statistically significant amount as compared with AUC of blood glucose excursion, following a glucose load, prior to treatment. Preferably, the statistically significant reduction in AUC of blood glucose excursion is a mean of about 10-30%, preferably about 20%.

Improved glycemic control can be demonstrated by decreased fasting blood glucose levels as measured by fasting blood glucose concentration that is reduced by a statistically significant amount as compared with baseline fasting blood glucose concentration prior to treatment. Preferably, the statistically significant reduction in fasting blood glucose concentration is a mean of about 10-30%, preferably about 19%.

Improved glycemic control can also be demonstrated by decreased serum fructosamine concentrations, as measured by serum fructosamine assay, that is reduced by a statistically significant amount as compared with baseline serum fructosamine concentrations prior to treatment. Preferably, the statistically significant reduction in serum fructosamine concentrations is a mean of about 5-20%, preferably about 9%.

Improved glycemic control can also be demonstrated by improved HbA1c levels after treatment compared with baseline levels prior to treatment. Preferably, the improved HbA1c levels are measured by a statistically significant decline in HbA1c levels. When treating a mammal with impaired glucose tolerance or with early or late stage diabetes, administration of the pharmaceutical formulation of the present invention can preferably be made to a mammal having an HbA$_{1c}$ level ranging from normal to elevated prior to treatment. In one embodiment, the mammal may have an HbA$_{1c}$ level preferably of less than about 8.0 prior to treatment.

Improved insulin utilization and insulin sensitivity of the patient's body can be measured by a statistically significant decline in HOMA (Homeostasis Model Assessment), and the improved insulin secretion capacity of the patient's body is measured by Stumvoll first-phase insulin secretion capacity index.

In preferred embodiments of the invention, by virtue of the chronic administration of oral dosage forms of the present invention, the patient achieves improved glucose tolerance and glycemic control as compared with baseline levels prior to treatment even without any statistically significant increase in weight, any statistically significant increase in risk of hypoglycemia or any statistically significant increase in risk of hyperinsulinemia in the mammal over the treatment period, and without the need for monitoring the mammal's blood glucose concentrations or HbA1c levels. Further, by virtue of the chronic administration of oral dosage forms of the present invention, the patient achieves improved insulin utilization, insulin sensitivity insulin secretion capacity and HbA1c levels as compared with baseline levels prior to treatment.

It is preferred that the administration of the oral pharmaceutical formulation will be about once daily to about four or more times daily, preprandially and/or at bedtime. In one embodiment of the invention, administration of the pharmaceutical formulation takes place once daily, either at bedtime or preprandially for one meal during the day time, e.g., for breakfast, lunch or dinner. In another embodiment, administration of the pharmaceutical formulation takes place multiple times daily, preferably at bedtime and preprandially for one meal during the day time, e.g., for breakfast, lunch or dinner. In a further embodiment, administration of the pharmaceutical formulation takes place multiple times daily, preferably at bedtime and preprandially for more than one meal during the day time. Administration of the pharmaceutical formulation can also be is at or shortly prior to bedtime and concurrently with or shortly prior to ingestion of each meal, i.e., within about 15 minutes or less of ingestion of each meal.

Preferably, the insulin formulations are administered to such human patients on a chronic basis, e.g., for at least about two weeks. The dosage form of the present invention can be administered for at least one day, for one week, for two weeks, for longer periods, for alternating on-off time periods, or for the life of the patient.

It is believed that the frequency of administration of the oral pharmaceutical formulation, on a daily basis (i.e., how often during one day-night period) and on a chronic basis (i.e., for how many days), will depend upon the patient's position along a "diabetes continuum", i.e., the extent of the patient's impaired glucose tolerance, the patient's stage of diabetes and the patient's need for exogenous glycemic control. This continuum ranges from normal glycemic control, to simple impaired glucose tolerance and insulin resistance seen in pre-diabetics or early stage type 2 diabetics, to failure of insulin production by the pancreas seen in type 1 diabetics and late stage type 2 diabetics. This can also be measured by the patient's $HbA_1c$ concentration, ranging from normal to elevated levels.

For example, if the patient has a need for fasting glycemic control, the oral pharmaceutical formulation should preferably be administered only at or shortly prior to bedtime. If the patient has some need for post-prandial glycemic control, the oral pharmaceutical formulation should preferably be administered preprandially for some meals. If the patient has a need for total post-prandial glycemic control, the oral pharmaceutical formulation should preferably be administered preprandially for all meals. If the patient has a need for comprehensive glycemic control, the oral pharmaceutical formulation should preferably be administered preprandially for all meals and at or shortly prior to bedtime.

Similarly, it is also believed that depending upon the patient's position along the "diabetes continuum", the oral insulin formulations of the present invention may be utilized in combination therapy, and may also include an additional treatment, either oral or subcutaneously administered, such as an anti-diabetic drug or insulin that has rapid action, intermediate action and/or slow action. It is believed that, in certain preferred embodiments of the present invention, the oral dosage forms described herein can be orally administered as described herein in combination with an additional yet separate therapy to treat diabetes or impaired glucose tolerance or to achieve glucose homeostasis, such as an additional drug such as sulfonylurea, a biguanide, an alpha-glucosidase, insulin delivered via a different pathway (e.g., parenteral insulin), an insulin sensitizer such as thiazolidinedione, and/or an insulin secretagogue.

In alternatively preferred embodiments of the invention, the additional treatment may comprise a second form of insulin, so as to provide the patient with two separate forms of insulin having different activity rates in order for the regimen to simulate the biphasic release of insulin in non-diabetic humans. For example, the oral formulations may include a rapid-acting form of insulin so as to provide a first insulin peak that occurs rapidly and is short-lived, and the fast-acting effect may be provided by the delivery agent that facilitates the absorption of insulin from the gastrointestinal tract. The slow acting form of insulin provides a second insulin peak that occurs later but has a longer duration. Such slower acting insulin may be provided by the same oral formulation as the rapid-acting insulin or by a separate dosage form that may be administered orally or subcutaneously.

It is further believed that the particular combination therapy and its frequency of administration, on a daily basis and on a chronic basis, will depend upon the patient's position along the "diabetes continuum". For example, if the patient has a need for fasting glycemic control, the oral pharmaceutical formulation should be administered only at or shortly prior to bedtime. If the patient has some need for post-prandial glycemic control, the oral pharmaceutical formulation should be administered preprandially for meals. If the patient has a need for basal insulin, as in late stage type 2 diabetes or type 1 diabetes, the supplemental slow-acting insulin or anti-diabetic drug should be administered daily. If the patient has a need for comprehensive glycemic control, the oral pharmaceutical formulation should preferably be administered preprandially for all meals and at or shortly prior to bedtime in combination with the slow-acting insulin or anti-diabetic drug.

It is also believed that the invention provides a method of achieving glucose homeostasis in mammals, comprising orally administering to a mammal a pharmaceutical formulation comprising a therapeutically effective amount of insulin or an insulin analog and a delivery agent in an amount effective to facilitate the absorption of the insulin from the gastrointestinal tract. It is preferred that the administration be on a chronic basis, e.g., for at least two weeks, and be preprandially and at bedtime such that, after two weeks of treatment, the mammal achieves improved glucose tolerance and glycemic control as compared with baseline levels prior to treatment.

It is further believed that the chronic administration of the oral dosage forms of the present invention will reduce the incidence and/or severity of systemic hyperinsulinemia associated with chronic dosing of insulin or of one or more disease states associated with chronic dosing of insulin in a mammal that has impaired glucose tolerance or early stage diabetes.

The chronic administration of oral dosage forms of the present invention result in a higher portal insulin concentration and lower systemic insulin concentration over time than that obtained with an equi-effective dose of insulin administered subcutaneously (i.e., which provide similar control of blood glucose levels). Transient peaks in insulin levels that may occur by virtue of the oral administration of insulin in accordance with the present invention are not believed to be associated with vascular diseases. By virtue of the chronic administration of oral dosage forms of the present invention instead of equi-effective subcutaneous doses of insulin, lower levels of hyperinsulinemia are obtained, e.g., systemic insulin concentrations are at least about 20% lower when compared to a comparably effective subcutaneous dose of insulin.

The present invention thus provides methods for reducing the incidence and/or severity of systemic hyperinsulinemia associated with chronic dosing of insulin, and it is believed that the present invention also provides a method for reducing the incidence and/or severity of one or more disease states associated with chronic dosing of insulin.

Such methods also comprise orally administering a therapeutically effective dose of a pharmaceutical formulation comprising insulin and a delivery agent that facilitates the absorption of the insulin from the gastrointestinal tract, to provide a therapeutically effective reduction and/or control in blood glucose concentration and a plasma insulin concentration that is reduced relative to the plasma insulin concentration provided by a therapeutically equivalent dose of subcutaneously injected insulin. Such methods also achieve a reduction in blood glucose concentration in human diabetic patients comparable to a subcutaneous insulin injection in those patients, while providing a lower (e.g., 20% or greater) total exposure of insulin to the peripheral blood circulation under acute, sub-acute and chronic conditions as compared to the peripheral blood insulin exposure achieved via subcutaneous injection. The determinations of blood or insulin concentration obtained in patients who have been administered subcutaneous insulin are well known to those skilled in the art.

It is still further believed that the chronic administration of oral dosage forms of the present invention to replace the endogenous insulin production in a mammal with impaired glucose tolerance or early stage diabetes mellitus will result in prophylactically sparing the function of the mammal's β-cells or will prevent death or dysfunction of the mammal's β-cells, and will thereby provide long-term protection to the mammal from developing overt or insulin dependent diabetes, or will delay the onset of overt or insulin dependent diabetes in the mammal. The rationale for this belief is as follows.

A two year observational study with SC insulin therapy initiated early in type 2 diabetic patients, as reported in Kalfhaus J and Berger M, Insulin Treatment With Preprandial Injections of Regular Insulin in Middle-Aged Type 2 Diabetic Patients: A Two Years Observational Study, *Diabetes Metab*, Volume 26, pp. 197-201 (2000), showed that a subcutaneous insulin treatment regimen is safe (with a very low incidence of hypoglycemia), and highly effective in terms of establishing long-term metabolic control by the preservation of β-cell function. Insulin/4-CNAB may have the potential to show similar or even better results, because, as an oral therapy, it will be much more easily accepted by patients.

The clinical studies with oral insulin in type 2 diabetic patients reported previously by Emisphere Technologies, Inc. and herein demonstrated a hypoglycemic effect of short duration, probably indicating that the half-life of systemic circulating insulin provided by oral administration is short to affect peripheral glucose disposal. It was hypothesized that orally administered insulin as set forth herein may, however, due to its portal delivery, have a more profound effect on hepatic glucose production, which is responsible for the fasting blood glucose levels.

In a non-diabetic individual, during times of fasting, such as during sleeping hours or between meals, the pancreas is able to store insulin for future use and is given a rest from secretion. In a diabetic or insulin resistant patients, the pancreas continues to secrete insulin without allowing a proper insulin store to be achieved. It is believed that one of the first defects of the pancreas in insulin resistance and type 2 diabetes is this defect in insulin storage.

In type 2 diabetics, blood glucose levels are often elevated after an overnight fast, presumably because of unrestrained glucose production by the liver as a result of a combination of insulin resistance and insufficient insulin secretion, which is the hallmark of the diabetes disease. Elevated blood glucose levels can lead to a vicious cycle to perpetuate the severity of a diabetic's condition because, if blood glucose concentration is elevated for an extended period of time, a corresponding "wear and tear" on the cells in the pancreas that secrete insulin to regulate blood glucose levels is possible. It is believed that hyperglycemia is toxic to the β-cells of the pancreas. Current literature shows that patients in the United States with type 2 diabetes are being diagnosed 8-10 years after the diabetic process has begun. The current American Diabetes Association guideline for diagnosing diabetes is two consecutive fasting blood glucose levels above 110 mg/dL. It is believed that, by the time of diagnosis, a diabetic patient has already lost function of about 50% of his islet cells.

In insulin resistant and early stage diabetic patients, the first phase insulin response is lost or impaired, depending on the stage of the disease. In addition, this lack of rest by the pancreas, especially the β-cells, can cause these cells to become dysfunctional or die from exhaustion. Thus, if a treatment were to spare insulin producing cell function, this "rest" to the cells may provide for long-term protection to develop overt diabetes.

In a study reported in International Patent Application No. PCT/US04/00273 and also discussed below, it was shown that administration of exogenous insulin at nighttime had an effect on hepatic glucose production and hence FBG (free blood glucose), thereby presumably allowing the patients' β-cells to rest and produce less insulin to achieve the same glycemic level. The suggested clinical implication is that, if nighttime oral insulin treatment were to be given alone, it is likely to spare β-cell function. This significance is supported by several reported studies that have shown that, by intervening "aggressively" with insulin at early stages of the disease (such as at the impaired glucose tolerance stage) by giving insulin even for a short time such as two week duration, the resulting rest to the β-cells may provide long term protection from developing overt diabetes. It is thus believed that a boost of exogenous insulin at nighttime can also be useful through the progression of the diabetes from a healthy state, to a pre-diabetic state and finally to a diabetic state.

It is believed that therapy can be initiated at an early stage to prophylactically spare β-cell function and aid in preventing β-cell death and the progression to overt diabetes. Many factors may be taken into account when therapy becomes necessary or desirable including, but not limited to: defects in GTT indicating signs of insulin resistance, reactive hypoglycemia, or early β-cell dysfunction, elevated fasting or postprandial blood glucose levels, family history for diabetes, obesity, $HbA_{1c}$ above approximately 6.5 or an elevation of $HbA_{1c}$ of more than about 10% over patient's past values, even if still within normal ranges. In accordance with the present invention, it is believed that a mammal at this early stage can be treated, prophylactically sparing β-cell function, aiding in preventing β-cell death and/or the progression to overt diabetes, by administering one time daily an effective dose of a pharmaceutical formulation, preferably an oral formulation, comprising insulin (as described herein) at nighttime, in the morning or preprandially, preferably at nighttime or in the morning. Preferably, the insulin formulation is administered to such human patients on a chronic basis, e.g., for at least about two weeks.

It is believed that, as the diabetes progresses, the patient may no longer be able to control his blood glucose at breakfast, even with the once a day dose as described above. This progression can be diagnosed using any method known in the art including but not limited to noting: further defects in the GTT, elevated fasting or postprandial blood glucose levels, $HbA_{1c}$ above approximately 6.5 or an elevation of $HbA_{1c}$ of more than about 10% over patient's past values, even if still within normal ranges, or no noticeable decrease in patients elevated HbA$_{1c}$ as described above despite treatment. In accordance with the present invention, it is believed that a mammal at this early stage of impaired glucose tolerance or early stage diabetes mellitus can be treated, prophylactically sparing remaining β-cell function, aiding in preventing β-cell death and/or the progression to overt diabetes and treating the current level of glycemic control dysfunction, by administering an effective dose of a pharmaceutical formulation, preferably an oral formulation, twice daily comprising insulin (as described herein) at nighttime, in the morning and/or preprandially, preferably at nighttime or morning and preprandially, more preferably at nighttime and preprandial for breakfast. Preferably, the insulin formulation is administered to such human patients on a chronic basis, e.g., for at least about two weeks.

Alternatively, it is believed that, even at this stage of impaired glucose tolerance or early stage diabetes, the patient can be treated, prophylactically sparing remaining β-cell function, aiding in preventing β-cell death and/or the progression to overt diabetes and treating the current level of glycemic control dysfunction, by administering an effective dose of a pharmaceutical formulation, preferably an oral formulation, three times daily comprising insulin (as described herein) preprandially or postprandially. This treatment regime can be carried through to later stages of the diabetes. Preferably, the insulin formulation is administered to such human patients on a chronic basis, e.g., for at least about two weeks.

It is believed that, as the diabetes progresses even further, the patient may no longer be able to control his blood glucose at lunch, even with the twice a day dose as described above. This progression can be diagnosed using any method known in the art including but not limited to noting: further defects in the GTT or defects in a lunchtime GTT, elevated fasting or postprandial blood glucose levels, HbA$_{1c}$ above approximately 6.5 or an elevation of HbA$_{1c}$ of more than about 10% over patient's past values, even if still within normal ranges, or no noticeable decrease in patients elevated HbA$_{1c}$ as described above despite treatment. In accordance with the present invention, it is believed that a mammal at this stage of impaired glucose tolerance or diabetes mellitus can be treated, prophylactically sparing remaining β-cell function, aiding in preventing β-cell death and/or the progression to overt diabetes and treating the current level of glycemic control dysfunction, by administering an effective dose of a pharmaceutical formulation, preferably an oral formulation, three times daily comprising insulin (as described herein) at nighttime, in the morning and/or preprandially, preferably at nighttime or morning and twice preprandially, more preferably at nighttime and preprandial for breakfast and lunch. Preferably, the insulin formulation is administered to such human patients on a chronic basis, e.g., for at least about two weeks.

It is believed that, as the diabetes progresses yet further, the patient may no longer be able to control his blood glucose at dinner, even with the three times a day dose as described above. This progression can be diagnosed using any method known in the art including but not limited to noting: further defects in the GTT, or defects in a dinnertime GTT, elevated fasting or postprandial blood glucose levels, HbA$_{1c}$ above 6.5 or an elevation of HbA$_{1c}$ of more than about 10% over patients past values, even if still within normal ranges, or no noticeable decrease in patients elevated HbA$_{1c}$ as described above, even with treatment. In accordance with the present invention, it is believed that a mammal at this stage of impaired glucose tolerance or diabetes mellitus can be treated, prophylactically sparing remaining β-cell function, and/or aiding in preventing β-cell death and treating the current level of glycemic control dysfunction, by administering an effective dose of a pharmaceutical formulation, preferably an oral formulation four times daily comprising insulin (as described herein) at nighttime, in the morning and/or preprandially, preferably at nighttime or morning and three times preprandially, more preferably at nighttime and preprandially for breakfast, lunch and dinner. Preferably, the insulin formulation is administered to such human patients on a chronic basis, e.g., for at least about two weeks.

It is believed that, as the diabetes progresses still further, the patient may no longer be able to control his blood glucose endogenously at all, even with the four time a day dose as described above. In accordance with the present invention, it is believed that a mammal at this stage of diabetes mellitus can be treated, prophylactically sparing any remaining β-cell function, and/or aiding in preventing β-cell death and treating the current level of glycemic control dysfunction, by administering an effective dose of a pharmaceutical formulation, preferably oral, comprising long-acting insulin; and an effective dose of a pharmaceutical formulation, preferably an oral formulation, four times daily comprising insulin (as described herein) at nighttime, in the morning and/or preprandially, preferably at nighttime or morning and three times preprandially, more preferably at nighttime and preprandially for breakfast, lunch and dinner. Preferably, the insulin formulations are administered to such human patients on a chronic basis, e.g., for at least about two weeks.

It is believed that, if it is determined that the pancreas has ceased to function, in accordance with the present invention, a mammal at this stage of diabetes mellitus can be treated by administering an effective dose of a pharmaceutical formulation, preferably oral, comprising long-acting insulin; and an effective dose of a pharmaceutical formulation, preferably an oral formulation, three or four times daily comprising insulin (as described herein) at nighttime, in the morning and/or preprandially, preferably nighttime, or in the morning and three preprandially, preferably at nighttime and three times preprandially. If three times a day dosing is chosen, it is believed that in addition to the long acting formulation described above, an effective dose of a pharmaceutical formulation of should be dosed, preferably preprandially. Preferably, the insulin formulations are administered to such human patients on a chronic basis, e.g., for at least about two weeks.

In another embodiment of the invention, a continuum of development of diabetes is identified comprising a pre-diabetic stage, an early stage diabetes and late stage diabetes, and the invention comprises identifying a patient's stage along the continuum of development of diabetes. A preferred embodiment of the invention comprises a method for treating a patient in accordance with his/her stage of development of diabetes comprising: identifying a patient's stage along the continuum of development of diabetes, devising a course of treatment for that patient in accordance with his stage along the continuum of development of diabetes and administering the treatment to the patient.

In order that this invention may be better understood, the following examples are set forth. These examples are for the purpose of illustration only and are not to be construed as limiting the scope of the invention in any manner.

Example 1

Comparison Between Oral Insulin and SC Short Acting Postprandial Blood Glucose Excursions A randomized, 3-period crossover, double-blind, double-dummy study was conducted in order to compare the effect (i.e., the postprandial pharmacokinetic and pharmacodynamic profiles) of an oral insulin formulation with that of subcutaneously administered short acting insulin on postprandial blood glucose excursions in type 2 diabetic subjects without any antidiabetic medication.

A primary objective of this study was to compare the effect of an oral insulin formulation (300 U insulin combined with 400 mg 4-CNAB in 2 capsules, each capsule containing 150 U insulin/200 mg 4-CNAB) with that of 12 U subcutaneous (SC) injected short acting insulin [Humalog® injection 100 U/ml from Eli Lilly and Company] on postprandial blood glucose excursions. The postprandial blood glucose excursions were assessed after a standardized breakfast intake.

Fifteen male subjects between 35 and 70 years old, inclusive, with type 2 diabetes mellitus as defined by the American Diabetes Association (1998 Diabetes care, 21: S5-S19) for more than one year were chosen. Subjects included in the study had BMI<36 kg/m$^2$, had stable glycemic control (HbA$_{1c}$<11%), were off all oral hypoglycemic agents 24 hours prior to each study dosing day and off any investigational drug for at least four (4) weeks prior to Visit 1, refrained from strenuous physical activity beginning 72 hrs prior to admission and through the duration of the study, and were confined to the clinical research unit as required by the protocol. Subjects maintained a constant body weight (+/−2 kg).

All patients received the same oral and SC injection treatments in a randomized sequence. At visit 1, each patient was randomized to one of six possible treatment sequences (see Table 1). On four separate occasions, patients received one of the four possible treatments prior to a standardized breakfast: 300 U oral Insulin/400 mg 4-CNAB (2 capsules, each capsule containing 150 U Insulin/200 mg 4-CNAB), 150 U oral Insulin/200 mg 4-CNAB (one capsule), 12 U SC short-acting insulin (Humalog®), and no supplemental insulin (placebo). During the first three treatment periods, 300 U oral, 12 U SC and placebo insulin were administered in random order and under blinded conditions (double-dummy technique). During the fourth treatment period, the patients received 150 U oral insulin in an open fashion. The overall study design is illustrated in Table 1 below.

days. The duration of each session was approximately 8-9 hours, and all experiments were performed after an overnight fast of approx. 12 hours.

At Visit 1 (screening visit), the patients came to the clinical research unit in a fasted state (i.e., not having had any caloric intake for at least 12 hours). The patients' physical statistics, medical history and social habits recorded, and a physical examination performed. Not more than 14 days later, at Visit 2, each patient was randomized to one of six treatment sequences shown in Table 2 below and received either one of the two active treatments (300 U oral Insulin/400 mg 4-CNAB or 12 U short-acting SC insulin) or no supplemental insulin (placebo). Thirty minutes after oral and fifteen minutes after SC drug administration, the patients ate a standardized breakfast, and postprandial blood glucose concentrations were monitored for six hours. Serial blood samples were also collected in regular intervals for measurement of plasma insulin, 4-CNAB, and C-peptide concentrations. The study patients were released from the institute at the end of the treatment session.

At Visits 3 and 4, the study patients returned to the clinical unit to receive the alternative treatments in conjunction with the test meal according to their treatment sequence. All experimental procedures and measurements were identical with those of the preceding treatment days. A final examination (Visit 5) was performed after Visit 4, preferably immediately after the experimental procedures were completed, but no longer than fourteen days after Visit 4.

The patients were invited to attend a fourth treatment session (Visit 7) with a single oral administration of 150 U Insulin/200 mg 4-CNAB thirty minutes prior to a test meal. All experimental procedures and measurements were the same as on the preceding treatment days. Patients attended a screening (Visit 6), no more than twenty days prior to the additional session, as well as a final examination (Visit 8), preferably immediately after the experimental procedures of Visit 7 were completed, but no longer than fourteen days thereafter. Visits 7 and 8 were generally combined (i.e., for all patients final examination was performed at Visit 7, immediately after completion of experimental procedures).

TABLE 1

Overall Study Design

| Visit 1 | Randomization ↓ Visit 2 | Visit 3 | Visit 4 | Visit 5 | Visit 6 | Visit 7 | Visit 8*) |
|---|---|---|---|---|---|---|---|
| Screening | Session 1 | Session 2 | Session 3 | Final Visit | Screening | Session 4 | Final Visit*) |
| | 300 U oral insulin or 12 U SC or placebo | | | | | 150 U oral | |

*)For all patients, Visits 7 and 8 were combined (i.e., final examination was performed at Visit 7, immediately after finishing experimental procedures).

The SC insulin dose of 12 U was selected to fall within a range typical for type 2 diabetic patients. The oral dose of 300 U insulin (in combination with 400 mg 4-CNBA) had been shown to be effective in Example 5 above. The oral dose of 150 U insulin (in combination with 200 mg 4-CNBA) was chosen to investigate whether or not an effect on hepatic glucose production could be achieved also by a lower insulin dose.

The time point of study drug administration (SC injection: 15 minutes prior to meal intake; oral administration: 30 minutes prior to meal intake) was selected in order to match the PK and PD properties of the administered insulin formulations with the postprandial rise of blood glucose. The washout period between the first three treatment sessions was 1-20

The patients were randomly assigned to one of the following treatment sequences:

TABLE 2

Treatments Administered

| Treatment Sequence | Treatment Period | | | |
|---|---|---|---|---|
| | 1 (Visit 2) | 2 (Visit 3) | 3 (Visit 4) | 4 (Visit 7) |
| 1 | 300 U Oral | 12 U SC | Placebo | 150 U Oral |
| 2 | 300 U Oral | Placebo | 12 U SC | 150 U Oral |
| 3 | 12 U SC | 300 U Oral | Placebo | 150 U Oral |
| 4 | 12 U SC | Placebo | 300 U Oral | 150 U Oral |

TABLE 2-continued

Treatments Administered

| Treatment Sequence | Treatment Period | | | |
|---|---|---|---|---|
| | 1 (Visit 2) | 2 (Visit 3) | 3 (Visit 4) | 4 (Visit 7) |
| 5 | Placebo | 12 U SC | 300 U Oral | 150 U Oral |
| 6 | Placebo | 300 U Oral | 12 U SC | 150 U Oral |

According to the double-dummy technique, each patient received on the first three treatment sessions (Visits 2-4), in addition to his scheduled treatment administration (oral or SC), the alternative administration (SC or oral) as placebo preparation. On sessions without supplemental insulin, both treatments (oral and SC) were placebo preparations. On the last treatment session (Visit 7), all patients received in an open fashion one oral dose of 150 U Insulin/200 mg 4-CNAB.

Based on the six sequences shown above, the following treatments were administered during the study:

Sequence 1:
Visit 2: Two insulin capsules 30 minutes, one SC placebo injection 15 minutes before meal.
Visit 3: Two placebo capsules 30 minutes, one SC insulin injection 15 minutes before meal
Visit 4: Two placebo capsules 30 minutes, one SC placebo injection 15 minutes before meal
Visit 7: One insulin capsule 30 minutes before meal Sequence 2:
Visit 2: Two insulin capsules 30 minutes, one SC placebo injection 15 minutes before meal.
Visit 3: Two placebo capsules 30 minutes, one SC placebo injection 15 minutes before meal
Visit 4: Two placebo capsules 30 minutes, one SC insulin injection 15 minutes before meal
Visit 7: One insulin capsule 30 minutes before meal Sequence 3:
Visit 2: Two placebo capsules 30 minutes, one SC insulin injection 15 minutes before meal.
Visit 3: Two insulin capsules 30 minutes, one SC insulin injection 15 minutes before meal
Visit 4: Two placebo capsules 30 minutes, one SC placebo injection 15 minutes before meal
Visit 7: One insulin capsule 30 minutes before meal Sequence 4:
Visit 2: Two placebo capsules 30 minutes, one SC insulin injection 15 minutes before meal.
Visit 3: Two placebo capsules 30 minutes, one SC placebo injection 15 minutes before meal
Visit 4: Two insulin capsules 30 minutes, one SC placebo injection 15 minutes before meal
Visit 7: One insulin capsule 30 minutes before meal Sequence 5:
Visit 2: Two placebo capsules 30 minutes, one SC placebo injection 15 minutes before meal.
Visit 3: Two placebo capsules 30 minutes, one SC insulin injection 15 minutes before meal
Visit 4: Two insulin capsules 30 minutes, one SC placebo injection 15 minutes before meal
Visit 7: One insulin capsule 30 minutes before meal Sequence 6:
Visit 2: Two placebo capsules 30 minutes, one SC placebo injection 15 minutes before meal.
Visit 3: Two insulin capsules 30 minutes, one SC placebo injection 15 minutes before meal
Visit 4: Two placebo capsules 30 minutes, one SC insulin injection 15 minutes before meal
Visit 7: One insulin capsule 30 minutes before meal The 4-CNAB used for the capsules was manufactured under GMP compliance. The Insulin used to prepare the capsules was Zinc-Insulin Crystals Human: Proinsulin Derived (Recombinant DNA Origin) USP Quality obtained from Eli Lilly and Company (Indianapolis, Ind.). The Insulin/4-CNAB capsules contained 150 Insulin Units USP and 200 mg 4-CNAB. The insulin/4-CNAB capsules were prepared by AAI Pharma Inc., Wilmington N.C.

Insulin/4-CNAB capsules were provided in HDPE bottles, each of which contained 40 capsules and a polyester coil. Each bottle had a heat-induction seal and a child-resistant cap, and were stored frozen at or less than minus 10° C. On the day of dosing, the appropriate number of capsules was removed from the freezer and brought to room temperature (between 15 and 30° C.) for about one hour. Capsules were used within four hours of dispensing, and unopened bottles were not left at room temperature for more than four hours.

The subjects ingested the meal thirty minutes after oral insulin administration. Blood glucose concentrations were monitored for six hours after glucose ingestion, and serial blood samples were collected in regular intervals for measurement of insulin concentration, 4-CNAB concentration, C-peptide, and blood glucose, providing information for pharmacokinetic and pharmacodynamic determinations. Blood glucose concentrations were determined immediately after sample collection and documented. All experiments were identical in their sample collections and monitoring period for all visits. The experimental procedure after the meal intake lasted for six hours (+1 hour baseline period for stabilization of blood glucose concentrations at the desired preprandial blood glucose level).

During each treatment session, blood samples were collected for determination of plasma concentrations of 4-CNAB, insulin and C-peptide, and for blood glucose concentration. Sampling started 1 hour before intake of the test meal and continued until 6 hours thereafter. Blood samples were drawn via a venous cannula and collected related to the start of the test meal at time point 0. The timing of scheduled samples could be adjusted according to clinical needs or needs for pharmacokinetic data. The duration of each session was approximately 8-9 hours. All experiments were performed after an overnight fast of approximately 12 hours.

The studies started in the morning. A 17-gauge PTFE catheter was inserted into an arm vein for blood sampling for measurement of blood glucose, and for plasma insulin, 4-CNAB and C-peptide concentrations. The line was kept patent with 0.15-mol/L (0.9%) sterile saline.

At time-point −15, exogenous insulin was administered by oral insulin administration or by subcutaneous injection at two of the three experimental days. At time point 0, subjects ingested a standardized breakfast at every study day (visits 2-4 and 7). The oral treatments (Insulin/4-CNAB capsules and placebo capsules) were administered 30 minutes, and the injections (short-acting insulin and placebo solution) 15 minutes, before start of meal intake. The pharmacodynamic response elicited was studied by measurements of blood glucose concentrations in 5 minute intervals for another six hours, and no food intake was allowed during this period, although water was consumed as desired.

Blood samples for blood glucose determination (0.25 mL per sample) were taken at −1 min (baseline), 5 minutes after start of meal intake and thereafter in 5 minute intervals until 120 minutes, 10 minute intervals until 240 minutes, and 15 minute intervals until 360 minutes after start of meal intake (45 samples per session). Blood glucose concentrations were measured immediately after sample collection using an automated GOD method (Super GL Ambulance Glucose Analyzer, Ruhrtal Labortechnik, Delecke-Möhnesee, Germany).

Blood samples for determination of 4-CNAB plasma concentrations (2 mL in sodium heparin tube) were drawn 10, 20, 30, 40, 60, 90, 120, 240 and 360 minutes after start of meal intake (9 samples per session). Blood samples for determination of insulin and C-peptide plasma concentrations (5 mL in sodium heparin tube) were drawn at −60 and −30 minutes, at time 0 (start of meal intake), and after 10, 20, 30, 40, 50, 60, 75, 90, 105, 120, 150, 180, 210, 240, 300, and 360 minutes (19 samples per session). Plasma concentrations of insulin were determined by a GLP-validated microparticle enzyme immunoassay (MEIA).

In case of a hypoglycemia (defined as blood glucose concentrations below 60 mg/dl), a blood glucose concentration of 60 mg/dl was maintained by means of a variable-rate intravenous infusion of 20% glucose. The glucose infusion rate was adopted, if necessary, in relation to the blood glucose concentrations measured to maintain this blood glucose level. In case of blood glucose values exceeding 350 mg/dl for more than 60 minutes, the experiments were aborted and the subject was treated with additional s.c. insulin to normalize his blood glucose concentrations.

Blood samples for the determination of plasma concentrations of insulin, 4-CNAB and C-peptide were collected at defined intervals, as discussed above. Plasma samples were stored at approximately −20° C. (4-CNAB at −70° C.) until determination by immunoassay is performed. After the end of the sampling period, the study subjects were released from the clinic.

Inter-subject variability for selected pharmacodynamic and pharmacokinetic parameters was assessed. Incidence of postprandial hypoglycemia was assessed for each subject and across the study population.

Blood glucose excursions (i.e., differences between preprandial and postprandial blood glucose concentrations) registered after the ingestion of the meal were used to evaluate pharmacodynamic parameters of the two insulin administration routes and compared with the same data obtained for the study day without any supplemental insulin. From these measurements, the area under the glucose infusion rate versus time curve from 0-6 hours (and other time intervals), the maximal blood glucose excursion ($C_{max}$) and time to the maximal blood glucose excursion ($t_{max}$) were analyzed.

For pharmacodynamic assessment, the following parameters were calculated: Maximal blood glucose excursion ($BG_{max}$), time to $BG_{max}$ ($t_{BG_{max}}$), Area under the blood glucose excursion curve in defined time-intervals ($AUC_{BG\ 0-1h}$, $AUC_{BG\ 0-2h}$, $AUC_{BG\ 0-3h}$, $AUC_{BG\ 0-4h}$, $AUC_{BG\ 0-6h}$), maximal absolute blood glucose concentrations ($BGabs_{max}$), time to $BGabs_{max}$ ($tBGabs_{max}$).

For pharmacokinetic assessment the following parameters were calculated: Maximal plasma insulin concentrations ($INS_{max}$), time to $INS_{max}$ ($t_{INS_{max}}$), Area under the glucose infusion rates in defined time-intervals ($AUC_{Ins\ 0-1h}$, $AUC_{Ins\ 0-2h}$, $AUC_{Ins\ 0-3h}$, $AUC_{Ins\ 0-4h}$, $AUC_{Ins\ 0-6h}$) and maximum reduction of C-peptide concentrations Plasma insulin concentrations were subjected to appropriate pharmacokinetic analyses. Parameters determined include $C_{max}$, $t_{max}$, and the area under the plasma concentration versus time curve from the time of dosing until a return to the baseline measurement ($AUC_{0-t'}$), where t' is the time that the level of plasma insulin concentration returns to the baseline. In addition, other pharmacokinetic parameters, such as $t_{1/2}$, elimination rate constant ($\lambda_z$) and partial AUC values, were calculated, if considered appropriate, for each individual subject enrolled within the study.

Pharmacodynamics

As measurement of a pharmacodynamic effect of oral Insulin/4-CNAB capsules, the blood glucose excursions measured over 6 hours were considered, and the area under the blood glucose excursion vs. time curve in the first two hours after start of meal intake ($AUC_{0-2h}$) was defined as primary pharmacodynamic endpoint.

From the blood samples taken, the individual blood glucose concentrations were determined, and summary concentration vs. time tables were prepared and profiles were plotted, as set forth in Tables 3-20 below.

TABLE 3

Patient Number 101

| | Treatment | | | | | | | |
|---|---|---|---|---|---|---|---|---|
| | Oral 150 U Insulin/ 200 mg 4-CNAB | | Oral 300 U Insulin/ 400 mg 4-CNAB | | SC 12 U Short-acting insulin | | Placebo | |
| Time (min) | Blood glucose (mg/dl) | Postprandial excursion (mg/dl) | Blood glucose (mg/dl) | Postprandial excursion (mg/dl) | Blood glucose (mg/dl) | Postprandial excursion (mg/dl) | Blood glucose (mg/dl) | Postprandial excursion (mg/dl) |
| −120 | | | NA | | NA | | NA | |
| −105 | | | NA | | NA | | NA | |
| −90 | | | NA | | NA | | NA | |
| −75 | | | NA | | NA | | NA | |
| −60 | | | 134 | | 149 | | 140 | |
| −45 | | | 135 | | 152 | | 141 | |
| −30 | | | 130 | | 150 | | 144 | |
| −16 | | | 124 | | 146 | | 139 | |
| −1 | | | 127 | 0 | 144 | 0 | 140 | 0 |
| 5 | | | 126 | −1 | 144 | 0 | 134 | −6 |
| 10 | | | 123 | −4 | 141 | −3 | 116 | −24 |
| 15 | | | 121 | −6 | 142 | −2 | 138 | −2 |
| 20 | | | 127 | 0 | 148 | 4 | 136 | −4 |
| 25 | | | 129 | 2 | 158 | 14 | 145 | 5 |
| 30 | | | 139 | 12 | 164 | 20 | 166 | 26 |
| 35 | | | 140 | 13 | 169 | 25 | 171 | 31 |
| 40 | | | 150 | 23 | 179 | 35 | 183 | 43 |
| 45 | | | 153 | 26 | 179 | 35 | 198 | 58 |
| 50 | | | 163 | 36 | 184 | 40 | 195 | 55 |

TABLE 3-continued

Patient Number 101

| | Treatment | | | | | | | |
|---|---|---|---|---|---|---|---|---|
| | Oral 150 U Insulin/ 200 mg 4-CNAB | | Oral 300 U Insulin/ 400 mg 4-CNAB | | SC 12 U Short-acting insulin | | Placebo | |
| Time (min) | Blood glucose (mg/dl) | Postprandial excursion (mg/dl) | Blood glucose (mg/dl) | Postprandial excursion (mg/dl) | Blood glucose (mg/dl) | Postprandial excursion (mg/dl) | Blood glucose (mg/dl) | Postprandial excursion (mg/dl) |
| 55 | | | 170 | 43 | 185 | 41 | 209 | 69 |
| 60 | | | 178 | 51 | 186 | 42 | 206 | 66 |
| 65 | | | 185 | 58 | 193 | 49 | 211 | 71 |
| 70 | | | 204 | 77 | 193 | 49 | 222 | 82 |
| 75 | | | 215 | 88 | 197 | 53 | 223 | 83 |
| 80 | | | 218 | 91 | 213 | 69 | 225 | 85 |
| 85 | | | 221 | 94 | 210 | 66 | 224 | 84 |
| 90 | | | 225 | 98 | 210 | 66 | 222 | 82 |
| 95 | | | 225 | 98 | 204 | 60 | 229 | 89 |
| 100 | | | 231 | 104 | 211 | 67 | 231 | 91 |
| 105 | | | 231 | 104 | 209 | 65 | 214 | 74 |
| 110 | | | 229 | 102 | 199 | 55 | 231 | 91 |
| 115 | | | 226 | 99 | 202 | 58 | 223 | 83 |
| 120 | | | 215 | 88 | 208 | 64 | 204 | 64 |
| 130 | | | 207 | 80 | 201 | 57 | 202 | 62 |
| 140 | | | 211 | 84 | 182 | 38 | 192 | 52 |
| 150 | | | 208 | 81 | 173 | 29 | 175 | 35 |
| 160 | | | 188 | 61 | 164 | 20 | 177 | 37 |
| 170 | | | 176 | 49 | 153 | 9 | 165 | 25 |
| 180 | | | 169 | 42 | 141 | −3 | 169 | 29 |
| 190 | | | 157 | 30 | 126 | −18 | 154 | 14 |
| 200 | | | 148 | 21 | 130 | −14 | 162 | 22 |
| 210 | | | 142 | 15 | 117 | −27 | 155 | 15 |
| 220 | | | 141 | 14 | 116 | −28 | 160 | 20 |
| 230 | | | 141 | 14 | 114 | −30 | 159 | 19 |
| 240 | | | 134 | 7 | 105 | −39 | 155 | 15 |
| 255 | | | 132 | 5 | 101 | −43 | 135 | −5 |
| 270 | | | 131 | 4 | 95 | −49 | 131 | −9 |
| 285 | | | 117 | −10 | 91.7 | −52.3 | 128 | −12 |
| 300 | | | 118 | −9 | 86.1 | −57.9 | 123 | −17 |
| 315 | | | 105 | −22 | 83.6 | −60.4 | 114 | −26 |
| 330 | | | 105 | −22 | 83 | −61 | 118 | −22 |
| 345 | | | 101 | −26 | 78.3 | −65.7 | 113 | −27 |
| 360 | | | 99.9 | −27.1 | 83.8 | −60.2 | 110 | −30 |

TABLE 4

Patient Number 102

| | Treatment | | | | | | | |
|---|---|---|---|---|---|---|---|---|
| | Oral 150 U Insulin/ 200 mg 4-CNAB | | Oral 300 U Insulin/ 400 mg 4-CNAB | | SC 12 U Short-acting insulin | | Placebo | |
| Time (min) | Blood glucose (mg/dl) | Postprandial excursion (mg/dl) | Blood glucose (mg/dl) | Postprandial excursion (mg/dl) | Blood glucose (mg/dl) | Postprandial excursion (mg/dl) | Blood glucose (mg/dl) | Postprandial excursion (mg/dl) |
| −120 | | | NA | | NA | | NA | |
| −105 | | | NA | | NA | | NA | |
| −90 | | | NA | | NA | | NA | |
| −75 | | | NA | | NA | | NA | |
| −60 | | | 135 | | 149 | | 164 | |
| −45 | | | 147 | | 157 | | 181 | |
| −30 | | | 139 | | 161 | | 169 | |
| −16 | | | 144 | | 164 | | 177 | |
| −1 | | | 146 | 0 | 151 | 0 | 172 | 0 |
| 5 | | | 157 | 11 | 157 | 6 | 177 | 5 |
| 10 | | | 154 | 8 | 155 | 4 | 178 | 6 |
| 15 | | | 152 | 6 | 158 | 7 | 180 | 8 |
| 20 | | | 154 | 8 | 167 | 16 | 167 | −5 |
| 25 | | | 159 | 13 | 164 | 13 | 174 | 2 |
| 30 | | | 175 | 29 | 160 | 9 | 184 | 12 |
| 35 | | | 182 | 36 | 179 | 28 | 184 | 12 |
| 40 | | | 191 | 45 | 184 | 33 | 199 | 27 |
| 45 | | | 206 | 60 | 167 | 16 | 208 | 36 |

TABLE 4-continued

Patient Number 102

| | Treatment | | | | | | | |
|---|---|---|---|---|---|---|---|---|
| | Oral 150 U Insulin/ 200 mg 4-CNAB | | Oral 300 U Insulin/ 400 mg 4-CNAB | | SC 12 U Short-acting insulin | | Placebo | |
| Time (min) | Blood glucose (mg/dl) | Postprandial excursion (mg/dl) | Blood glucose (mg/dl) | Postprandial excursion (mg/dl) | Blood glucose (mg/dl) | Postprandial excursion (mg/dl) | Blood glucose (mg/dl) | Postprandial excursion (mg/dl) |
| 50 | | | 202 | 56 | 177 | 26 | 217 | 45 |
| 55 | | | 209 | 63 | 175 | 24 | 223 | 51 |
| 60 | | | 217 | 71 | 168 | 17 | 234 | 62 |
| 65 | | | 239 | 93 | 188 | 37 | 252 | 80 |
| 70 | | | 247 | 101 | 188 | 37 | 239 | 67 |
| 75 | | | 241 | 95 | 194 | 43 | 260 | 88 |
| 80 | | | 246 | 100 | 194 | 43 | 279 | 107 |
| 85 | | | 249 | 103 | 213 | 62 | 271 | 99 |
| 90 | | | 255 | 109 | 196 | 45 | 255 | 83 |
| 95 | | | 253 | 107 | 211 | 60 | 275 | 103 |
| 100 | | | 261 | 115 | 197 | 46 | 256 | 84 |
| 105 | | | 258 | 112 | 214 | 63 | 279 | 107 |
| 110 | | | 276 | 130 | 209 | 58 | 264 | 92 |
| 115 | | | 270 | 124 | 201 | 50 | 270 | 98 |
| 120 | | | 275 | 129 | 198 | 47 | 270 | 98 |
| 130 | | | 265 | 119 | 199 | 48 | 281 | 109 |
| 140 | | | 266 | 120 | 190 | 39 | 295 | 123 |
| 150 | | | 271 | 125 | 186 | 35 | 254 | 82 |
| 160 | | | 252 | 106 | 194 | 43 | 275 | 103 |
| 170 | | | 254 | 108 | 188 | 37 | 259 | 87 |
| 180 | | | 249 | 103 | 184 | 33 | 251 | 79 |
| 190 | | | 243 | 97 | 172 | 21 | 252 | 80 |
| 200 | | | 247 | 101 | 171 | 20 | 247 | 75 |
| 210 | | | 243 | 97 | 180 | 29 | 248 | 76 |
| 220 | | | 244 | 98 | 170 | 19 | 227 | 55 |
| 230 | | | 245 | 99 | 170 | 19 | 231 | 59 |
| 240 | | | 233 | 87 | 163 | 12 | 226 | 54 |
| 255 | | | 225 | 79 | 162 | 11 | 222 | 50 |
| 270 | | | 218 | 72 | 153 | 2 | 223 | 51 |
| 285 | | | 219 | 73 | 158 | 7 | 212 | 40 |
| 300 | | | 213 | 67 | 147 | −4 | 212 | 40 |
| 315 | | | 210 | 64 | 129 | −22 | 205 | 33 |
| 330 | | | 210 | 64 | 145 | −6 | 196 | 24 |
| 345 | | | 204 | 58 | 105 | −46 | 199 | 27 |
| 360 | | | 199 | 53 | 130 | −21 | 204 | 32 |

TABLE 5

Patient Number 103

| | Treatment | | | | | | | |
|---|---|---|---|---|---|---|---|---|
| | Oral 150 U Insulin/ 200 mg 4-CNAB | | Oral 300 U Insulin/ 400 mg 4-CNAB | | SC 12 U Short-acting insulin | | Placebo | |
| Time (min) | Blood glucose (mg/dl) | Postprandial excursion (mg/dl) | Blood glucose (mg/dl) | Postprandial excursion (mg/dl) | Blood glucose (mg/dl) | Postprandial excursion (mg/dl) | Blood glucose (mg/dl) | Postprandial excursion (mg/dl) |
| −120 | NA | | NA | | NA | | NA | |
| −105 | NA | | NA | | NA | | NA | |
| −90 | NA | | NA | | NA | | NA | |
| −75 | NA | | NA | | NA | | NA | |
| −60 | 162 | | 172 | | 177 | | 170 | |
| −45 | 144 | | 177 | | 175 | | 167 | |
| −30 | 146 | | 174 | | 179 | | 165 | |
| −16 | 139 | | 162 | | 166 | | 164 | |
| −1 | 137 | 0 | 169 | 0 | 162 | 0 | 160 | 0 |
| 5 | 135 | −2 | 167 | −2 | 166 | 4 | 159 | −1 |
| 10 | 135 | −2 | 165 | −4 | 159 | −3 | 159 | −1 |
| 15 | 137 | 0 | 161 | −8 | 164 | 2 | 160 | 0 |
| 20 | 150 | 13 | 166 | −3 | 159 | −3 | 167 | 7 |
| 25 | 161 | 24 | 170 | 1 | 175 | 13 | 174 | 14 |
| 30 | 180 | 43 | 168 | −1 | 179 | 17 | 188 | 28 |
| 35 | 172 | 35 | 186 | 17 | 184 | 22 | 188 | 28 |
| 40 | 187 | 50 | 198 | 29 | 188 | 26 | 202 | 42 |

TABLE 5-continued

Patient Number 103

| | Treatment | | | | | | | |
|---|---|---|---|---|---|---|---|---|
| | Oral 150 U Insulin/ 200 mg 4-CNAB | | Oral 300 U Insulin/ 400 mg 4-CNAB | | SC 12 U Short-acting insulin | | Placebo | |
| Time (min) | Blood glucose (mg/dl) | Postprandial excursion (mg/dl) | Blood glucose (mg/dl) | Postprandial excursion (mg/dl) | Blood glucose (mg/dl) | Postprandial excursion (mg/dl) | Blood glucose (mg/dl) | Postprandial excursion (mg/dl) |
| 45 | 190 | 53 | 203 | 34 | 190 | 28 | 201 | 41 |
| 50 | 216 | 79 | 203 | 34 | 194 | 32 | 209 | 49 |
| 55 | 207 | 70 | 214 | 45 | 199 | 37 | 215 | 55 |
| 60 | 218 | 81 | 219 | 50 | 200 | 38 | 214 | 54 |
| 65 | 223 | 86 | 224 | 55 | 201 | 39 | 203 | 43 |
| 70 | 222 | 85 | 228 | 59 | 209 | 47 | 225 | 65 |
| 75 | 216 | 79 | 205 | 36 | 205 | 43 | 226 | 66 |
| 80 | 229 | 92 | 229 | 60 | 204 | 42 | 214 | 54 |
| 85 | 228 | 91 | 233 | 64 | 196 | 34 | 217 | 57 |
| 90 | 226 | 89 | 250 | 81 | 193 | 31 | 214 | 54 |
| 95 | 238 | 101 | 246 | 77 | 190 | 28 | 219 | 59 |
| 100 | 227 | 90 | 244 | 75 | 189 | 27 | 209 | 49 |
| 105 | 235 | 98 | 248 | 79 | 186 | 24 | 217 | 57 |
| 110 | 233 | 96 | 231 | 62 | 179 | 17 | 216 | 56 |
| 115 | 220 | 83 | 249 | 80 | 172 | 10 | 222 | 62 |
| 120 | 225 | 88 | 254 | 85 | 172 | 10 | 214 | 54 |
| 130 | 204 | 67 | 245 | 76 | 157 | −5 | 217 | 57 |
| 140 | 215 | 78 | 249 | 80 | 156 | −6 | 216 | 56 |
| 150 | 215 | 78 | 246 | 77 | 146 | −16 | 199 | 39 |
| 160 | 222 | 85 | 248 | 79 | 151 | −11 | 194 | 34 |
| 170 | 220 | 83 | 257 | 88 | 147 | −15 | 200 | 40 |
| 180 | 212 | 75 | 250 | 81 | 144 | −18 | 199 | 39 |
| 190 | 204 | 67 | 248 | 79 | 144 | −18 | 192 | 32 |
| 200 | 193 | 56 | 235 | 66 | 145 | −17 | 188 | 28 |
| 210 | 168 | 31 | 240 | 71 | 129 | −33 | 187 | 27 |
| 220 | 188 | 51 | 205 | 36 | 127 | −35 | 188 | 28 |
| 230 | 189 | 52 | 222 | 53 | 116 | −46 | 181 | 21 |
| 240 | 178 | 41 | 217 | 48 | 112 | −50 | 185 | 25 |
| 255 | 189 | 52 | 204 | 35 | 112 | −50 | 175 | 15 |
| 270 | 151 | 14 | 192 | 23 | 108 | −54 | 163 | 3 |
| 285 | 142 | 5 | 181 | 12 | 106 | −56 | 157 | −3 |
| 300 | 135 | −2 | 178 | 9 | 101 | −61 | 155 | −5 |
| 315 | 135 | −2 | 170 | 1 | 101 | −61 | 148 | −12 |
| 330 | 122 | −15 | 161 | −8 | 99.8 | −62.2 | 140 | −20 |
| 345 | 111 | −26 | 164 | −5 | 96.6 | −65.4 | 136 | −24 |
| 360 | 104 | −33 | 157 | −12 | 92.8 | −69.2 | 136 | −24 |

TABLE 6

Patient Number 104

| | Treatment | | | | | | | |
|---|---|---|---|---|---|---|---|---|
| | Oral 150 U Insulin/ 200 mg 4-CNAB | | Oral 300 U Insulin/ 400 mg 4-CNAB | | SC 12 U Short-acting insulin | | Placebo | |
| Time (min) | Blood glucose (mg/dl) | Postprandial excursion (mg/dl) | Blood glucose (mg/dl) | Postprandial excursion (mg/dl) | Blood glucose (mg/dl) | Postprandial excursion (mg/dl) | Blood glucose (mg/dl) | Postprandial excursion (mg/dl) |
| −120 | NA | | NA | | NA | | NA | |
| −105 | NA | | NA | | NA | | NA | |
| −90 | NA | | NA | | NA | | NA | |
| −75 | NA | | NA | | NA | | NA | |
| −60 | 164 | | 166 | | 149 | | 184 | |
| −45 | 164 | | 137 | | 135 | | 180 | |
| −30 | 165 | | 177 | | 139 | | 178 | |
| −16 | 163 | | 135 | | 168 | | 185 | |
| −1 | 164 | 0 | 157 | 0 | 173 | 0 | 183 | 0 |
| 5 | 161 | −3 | 154 | −3 | 182 | 9 | 172 | −11 |
| 10 | 161 | −3 | 151 | −6 | 178 | 5 | 173 | −10 |
| 15 | 159 | −5 | 118 | −39 | 190 | 17 | 169 | −14 |
| 20 | 164 | 0 | 150 | −7 | 195 | 22 | 192 | 9 |
| 25 | 163 | −1 | 163 | 6 | 193 | 20 | 202 | 19 |
| 30 | 170 | 6 | 164 | 7 | 208 | 35 | 213 | 30 |
| 35 | 177 | 13 | 171 | 14 | 208 | 35 | 214 | 31 |

TABLE 6-continued

Patient Number 104

Treatment

| Time (min) | Oral 150 U Insulin/ 200 mg 4-CNAB | | Oral 300 U Insulin/ 400 mg 4-CNAB | | SC 12 U Short-acting insulin | | Placebo | |
|---|---|---|---|---|---|---|---|---|
| | Blood glucose (mg/dl) | Postprandial excursion (mg/dl) | Blood glucose (mg/dl) | Postprandial excursion (mg/dl) | Blood glucose (mg/dl) | Postprandial excursion (mg/dl) | Blood glucose (mg/dl) | Postprandial excursion (mg/dl) |
| 40 | 179 | 15 | 176 | 19 | 214 | 41 | 220 | 37 |
| 45 | 185 | 21 | 184 | 27 | 218 | 45 | 224 | 41 |
| 50 | 196 | 32 | 195 | 38 | 193 | 20 | 235 | 52 |
| 55 | 189 | 25 | 207 | 50 | 211 | 38 | 251 | 68 |
| 60 | 203 | 39 | 224 | 67 | 213 | 40 | 229 | 46 |
| 65 | 206 | 42 | 214 | 57 | 216 | 43 | 262 | 79 |
| 70 | 211 | 47 | 228 | 71 | 213 | 40 | 267 | 84 |
| 75 | 223 | 59 | 240 | 83 | 198 | 25 | 267 | 84 |
| 80 | 232 | 68 | 220 | 63 | 210 | 37 | 267 | 84 |
| 85 | 220 | 56 | 238 | 81 | 207 | 34 | 263 | 80 |
| 90 | 212 | 48 | 248 | 91 | 198 | 25 | 271 | 88 |
| 95 | 213 | 49 | 242 | 85 | 189 | 16 | 282 | 99 |
| 100 | 218 | 54 | 265 | 108 | 191 | 18 | 284 | 101 |
| 105 | 205 | 41 | 250 | 93 | 183 | 10 | 259 | 76 |
| 110 | 207 | 43 | 253 | 96 | 194 | 21 | 276 | 93 |
| 115 | 208 | 44 | 246 | 89 | 188 | 15 | 281 | 98 |
| 120 | 207 | 43 | 244 | 87 | 188 | 15 | 256 | 73 |
| 130 | 204 | 40 | 238 | 81 | 179 | 6 | 240 | 57 |
| 140 | 209 | 45 | 250 | 93 | 185 | 12 | 228 | 45 |
| 150 | 220 | 56 | 249 | 92 | 164 | −9 | 239 | 56 |
| 160 | 220 | 56 | 241 | 84 | 165 | −8 | 252 | 69 |
| 170 | 216 | 52 | 246 | 89 | 153 | −20 | 251 | 68 |
| 180 | 220 | 56 | 218 | 61 | 145 | −28 | 252 | 69 |
| 190 | 225 | 61 | 228 | 71 | 152 | −21 | 256 | 73 |
| 200 | 228 | 64 | 213 | 56 | 162 | −11 | 268 | 85 |
| 210 | 224 | 60 | 203 | 46 | 160 | −13 | 264 | 81 |
| 220 | 230 | 66 | 217 | 60 | 155 | −18 | 237 | 54 |
| 230 | 218 | 54 | 218 | 61 | 151 | −22 | 271 | 88 |
| 240 | 226 | 62 | 211 | 54 | 150 | −23 | 252 | 69 |
| 255 | 227 | 63 | 195 | 38 | 138 | −35 | 234 | 51 |
| 270 | 215 | 51 | 196 | 39 | 135 | −38 | 227 | 44 |
| 285 | 218 | 54 | 176 | 19 | 128 | −45 | 225 | 42 |
| 300 | 213 | 49 | 175 | 18 | 131 | −42 | 218 | 35 |
| 315 | 206 | 42 | 171 | 14 | 132 | −41 | 195 | 12 |
| 330 | 200 | 36 | 160 | 3 | 129 | −44 | 201 | 18 |
| 345 | 188 | 24 | 159 | 2 | 133 | −40 | 195 | 12 |
| 360 | 172 | 8 | 156 | −1 | 130 | −43 | 184 | 1 |

TABLE 7

Patient Number 105

Treatment

| Time (min) | Oral 150 U Insulin/ 200 mg 4-CNAB | | Oral 300 U Insulin/ 400 mg 4-CNAB | | SC 12 U Short-acting insulin | | Placebo | |
|---|---|---|---|---|---|---|---|---|
| | Blood glucose (mg/dl) | Postprandial excursion (mg/dl) | Blood glucose (mg/dl) | Postprandial excursion (mg/dl) | Blood glucose (mg/dl) | Postprandial excursion (mg/dl) | Blood glucose (mg/dl) | Postprandial excursion (mg/dl) |
| −120 | NA | | NA | | NA | | NA | |
| −105 | NA | | NA | | NA | | NA | |
| −90 | NA | | NA | | NA | | NA | |
| −75 | NA | | NA | | NA | | NA | |
| −60 | 131 | | 114 | | 111 | | 125 | |
| −45 | 111 | | 108 | | 112 | | 114 | |
| −30 | 116 | | 109 | | 110 | | 98.6 | |
| −16 | 109 | | 106 | | 105 | | 84.2 | |
| −1 | 99.1 | 0 | 107 | 0 | 106 | 0 | 93.1 | 0 |
| 5 | 95.5 | −3.6 | 105 | −2 | 102 | −4 | 96.1 | 3 |
| 10 | 96.8 | −2.3 | 99.9 | −7.1 | 99.7 | −6.3 | 95.2 | 2.1 |
| 15 | 108 | 8.9 | 92.1 | −14.9 | 104 | −2 | 92.8 | −0.3 |
| 20 | 111 | 11.9 | 112 | 5 | 107 | 1 | 99.6 | 6.5 |
| 25 | 137 | 37.9 | 107 | 0 | 120 | 14 | 118 | 24.9 |
| 30 | 149 | 49.9 | 118 | 11 | 119 | 13 | 120 | 26.9 |

TABLE 7-continued

Patient Number 105

Treatment

| Time (min) | Oral 150 U Insulin/ 200 mg 4-CNAB | | Oral 300 U Insulin/ 400 mg 4-CNAB | | SC 12 U Short-acting insulin | | Placebo | |
|---|---|---|---|---|---|---|---|---|
| | Blood glucose (mg/dl) | Postprandial excursion (mg/dl) | Blood glucose (mg/dl) | Postprandial excursion (mg/dl) | Blood glucose (mg/dl) | Postprandial excursion (mg/dl) | Blood glucose (mg/dl) | Postprandial excursion (mg/dl) |
| 35 | 157 | 57.9 | 120 | 13 | 120 | 14 | 119 | 25.9 |
| 40 | 156 | 56.9 | 126 | 19 | 133 | 27 | 117 | 23.9 |
| 45 | 176 | 76.9 | 119 | 12 | 130 | 24 | 102 | 8.9 |
| 50 | 178 | 78.9 | 136 | 29 | 133 | 27 | 144 | 50.9 |
| 55 | 184 | 84.9 | 119 | 12 | 126 | 20 | 151 | 57.9 |
| 60 | 186 | 86.9 | 133 | 26 | 137 | 31 | 160 | 66.9 |
| 65 | 179 | 79.9 | 133 | 26 | 138 | 32 | 160 | 66.9 |
| 70 | 182 | 82.9 | 157 | 50 | 140 | 34 | 147 | 53.9 |
| 75 | 185 | 85.9 | 155 | 48 | 138 | 32 | 161 | 67.9 |
| 80 | 190 | 90.9 | 156 | 49 | 130 | 24 | 162 | 68.9 |
| 85 | 178 | 78.9 | 167 | 60 | 141 | 35 | 147 | 53.9 |
| 90 | 181 | 81.9 | 154 | 47 | 134 | 28 | 161 | 67.9 |
| 95 | 164 | 64.9 | 155 | 48 | 147 | 41 | 159 | 65.9 |
| 100 | 162 | 62.9 | 156 | 49 | 146 | 40 | 161 | 67.9 |
| 105 | 152 | 52.9 | 168 | 61 | 147 | 41 | 159 | 65.9 |
| 110 | 139 | 39.9 | 168 | 61 | 139 | 33 | 165 | 71.9 |
| 115 | 133 | 33.9 | 168 | 61 | 138 | 32 | 158 | 64.9 |
| 120 | 120 | 20.9 | 178 | 71 | 148 | 42 | 157 | 63.9 |
| 130 | 112 | 12.9 | 171 | 64 | 132 | 26 | 156 | 62.9 |
| 140 | 106 | 6.9 | 159 | 52 | 137 | 31 | 159 | 65.9 |
| 150 | 97.3 | −1.8 | 153 | 46 | 135 | 29 | 158 | 64.9 |
| 160 | 102 | 2.9 | 146 | 39 | 117 | 11 | 143 | 49.9 |
| 170 | 101 | 1.9 | 147 | 40 | 119 | 13 | 145 | 51.9 |
| 180 | 109 | 9.9 | 143 | 36 | 108 | 2 | 132 | 38.9 |
| 190 | 116 | 16.9 | 138 | 31 | 93.7 | −12.3 | 132 | 38.9 |
| 200 | 113 | 13.9 | 127 | 20 | 85.1 | −20.9 | 127 | 33.9 |
| 210 | 108 | 8.9 | 132 | 25 | 77.6 | −28.4 | 119 | 25.9 |
| 220 | 109 | 9.9 | 132 | 25 | 70.3 | −35.7 | 117 | 23.9 |
| 230 | 101 | 1.9 | 113 | 6 | 67.4 | −38.6 | 109 | 15.9 |
| 240 | 90.6 | −8.5 | 110 | 3 | 62.5 | −43.5 | 102 | 8.9 |
| 255 | 79.6 | −19.5 | 123 | 16 | 64.5 | −41.5 | 94.1 | 1 |
| 270 | 75 | −24.1 | 95.7 | −11.3 | 68.3 | −37.7 | 92.9 | −0.2 |
| 285 | 71.4 | −27.7 | 81.1 | −25.9 | 72.8 | −33.2 | 82.3 | −10.8 |
| 300 | 70.9 | −28.2 | 87.9 | −19.1 | 66.9 | −39.1 | 76.2 | −16.9 |
| 315 | 68 | −31.1 | 85.4 | −21.6 | 67.6 | −38.4 | 74.1 | −19 |
| 330 | 68.7 | −30.4 | 80.4 | −26.6 | 66.9 | −39.1 | 69.2 | −23.9 |
| 345 | 68.9 | −30.2 | 74.5 | −32.5 | 73.7 | −32.3 | 69.9 | −23.2 |
| 360 | 69.1 | −30 | 80.4 | −26.6 | 72.5 | −33.5 | 71 | −22.1 |

TABLE 8

Patient Number 106

Treatment

| Time (min) | Oral 150 U Insulin/ 200 mg 4-CNAB | | Oral 300 U Insulin/ 400 mg 4-CNAB | | SC 12 U Short-acting insulin | | Placebo | |
|---|---|---|---|---|---|---|---|---|
| | Insulin (pmol/l) | C-Peptide (nmol/l) | Insulin (pmol/l) | C-Peptide (nmol/l) | Insulin (pmol/l) | C-Peptide (nmol/l) | Insulin (pmol/l) | C-Peptide (nmol/l) |
| −60 | 65 | 0.82 | 42 | 0.71 | 24 | 0.51 | 24 | 0.69 |
| −30 | 55 | 0.86 | 30 | 0.74 | 19 | 0.49 | 24 | 0.58 |
| 0 | 62 | 0.71 | 48 | 0.61 | 26 | 0.55 | 32 | 0.66 |
| 10 | 46 | 0.75 | 48 | 0.66 | 38 | 0.61 | 39 | 0.68 |
| 20 | 38 | 0.76 | 27 | 0.58 | 52 | 0.75 | 71 | 0.81 |
| 30 | 82 | 0.88 | 33 | 0.57 | 69 | 0.76 | 90 | 0.93 |
| 40 | 106 | 1.00 | 42 | 0.68 | 39 | 0.74 | 122 | 1.12 |
| 50 | 123 | 1.33 | 55 | 0.74 | 63 | 0.77 | 136 | 1.32 |
| 60 | 118 | 1.39 | 78 | 0.82 | 58 | 0.72 | 130 | 1.63 |
| 75 | 94 | 1.44 | 53 | 0.77 | BLQ* | 0.51* | 155 | 1.76 |
| 90 | 127 | 1.42 | 121 | 1.22 | BLQ* | 0.43* | 173 | 1.96 |
| 105 | 123 | 1.90 | 62 | 1.05 | BLQ | 0.34 | 166 | 2.30 |
| 120 | 140 | 2.10 | 73 | 1.09 | 13 | 0.32 | 159 | 2.40 |
| 150 | 155 | 2.30 | 88 | 1.36 | 17 | 0.35 | 97 | 1.91 |
| 180 | 121 | 2.50 | 146 | 1.58 | 26 | 0.46 | 108 | 1.73 |

TABLE 8-continued

Patient Number 106

| | Treatment | | | | | | | |
|---|---|---|---|---|---|---|---|---|
| | Oral 150 U Insulin/ 200 mg 4-CNAB | | Oral 300 U Insulin/ 400 mg 4-CNAB | | SC 12 U Short-acting insulin | | Placebo | |
| Time (min) | Insulin (pmol/l) | C-Peptide (nmol/l) | Insulin (pmol/l) | C-Peptide (nmol/l) | Insulin (pmol/l) | C-Peptide (nmol/l) | Insulin (pmol/l) | C-Peptide (nmol/l) |
| 210 | 84 | 1.98 | 135 | 2.10 | 12* | 0.44* | 104 | 1.75 |
| 240 | 112 | 2.00 | 137 | 2.20 | 31 | 0.50 | 90 | 1.90 |
| 300 | 87 | 1.68 | 51 | 1.30 | BLQ* | 0.41* | 22 | 0.84 |
| 360 | 35 | 0.88 | 30 | 0.70 | BLQ | 0.31 | 18 | 0.57 |

TABLE 9

Patient Number 107

| | Treatment | | | | | | | |
|---|---|---|---|---|---|---|---|---|
| | Oral 150 U Insulin/ 200 mg 4-CNAB | | Oral 300 U Insulin/ 400 mg 4-CNAB | | SC 12 U Short-acting insulin | | Placebo | |
| Time (min) | Blood glucose (mg/dl) | Postprandial excursion (mg/dl) | Blood glucose (mg/dl) | Postprandial excursion (mg/dl) | Blood glucose (mg/dl) | Postprandial excursion (mg/dl) | Blood glucose (mg/dl) | Postprandial excursion (mg/dl) |
| −120 | NA | | NA | | NA | | NA | |
| −105 | NA | | NA | | NA | | NA | |
| −90 | NA | | NA | | NA | | NA | |
| −75 | NA | | NA | | NA | | NA | |
| −60 | 145 | | 140 | | 147 | | 139 | |
| −45 | 145 | | 136 | | 154 | | 138 | |
| −30 | 142 | | 151 | | 147 | | 141 | |
| −16 | 129 | | 141 | | 145 | | 136 | |
| −1 | 123 | 0 | 130 | 0 | 140 | 0 | 128 | 0 |
| 5 | 120 | −3 | 125 | −5 | 141 | 1 | 131 | 3 |
| 10 | 114 | −9 | 140 | 10 | 139 | −1 | 128 | 0 |
| 15 | 114 | −9 | 136 | 6 | 141 | 1 | 124 | −4 |
| 20 | 119 | −4 | 142 | 12 | 141 | 1 | 126 | −2 |
| 25 | 140 | 17 | 144 | 14 | 147 | 7 | 127 | −1 |
| 30 | 141 | 18 | 156 | 26 | 152 | 12 | 140 | 12 |
| 35 | 151 | 28 | 162 | 32 | 159 | 19 | 142 | 14 |
| 40 | 155 | 32 | 164 | 34 | 149 | 9 | 152 | 24 |
| 45 | 163 | 40 | 164 | 34 | 154 | 14 | 164 | 36 |
| 50 | 166 | 43 | 172 | 42 | 158 | 18 | 165 | 37 |
| 55 | 174 | 51 | 167 | 37 | 154 | 14 | 170 | 42 |
| 60 | 174 | 51 | 170 | 40 | 160 | 20 | 171 | 43 |
| 65 | 176 | 53 | 171 | 41 | 164 | 24 | 176 | 48 |
| 70 | 186 | 63 | 172 | 42 | 168 | 28 | 173 | 45 |
| 75 | 183 | 60 | 188 | 58 | 164 | 24 | 187 | 59 |
| 80 | 175 | 52 | 187 | 57 | 162 | 22 | 184 | 56 |
| 85 | 181 | 58 | 175 | 45 | 169 | 29 | 184 | 56 |
| 90 | 181 | 58 | 197 | 67 | 170 | 30 | 185 | 57 |
| 95 | 179 | 56 | 189 | 59 | 166 | 26 | 185 | 57 |
| 100 | 174 | 51 | 180 | 50 | 169 | 29 | 184 | 56 |
| 105 | 176 | 53 | 192 | 62 | 165 | 25 | 183 | 55 |
| 110 | 175 | 52 | 187 | 57 | 165 | 25 | 180 | 52 |
| 115 | 175 | 52 | 183 | 53 | 167 | 27 | 183 | 55 |
| 120 | 182 | 59 | 189 | 59 | 160 | 20 | 185 | 57 |
| 130 | 178 | 55 | 181 | 51 | 154 | 14 | 186 | 58 |
| 140 | 167 | 44 | 183 | 53 | 157 | 17 | 182 | 54 |
| 150 | 156 | 33 | 190 | 60 | 141 | 1 | 174 | 46 |
| 160 | 152 | 29 | 182 | 52 | 133 | −7 | 170 | 42 |
| 170 | 148 | 25 | 173 | 43 | 130 | −10 | 170 | 42 |
| 180 | 149 | 26 | 169 | 39 | 128 | −12 | 170 | 42 |
| 190 | 146 | 23 | 162 | 32 | 121 | −19 | 170 | 42 |
| 200 | 149 | 26 | 150 | 20 | 120 | −20 | 168 | 40 |
| 210 | 146 | 23 | 137 | 7 | 115 | −25 | 162 | 34 |
| 220 | 141 | 18 | 127 | −3 | 112 | −28 | 155 | 27 |
| 230 | 147 | 24 | 140 | 10 | 107 | −33 | 149 | 21 |
| 240 | 140 | 17 | 126 | −4 | 102 | −38 | 147 | 19 |
| 255 | 139 | 16 | 113 | −17 | 101 | −39 | 135 | 7 |
| 270 | 138 | 15 | 115 | −15 | 98.6 | −41.4 | 120 | −8 |
| 285 | 136 | 13 | 106 | −24 | 97.9 | −42.1 | 111 | −17 |
| 300 | 127 | 4 | 102 | −28 | 99.2 | −40.8 | 104 | −24 |

TABLE 9-continued

| | Patient Number 107 | | | | | | | |
|---|---|---|---|---|---|---|---|---|
| | Treatment | | | | | | | |
| | Oral 150 U Insulin/ 200 mg 4-CNAB | | Oral 300 U Insulin/ 400 mg 4-CNAB | | SC 12 U Short-acting insulin | | Placebo | |
| Time (min) | Blood glucose (mg/dl) | Postprandial excursion (mg/dl) | Blood glucose (mg/dl) | Postprandial excursion (mg/dl) | Blood glucose (mg/dl) | Postprandial excursion (mg/dl) | Blood glucose (mg/dl) | Postprandial excursion (mg/dl) |
| 315 | 120 | −3 | 97 | −33 | 100 | −40 | 98.3 | −29.7 |
| 330 | 117 | −6 | 100 | −30 | 98.8 | −41.2 | 94.4 | −33.6 |
| 345 | 111 | −12 | 99.5 | −30.5 | 101 | −39 | 95.5 | −32.5 |
| 360 | 108 | −15 | 88.5 | −41.5 | 95.8 | −44.2 | 92.1 | −35.9 |

TABLE 10

| | Patient Number 108 | | | | | | | |
|---|---|---|---|---|---|---|---|---|
| | Treatment | | | | | | | |
| | Oral 150 U Insulin/ 200 mg 4-CNAB | | Oral 300 U Insulin/ 400 mg 4-CNAB | | SC 12 U Short-acting insulin | | Placebo | |
| Time (min) | Blood glucose (mg/dl) | Postprandial excursion (mg/dl) | Blood glucose (mg/dl) | Postprandial excursion (mg/dl) | Blood glucose (mg/dl) | Postprandial excursion (mg/dl) | Blood glucose (mg/dl) | Postprandial excursion (mg/dl) |
| −120 | NA | | NA | | NA | | NA | |
| −105 | NA | | NA | | NA | | NA | |
| −90 | NA | | NA | | NA | | NA | |
| −75 | NA | | NA | | NA | | NA | |
| −60 | 150 | | 148 | | 150 | | 162 | |
| −45 | 146 | | 148 | | 154 | | 163 | |
| −30 | 147 | | 147 | | 151 | | 156 | |
| −16 | 154 | | 151 | | 151 | | 158 | |
| −1 | 144 | 0 | 129 | 0 | 147 | 0 | 150 | 0 |
| 5 | 142 | −2 | 122 | −7 | 151 | 4 | 151 | 1 |
| 10 | 139 | −5 | 123 | −6 | 148 | 1 | 152 | 2 |
| 15 | 142 | −2 | 118 | −11 | 146 | −1 | 151 | 1 |
| 20 | 164 | 20 | 119 | −10 | 148 | 1 | 158 | 8 |
| 25 | 170 | 26 | 113 | −16 | 155 | 8 | 179 | 29 |
| 30 | 200 | 56 | 133 | 4 | 166 | 19 | 200 | 50 |
| 35 | 205 | 61 | 137 | 8 | 172 | 25 | 210 | 60 |
| 40 | 212 | 68 | 168 | 39 | 177 | 30 | 227 | 77 |
| 45 | 213 | 69 | 179 | 50 | 184 | 37 | 221 | 71 |
| 50 | 223 | 79 | 196 | 67 | 184 | 37 | 219 | 69 |
| 55 | 215 | 71 | 189 | 60 | 186 | 39 | 219 | 69 |
| 60 | 222 | 78 | 200 | 71 | 194 | 47 | 238 | 88 |
| 65 | 231 | 87 | 197 | 68 | 194 | 47 | 242 | 92 |
| 70 | 238 | 94 | 207 | 78 | 209 | 62 | 239 | 89 |
| 75 | 238 | 94 | 214 | 85 | 219 | 72 | 256 | 106 |
| 80 | 256 | 112 | 214 | 85 | 213 | 66 | 257 | 107 |
| 85 | 262 | 118 | 222 | 93 | 220 | 73 | 244 | 94 |
| 90 | 268 | 124 | 211 | 82 | 222 | 75 | 252 | 102 |
| 95 | 277 | 133 | 208 | 79 | 228 | 81 | 256 | 106 |
| 100 | 273 | 129 | 223 | 94 | 219 | 72 | 251 | 101 |
| 105 | 280 | 136 | 228 | 99 | 226 | 79 | 249 | 99 |
| 110 | 281 | 137 | 220 | 91 | 222 | 75 | 246 | 96 |
| 115 | 277 | 133 | 212 | 83 | 226 | 79 | 244 | 94 |
| 120 | 270 | 126 | 214 | 85 | 231 | 84 | 241 | 91 |
| 130 | 284 | 140 | 208 | 79 | 220 | 73 | 244 | 94 |
| 140 | 294 | 150 | 213 | 84 | 227 | 80 | 241 | 91 |
| 150 | 298 | 154 | 214 | 85 | 235 | 88 | 255 | 105 |
| 160 | 252 | 108 | 225 | 96 | 231 | 84 | 264 | 114 |
| 170 | 293 | 149 | 227 | 98 | 233 | 86 | 257 | 107 |
| 180 | 286 | 142 | 214 | 85 | 224 | 77 | 252 | 102 |
| 190 | 281 | 137 | 211 | 82 | 232 | 85 | 252 | 102 |
| 200 | 288 | 144 | 213 | 84 | 234 | 87 | 255 | 105 |
| 210 | 270 | 126 | 204 | 75 | 232 | 85 | 230 | 80 |
| 220 | 254 | 110 | 198 | 69 | 219 | 72 | 234 | 84 |
| 230 | 244 | 100 | 193 | 64 | 212 | 65 | 218 | 68 |
| 240 | 236 | 92 | 184 | 55 | 202 | 55 | 208 | 58 |
| 255 | 225 | 81 | 172 | 43 | 197 | 50 | 198 | 48 |
| 270 | 212 | 68 | 171 | 42 | 158 | 11 | 195 | 45 |
| 285 | 207 | 63 | 161 | 32 | 149 | 2 | 179 | 29 |

TABLE 10-continued

| | Patient Number 108 | | | | | | | |
|---|---|---|---|---|---|---|---|---|
| | Treatment | | | | | | | |
| | Oral 150 U Insulin/ 200 mg 4-CNAB | | Oral 300 U Insulin/ 400 mg 4-CNAB | | SC 12 U Short-acting insulin | | Placebo | |
| Time (min) | Blood glucose (mg/dl) | Postprandial excursion (mg/dl) | Blood glucose (mg/dl) | Postprandial excursion (mg/dl) | Blood glucose (mg/dl) | Postprandial excursion (mg/dl) | Blood glucose (mg/dl) | Postprandial excursion (mg/dl) |
| 300 | 189 | 45 | 153 | 24 | 141 | −6 | 170 | 20 |
| 315 | 178 | 34 | 147 | 18 | 128 | −19 | 159 | 9 |
| 330 | 168 | 24 | 139 | 10 | 123 | −24 | 152 | 2 |
| 345 | 158 | 14 | 133 | 4 | 113 | −34 | 142 | −8 |
| 360 | 140 | −4 | 121 | −8 | 103 | −44 | 134 | −16 |

TABLE 11

| | Patient Number 109 | | | | | | | |
|---|---|---|---|---|---|---|---|---|
| | Treatment | | | | | | | |
| | Oral 150 U Insulin/ 200 mg 4-CNAB | | Oral 300 U Insulin/ 400 mg 4-CNAB | | SC 12 U Short-acting insulin | | Placebo | |
| Time (min) | Blood glucose (mg/dl) | Postprandial excursion (mg/dl) | Blood glucose (mg/dl) | Postprandial excursion (mg/dl) | Blood glucose (mg/dl) | Postprandial excursion (mg/dl) | Blood glucose (mg/dl) | Postprandial excursion (mg/dl) |
| −120 | NA | | NA | | NA | | NA | |
| −105 | NA | | NA | | NA | | NA | |
| −90 | NA | | NA | | NA | | NA | |
| −75 | NA | | NA | | NA | | NA | |
| −60 | 171 | | 187 | | 171 | | 179 | |
| −45 | 182 | | 195 | | 171 | | 179 | |
| −30 | 176 | | 193 | | 170 | | 169 | |
| −16 | 172 | | 185 | | 168 | | 177 | |
| −1 | 172 | 0 | 175 | 0 | 166 | 0 | 173 | 0 |
| 5 | 170 | −2 | 170 | −5 | 170 | 4 | 171 | −2 |
| 10 | 171 | −1 | 170 | −5 | 166 | 0 | 171 | −2 |
| 15 | 174 | 2 | 171 | −4 | 165 | −1 | 171 | −2 |
| 20 | 187 | 15 | 164 | −11 | 179 | 13 | 177 | 4 |
| 25 | 195 | 23 | 180 | 5 | 188 | 22 | 186 | 13 |
| 30 | 206 | 34 | 190 | 15 | 201 | 35 | 199 | 26 |
| 35 | 210 | 38 | 193 | 18 | 209 | 43 | 202 | 29 |
| 40 | 234 | 62 | 202 | 27 | 216 | 50 | 220 | 47 |
| 45 | 237 | 65 | 211 | 36 | 208 | 42 | 221 | 48 |
| 50 | 239 | 67 | 213 | 38 | 211 | 45 | 225 | 52 |
| 55 | 246 | 74 | 196 | 21 | 200 | 34 | 227 | 54 |
| 60 | 258 | 86 | 208 | 33 | 213 | 47 | 233 | 60 |
| 65 | 255 | 83 | 199 | 24 | 220 | 54 | 247 | 74 |
| 70 | 256 | 84 | 221 | 46 | 223 | 57 | 249 | 76 |
| 75 | 256 | 84 | 232 | 57 | 226 | 60 | 243 | 70 |
| 80 | 258 | 86 | 233 | 58 | 227 | 61 | 239 | 66 |
| 85 | 266 | 94 | 241 | 66 | 226 | 60 | 226 | 53 |
| 90 | 266 | 94 | 230 | 55 | 217 | 51 | 230 | 57 |
| 95 | 273 | 101 | 245 | 70 | 220 | 54 | 228 | 55 |
| 100 | 275 | 103 | 252 | 77 | 218 | 52 | 236 | 63 |
| 105 | 280 | 108 | 256 | 81 | 206 | 40 | 233 | 60 |
| 110 | 275 | 103 | 262 | 87 | 184 | 18 | 242 | 69 |
| 115 | 264 | 92 | 249 | 74 | 189 | 23 | 235 | 62 |
| 120 | 262 | 90 | 240 | 65 | 191 | 25 | 225 | 52 |
| 130 | 250 | 78 | 247 | 72 | 195 | 29 | 228 | 55 |
| 140 | 256 | 84 | 251 | 76 | 196 | 30 | 219 | 46 |
| 150 | 253 | 81 | 267 | 92 | 195 | 29 | 213 | 40 |
| 160 | 253 | 81 | 267 | 92 | 187 | 21 | 224 | 51 |
| 170 | 244 | 72 | 268 | 93 | 188 | 22 | 211 | 38 |
| 180 | 257 | 85 | 265 | 90 | 190 | 24 | 206 | 33 |
| 190 | 267 | 95 | 262 | 87 | 171 | 5 | 195 | 22 |
| 200 | 273 | 101 | 256 | 81 | 166 | 0 | 197 | 24 |
| 210 | 285 | 113 | 239 | 64 | 173 | 7 | 189 | 16 |
| 220 | 280 | 108 | 245 | 70 | 148 | −18 | 185 | 12 |
| 230 | 268 | 96 | 234 | 59 | 153 | −13 | 178 | 5 |
| 240 | 255 | 83 | 232 | 57 | 148 | −18 | 177 | 4 |
| 255 | 246 | 74 | 211 | 36 | 135 | −31 | 164 | −9 |
| 270 | 232 | 60 | 231 | 56 | 132 | −34 | 154 | −19 |

TABLE 11-continued

Patient Number 109

Treatment

| | Oral 150 U Insulin/ 200 mg 4-CNAB | | Oral 300 U Insulin/ 400 mg 4-CNAB | | SC 12 U Short-acting insulin | | Placebo | |
|---|---|---|---|---|---|---|---|---|
| Time (min) | Blood glucose (mg/dl) | Postprandial excursion (mg/dl) | Blood glucose (mg/dl) | Postprandial excursion (mg/dl) | Blood glucose (mg/dl) | Postprandial excursion (mg/dl) | Blood glucose (mg/dl) | Postprandial excursion (mg/dl) |
| 285 | 224 | 52 | 222 | 47 | 131 | −35 | 153 | −20 |
| 300 | 219 | 47 | 225 | 50 | 118 | −48 | 146 | −27 |
| 315 | 214 | 42 | 222 | 47 | 117 | −49 | 143 | −30 |
| 330 | 192 | 20 | 212 | 37 | 111 | −55 | 137 | −36 |
| 345 | 189 | 17 | 211 | 36 | 111 | −55 | 127 | −46 |
| 360 | 181 | 9 | 210 | 35 | 107 | −59 | 119 | −54 |

TABLE 12

Patient Number 110

Treatment

| | Oral 150 U Insulin/ 200 mg 4-CNAB | | Oral 300 U Insulin/ 400 mg 4-CNAB | | SC 12 U Short-acting insulin | | Placebo | |
|---|---|---|---|---|---|---|---|---|
| Time (min) | Blood glucose (mg/dl) | Postprandial excursion (mg/dl) | Blood glucose (mg/dl) | Postprandial excursion (mg/dl) | Blood glucose (mg/dl) | Postprandial excursion (mg/dl) | Blood glucose (mg/dl) | Postprandial excursion (mg/dl) |
| −120 | NA | | NA | | NA | | NA | |
| −105 | NA | | NA | | NA | | NA | |
| −90 | NA | | NA | | NA | | NA | |
| −75 | NA | | NA | | NA | | NA | |
| −60 | 142 | | 142 | | 151 | | 141 | |
| −45 | 141 | | 138 | | 148 | | 141 | |
| −30 | 143 | | 141 | | 117 | | 143 | |
| −16 | 136 | | 140 | | 144 | | 141 | |
| −1 | 131 | 0 | 121 | 0 | 141 | 0 | 139 | 0 |
| 5 | 128 | −3 | 84.8 | −36.2 | 133 | −8 | 135 | −4 |
| 10 | 135 | 4 | 80 | −41 | 129 | −12 | 134 | −5 |
| 15 | 138 | 7 | 68.8 | −52.2 | 132 | −9 | 144 | 5 |
| 20 | 144 | 13 | 79.2 | −41.8 | 134 | −7 | 150 | 11 |
| 25 | 149 | 18 | 73.9 | −47.1 | 145 | 4 | 162 | 23 |
| 30 | 154 | 23 | 75.8 | −45.2 | 147 | 6 | 176 | 37 |
| 35 | 149 | 18 | 73.9 | −47.1 | 147 | 6 | 181 | 42 |
| 40 | 158 | 27 | 80 | −41 | 145 | 4 | 191 | 52 |
| 45 | 156 | 25 | 87.3 | −33.7 | 146 | 5 | 191 | 52 |
| 50 | 168 | 37 | 88.4 | −32.6 | 151 | 10 | 188 | 49 |
| 55 | 162 | 31 | 93.5 | −27.5 | 144 | 3 | 189 | 50 |
| 60 | 164 | 33 | 113 | −8 | 151 | 10 | 190 | 51 |
| 65 | 156 | 25 | 110 | −11 | 156 | 15 | 186 | 47 |
| 70 | 160 | 29 | 120 | −1 | 155 | 14 | 189 | 50 |
| 75 | 169 | 38 | 130 | 9 | 156 | 15 | 194 | 55 |
| 80 | 165 | 34 | 135 | 14 | 161 | 20 | 199 | 60 |
| 85 | 170 | 39 | 142 | 21 | 164 | 23 | 199 | 60 |
| 90 | 170 | 39 | 142 | 21 | 158 | 17 | 196 | 57 |
| 95 | 176 | 45 | 139 | 18 | 156 | 15 | 197 | 58 |
| 100 | 171 | 40 | 139 | 18 | 161 | 20 | 191 | 52 |
| 105 | 176 | 45 | 137 | 16 | 155 | 14 | 196 | 57 |
| 110 | 185 | 54 | 137 | 16 | 159 | 18 | 185 | 46 |
| 115 | 172 | 41 | 142 | 21 | 136 | −5 | 189 | 50 |
| 120 | 180 | 49 | 143 | 22 | 135 | −6 | 197 | 58 |
| 130 | 186 | 55 | 151 | 30 | 144 | 3 | 188 | 49 |
| 140 | 186 | 55 | 138 | 17 | 119 | −22 | 188 | 49 |
| 150 | 191 | 60 | 144 | 23 | 116 | −25 | 180 | 41 |
| 160 | 181 | 50 | 142 | 21 | 113 | −28 | 170 | 31 |
| 170 | 186 | 55 | 145 | 24 | 102 | −39 | 159 | 20 |
| 180 | 183 | 52 | 146 | 25 | 104 | −37 | 158 | 19 |
| 190 | 181 | 50 | 148 | 27 | 95.9 | −45.1 | 160 | 21 |
| 200 | 177 | 46 | 139 | 18 | 90.1 | −50.9 | 158 | 19 |
| 210 | 171 | 40 | 139 | 18 | 83.4 | −57.6 | 153 | 14 |
| 220 | 154 | 23 | 134 | 13 | 83.8 | −57.2 | 146 | 7 |
| 230 | 130 | −1 | 127 | 6 | 81.8 | −59.2 | 142 | 3 |
| 240 | 126 | −5 | 126 | 5 | 82.4 | −58.6 | 137 | −2 |
| 255 | 127 | −4 | 111 | −10 | 78.9 | −62.1 | 133 | −6 |

TABLE 12-continued

Patient Number 110

| | Treatment | | | | | | | |
|---|---|---|---|---|---|---|---|---|
| | Oral 150 U Insulin/ 200 mg 4-CNAB | | Oral 300 U Insulin/ 400 mg 4-CNAB | | SC 12 U Short-acting insulin | | Placebo | |
| Time (min) | Blood glucose (mg/dl) | Postprandial excursion (mg/dl) | Blood glucose (mg/dl) | Postprandial excursion (mg/dl) | Blood glucose (mg/dl) | Postprandial excursion (mg/dl) | Blood glucose (mg/dl) | Postprandial excursion (mg/dl) |
| 270 | 122 | −9 | 109 | −12 | 78.8 | −62.2 | 129 | −10 |
| 285 | 122 | −9 | 103 | −18 | 80.9 | −60.1 | 124 | −15 |
| 300 | 130 | −1 | 99 | −22 | 79 | −62 | 120 | −19 |
| 315 | 124 | −7 | 99 | −22 | 79.9 | −61.1 | 117 | −22 |
| 330 | 123 | −8 | 97 | −24 | 77.7 | −63.3 | 115 | −24 |
| 345 | 113 | −18 | 96 | −25 | 79.7 | −61.3 | 109 | −30 |
| 360 | 104 | −27 | 92.1 | −28.9 | 80.4 | −60.6 | 104 | −35 |

TABLE 13

Patient Number 111

| | Treatment | | | | | | | |
|---|---|---|---|---|---|---|---|---|
| | Oral 150 U Insulin/ 200 mg 4-CNAB | | Oral 300 U Insulin/ 400 mg 4-CNAB | | SC 12 U Short-acting insulin | | Placebo | |
| Time (min) | Blood glucose (mg/dl) | Postprandial excursion (mg/dl) | Blood glucose (mg/dl) | Postprandial excursion (mg/dl) | Blood glucose (mg/dl) | Postprandial excursion (mg/dl) | Blood glucose (mg/dl) | Postprandial excursion (mg/dl) |
| −120 | NA | | NA | | NA | | NA | |
| −105 | NA | | NA | | NA | | NA | |
| −90 | NA | | NA | | NA | | NA | |
| −75 | NA | | NA | | NA | | NA | |
| −60 | 109 | | 110 | | 134 | | 129 | |
| −45 | 117 | | 113 | | 132 | | 127 | |
| −30 | 118 | | 112 | | 142 | | 127 | |
| −16 | 122 | | 120 | | 141 | | 126 | |
| −1 | 106 | 0 | 109 | 0 | 138 | 0 | 118 | 0 |
| 5 | 112 | 6 | 96.2 | −12.8 | 138 | 0 | 127 | 9 |
| 10 | 124 | 18 | 90.5 | −18.5 | 138 | 0 | 128 | 10 |
| 15 | 108 | 2 | 80.6 | −28.4 | 135 | −3 | 127 | 9 |
| 20 | 108 | 2 | 92.1 | −16.9 | 138 | 0 | 136 | 18 |
| 25 | 114 | 8 | 106 | −3 | 149 | 11 | 142 | 24 |
| 30 | 119 | 13 | 110 | 1 | 147 | 9 | 144 | 26 |
| 35 | 121 | 15 | 127 | 18 | 161 | 23 | NA | |
| 40 | 129 | 23 | 120 | 11 | 165 | 27 | 160 | 42 |
| 45 | 154 | 48 | 144 | 35 | 174 | 36 | 165 | 47 |
| 50 | 144 | 38 | 146 | 37 | 166 | 28 | 168 | 50 |
| 55 | 147 | 41 | 134 | 25 | 181 | 43 | 183 | 65 |
| 60 | 156 | 50 | 157 | 48 | 137 | −1 | 183 | 65 |
| 65 | 154 | 48 | 161 | 52 | 155 | 17 | 176 | 58 |
| 70 | 146 | 40 | 154 | 45 | 165 | 27 | 183 | 65 |
| 75 | 153 | 47 | 161 | 52 | 165 | 27 | 191 | 73 |
| 80 | 150 | 44 | 147 | 38 | 150 | 12 | 184 | 66 |
| 85 | 160 | 54 | 159 | 50 | 147 | 9 | 183 | 65 |
| 90 | 152 | 46 | 142 | 33 | 135 | −3 | 191 | 73 |
| 95 | 153 | 47 | 160 | 51 | 119 | −19 | 189 | 71 |
| 100 | 153 | 47 | 146 | 37 | 142 | 4 | 194 | 76 |
| 105 | 150 | 44 | 149 | 40 | 133 | −5 | 195 | 77 |
| 110 | 151 | 45 | 143 | 34 | 147 | 9 | 191 | 73 |
| 115 | 160 | 54 | 137 | 28 | 134 | −4 | 188 | 70 |
| 120 | 160 | 54 | 146 | 37 | 77.6 | −60.4 | 180 | 62 |
| 130 | 163 | 57 | 145 | 36 | 117 | −21 | 176 | 58 |
| 140 | 155 | 49 | 134 | 25 | 131 | −7 | 167 | 49 |
| 150 | 164 | 58 | 143 | 34 | 134 | −4 | 183 | 65 |
| 160 | 152 | 46 | 151 | 42 | 135 | −3 | 176 | 58 |
| 170 | 156 | 50 | 129 | 20 | 145 | 7 | 165 | 47 |
| 180 | 149 | 43 | 118 | 9 | 152 | 14 | 183 | 65 |
| 190 | 154 | 48 | 153 | 44 | 147 | 9 | 154 | 36 |
| 200 | 147 | 41 | 148 | 39 | 145 | 7 | 154 | 36 |
| 210 | 139 | 33 | 148 | 39 | 152 | 14 | 161 | 43 |
| 220 | 138 | 32 | 137 | 28 | 142 | 4 | 145 | 27 |
| 230 | 133 | 27 | 150 | 41 | 119 | −19 | 130 | 12 |
| 240 | 142 | 36 | 152 | 43 | 144 | 6 | 131 | 13 |

TABLE 13-continued

Patient Number 111

Treatment

| | Oral 150 U Insulin/ 200 mg 4-CNAB | | Oral 300 U Insulin/ 400 mg 4-CNAB | | SC 12 U Short-acting insulin | | Placebo | |
|---|---|---|---|---|---|---|---|---|
| Time (min) | Blood glucose (mg/dl) | Postprandial excursion (mg/dl) | Blood glucose (mg/dl) | Postprandial excursion (mg/dl) | Blood glucose (mg/dl) | Postprandial excursion (mg/dl) | Blood glucose (mg/dl) | Postprandial excursion (mg/dl) |
| 255 | 147 | 41 | 133 | 24 | 138 | 0 | 121 | 3 |
| 270 | 133 | 27 | 122 | 13 | 118 | −20 | 118 | 0 |
| 285 | 134 | 28 | 124 | 15 | 112 | −26 | 111 | −7 |
| 300 | 121 | 15 | 118 | 9 | 108 | −30 | 114 | −4 |
| 315 | 96.7 | −9.3 | 120 | 11 | 99.6 | −38.4 | 108 | −10 |
| 330 | 110 | 4 | 111 | 2 | 97.4 | −40.6 | 107 | −11 |
| 345 | 107 | 1 | 107 | −2 | 95.1 | −42.9 | 106 | −12 |
| 360 | 105 | −1 | 108 | −1 | 91.6 | −46.4 | 105 | −13 |

TABLE 14

Patient Number 112

Treatment

| | Oral 150 U Insulin/ 200 mg 4-CNAB | | Oral 300 U Insulin/ 400 mg 4-CNAB | | SC 12 U Short-acting insulin | | Placebo | |
|---|---|---|---|---|---|---|---|---|
| Time (min) | Blood glucose (mg/dl) | Postprandial excursion (mg/dl) | Blood glucose (mg/dl) | Postprandial excursion (mg/dl) | Blood glucose (mg/dl) | Postprandial excursion (mg/dl) | Blood glucose (mg/dl) | Postprandial excursion (mg/dl) |
| −120 | NA | | NA | | NA | | NA | |
| −105 | NA | | NA | | NA | | NA | |
| −90 | NA | | NA | | NA | | NA | |
| −75 | NA | | NA | | NA | | NA | |
| −60 | 108 | | 112 | | 120 | | 117 | |
| −45 | 108 | | 108 | | 117 | | 116 | |
| −30 | 92.6 | | 111 | | 117 | | 116 | |
| −16 | 101 | | 105 | | 109 | | 112 | |
| −1 | 99.3 | 0 | 86.6 | 0 | 104 | 0 | 110 | 0 |
| 5 | 96.7 | −2.6 | 76.6 | −10 | 106 | 2 | 107 | −3 |
| 10 | 96.7 | −2.6 | 74.3 | −12.3 | 103 | −1 | 107 | −3 |
| 15 | 98.4 | −0.9 | 60.1 | −26.5 | 101 | −3 | 111 | 1 |
| 20 | 93.3 | −6 | 81.1 | −5.5 | 98 | −6 | 120 | 10 |
| 25 | 96 | −3.3 | 84.6 | −2 | 101 | −3 | 128 | 18 |
| 30 | 103 | 3.7 | 84.9 | −1.7 | 109 | 5 | 132 | 22 |
| 35 | 109 | 9.7 | 95 | 8.4 | 111 | 7 | 134 | 24 |
| 40 | 108 | 8.7 | 99.1 | 12.5 | 109 | 5 | 141 | 31 |
| 45 | 118 | 18.7 | 106 | 19.4 | 107 | 3 | 138 | 28 |
| 50 | 125 | 25.7 | 101 | 14.4 | 112 | 8 | 137 | 27 |
| 55 | 129 | 29.7 | 107 | 20.4 | 100 | −4 | 137 | 27 |
| 60 | 137 | 37.7 | 107 | 20.4 | NA | | 144 | 34 |
| 65 | 140 | 40.7 | 111 | 24.4 | 117 | 13 | 144 | 34 |
| 70 | 143 | 43.7 | 116 | 29.4 | 108 | 4 | 137 | 27 |
| 75 | 146 | 46.7 | 120 | 33.4 | 109 | 5 | 137 | 27 |
| 80 | 151 | 51.7 | 121 | 34.4 | 102 | −2 | 144 | 34 |
| 85 | 147 | 47.7 | 120 | 33.4 | 99.9 | −4.1 | 137 | 27 |
| 90 | 143 | 43.7 | 132 | 45.4 | 104 | 0 | 136 | 26 |
| 95 | 139 | 39.7 | 133 | 46.4 | 105 | 1 | 140 | 30 |
| 100 | 143 | 43.7 | 129 | 42.4 | 112 | 8 | 141 | 31 |
| 105 | 147 | 47.7 | 134 | 47.4 | 110 | 6 | 138 | 28 |
| 110 | 148 | 48.7 | 127 | 40.4 | 105 | 1 | 143 | 33 |
| 115 | 145 | 45.7 | 125 | 38.4 | 110 | 6 | 141 | 31 |
| 120 | 141 | 41.7 | 138 | 51.4 | 108 | 4 | 141 | 31 |
| 130 | 139 | 39.7 | 130 | 43.4 | 99.2 | −4.8 | 136 | 26 |
| 140 | 134 | 34.7 | 121 | 34.4 | 96.2 | −7.8 | 144 | 34 |
| 150 | 124 | 24.7 | 119 | 32.4 | 100 | −4 | 147 | 37 |
| 160 | 91 | −8.3 | 129 | 42.4 | 87.6 | −16.4 | 143 | 33 |
| 170 | 90.3 | −9 | 129 | 42.4 | 92.9 | −11.1 | 114 | 4 |
| 180 | 96.8 | −2.5 | 143 | 56.4 | 83.5 | −20.5 | 111 | 1 |
| 190 | 96.6 | −2.7 | 139 | 52.4 | 85.7 | −18.3 | 113 | 3 |
| 200 | 100 | 0.7 | 126 | 39.4 | 86.1 | −17.9 | 124 | 14 |
| 210 | 88.9 | −10.4 | 108 | 21.4 | 84.1 | −19.9 | 119 | 9 |
| 220 | 96.6 | −2.7 | 111 | 24.4 | 87.7 | −16.3 | 120 | 10 |
| 230 | 96.7 | −2.6 | 118 | 31.4 | 96.1 | −7.9 | 120 | 10 |

TABLE 14-continued

Patient Number 112

| | Treatment | | | | | | | |
|---|---|---|---|---|---|---|---|---|
| | Oral 150 U Insulin/ 200 mg 4-CNAB | | Oral 300 U Insulin/ 400 mg 4-CNAB | | SC 12 U Short-acting insulin | | Placebo | |
| Time (min) | Blood glucose (mg/dl) | Postprandial excursion (mg/dl) | Blood glucose (mg/dl) | Postprandial excursion (mg/dl) | Blood glucose (mg/dl) | Postprandial excursion (mg/dl) | Blood glucose (mg/dl) | Postprandial excursion (mg/dl) |
| 240 | 97.3 | −2 | 121 | 34.4 | 101 | −3 | 120 | 10 |
| 255 | 90.4 | −8.9 | 115 | 28.4 | 104 | 0 | 110 | 0 |
| 270 | 86.2 | −13.1 | 109 | 22.4 | 102 | −2 | 109 | −1 |
| 285 | 79.4 | −19.9 | 111 | 24.4 | 102 | −2 | 96.2 | −13.8 |
| 300 | 75.3 | −24 | 105 | 18.4 | 97.9 | −6.1 | 96.5 | −13.5 |
| 315 | 72.1 | −27.2 | 105 | 18.4 | 93.6 | −10.4 | 94.8 | −15.2 |
| 330 | 81.4 | −17.9 | 103 | 16.4 | 87.7 | −16.3 | 91.8 | −18.2 |
| 345 | 83.7 | −15.6 | 101 | 14.4 | 84.1 | −19.9 | 85.9 | −24.1 |
| 360 | 78.8 | −20.5 | 95.6 | 9 | 82.6 | −21.4 | 82.7 | −27.3 |

TABLE 15

Patient Number 113

| | Treatment | | | | | | | |
|---|---|---|---|---|---|---|---|---|
| | Oral 150 U Insulin/ 200 mg 4-CNAB | | Oral 300 U Insulin/ 400 mg 4-CNAB | | SC 12 U Short-acting insulin | | Placebo | |
| Time (min) | Blood glucose (mg/dl) | Postprandial excursion (mg/dl) | Blood glucose (mg/dl) | Postprandial excursion (mg/dl) | Blood glucose (mg/dl) | Postprandial excursion (mg/dl) | Blood glucose (mg/dl) | Postprandial excursion (mg/dl) |
| −120 | NA | | NA | | NA | | NA | |
| −105 | NA | | NA | | NA | | NA | |
| −90 | NA | | NA | | NA | | NA | |
| −75 | NA | | NA | | NA | | NA | |
| −60 | 110 | | 144 | | 174 | | 115 | |
| −45 | 108 | | 139 | | 174 | | 113 | |
| −30 | 103 | | 136 | | 171 | | 106 | |
| −16 | 103 | | 130 | | 164 | | 115 | |
| −1 | 99.2 | 0 | 129 | 0 | 168 | 0 | 111 | 0 |
| 5 | 98.8 | −0.4 | 123 | −6 | 168 | 0 | 102 | −9 |
| 10 | 98.8 | −0.4 | 120 | −9 | 168 | 0 | 107 | −4 |
| 15 | 96.1 | −3.1 | 125 | −4 | 153 | −15 | 100 | −11 |
| 20 | 97.5 | −1.7 | 123 | −6 | 164 | −4 | 104 | −7 |
| 25 | 102 | 2.8 | 122 | −7 | 168 | 0 | 113 | 2 |
| 30 | 112 | 12.8 | 128 | −1 | 174 | 6 | 108 | −3 |
| 35 | 119 | 19.8 | 129 | 0 | 184 | 16 | 116 | 5 |
| 40 | 128 | 28.8 | 144 | 15 | 184 | 16 | 123 | 12 |
| 45 | 127 | 27.8 | 144 | 15 | 188 | 20 | 131 | 20 |
| 50 | 138 | 38.8 | 156 | 27 | 179 | 11 | 132 | 21 |
| 55 | 146 | 46.8 | 153 | 24 | 188 | 20 | 129 | 18 |
| 60 | 156 | 56.8 | 156 | 27 | 201 | 33 | 131 | 20 |
| 65 | 159 | 59.8 | 185 | 56 | 224 | 56 | 139 | 28 |
| 70 | 166 | 66.8 | 183 | 54 | 219 | 51 | 141 | 30 |
| 75 | 168 | 68.8 | 187 | 58 | 228 | 60 | 136 | 25 |
| 80 | 165 | 65.8 | 197 | 68 | 236 | 68 | 148 | 37 |
| 85 | 168 | 68.8 | 194 | 65 | 223 | 55 | 157 | 46 |
| 90 | 163 | 63.8 | 195 | 66 | 231 | 63 | 167 | 56 |
| 95 | 169 | 69.8 | 188 | 59 | 222 | 54 | 168 | 57 |
| 100 | 171 | 71.8 | 199 | 70 | 229 | 61 | 162 | 51 |
| 105 | 170 | 70.8 | 200 | 71 | 229 | 61 | 187 | 76 |
| 110 | 171 | 71.8 | 204 | 75 | 233 | 65 | 176 | 65 |
| 115 | 174 | 74.8 | 212 | 83 | 238 | 70 | 177 | 66 |
| 120 | 173 | 73.8 | 206 | 77 | 237 | 69 | 199 | 88 |
| 130 | 176 | 76.8 | 215 | 86 | 232 | 64 | 190 | 79 |
| 140 | 186 | 86.8 | 220 | 91 | 234 | 66 | 178 | 67 |
| 150 | 195 | 95.8 | 219 | 90 | 241 | 73 | 198 | 87 |
| 160 | 199 | 99.8 | 207 | 78 | 269 | 101 | 187 | 76 |
| 170 | 204 | 104.8 | 218 | 89 | 241 | 73 | 184 | 73 |
| 180 | 210 | 110.8 | 224 | 95 | 245 | 77 | 195 | 84 |
| 190 | 223 | 123.8 | 221 | 92 | 236 | 68 | 178 | 67 |
| 200 | 225 | 125.8 | 226 | 97 | 243 | 75 | 176 | 65 |
| 210 | 220 | 120.8 | 227 | 98 | 224 | 56 | 164 | 53 |
| 220 | 216 | 116.8 | 241 | 112 | 220 | 52 | 180 | 69 |

TABLE 15-continued

Patient Number 113

| | Treatment | | | | | | | |
|---|---|---|---|---|---|---|---|---|
| | Oral 150 U Insulin/ 200 mg 4-CNAB | | Oral 300 U Insulin/ 400 mg 4-CNAB | | SC 12 U Short-acting insulin | | Placebo | |
| Time (min) | Blood glucose (mg/dl) | Postprandial excursion (mg/dl) | Blood glucose (mg/dl) | Postprandial excursion (mg/dl) | Blood glucose (mg/dl) | Postprandial excursion (mg/dl) | Blood glucose (mg/dl) | Postprandial excursion (mg/dl) |
| 230 | 219 | 119.8 | 222 | 93 | 213 | 45 | 176 | 65 |
| 240 | 211 | 111.8 | 224 | 95 | 210 | 42 | 184 | 73 |
| 255 | 215 | 115.8 | 228 | 99 | 192 | 24 | 179 | 68 |
| 270 | 221 | 121.8 | 228 | 99 | 187 | 19 | 187 | 76 |
| 285 | 218 | 118.8 | 231 | 102 | 179 | 11 | 168 | 57 |
| 300 | 218 | 118.8 | 218 | 89 | 174 | 6 | 165 | 54 |
| 315 | 211 | 111.8 | 210 | 81 | 170 | 2 | 152 | 41 |
| 330 | 209 | 109.8 | 210 | 81 | 164 | −4 | 170 | 59 |
| 345 | 204 | 104.8 | 201 | 72 | 167 | −1 | 156 | 45 |
| 360 | 198 | 98.8 | 200 | 71 | 154 | −14 | 147 | 36 |

TABLE 16

Patient Number 114

| | Treatment | | | | | | | |
|---|---|---|---|---|---|---|---|---|
| | Oral 150 U Insulin/ 200 mg 4-CNAB | | Oral 300 U Insulin/ 400 mg 4-CNAB | | SC 12 U Short-acting insulin | | Placebo | |
| Time (min) | Blood glucose (mg/dl) | Postprandial excursion (mg/dl) | Blood glucose (mg/dl) | Postprandial excursion (mg/dl) | Blood glucose (mg/dl) | Postprandial excursion (mg/dl) | Blood glucose (mg/dl) | Postprandial excursion (mg/dl) |
| −120 | | | NA | | NA | | NA | |
| −105 | | | NA | | NA | | NA | |
| −90 | | | NA | | NA | | NA | |
| −75 | | | NA | | NA | | NA | |
| −60 | | | 141 | | 140 | | 142 | |
| −45 | | | 144 | | 138 | | 154 | |
| −30 | | | 138 | | 140 | | 156 | |
| −16 | | | 133 | | 138 | | 157 | |
| −1 | | | 94 | 0 | 132 | 0 | 135 | 0 |
| 5 | | | 70.4 | −23.6 | 131 | −1 | 151 | 16 |
| 10 | | | 65.9 | −28.1 | 125 | −7 | 143 | 8 |
| 15 | | | 67.9 | −26.1 | 126 | −6 | 142 | 7 |
| 20 | | | 79.6 | −14.4 | 136 | 4 | 157 | 22 |
| 25 | | | 90.4 | −3.6 | 141 | 9 | 172 | 37 |
| 30 | | | 98.9 | 4.9 | 148 | 16 | 172 | 37 |
| 35 | | | 110 | 16 | 155 | 23 | 154 | 19 |
| 40 | | | 125 | 31 | 157 | 25 | 205 | 70 |
| 45 | | | 127 | 33 | 152 | 20 | 200 | 65 |
| 50 | | | 135 | 41 | 156 | 24 | 161 | 26 |
| 55 | | | 144 | 50 | 149 | 17 | 204 | 69 |
| 60 | | | 143 | 49 | 142 | 10 | 225 | 90 |
| 65 | | | 162 | 68 | 156 | 24 | 200 | 65 |
| 70 | | | 172 | 78 | 143 | 11 | 212 | 77 |
| 75 | | | 189 | 95 | 140 | 8 | 224 | 89 |
| 80 | | | 199 | 105 | 138 | 6 | 223 | 88 |
| 85 | | | 190 | 96 | 134 | 2 | 179 | 44 |
| 90 | | | 194 | 100 | 130 | −2 | 222 | 87 |
| 95 | | | 186 | 92 | 126 | −6 | 226 | 91 |
| 100 | | | 186 | 92 | 123 | −9 | 203 | 68 |
| 105 | | | 177 | 83 | 115 | −17 | 207 | 72 |
| 110 | | | 177 | 83 | 112 | −20 | 177 | 42 |
| 115 | | | 178 | 84 | 114 | −18 | 218 | 83 |
| 120 | | | 185 | 91 | 108 | −24 | 225 | 90 |
| 130 | | | 195 | 101 | 119 | −13 | 204 | 69 |
| 140 | | | 195 | 101 | 120 | −12 | 185 | 50 |
| 150 | | | 193 | 99 | 123 | −9 | 194 | 59 |
| 160 | | | 185 | 91 | 127 | −5 | 167 | 32 |
| 170 | | | 183 | 89 | 127 | −5 | 195 | 60 |
| 180 | | | 176 | 82 | 111 | −21 | 155 | 20 |
| 190 | | | 166 | 72 | 93 | −39 | 159 | 24 |
| 200 | | | 169 | 75 | 73 | −59 | 150 | 15 |
| 210 | | | 167 | 73 | 65.5 | −66.5 | 159 | 24 |

TABLE 16-continued

Patient Number 114

| | Treatment | | | | | | | |
|---|---|---|---|---|---|---|---|---|
| | Oral 150 U Insulin/ 200 mg 4-CNAB | | Oral 300 U Insulin/ 400 mg 4-CNAB | | SC 12 U Short-acting insulin | | Placebo | |
| Time (min) | Blood glucose (mg/dl) | Postprandial excursion (mg/dl) | Blood glucose (mg/dl) | Postprandial excursion (mg/dl) | Blood glucose (mg/dl) | Postprandial excursion (mg/dl) | Blood glucose (mg/dl) | Postprandial excursion (mg/dl) |
| 220 | | | 164 | 70 | 57.9 | −74.1 | 161 | 26 |
| 230 | | | 153 | 59 | 65.1 | −66.9 | 142 | 7 |
| 240 | | | 136 | 42 | 54.1 | −77.9 | 136 | 1 |
| 255 | | | 134 | 40 | 80.7 | −51.3 | 131 | −4 |
| 270 | | | 127 | 33 | 67.7 | −64.3 | 137 | 2 |
| 285 | | | 117 | 23 | 65.9 | −66.1 | 130 | −5 |
| 300 | | | 111 | 17 | 68.2 | −63.8 | 128 | −7 |
| 315 | | | 112 | 18 | 70.5 | −61.5 | 119 | −16 |
| 330 | | | 112 | 18 | 82 | −50 | 119 | −16 |
| 345 | | | 108 | 14 | 84 | −48 | 115 | −20 |
| 360 | | | 111 | 17 | 87.1 | −44.9 | 114 | −21 |

TABLE 17

Patient Number 115

| | Treatment | | | | | | | |
|---|---|---|---|---|---|---|---|---|
| | Oral 150 U Insulin/ 200 mg 4-CNAB | | Oral 300 U Insulin/ 400 mg 4-CNAB | | SC 12 U Short-acting insulin | | Placebo | |
| Time (min) | Blood glucose (mg/dl) | Postprandial excursion (mg/dl) | Blood glucose (mg/dl) | Postprandial excursion (mg/dl) | Blood glucose (mg/dl) | Postprandial excursion (mg/dl) | Blood glucose (mg/dl) | Postprandial excursion (mg/dl) |
| −120 | | | NA | | NA | | NA | |
| −105 | | | NA | | NA | | NA | |
| −90 | | | NA | | NA | | NA | |
| −75 | | | NA | | NA | | NA | |
| −60 | | | 136 | | 175 | | 176 | |
| −45 | | | 136 | | 170 | | 176 | |
| −30 | | | 135 | | 166 | | 174 | |
| −16 | | | 136 | | 169 | | 170 | |
| −1 | | | 126 | 0 | 168 | 0 | 174 | 0 |
| 5 | | | 123 | −3 | 165 | −3 | 180 | 6 |
| 10 | | | 111 | −15 | 161 | −7 | 175 | 1 |
| 15 | | | 105 | −21 | 161 | −7 | 179 | 5 |
| 20 | | | 104 | −22 | 162 | −6 | 169 | −5 |
| 25 | | | 103 | −23 | 162 | −6 | 175 | 1 |
| 30 | | | 114 | −12 | 170 | 2 | 191 | 17 |
| 35 | | | 122 | −4 | 168 | 0 | 189 | 15 |
| 40 | | | 135 | 9 | 203 | 35 | 219 | 45 |
| 45 | | | 143 | 17 | 203 | 35 | 228 | 54 |
| 50 | | | 147 | 21 | 193 | 25 | 235 | 61 |
| 55 | | | 168 | 42 | 184 | 16 | 249 | 75 |
| 60 | | | 172 | 46 | 194 | 26 | 231 | 57 |
| 65 | | | 171 | 45 | 194 | 26 | 251 | 77 |
| 70 | | | 173 | 47 | 199 | 31 | 274 | 100 |
| 75 | | | 183 | 57 | 198 | 30 | 284 | 110 |
| 80 | | | 196 | 70 | 203 | 35 | 275 | 101 |
| 85 | | | 184 | 58 | 204 | 36 | 286 | 112 |
| 90 | | | 206 | 80 | 212 | 44 | 286 | 112 |
| 95 | | | 200 | 74 | 212 | 44 | 283 | 109 |
| 100 | | | 204 | 78 | 210 | 42 | 281 | 107 |
| 105 | | | 213 | 87 | 214 | 46 | 287 | 113 |
| 110 | | | 217 | 91 | 221 | 53 | 298 | 124 |
| 115 | | | 210 | 84 | 230 | 62 | 291 | 117 |
| 120 | | | 222 | 96 | 230 | 62 | 300 | 126 |
| 130 | | | 218 | 92 | 222 | 54 | 308 | 134 |
| 140 | | | 217 | 91 | 214 | 46 | 302 | 128 |
| 150 | | | 224 | 98 | 202 | 34 | 302 | 128 |
| 160 | | | 239 | 113 | 183 | 15 | 302 | 128 |
| 170 | | | 233 | 107 | 160 | −8 | 281 | 107 |
| 180 | | | 235 | 109 | 149 | −19 | 276 | 102 |
| 190 | | | 239 | 113 | 122 | −46 | 278 | 104 |
| 200 | | | 238 | 112 | 112 | −56 | 271 | 97 |

TABLE 17-continued

Patient Number 115

| | Treatment | | | | | | | |
|---|---|---|---|---|---|---|---|---|
| | Oral 150 U Insulin/ 200 mg 4-CNAB | | Oral 300 U Insulin/ 400 mg 4-CNAB | | SC 12 U Short-acting insulin | | Placebo | |
| Time (min) | Blood glucose (mg/dl) | Postprandial excursion (mg/dl) | Blood glucose (mg/dl) | Postprandial excursion (mg/dl) | Blood glucose (mg/dl) | Postprandial excursion (mg/dl) | Blood glucose (mg/dl) | Postprandial excursion (mg/dl) |
| 210 | | | 243 | 117 | 98.6 | −69.4 | 270 | 96 |
| 220 | | | 236 | 110 | 97.7 | −70.3 | 268 | 94 |
| 230 | | | 231 | 105 | 89.9 | −78.1 | 260 | 86 |
| 240 | | | 236 | 110 | 84.4 | −83.6 | 253 | 79 |
| 255 | | | 239 | 113 | 73.5 | −94.5 | 254 | 80 |
| 270 | | | 234 | 108 | 64.2 | −104 | 249 | 75 |
| 285 | | | 224 | 98 | 68.5 | −99.5 | 237 | 63 |
| 300 | | | 217 | 91 | 73 | −95 | 230 | 56 |
| 315 | | | 208 | 82 | 78.9 | −89.1 | 223 | 49 |
| 330 | | | 206 | 80 | 77.7 | −90.3 | 218 | 44 |
| 345 | | | 194 | 68 | 80.1 | −87.9 | 216 | 42 |
| 360 | | | 184 | 58 | 77.6 | −90.4 | 196 | 22 |

TABLE 18

Patient Number 116

| | Treatment | | | | | | | |
|---|---|---|---|---|---|---|---|---|
| | Oral 150 U Insulin/ 200 mg 4-CNAB | | Oral 300 U Insulin/ 400 mg 4-CNAB | | SC 12 U Short-acting insulin | | Placebo | |
| Time (min) | Blood glucose (mg/dl) | Postprandial excursion (mg/dl) | Blood glucose (mg/dl) | Postprandial excursion (mg/dl) | Blood glucose (mg/dl) | Postprandial excursion (mg/dl) | Blood glucose (mg/dl) | Postprandial excursion (mg/dl) |
| −120 | NA | | NA | | NA | | NA | |
| −105 | NA | | NA | | NA | | NA | |
| −90 | NA | | NA | | NA | | NA | |
| −75 | NA | | NA | | NA | | NA | |
| −60 | 113 | | 107 | | 106 | | 117 | |
| −45 | 117 | | 104 | | 115 | | 115 | |
| −30 | 117 | | 98.3 | | 110 | | 118 | |
| −16 | 105 | | 92.2 | | 102 | | 117 | |
| −1 | 112 | 0 | 72.2 | 0 | 108 | 0 | 111 | 0 |
| 5 | 111 | −1 | 57.4 | −14.8 | 107 | −1 | 124 | 13 |
| 10 | 111 | −1 | 44.7 | −27.5 | 105 | −3 | 105 | −6 |
| 15 | 116 | 4 | 41.7 | −30.5 | 105 | −3 | 113 | 2 |
| 20 | 119 | 7 | 50.7 | −21.5 | 107 | −1 | 131 | 20 |
| 25 | 137 | 25 | 61.8 | −10.4 | 127 | 19 | 130 | 19 |
| 30 | 160 | 48 | 79.4 | 7.2 | 131 | 23 | NA | |
| 35 | 169 | 57 | 112 | 39.8 | 141 | 33 | NA | |
| 40 | 197 | 85 | 125 | 52.8 | 155 | 47 | 166 | 55 |
| 45 | 216 | 104 | 136 | 63.8 | 156 | 48 | 165 | 54 |
| 50 | 219 | 107 | 136 | 63.8 | 164 | 56 | 205 | 94 |
| 55 | 220 | 108 | 153 | 80.8 | 159 | 51 | 222 | 111 |
| 60 | 233 | 121 | 154 | 81.8 | 192 | 84 | 206 | 95 |
| 65 | 248 | 136 | 163 | 90.8 | 181 | 73 | 212 | 101 |
| 70 | 242 | 130 | 157 | 84.8 | 179 | 71 | 205 | 94 |
| 75 | 239 | 127 | 165 | 92.8 | 176 | 68 | 199 | 88 |
| 80 | 244 | 132 | 182 | 109.8 | 170 | 62 | NA | |
| 85 | 252 | 140 | 186 | 113.8 | 177 | 69 | 203 | 92 |
| 90 | 260 | 148 | 186 | 113.8 | 165 | 57 | 203 | 92 |
| 95 | 263 | 151 | 187 | 114.8 | 165 | 57 | 194 | 83 |
| 100 | 244 | 132 | 188 | 115.8 | 163 | 55 | 200 | 89 |
| 105 | 241 | 129 | 184 | 111.8 | 175 | 67 | 184 | 73 |
| 110 | 248 | 136 | 178 | 105.8 | 158 | 50 | 188 | 77 |
| 115 | 248 | 136 | 172 | 99.8 | 157 | 49 | 181 | 70 |
| 120 | 235 | 123 | 177 | 104.8 | 162 | 54 | 174 | 63 |
| 130 | 219 | 107 | 180 | 107.8 | 150 | 42 | 172 | 61 |
| 140 | 205 | 93 | 156 | 83.8 | 138 | 30 | 169 | 58 |
| 150 | 175 | 63 | 134 | 61.8 | 127 | 19 | 157 | 46 |
| 160 | 167 | 55 | 132 | 59.8 | 112 | 4 | 136 | 25 |
| 170 | 171 | 59 | 117 | 44.8 | 105 | −3 | 138 | 27 |
| 180 | 151 | 39 | 115 | 42.8 | 89.2 | −18.8 | 130 | 19 |
| 190 | 119 | 7 | 108 | 35.8 | 73.3 | −34.7 | 111 | 0 |

TABLE 18-continued

Patient Number 116

Treatment

| Time (min) | Oral 150 U Insulin/ 200 mg 4-CNAB | | Oral 300 U Insulin/ 400 mg 4-CNAB | | SC 12 U Short-acting insulin | | Placebo | |
|---|---|---|---|---|---|---|---|---|
| | Blood glucose (mg/dl) | Postprandial excursion (mg/dl) | Blood glucose (mg/dl) | Postprandial excursion (mg/dl) | Blood glucose (mg/dl) | Postprandial excursion (mg/dl) | Blood glucose (mg/dl) | Postprandial excursion (mg/dl) |
| 200 | 104 | −8 | 97.5 | 25.3 | 62.3 | −45.7 | 93.8 | −17.2 |
| 210 | 91 | −21 | 98.5 | 26.3 | 57.8 | −50.2 | 85.7 | −25.3 |
| 220 | 94.2 | −17.8 | 94.5 | 22.3 | 53.6 | −54.4 | 74 | −37 |
| 230 | 91.6 | −20.4 | 83.8 | 11.6 | 73.2 | −34.8 | 75.9 | −35.1 |
| 240 | 86.4 | −25.6 | 78.7 | 6.5 | 77.8 | −30.2 | 73.5 | −37.5 |
| 255 | 81 | −31 | 80.3 | 8.1 | 73.1 | −34.9 | 70.5 | −40.5 |
| 270 | 80.8 | −31.2 | 75 | 2.8 | 72.9 | −35.1 | 73.1 | −37.9 |
| 285 | 77.7 | −34.3 | 78.7 | 6.5 | 69.3 | −38.7 | 71.1 | −39.9 |
| 300 | 77.8 | −34.2 | 79.4 | 7.2 | 75 | −33 | 70.8 | −40.2 |
| 315 | 71.4 | −40.6 | 76.2 | 4 | 77.7 | −30.3 | 69.1 | −41.9 |
| 330 | 74.5 | −37.5 | 76.2 | 4 | 77.1 | −30.9 | 72.3 | −38.7 |
| 345 | 78.5 | −33.5 | 75.8 | 3.6 | 75.8 | −32.2 | 73.3 | −37.7 |
| 360 | 78.5 | −33.5 | 76.8 | 4.6 | 85.6 | −22.4 | 75.9 | −35.1 |

TABLE 19

Patient Number 117

Treatment

| Time (min) | Oral 150 U Insulin/ 200 mg 4-CNAB | | Oral 300 U Insulin/ 400 mg 4-CNAB | | SC 12 U Short-acting insulin | | Placebo | |
|---|---|---|---|---|---|---|---|---|
| | Blood glucose (mg/dl) | Postprandial excursion (mg/dl) | Blood glucose (mg/dl) | Postprandial excursion (mg/dl) | Blood glucose (mg/dl) | Postprandial excursion (mg/dl) | Blood glucose (mg/dl) | Postprandial excursion (mg/dl) |
| −120 | | | NA | | NA | | NA | |
| −105 | | | NA | | NA | | NA | |
| −90 | | | NA | | NA | | NA | |
| −75 | | | NA | | NA | | NA | |
| −60 | | | 160 | | 133 | | 145 | |
| −45 | | | 161 | | 139 | | 140 | |
| −30 | | | 157 | | 135 | | 146 | |
| −16 | | | 156 | | 135 | | 140 | |
| −1 | | | 142 | 0 | 134 | 0 | 138 | 0 |
| 5 | | | 139 | −3 | 134 | 0 | 140 | 2 |
| 10 | | | 125 | −17 | 132 | −2 | 141 | 3 |
| 15 | | | 119 | −23 | 130 | −4 | 138 | 0 |
| 20 | | | 125 | −17 | 136 | 2 | 141 | 3 |
| 25 | | | 129 | −13 | 147 | 13 | 160 | 22 |
| 30 | | | 146 | 4 | 155 | 21 | 170 | 32 |
| 35 | | | 157 | 15 | 165 | 31 | 179 | 41 |
| 40 | | | 172 | 30 | 168 | 34 | 193 | 55 |
| 45 | | | 182 | 40 | 166 | 32 | 191 | 53 |
| 50 | | | 199 | 57 | 163 | 29 | 207 | 69 |
| 55 | | | 203 | 61 | 175 | 41 | 213 | 75 |
| 60 | | | 221 | 79 | 170 | 36 | 221 | 83 |
| 65 | | | 215 | 73 | 184 | 50 | 220 | 82 |
| 70 | | | 230 | 88 | 184 | 50 | 222 | 84 |
| 75 | | | 222 | 80 | 178 | 44 | 234 | 96 |
| 80 | | | 227 | 85 | 196 | 62 | 237 | 99 |
| 85 | | | 227 | 85 | 191 | 57 | 238 | 100 |
| 90 | | | 216 | 74 | 181 | 47 | 250 | 112 |
| 95 | | | 221 | 79 | 187 | 53 | 254 | 116 |
| 100 | | | 228 | 86 | 179 | 45 | 258 | 120 |
| 105 | | | 229 | 87 | 184 | 50 | 267 | 129 |
| 110 | | | 226 | 84 | 180 | 46 | 269 | 131 |
| 115 | | | 226 | 84 | 173 | 39 | 270 | 132 |
| 120 | | | 230 | 88 | 165 | 31 | 269 | 131 |
| 130 | | | 228 | 86 | 176 | 42 | 267 | 129 |
| 140 | | | 231 | 89 | 176 | 42 | 270 | 132 |
| 150 | | | 232 | 90 | 175 | 41 | 268 | 130 |
| 160 | | | 223 | 81 | 155 | 21 | 255 | 117 |
| 170 | | | 213 | 71 | 137 | 3 | 249 | 111 |
| 180 | | | 209 | 67 | 124 | −10 | 255 | 117 |

TABLE 19-continued

Patient Number 117

| | Treatment | | | | | | | |
|---|---|---|---|---|---|---|---|---|
| | Oral 150 U Insulin/ 200 mg 4-CNAB | | Oral 300 U Insulin/ 400 mg 4-CNAB | | SC 12 U Short-acting insulin | | Placebo | |
| Time (min) | Blood glucose (mg/dl) | Postprandial excursion (mg/dl) | Blood glucose (mg/dl) | Postprandial excursion (mg/dl) | Blood glucose (mg/dl) | Postprandial excursion (mg/dl) | Blood glucose (mg/dl) | Postprandial excursion (mg/dl) |
| 190 | | | 220 | 78 | 118 | −16 | 259 | 121 |
| 200 | | | 228 | 86 | 121 | −13 | 263 | 125 |
| 210 | | | 237 | 95 | 129 | −5 | 260 | 122 |
| 220 | | | 223 | 81 | 139 | 5 | 256 | 118 |
| 230 | | | 214 | 72 | 137 | 3 | 249 | 111 |
| 240 | | | 214 | 72 | 138 | 4 | 242 | 104 |
| 255 | | | 218 | 76 | 136 | 2 | 233 | 95 |
| 270 | | | 225 | 83 | 133 | −1 | 228 | 90 |
| 285 | | | 217 | 75 | 124 | −10 | 214 | 76 |
| 300 | | | 211 | 69 | 123 | −11 | 209 | 71 |
| 315 | | | 194 | 52 | 119 | −15 | 202 | 64 |
| 330 | | | 191 | 49 | 109 | −25 | 184 | 46 |
| 345 | | | 187 | 45 | 123 | −11 | 178 | 40 |
| 360 | | | 169 | 27 | 118 | −16 | 165 | 27 |

TABLE 20

Patient Number 118

| | Treatment | | | | | | | |
|---|---|---|---|---|---|---|---|---|
| | Oral 150 U Insulin/ 200 mg 4-CNAB | | Oral 300 U Insulin/ 400 mg 4-CNAB | | SC 12 U Short-acting insulin | | Placebo | |
| Time | Blood glucose (mg/dl) | Postprandial excursion (mg/dl) | Blood glucose (mg/dl) | Postprandial excursion (mg/dl) | Blood glucose (mg/dl) | Postprandial excursion (mg/dl) | Blood glucose (mg/dl) | Postprandial excursion (mg/dl) |
| −120 | | | | | NA | | | |
| −105 | | | | | NA | | | |
| −90 | | | | | NA | | | |
| −75 | | | | | NA | | | |
| −60 | | | | | 175 | | | |
| −45 | | | | | 181 | | | |
| −30 | | | | | 181 | | | |
| −16 | | | | | 184 | | | |
| −1 | | | | | 190 | 0 | | |
| 5 | | | | | 193 | 3 | | |
| 10 | | | | | 191 | 1 | | |
| 15 | | | | | 185 | −5 | | |
| 20 | | | | | 184 | −6 | | |
| 25 | | | | | 185 | −5 | | |
| 30 | | | | | 190 | 0 | | |
| 35 | | | | | 202 | 12 | | |
| 40 | | | | | 201 | 11 | | |
| 45 | | | | | 210 | 20 | | |
| 50 | | | | | 215 | 25 | | |
| 55 | | | | | 227 | 37 | | |
| 60 | | | | | 214 | 24 | | |
| 65 | | | | | 228 | 38 | | |
| 70 | | | | | 233 | 43 | | |
| 75 | | | | | 239 | 49 | | |
| 80 | | | | | 218 | 28 | | |
| 85 | | | | | 211 | 21 | | |
| 90 | | | | | 224 | 34 | | |
| 95 | | | | | 223 | 33 | | |
| 100 | | | | | 233 | 43 | | |
| 105 | | | | | 225 | 35 | | |
| 110 | | | | | 226 | 36 | | |
| 115 | | | | | 226 | 36 | | |
| 120 | | | | | 225 | 35 | | |
| 130 | | | | | 215 | 25 | | |
| 140 | | | | | 212 | 22 | | |
| 150 | | | | | 214 | 24 | | |
| 160 | | | | | 214 | 24 | | |
| 170 | | | | | 205 | 15 | | |

TABLE 20-continued

Patient Number 118

| | Treatment | | | | | | | |
|---|---|---|---|---|---|---|---|---|
| | Oral 150 U Insulin/ 200 mg 4-CNAB | | Oral 300 U Insulin/ 400 mg 4-CNAB | | SC 12 U Short-acting insulin | | Placebo | |
| Time | Blood glucose (mg/dl) | Postprandial excursion (mg/dl) | Blood glucose (mg/dl) | Postprandial excursion (mg/dl) | Blood glucose (mg/dl) | Postprandial excursion (mg/dl) | Blood glucose (mg/dl) | Postprandial excursion (mg/dl) |
| 180 | | | | | 201 | 11 | | |
| 190 | | | | | 192 | 2 | | |
| 200 | | | | | 189 | −1 | | |
| 210 | | | | | 188 | −2 | | |
| 220 | | | | | 176 | −14 | | |
| 230 | | | | | 179 | −11 | | |
| 240 | | | | | 177 | −13 | | |
| 255 | | | | | 167 | −23 | | |
| 270 | | | | | 148 | −42 | | |
| 285 | | | | | 138 | −52 | | |
| 300 | | | | | 136 | −54 | | |
| 315 | | | | | 136 | −54 | | |
| 330 | | | | | 136 | −54 | | |
| 345 | | | | | 125 | −65 | | |
| 360 | | | | | 129 | −61 | | |

Based upon individual blood glucose excursion data, the mean time data (with standard deviation) of the blood glucose excursions per treatment were calculated. Table 21 below presents the mean time profiles (with standard deviation) of the blood glucose excursions per treatment.

TABLE 21

Statistics on Blood Glucose Excursions (mg/dL) versus Time

| | Treatment | | | | | | | |
|---|---|---|---|---|---|---|---|---|
| | Oral 150 U Insulin/ 200 mg 4-CNAB | | Oral 300 U Insulin/ 400 mg 4-CNAB | | SC 12 U Short-acting insulin | | Placebo | |
| Time | MEAN | STD | Mean | STD | Mean | STD | Mean | STD |
| −1 min | 0.00 | 0.00 | 0.00 | 0.00 | 0.00 | 0.00 | 0.00 | 0.00 |
| 5 min | −1.88 | 2.85 | −10.28 | 9.82 | 0.83 | 3.90 | 1.26 | 7.21 |
| 10 min | −0.94 | 6.82 | −14.32 | 12.79 | −2.02 | 4.12 | −1.34 | 7.73 |
| 15 min | −0.90 | 6.60 | −20.80 | 15.85 | −1.83 | 6.65 | 0.67 | 6.27 |
| 20 min | 5.17 | 9.34 | −13.10 | 12.28 | 2.00 | 7.99 | 6.36 | 8.95 |
| 25 min | 14.45 | 13.65 | −7.73 | 15.37 | 8.78 | 8.34 | 15.98 | 10.94 |
| 30 min | 25.78 | 19.53 | 0.96 | 16.45 | 13.94 | 10.32 | 25.04 | 12.13 |
| 35 min | 30.03 | 19.59 | 9.65 | 20.71 | 20.22 | 11.84 | 27.17 | 13.77 |
| 40 min | 38.70 | 25.11 | 19.44 | 22.26 | 25.61 | 14.29 | 42.09 | 16.75 |
| 45 min | 46.62 | 28.06 | 27.22 | 23.02 | 25.39 | 14.72 | 44.27 | 15.74 |
| 50 min | 53.20 | 28.13 | 34.15 | 25.35 | 25.17 | 14.72 | 50.21 | 17.62 |
| 55 min | 53.78 | 28.10 | 36.32 | 26.55 | 25.23 | 18.21 | 59.15 | 20.77 |
| 60 min | 61.53 | 29.36 | 45.12 | 25.43 | 28.61 | 22.60 | 60.68 | 20.18 |
| 65 min | 62.95 | 33.22 | 47.66 | 26.40 | 34.27 | 20.98 | 64.92 | 20.20 |
| 70 min | 65.28 | 31.71 | 53.43 | 25.78 | 34.80 | 23.89 | 67.21 | 21.48 |
| 75 min | 67.03 | 29.53 | 60.82 | 26.01 | 35.18 | 24.69 | 73.09 | 24.03 |
| 80 min | 71.62 | 31.52 | 63.58 | 28.07 | 34.76 | 27.55 | 72.98 | 23.59 |
| 85 min | 72.78 | 33.07 | 65.35 | 27.24 | 34.84 | 28.91 | 70.15 | 23.72 |
| 90 min | 72.45 | 35.93 | 66.43 | 27.65 | 31.73 | 28.64 | 74.27 | 23.37 |
| 95 min | 73.95 | 38.85 | 65.43 | 26.86 | 30.77 | 32.19 | 77.04 | 24.40 |
| 100 min | 72.03 | 33.65 | 68.82 | 31.37 | 31.89 | 29.45 | 73.86 | 24.91 |
| 105 min | 71.70 | 36.28 | 70.05 | 28.56 | 30.43 | 34.39 | 74.98 | 24.90 |
| 110 min | 72.53 | 36.31 | 68.66 | 29.11 | 28.94 | 29.69 | 74.21 | 27.63 |
| 115 min | 69.95 | 34.89 | 66.82 | 25.86 | 27.78 | 30.69 | 75.51 | 26.02 |
| 120 min | 67.62 | 33.17 | 68.74 | 26.84 | 24.39 | 38.20 | 73.09 | 27.51 |
| 130 min | 64.20 | 33.66 | 69.66 | 26.29 | 23.58 | 29.38 | 69.92 | 30.50 |
| 140 min | 64.12 | 36.90 | 67.05 | 29.96 | 21.13 | 29.04 | 65.21 | 34.05 |
| 150 min | 61.81 | 39.39 | 69.82 | 27.52 | 18.24 | 30.41 | 63.09 | 33.30 |
| 160 min | 52.45 | 36.58 | 69.89 | 26.44 | 14.70 | 33.22 | 60.04 | 35.19 |
| 170 min | 56.14 | 43.50 | 66.58 | 29.68 | 8.18 | 31.08 | 54.62 | 33.10 |
| 180 min | 53.43 | 43.74 | 63.05 | 29.07 | 2.46 | 32.61 | 52.51 | 34.37 |
| 190 min | 52.50 | 46.66 | 65.51 | 25.89 | −5.92 | 35.08 | 47.62 | 36.83 |
| 200 min | 51.87 | 49.16 | 61.24 | 30.87 | −7.98 | 38.93 | 47.20 | 38.33 |
| 210 min | 43.86 | 50.96 | 56.55 | 34.19 | −11.50 | 40.57 | 42.43 | 37.39 |
| 220 min | 44.02 | 46.33 | 54.32 | 35.95 | −16.28 | 38.64 | 38.04 | 37.33 |

TABLE 21-continued

Statistics on Blood Glucose Excursions (mg/dL) versus Time

| | Treatment | | | | | | | |
|---|---|---|---|---|---|---|---|---|
| | Oral 150 U Insulin/ 200 mg 4-CNAB | | Oral 300 U Insulin/ 400 mg 4-CNAB | | SC 12 U Short-acting insulin | | Placebo | |
| Time | MEAN | STD | Mean | STD | Mean | STD | Mean | STD |
| 230 min | 39.06 | 45.66 | 51.03 | 30.63 | −18.03 | 36.67 | 34.38 | 38.38 |
| 240 min | 35.81 | 43.81 | 47.56 | 33.31 | −19.99 | 37.25 | 30.18 | 36.50 |
| 255 min | 34.03 | 45.16 | 38.68 | 38.20 | −23.24 | 34.66 | 21.01 | 37.12 |
| 270 min | 25.78 | 44.25 | 37.74 | 39.55 | −30.94 | 31.16 | 17.26 | 38.00 |
| 285 min | 22.66 | 44.50 | 32.02 | 39.22 | −33.17 | 29.93 | 9.15 | 34.35 |
| 300 min | 17.62 | 42.95 | 27.00 | 37.62 | −36.51 | 27.14 | 5.46 | 33.57 |
| 315 min | 9.72 | 42.22 | 22.73 | 34.64 | −38.84 | 23.55 | −1.79 | 31.13 |
| 330 min | 6.50 | 39.10 | 19.07 | 34.40 | −40.00 | 22.81 | −3.87 | 30.70 |
| 345 min | 2.29 | 37.43 | 15.57 | 31.59 | −42.37 | 22.24 | −7.80 | 29.53 |
| 360 min | −3.60 | 36.03 | 10.60 | 31.52 | −42.68 | 21.48 | −12.44 | 26.69 |

Based upon individual blood glucose excursion data, the mean time profiles (with standard deviation) of the blood glucose excursions per treatment were plotted. FIG. 1 shows a plot of the arithmetic means of postprandial blood glucose excursions (mg/dL) vs. time for all subjects. As indicated in FIG. 1, mean blood glucose excursions of the different treatments reach their maxima between 1 and 2 hours after start of meal intake and then return towards baseline. The time to maximal glucose excursion (median) was 1.3 hours for SC 12 U short-acting insulin, 1.7 hours for placebo, 1.8 hours for oral 150 U Insulin/200 mg 4-CNAB, and 2.2 hours for oral 300 U Insulin/400 mg 4-CNAB.

The lowest overall excursions were achieved with the 12 U SC short-acting insulin injection. Compared to both oral insulin treatments and placebo, blood glucose excursions after SC injection are markedly lower during the period from 45 to 360 minutes and, after crossing the baseline at about 180 minutes, values become increasingly negative until 360 minutes after meal intake.

After oral 300 U Insulin/400 mg 4-CNAB, a sharp decline from baseline can be seen until −20.8 mg/dL at 15 minutes, followed by a return to baseline at 30 minutes. Thus, during approximately the first hour, the dose of 300 U oral Insulin/400 mg 4-CNAB led to lower excursions even when compared to injection. Thereafter, rise and subsequent decline of the curve follows the pattern seen for oral 150 U Insulin/200 mg 4-CNAB dosage and no treatment (placebo). No differences could be seen between 150 U oral Insulin/200 mg 4-CNAB and no treatment (placebo).

Based on the profiles, the derived parameters, $AUC_{0-1h}$, $AUC_{0-1h}$, $AUC_{0-3h}$, $AUC_{0-4h}$, $AUC_{0-6h}$ and $C_{max}$ were calculated, as presented in Table 22 below.

This data indicates that $AUC_{0-1h}$ is lowest following the 300 U oral Insulin/400 mg 4-CNAB dosage. Up to 2 hours and 3 hours, the AUCs are still smaller than the AUCs of 150 U oral Insulin/200 mg 4-CNAB and no treatment (placebo), but larger than the AUCs of 12 U SC short-acting insulin. However, for 4 hours and 6 hours, no difference can be seen between the oral applications and no treatment. For 150 U oral Insulin/200 mg 4-CNAB, all AUCs are more or less equal to those obtained under no treatment. Mean maximum blood glucose excursions ($C_{max}$) after both oral insulin administrations and after no treatment are similar and clearly higher than $C_{max}$ after the SC injection.

Figure 3:
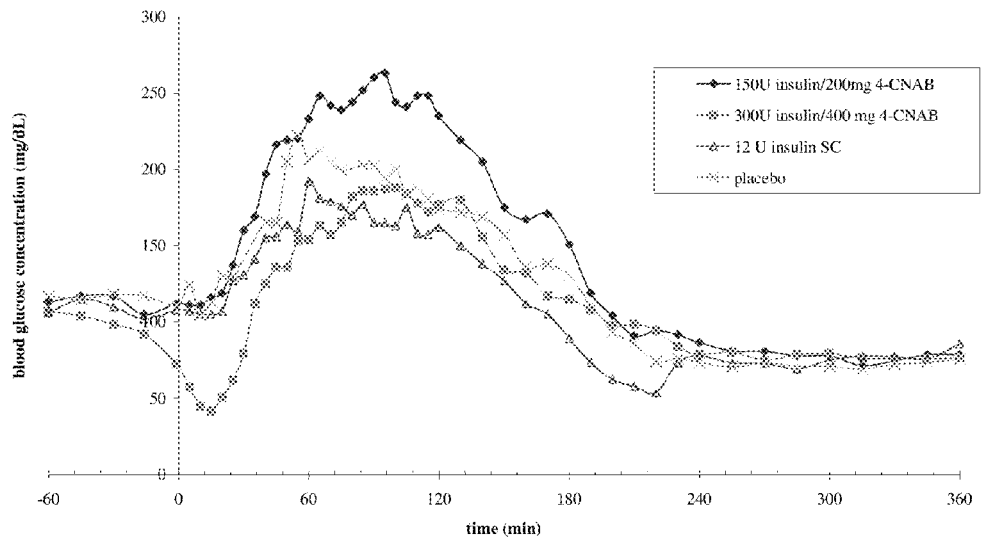
FIG. 3 shows a plot of the postprandial blood glucose excursion (blood glucose concentration (SuperGL) (mg/dl) vs. time) for Type 2 Diabetic subject no. 116 after oral or subcutaneous administration of insulin or insulin/4-CNAB 30 minutes prior to a standard meal (meal at time=0).
Figure 4:
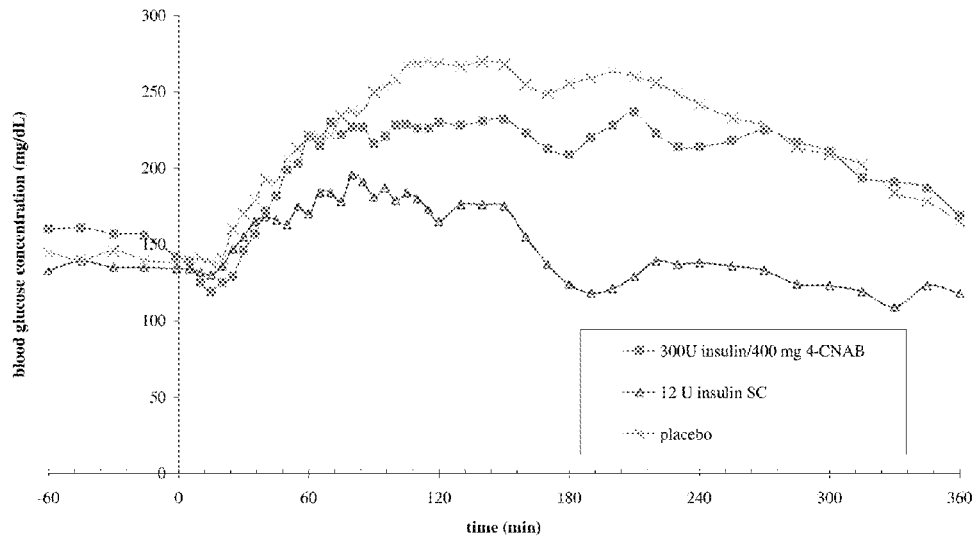
FIG. 4 shows a plot of the postprandial blood glucose excursion (blood glucose concentration (SuperGL) (mg/dl) vs. time) for Type 2 Diabetic subject no. 117 after oral or subcutaneous administration of insulin or insulin/4-CNAB 30 minutes prior to a standard meal (meal at time=0).

FIGS. 3 and 4 show the blood glucose concentration vs. time curves for subjects 116 and 117, respectively. Subject 116 was chosen because he was a Type II diabetic in an early stage of the disease, i.e., was able to produce his own insulin, and the glucose curve for subject 116 shown in FIG. 3 paralleled that of healthy (normal) non-diabetic humans. By contrast, subject 117 was a type II diabetic in an advanced stage of the disease, i.e., having very little pancreatic function left and producing very little endogenous insulin. Accordingly, as shown in the glucose curve of FIG. 4 for subject 117, it took much longer to lower the glucose level for this subject back to a level found in healthy (normal) non-diabetic humans.

The test results can be summarized as follows: When $C_{max}$ and AUCs for 3 hours and more are considered, no statistically significant differences of the oral treatments compared to no treatment (placebo) could be established. On the other hand, both oral treatments differ significantly from SC insulin injection, with oral treatments leading to higher mean values.

With regard to the primary endpoint $AUC_{0-2h}$, a single oral dose of 300 U Insulin/400 mg 4-CNAB, administered 30

TABLE 22

| | Treatment | | | | | | | |
|---|---|---|---|---|---|---|---|---|
| | Oral 150 U Insulin/200 mg 4-CNAB | | Oral 300 U Insulin/400 mg 4-CNAB | | SC 12 U Short-acting insulin | | Placebo | |
| Parameter | Mean | STD | Mean | STD | Mean | STD | Mean | STD |
| $AUC_{0-1h}$ (h*mg/dL) | 24.5 | 15.2 | 6.9 | 15.0 | 13.1 | 8.5 | 25.3 | 9.1 |
| $AUC_{0-2h}$ (h*mg/dL) | 94.3 | 46.3 | 69.8 | 38.0 | 44.9 | 32.8 | 97.8 | 28.5 |
| $AUC_{0-3h}$ (h*mg/dL) | 154.1 | 74.1 | 138.2 | 60.4 | 61.4 | 57.5 | 160.2 | 54.0 |
| $AUC_{0-4h}$ (h*mg/dL) | 200.1 | 105.9 | 195.2 | 81.4 | 50.0 | 83.6 | 202.1 | 84.9 |
| $AUC_{0-6h}$ (h*mg/dL) | 233.9 | 164.3 | 250.8 | 140.6 | −21.1 | 119.4 | 214.2 | 143.7 |
| $C_{max}$ (mg/dL) | 90.5 | 38.1 | 85.8 | 28.3 | 50.7 | 25.8 | 88.3 | 27.7 | minutes prior to a standardized test meal, caused a statistically significant reduction of postprandial blood glucose excursions in comparison to no treatment (placebo). However, the effect was significantly lower than after SC injection of 12 U short-acting insulin. The effect of 150 U oral Insulin/200 mg 4-CNAB was not significantly different from no treatment (placebo).

Pharmacokinetics

From the blood samples taken, the individual plasma concentrations of 4-CNAB, insulin and C-peptide were also determined, and summary concentration vs. time tables were prepared and profiles were plotted, as set forth in Tables 23-40 for insulin and C-peptide concentrations below.

TABLE 23

Patient Number 101

| | Treatment | | | | | | | |
|---|---|---|---|---|---|---|---|---|
| | Oral 150 U Insulin/ 200 mg 4-CNAB | | Oral 300 U Insulin/ 400 mg 4-CNAB | | SC 12 U Short-acting insulin | | Placebo | |
| Time (min) | Insulin (pmol/l) | C-Peptide (nmol/l) | Insulin (pmol/l) | C-Peptide (nmol/l) | Insulin (pmol/l) | C-Peptide (nmol/l) | Insulin (pmol/l) | C-Peptide (nmol/l) |
| −60 | | | 63 | 0.73 | 134 | 0.97 | 72 | 0.85 |
| −30 | | | 78 | 0.80 | 66 | 0.76 | 95 | 0.90 |
| 0 | | | 277 | 0.76 | 112 | 0.90 | 74 | 0.81 |
| 10 | | | 334 | 0.81 | 111 | 0.98 | 105 | 0.98 |
| 20 | | | 159 | 0.85 | 140 | 1.13 | 136 | 1.15 |
| 30 | | | 222 | 1.19 | 280 | 1.58 | 229 | 1.53 |
| 40 | | | 202 | 1.17 | 339 | 1.66 | 281 | 1.71 |
| 50 | | | 222 | 1.27 | 281 | 1.73 | 322 | 1.96 |
| 60 | | | 311 | 1.70 | 270 | 1.66 | 338 | 2.20 |
| 75 | | | 311 | 1.95 | 349 | 1.98 | 352 | 2.30 |
| 90 | | | 339 | 2.10 | 384 | 2.20 | 430 | 2.50 |
| 105 | | | 386 | 2.40 | 397 | 2.30 | 349 | 2.50 |
| 120 | | | 433 | 2.70 | 501 | 2.60 | 441 | 2.90 |
| 150 | | | 452 | 2.90 | 395 | 2.70 | 299 | 2.60 |
| 180 | | | 285 | 2.60 | 252 | 2.30 | 192 | 2.30 |
| 210 | | | 220 | 2.20 | 186 | 1.88 | 273 | 2.60 |
| 240 | | | 165 | 2.10 | 93 | 1.32 | 175 | 2.20 |
| 300 | | | 95 | 1.42 | 68 | 0.93 | 98 | 1.51 |
| 360 | | | 102 | 1.14 | 43 | 0.71 | 67 | 0.86 |

TABLE 24

Patient Number 102

| | Treatment | | | | | | | |
|---|---|---|---|---|---|---|---|---|
| | Oral 150 U Insulin/ 200 mg 4-CNAB | | Oral 300 U Insulin/ 400 mg 4-CNAB | | SC 12 U Short-acting insulin | | Placebo | |
| Time | Insulin (pmol/l) | C-Peptide (nmol/l) | Insulin (pmol/l) | C-Peptide (nmol/l) | Insulin (pmol/l) | C-Peptide (nmol/l) | Insulin (pmol/l) | C-Peptide (nmol/l) |
| −60 | | | 44 | 0.78 | 30 | 0.55 | 51 | 0.71 |
| −30 | | | 35 | 0.69 | 23 | 0.50 | 47 | 0.76 |
| 0 | | | 52 | 0.68 | 48 | 0.59 | 45 | 0.69 |
| 10 | | | 68 | 0.72 | 60 | 0.62 | 67 | 0.76 |
| 20 | | | 54 | 0.70 | 50 | 0.60 | 66 | 0.75 |
| 30 | | | 113 | 0.93 | 41 | 0.85 | 128 | 0.93 |
| 40 | | | 169 | 1.16 | 212 | 1.22 | 153 | 1.13 |
| 50 | | | 250 | 1.47 | 163 | 1.14 | 264 | 1.47 |
| 60 | | | 256 | 1.50 | 153 | 1.15 | 282 | 1.61 |
| 75 | | | 336 | 2.00 | 300 | 1.71 | 322 | 1.88 |
| 90 | | | 362 | 2.20 | 128 | 1.53 | 556 | 2.70 |
| 105 | | | 343 | 2.40 | 267 | 1.73 | 602 | 2.80 |
| 120 | | | 344 | 2.50 | 209 | 1.72 | 763 | 3.20 |
| 150 | | | 213 | 2.30 | 162 | 1.61 | 488 | 3.10 |
| 180 | | | 142 | 1.83 | 139 | 1.52 | 416 | 3.00 |
| 210 | | | 135 | 2.10 | 219 | 1.70 | 281 | 2.70 |
| 240 | | | 95 | 1.49 | 108 | 1.38 | 213 | 2.20 |
| 300 | | | 83 | 1.28 | 70 | 1.01 | 140 | 1.61 |
| 360 | | | 83 | 1.24 | 56 | 0.88 | 86 | 1.35 |

TABLE 25

Patient Number 103

Treatment

| | Oral 150 U Insulin/ 200 mg 4-CNAB | | Oral 300 U Insulin/ 400 mg 4-CNAB | | SC 12 U Short-acting insulin | | Placebo | |
|---|---|---|---|---|---|---|---|---|
| Time (min) | Insulin (pmol/l) | C-Peptide (nmol/l) | Insulin (pmol/l) | C-Peptide (nmol/l) | Insulin (pmol/l) | C-Peptide (nmol/l) | Insulin (pmol/l) | C-Peptide (nmol/l) |
| −60 | 70 | 0.88 | 35 | 1.11 | 77 | 1.01 | 58 | 1.01 |
| −30 | 70 | 0.83 | 79 | 1.09 | 65 | 1.00 | 25 | 0.97 |
| 0 | 68 | 0.85 | 95 | 0.97 | 61 | 0.94 | 78 | 1.00 |
| 10 | 82 | 0.90 | 73 | 1.13 | 84 | 1.05 | 80 | 1.16 |
| 20 | 101 | 0.99 | 84 | 1.17 | 81 | 1.07 | 120 | 1.26 |
| 30 | 132 | 1.12 | 147 | 1.41 | 150 | 1.25 | 152 | 1.44 |
| 40 | 174 | 1.38 | 178 | 1.46 | 191 | 1.41 | 73* | 1.59 |
| 50 | 253 | 1.69 | 180 | 1.63 | 208 | 1.52 | 196 | 1.77 |
| 60 | 275 | 1.74 | 237 | 1.84 | 249 | 1.68 | 271 | 1.87 |
| 75 | 350 | 2.40 | 305 | 1.99 | 291 | 1.94 | 274 | 2.20 |
| 90 | 483 | 2.80 | 271 | 2.30 | 343 | 2.10 | 278 | 2.50 |
| 105 | 530 | 3.60 | 173 | 2.40 | 301 | 2.20 | 96* | 2.50 |
| 120 | 558 | 3.90 | 227 | 2.70 | 318 | 2.20 | 320 | 2.70 |
| 150 | 596 | 4.30 | 260 | 2.70 | 211 | 2.10 | 292 | 2.80 |
| 180 | 469 | 4.80 | 288 | 2.90 | 148 | 1.82 | 256 | 3.00 |
| 210 | 410 | 4.40 | 164 | 3.00 | 100 | 1.55 | 224 | 2.90 |
| 240 | 304 | 3.90 | 126 | 2.10 | 68 | 1.33 | 122 | 2.40 |
| 300 | 167 | 2.50 | 119 | 1.90 | 74 | 1.12 | 93 | 1.74 |
| 360 | 93* | 2.10 | 122 | 1.88 | 61 | 1.00 | 44* | 1.43 |

TABLE 26

Patient Number 104

Treatment

| | Oral 150 U Insulin/ 200 mg 4-CNAB | | Oral 300 U Insulin/ 400 mg 4-CNAB | | SC 12 U Short-acting insulin | | Placebo | |
|---|---|---|---|---|---|---|---|---|
| Time (min) | Insulin (pmol/l) | C-Peptide (nmol/l) | Insulin (pmol/l) | C-Peptide (nmol/l) | Insulin (pmol/l) | C-Peptide (nmol/l) | Insulin (pmol/l) | C-Peptide (nmol/l) |
| −60 | 22 | 0.48 | BLQ | 0.52 | 27 | 0.55 | 23 | 0.52 |
| −30 | 23 | 0.51 | 15 | 0.47 | BLQ | BLQ | 14 | 0.47 |
| 0 | 62 | 0.59 | 47 | 0.50 | 25 | 0.53 | 31 | 0.60 |
| 10 | 95 | 0.83 | 35 | 0.53 | 24 | 0.54 | 53 | 0.73 |
| 20 | 130 | 1.14 | 61 | 0.77 | 84 | 0.78 | 100 | 0.94 |
| 30 | 94 | 0.99 | 56 | 0.72 | 71 | 0.76 | 73 | 0.92 |
| 40 | 50* | 0.95 | BLQ | BLQ | 112 | 0.83 | 89 | 1.05 |
| 50 | 108 | 1.11 | 64 | 0.82 | 124 | 0.98 | 14 | 1.23 |
| 60 | 141 | 1.34 | 65 | 1.04 | 114 | 0.94 | 98 | 1.37 |
| 75 | 135 | 1.39 | 113 | 1.23 | 82 | 0.90 | 22 | 1.65 |
| 90 | 115 | 1.36 | 129 | 1.18 | 51 | 0.91 | 117 | 1.67 |
| 105 | 83 | 1.45 | 142 | 1.75 | 85 | 1.07 | 117 | 1.70 |
| 120 | 107 | 1.54 | 162 | 2.00 | 82 | 0.94 | 98 | 1.80 |
| 150 | 117 | 1.57 | 158 | 2.30 | 54 | 0.83 | 74 | 1.46 |
| 180 | 116 | 1.58 | 118 | 2.00 | 32 | 0.75 | 44 | 1.43 |
| 210 | 94 | 1.53 | 89 | 1.96 | 42 | 0.71 | 64 | 1.64 |
| 240 | 122 | 1.63 | 77 | 1.76 | 27 | 0.61 | 56 | 1.38 |
| 300 | 48 | 1.41 | 35 | 1.19 | 14 | 0.47 | 40 | 1.01 |
| 360 | 43 | 1.01 | 28 | 0.91 | 19 | 0.43 | 23 | 0.78 |

TABLE 27

Patient Number 105

Treatment

| | Oral 150 U Insulin/ 200 mg 4-CNAB | | Oral 300 U Insulin/ 400 mg 4-CNAB | | SC 12 U Short-acting insulin | | Placebo | |
|---|---|---|---|---|---|---|---|---|
| Time (min) | Insulin (pmol/l) | C-Peptide (nmol/l) | Insulin (pmol/l) | C-Peptide (nmol/l) | Insulin (pmol/l) | C-Peptide (nmol/l) | Insulin (pmol/l) | C-Peptide (nmol/l) |
| −60 | 44 | 0.95 | 36 | 0.79 | 23 | 0.72 | 23 | 0.76 |
| −30 | 40 | 1.04 | 39 | 0.85 | 19 | 0.72 | 23 | 0.73 |
| 0 | 38 | 1.01 | 76 | 0.82 | 25 | 0.70 | 22 | 0.71 |
| 10 | 48 | 1.03 | 114 | 0.83 | 40 | 0.76 | 42 | 0.83 |

TABLE 27-continued

Patient Number 105

| | Treatment | | | | | | | |
|---|---|---|---|---|---|---|---|---|
| | Oral 150 U Insulin/ 200 mg 4-CNAB | | Oral 300 U Insulin/ 400 mg 4-CNAB | | SC 12 U Short-acting insulin | | Placebo | |
| Time (min) | Insulin (pmol/l) | C-Peptide (nmol/l) | Insulin (pmol/l) | C-Peptide (nmol/l) | Insulin (pmol/l) | C-Peptide (nmol/l) | Insulin (pmol/l) | C-Peptide (nmol/l) |
| 20 | 53 | 1.03 | 61 | 0.79 | 38 | 0.75 | 43 | 0.77 |
| 30 | 146 | 1.65 | 98 | 1.01 | 106 | 1.10 | 100 | 1.12 |
| 40 | 165 | 1.78 | 95 | 1.19 | 120 | 1.10 | 135 | 1.30 |
| 50 | 193 | 1.83 | 97 | 1.05 | 122 | 1.11 | 144 | 1.18 |
| 60 | 49* | 2.60* | 111 | 1.22 | 119 | 1.24 | 148 | 1.43 |
| 75 | 360 | 3.20 | 149 | 1.57 | 159 | 1.62 | 239 | 2.00 |
| 90 | 245* | 3.70 | 148 | 1.68 | 170 | 1.75 | 283 | 2.30 |
| 105 | 498 | 3.80 | 233 | 2.00 | 197 | 2.20 | 289 | 2.50 |
| 120 | 430 | 4.30 | 232 | 2.10 | 193 | 1.81 | 321 | 2.60 |
| 150 | 188 | 3.00 | 286 | 2.40 | 207 | 2.30 | 260 | 2.80 |
| 180 | 244 | 3.10 | 281 | 2.50 | 135 | 1.99 | 213 | 2.60 |
| 210 | 121 | 3.20 | 229 | 2.50 | 40 | 1.28 | 134* | 2.40 |
| 240 | 103 | 1.90 | 169 | 2.40 | 18 | 0.83 | 84 | 1.97 |
| 300 | 28 | 1.26 | 48 | 1.29 | 14 | 0.74 | 32 | 1.11 |
| 360 | 25 | 0.91 | 34 | 0.92 | BLQ | 0.58 | 25 | 0.86 |

TABLE 28

Patient Number 106

| | Treatment | | | | | | | |
|---|---|---|---|---|---|---|---|---|
| | Oral 150 U Insulin/ 200 mg 4-CNAB | | Oral 300 U Insulin/ 400 mg 4-CNAB | | SC 12 U Short-acting insulin | | Placebo | |
| Time (min) | Insulin (pmol/l) | C-Peptide (nmol/l) | Insulin (pmol/l) | C-Peptide (nmol/l) | Insulin (pmol/l) | C-Peptide (nmol/l) | Insulin (pmol/l) | C-Peptide (nmol/l) |
| −60 | 65 | 0.82 | 42 | 0.71 | 24 | 0.51 | 24 | 0.69 |
| −30 | 55 | 0.86 | 30 | 0.74 | 19 | 0.49 | 24 | 0.58 |
| 0 | 62 | 0.71 | 48 | 0.61 | 26 | 0.55 | 32 | 0.66 |
| 10 | 46 | 0.75 | 48 | 0.66 | 38 | 0.61 | 39 | 0.68 |
| 20 | 38 | 0.76 | 27 | 0.58 | 52 | 0.75 | 71 | 0.81 |
| 30 | 82 | 0.88 | 33 | 0.57 | 69 | 0.76 | 90 | 0.93 |
| 40 | 106 | 1.00 | 42 | 0.68 | 39 | 0.74 | 122 | 1.12 |
| 50 | 123 | 1.33 | 55 | 0.74 | 63 | 0.77 | 136 | 1.32 |
| 60 | 118 | 1.39 | 78 | 0.82 | 58 | 0.72 | 130 | 1.63 |
| 75 | 94 | 1.44 | 53 | 0.77 | BLQ* | 0.51* | 155 | 1.76 |
| 90 | 127 | 1.42 | 121 | 1.22 | BLQ* | 0.43* | 173 | 1.96 |
| 105 | 123 | 1.90 | 62 | 1.05 | BLQ | 0.34 | 166 | 2.30 |
| 120 | 140 | 2.10 | 73 | 1.09 | 13 | 0.32 | 159 | 2.40 |
| 150 | 155 | 2.30 | 88 | 1.36 | 17 | 0.35 | 97 | 1.91 |
| 180 | 121 | 2.50 | 146 | 1.58 | 26 | 0.46 | 108 | 1.73 |
| 210 | 84 | 1.98 | 135 | 2.10 | 12* | 0.44* | 104 | 1.75 |
| 240 | 112 | 2.00 | 137 | 2.20 | 31 | 0.50 | 90 | 1.90 |
| 300 | 87 | 1.68 | 51 | 1.30 | BLQ* | 0.41* | 22 | 0.84 |
| 360 | 35 | 0.88 | 30 | 0.70 | BLQ | 0.31 | 18 | 0.57 |

TABLE 29

Patient Number 107

| | Treatment | | | | | | | |
|---|---|---|---|---|---|---|---|---|
| | Oral 150 U Insulin/ 200 mg 4-CNAB | | Oral 300 U Insulin/ 400 mg 4-CNAB | | SC 12 U Short-acting insulin | | Placebo | |
| Time (min) | Insulin (pmol/l) | C-Peptide (nmol/l) | Insulin (pmol/l) | C-Peptide (nmol/l) | Insulin (pmol/l) | C-Peptide (nmol/l) | Insulin (pmol/l) | C-Peptide (nmol/l) |
| −60 | 42 | 0.76 | 43 | 0.73 | 38 | 0.70 | 36 | 0.74 |
| −30 | 43 | 0.77 | 43 | 0.74 | 46 | 0.77 | 40 | 0.75 |

TABLE 29-continued

Patient Number 107

| | Treatment | | | | | | | |
|---|---|---|---|---|---|---|---|---|
| | Oral 150 U Insulin/ 200 mg 4-CNAB | | Oral 300 U Insulin/ 400 mg 4-CNAB | | SC 12 U Short-acting insulin | | Placebo | |
| Time (min) | Insulin (pmol/l) | C-Peptide (nmol/l) | Insulin (pmol/l) | C-Peptide (nmol/l) | Insulin (pmol/l) | C-Peptide (nmol/l) | Insulin (pmol/l) | C-Peptide (nmol/l) |
| 0 | 134 | 0.85 | 98 | 0.94 | 52 | 0.81 | 53 | 0.84 |
| 10 | 86 | 0.84 | 163 | 1.30 | 103 | 1.08 | 83 | 1.01 |
| 20 | 145 | 1.28 | 143 | 1.35 | 135 | 1.22 | 70 | 0.92 |
| 30 | 153 | 1.37 | 221 | 1.55 | 220 | 1.46 | 138 | 1.26 |
| 40 | 163 | 1.37 | 217 | 1.58 | 184 | 1.48 | 258 | 1.48 |
| 50 | 214 | 1.63 | 190 | 1.60 | 184 | 1.49 | 235 | 1.49 |
| 60 | 245 | 1.95 | 210 | 1.86 | 219 | 1.66 | 203 | 1.78 |
| 75 | 306 | 2.30 | 263 | 2.10 | 330 | 2.10 | 326 | 2.10 |
| 90 | 306 | 2.50 | 268 | 2.20 | 260 | 2.10 | 455 | 2.50 |
| 105 | 251 | 2.40 | 261 | 2.20 | 273 | 2.20 | 346 | 2.50 |
| 120 | 275 | 2.70 | 269 | 2.50 | 253 | 2.10 | 386 | 2.80 |
| 150 | 229 | 2.50 | 40* | 2.30* | 159 | 2.00 | 280 | 2.60 |
| 180 | 172 | 2.30 | 148 | 2.00 | 111 | 1.67 | 237 | 2.50 |
| 210 | 87 | 1.97 | 114 | 1.75 | 86 | 1.54 | 165 | 2.40 |
| 240 | 98 | 1.80 | 156 | 1.96 | 59 | 1.28 | 121 | 2.00 |
| 300 | 56 | 1.30 | 65 | 1.05 | 33 | 0.96 | 55 | 1.29 |
| 360 | 50 | 1.15 | 50 | 0.92 | 28 | 0.76 | 38 | 0.86 |

TABLE 30

Patient Number 108

| | Treatment | | | | | | | |
|---|---|---|---|---|---|---|---|---|
| | Oral 150 U Insulin/ 200 mg 4-CNAB | | Oral 300 U Insulin/ 400 mg 4-CNAB | | SC 12 U Short-acting insulin | | Placebo | |
| Time (min) | Insulin (pmol/l) | C-Peptide (nmol/l) | Insulin (pmol/l) | C-Peptide (nmol/l) | Insulin (pmol/l) | C-Peptide (nmol/l) | Insulin (pmol/l) | C-Peptide (nmol/l) |
| −60 | 158 | 1.62 | 71 | 0.88 | 92 | 1.00 | 134 | 1.12 |
| −30 | 128 | 1.43 | BLQ* | 0.83* | 90 | 0.87 | 91 | 1.06 |
| 0 | 313 | 1.43 | 330 | 0.72 | 143 | 1.20 | 120 | 1.20 |
| 10 | 247 | 1.58 | 155 | 0.82 | 138 | 1.21 | 130 | 1.28 |
| 20 | 364 | 2.20 | 144 | 0.98 | 242 | 1.49 | 419 | 2.20 |
| 30 | 379 | 2.20 | 137 | 1.03 | 192 | 1.58 | 616 | 2.60 |
| 40 | 438 | 2.40 | 224 | 1.38 | 332 | 1.71 | 533 | 2.30 |
| 50 | 467 | 2.60 | 297 | 1.81 | 337 | 1.83 | 458 | 2.90 |
| 60 | 559 | 2.80 | 260 | 1.79 | 369 | 2.00 | 489 | 3.20 |
| 75 | 573 | 3.20 | 141 | 1.80 | 403 | 2.10 | 518 | 3.50 |
| 90 | 515 | 3.70 | 254 | 2.00 | 473 | 2.40 | 441 | 2.60 |
| 105 | 657 | 3.80 | 66* | 2.00 | 414 | 2.50 | 388 | 3.30 |
| 120 | 586 | 3.90 | 209 | 2.00 | 389 | 2.40 | 386 | 3.60 |
| 150 | 853 | 5.30 | 235 | 2.10 | 268 | 2.60 | 463 | 2.60 |
| 180 | 569 | 4.90 | 241 | 3.00 | 281 | 2.40 | 364 | 3.30 |
| 210 | 540 | 3.10 | 341 | 3.10 | 352 | 2.50 | 240 | 3.00 |
| 240 | 481 | 3.70 | 204 | 2.20 | 225 | 2.20 | 290 | 3.40 |
| 300 | 391 | 2.90 | 141 | 1.82 | 116 | 1.73 | 196 | 2.20 |
| 360 | 229 | 2.00 | 126 | 1.70 | 95 | 1.07 | 109 | 1.77 |

TABLE 31

Patient Number 109

| | Treatment | | | | | | | |
|---|---|---|---|---|---|---|---|---|
| | Oral 150 U Insulin/ 200 mg 4-CNAB | | Oral 300 U Insulin/ 400 mg 4-CNAB | | SC 12 U Short-acting insulin | | Placebo | |
| Time (min) | Insulin (pmol/l) | C-Peptide (nmol/l) | Insulin (pmol/l) | C-Peptide (nmol/l) | Insulin (pmol/l) | C-Peptide (nmol/l) | Insulin (pmol/l) | C-Peptide (nmol/l) |
| −60 | 82 | 0.89 | 64 | 1.18 | 69 | 1.18 | 36 | 0.66 |
| −30 | 82 | 0.97 | 59 | 1.38 | 38 | 0.86 | 36 | 0.63 |
| 0 | 83 | 0.95 | 273 | 1.19 | 63 | 1.17 | 63 | 0.77 |

TABLE 31-continued

Patient Number 109

Treatment

| Time (min) | Oral 150 U Insulin/ 200 mg 4-CNAB | | Oral 300 U Insulin/ 400 mg 4-CNAB | | SC 12 U Short-acting insulin | | Placebo | |
|---|---|---|---|---|---|---|---|---|
| | Insulin (pmol/l) | C-Peptide (nmol/l) | Insulin (pmol/l) | C-Peptide (nmol/l) | Insulin (pmol/l) | C-Peptide (nmol/l) | Insulin (pmol/l) | C-Peptide (nmol/l) |
| 10 | 47* | 0.96* | 114 | 1.04 | 81 | 1.36 | 61 | 0.76 |
| 20 | 149 | 1.27 | 74 | 0.83 | 101 | 1.34 | 141 | 1.01 |
| 30 | 595 | 2.30 | 302 | 1.43 | 460 | 2.60 | 222 | 1.45 |
| 40 | 388 | 2.00 | 303 | 2.10 | 436 | 3.40 | 362 | 1.88 |
| 50 | 482 | 2.30 | 265 | 1.94 | 276 | 2.70 | 416 | 2.00 |
| 60 | 406 | 2.20 | 174 | 1.69 | 418 | 2.70 | 379 | 2.10 |
| 75 | 415 | 2.20 | 225 | 2.20 | 457 | 3.80 | 569 | 2.50 |
| 90 | 511 | 2.60 | 329 | 2.50 | 499 | 4.10 | 416 | 2.30 |
| 105 | 582 | 3.30 | 475 | 2.70 | 352 | 3.30 | 635 | 3.00 |
| 120 | 470 | 3.00 | 408 | 2.70 | 265 | 2.60 | 594 | 3.00 |
| 150 | 565 | 3.40 | 375 | 2.50 | 494 | 4.70 | 514 | 3.30 |
| 180 | 435 | 3.10 | 321 | 2.40 | 240 | 3.80 | 333 | 2.60 |
| 210 | 447 | 3.40 | 196 | 3.20 | 140 | 2.50 | 183 | 2.40 |
| 240 | 271 | 2.70 | 203 | 2.70 | 92 | 2.10 | 122 | 1.93 |
| 300 | 204 | 2.30 | 137 | 2.20 | 57 | 1.81 | 62 | 1.37 |
| 360 | 98 | 1.54 | 93 | 1.87 | 39 | 1.01 | 76 | 1.32 |

TABLE 32

Patient Number 110

Treatment

| Time (min) | Oral 150 U Insulin/ 200 mg 4-CNAB | | Oral 300 U Insulin/ 400 mg 4-CNAB | | SC 12 U Short-acting insulin | | Placebo | |
|---|---|---|---|---|---|---|---|---|
| | Insulin (pmol/l) | C-Peptide (nmol/l) | Insulin (pmol/l) | C-Peptide (nmol/l) | Insulin (pmol/l) | C-Peptide (nmol/l) | Insulin (pmol/l) | C-Peptide (nmol/l) |
| −60 | 52 | 0.62 | 24 | 0.44 | 36 | 0.50 | 37 | 0.57 |
| −30 | 40 | 0.55 | 24 | 0.43 | 39 | 0.54 | 27 | 0.55 |
| 0 | 51 | 0.60 | 1803 | 0.52 | 50 | 0.61 | 32 | 0.56 |
| 10 | 219 | 1.21 | 890 | 0.64 | 67 | 0.67 | 153 | 0.94 |
| 20 | 227 | 1.24 | 351 | 0.78 | 271 | 1.26 | 348 | 1.57 |
| 30 | 270 | 1.27 | 197 | 0.73 | 275 | 1.22 | 473 | 2.00 |
| 40 | 242 | 1.42 | 189 | 0.79 | 275 | 1.28 | 511 | 2.20 |
| 50 | 348 | 1.81 | 184 | 0.87 | 348 | 1.58 | 445 | 2.20 |
| 60 | 359 | 1.86 | 171 | 0.99 | 471 | 1.74 | 356 | 2.10 |
| 75 | 477 | 2.30 | 153 | 1.08 | 455 | 1.89 | 383 | 2.20 |
| 90 | 411 | 2.40 | 161 | 1.20 | 427 | 2.10 | 422 | 2.60 |
| 105 | 396 | 2.40 | 112 | 1.14 | 461 | 2.10 | 329 | 2.60 |
| 120 | 375 | 2.40 | 223 | 1.61 | 252 | 1.72 | 492 | 3.00 |
| 150 | 437 | 2.80 | 165 | 1.67 | 248 | 1.75 | 233 | 2.40 |
| 180 | 444 | 2.90 | 152 | 1.47 | 76 | 1.27 | 174 | 2.20 |
| 210 | 342 | 2.60 | 139 | 1.56 | 51 | 0.81 | 142 | 2.00 |
| 240 | 179 | 1.97 | 59 | 1.16 | 42 | 0.63 | 96 | 1.63 |
| 300 | 149 | 1.57 | 35 | 0.63 | 27 | 0.47 | 44 | 1.00 |
| 360 | 51 | 0.96 | 24 | 0.51 | 22 | 0.37 | 33 | 0.62 |

TABLE 33

Patient Number 111

Treatment

| Time (min) | Oral 150 U Insulin/ 200 mg 4-CNAB | | Oral 300 U Insulin/ 400 mg 4-CNAB | | SC 12 U Short-acting insulin | | Placebo | |
|---|---|---|---|---|---|---|---|---|
| | Insulin (pmol/l) | C-Peptide (nmol/l) | Insulin (pmol/l) | C-Peptide (nmol/l) | Insulin (pmol/l) | C-Peptide (nmol/l) | Insulin (pmol/l) | C-Peptide (nmol/l) |
| −60 | 78 | 1.29 | 68 | 1.11 | 131 | 1.53 | 87 | 1.12 |
| −30 | 83 | 1.19 | 71 | 1.11 | 108 | 1.38 | 51 | 0.99 |
| 0 | 67 | 1.07 | 373 | 1.02 | 142 | 1.27 | 43 | 0.78 |
| 10 | 62 | 1.02 | 127 | 0.97 | 105 | 1.38 | 46 | 0.80 |

TABLE 33-continued

Patient Number 111

Treatment

| | Oral 150 U Insulin/ 200 mg 4-CNAB | | Oral 300 U Insulin/ 400 mg 4-CNAB | | SC 12 U Short-acting insulin | | Placebo | |
|---|---|---|---|---|---|---|---|---|
| Time (min) | Insulin (pmol/l) | C-Peptide (nmol/l) | Insulin (pmol/l) | C-Peptide (nmol/l) | Insulin (pmol/l) | C-Peptide (nmol/l) | Insulin (pmol/l) | C-Peptide (nmol/l) |
| 20 | 83 | 1.10 | 85 | 0.89 | BLQ | BLQ | 51 | 0.85 |
| 30 | 242 | 1.84 | 221 | 1.43 | 215 | 1.77 | 137 | 1.17 |
| 40 | 330 | 2.10 | 292 | 1.80 | 305 | 1.94 | 129 | 1.25 |
| 50 | 257 | 1.91 | 351 | 2.00 | 383 | 2.10 | 234 | 1.66 |
| 60 | 309 | 2.20 | 329 | 1.93 | 482 | 2.50 | 131 | 1.95 |
| 75 | 312 | 2.40 | 407 | 2.50 | 507 | 2.70 | 296 | 2.40 |
| 90 | 281 | 2.30 | 550 | 2.80 | 384 | 2.30 | 332 | 2.60 |
| 105 | 266 | 2.40 | 398 | 2.80 | 409 | 2.40 | 409 | 3.00 |
| 120 | 356 | 2.70 | 408 | 2.90 | 296 | 1.86 | 361 | 3.00 |
| 150 | 407 | 3.40 | 380 | 3.20 | 221 | 2.00 | 324 | 3.70 |
| 180 | 325 | 3.60 | 384 | 2.80 | 291 | 2.30 | 455 | 4.40 |
| 210 | 275 | 3.20 | 303 | 2.90 | 529 | 2.30 | 244 | 3.00 |
| 240 | 352 | 3.90 | 210 | 2.20 | 197 | 1.95 | 148 | 2.30 |
| 300 | 191 | 3.00 | 73 | 1.42 | 40 | 1.04 | 85 | 1.46 |
| 360 | 93 | 1.92 | 63 | 1.19 | 44 | 0.81 | 64 | 1.06 |

TABLE 34

Patient Number 112

Treatment

| | Oral 150 U Insulin/ 200 mg 4-CNAB | | Oral 300 U Insulin/ 400 mg 4-CNAB | | SC 12 U Short-acting insulin | | Placebo | |
|---|---|---|---|---|---|---|---|---|
| Time (min) | Insulin (pmol/l) | C-Peptide (nmol/l) | Insulin (pmol/l) | C-Peptide (nmol/l) | Insulin (pmol/l) | C-Peptide (nmol/l) | Insulin (pmol/l) | C-Peptide (nmol/l) |
| −60 | 74 | 0.88 | 42 | 0.67 | 37* | 0.64* | 79 | 0.74 |
| −30 | 66 | 0.90 | 47 | 0.70 | 40 | 0.64 | 54 | 0.64 |
| 0 | 63 | 0.89 | 241 | 0.61 | 49 | 0.62 | 52 | 0.69 |
| 10 | 71 | 0.89 | 13* | 0.54* | 57 | 0.67 | 44 | 0.67 |
| 20 | 68 | 0.90 | 38 | 0.55 | 40 | 0.63 | 149 | 0.87 |
| 30 | 76 | 0.94 | 82 | 0.69 | 149 | 0.91 | 246 | 1.22 |
| 40 | 219 | 1.49 | 106 | 0.82 | 216 | 1.05 | 270 | 1.52 |
| 50 | 239* | 1.81* | 100 | 0.85 | 216 | 1.22 | 281 | 1.34 |
| 60 | 293 | 1.99 | 85 | 0.87 | 200 | 1.25 | 304 | 1.71 |
| 75 | 383 | 2.30 | 83 | 0.95 | 201 | 1.33 | 272 | 1.74 |
| 90 | 372 | 2.60 | 96 | 1.21 | 188 | 1.49 | 260 | 1.87 |
| 105 | 407 | 2.80 | 87 | 1.40 | 189 | 1.48 | 298 | 2.00 |
| 120 | 484 | 3.60 | 103 | 1.57 | 176 | 1.47 | 308* | 2.40* |
| 150 | 470 | 4.00 | 142 | 1.95 | 156 | 1.56 | 417* | 3.30* |
| 180 | 402 | 3.70 | 212 | 2.50 | 103 | 1.27 | 370 | 3.00 |
| 210 | 327 | 2.90 | 126 | 2.50 | 62 | 0.99 | 335 | 3.10 |
| 240 | 279 | 3.10 | 189 | 2.90 | 72 | 0.96 | 362 | 3.30 |
| 300 | 91 | 1.96 | 101 | 1.94 | 56 | 0.94 | 132 | 2.20 |
| 360 | 62 | 1.26 | 54 | 1.33 | 25 | 0.63 | 41 | 1.15 |

TABLE 35

Patient Number 113

Treatment

| | Oral 150 U Insulin/ 200 mg 4-CNAB | | Oral 300 U Insulin/ 400 mg 4-CNAB | | SC 12 U Short-acting insulin | | Placebo | |
|---|---|---|---|---|---|---|---|---|
| Time (min) | Insulin (pmol/l) | C-Peptide (nmol/l) | Insulin (pmol/l) | C-Peptide (nmol/l) | Insulin (pmol/l) | C-Peptide (nmol/l) | Insulin (pmol/l) | C-Peptide (nmol/l) |
| −60 | 89 | 1.68 | 56 | 1.20 | 80 | 1.66 | 63 | 1.18 |
| −30 | 79 | 1.60 | 60 | 1.15 | 72 | 1.63 | 37 | 1.12 |
| 0 | 80 | 1.46 | 166 | 1.19 | 82 | 1.72 | 58 | 1.08 |
| 10 | 89 | 1.59 | 62 | 1.21 | 98 | 1.74 | 55 | 1.16 |
| 20 | 95 | 1.62 | 72 | 1.21 | 97 | 1.72 | 63 | 1.16 |

TABLE 35-continued

Patient Number 113

Treatment

| Time (min) | Oral 150 U Insulin/ 200 mg 4-CNAB | | Oral 300 U Insulin/ 400 mg 4-CNAB | | SC 12 U Short-acting insulin | | Placebo | |
|---|---|---|---|---|---|---|---|---|
| | Insulin (pmol/l) | C-Peptide (nmol/l) | Insulin (pmol/l) | C-Peptide (nmol/l) | Insulin (pmol/l) | C-Peptide (nmol/l) | Insulin (pmol/l) | C-Peptide (nmol/l) |
| 30 | 126 | 1.77 | 75 | 1.17 | 135 | 1.87 | 99 | 1.29 |
| 40 | 189 | 1.93 | 179 | 1.40 | 201 | 2.10 | 131 | 1.48 |
| 50 | 157 | 2.00 | 168 | 1.62 | 187 | 2.10 | 146 | 1.64 |
| 60 | 223 | 2.30 | 230 | 1.72 | 216 | 2.30 | 163 | 1.68 |
| 75 | 236 | 2.50 | 197 | 1.95 | 221 | 2.50 | 158 | 1.82 |
| 90 | 199 | 2.40 | 246 | 2.20 | 232 | 2.60 | 200 | 2.20 |
| 105 | 202 | 2.60 | 241 | 2.30 | 91 | 2.60 | 230 | 2.40 |
| 120 | 187 | 2.60 | 241 | 2.50 | 245 | 2.80 | 241 | 2.60 |
| 150 | 197 | 2.80 | 221 | 2.70 | 226 | 3.10 | 400 | 2.80 |
| 180 | 280 | 3.20 | 226 | 3.00 | 179 | 3.20 | 218 | 3.40 |
| 210 | 252 | 3.60 | 222 | 3.20 | 184 | 3.10 | 141 | 3.10 |
| 240 | 193 | 3.60 | 169 | 3.70 | 123 | 2.40 | 161 | 3.10 |
| 300 | 232 | 4.10 | 163 | 3.60 | 106 | 2.20 | 113 | 3.00 |
| 360 | 196 | 3.80 | 148 | 2.70 | 88 | 2.00 | 83 | 2.70 |

TABLE 36

Patient Number 114

Treatment

| Time (min) | Oral 150 U Insulin/ 200 mg 4-CNAB | | Oral 300 U Insulin/ 400 mg 4-CNAB | | SC 12 U Short-acting insulin | | Placebo | |
|---|---|---|---|---|---|---|---|---|
| | Insulin (pmol/l) | C-Peptide (nmol/l) | Insulin (pmol/l) | C-Peptide (nmol/l) | Insulin (pmol/l) | C-Peptide (nmol/l) | Insulin (pmol/l) | C-Peptide (nmol/l) |
| −60 | | | 19 | 0.51 | 20 | 0.55 | 153 | 0.53 |
| −30 | | | BLQ | 0.49 | 16 | 0.58 | 28 | 0.61 |
| 0 | | | BLQ | BLQ | 21 | 0.54 | 103 | 0.59 |
| 10 | | | 63 | 0.39 | 35 | 0.70 | 125 | 1.22 |
| 20 | | | 56 | 0.47 | 95 | 0.85 | 121 | 1.37 |
| 30 | | | 71 | 0.59 | 148 | 1.09 | 128 | 1.42 |
| 40 | | | 99 | 0.76 | 222 | 1.24 | 121 | 1.54 |
| 50 | | | 117 | 0.88 | 240 | 1.69 | 154 | 1.52 |
| 60 | | | 115 | 1.09 | 257 | 1.72 | 218 | 2.20 |
| 75 | | | 152 | 1.43 | 250 | 1.88 | BLQ* | 2.10* |
| 90 | | | 113 | 1.70 | 191 | 1.82 | 246 | 2.40 |
| 105 | | | 107 | 1.63 | 126 | 1.66 | 172 | 2.50 |
| 120 | | | 181 | 2.20 | 125 | 1.70 | 209 | 2.60 |
| 150 | | | 154 | 2.20 | 105 | 1.56 | 224 | 2.80 |
| 180 | | | 119 | 2.10 | 70 | 1.40 | 48* | 2.40* |
| 210 | | | 71 | 1.89 | 23 | 0.80 | 48 | 1.94 |
| 240 | | | 45 | 1.44 | BLQ | 0.51 | 26 | 1.35 |
| 300 | | | 23 | 0.84 | BLQ | 0.30 | 17 | 0.83 |
| 360 | | | 15 | 0.64* | BLQ | 0.25 | BLQ* | 0.62* |

TABLE 37

Patient Number 115

Treatment

| Time (min) | Oral 150 U Insulin/ 200 mg 4-CNAB | | Oral 300 U Insulin/ 400 mg 4-CNAB | | SC 12 U Short-acting insulin | | Placebo | |
|---|---|---|---|---|---|---|---|---|
| | Insulin (pmol/l) | C-Peptide (nmol/l) | Insulin (pmol/l) | C-Peptide (nmol/l) | Insulin (pmol/l) | C-Peptide (nmol/l) | Insulin (pmol/l) | C-Peptide (nmol/l) |
| −60 | | | 31 | 0.66 | 47 | 0.72 | 42 | 0.67 |
| −30 | | | 31 | 0.67 | 27 | 0.75 | 38 | 0.74 |
| 0 | | | 199 | 0.70 | 41 | 0.75 | 37 | 0.75 |
| 10 | | | 71 | 0.67 | 24 | 0.83 | 45 | 0.80 |
| 20 | | | 47 | 0.65 | 140 | 0.76 | 43 | 0.71 |
| 30 | | | 62 | 0.81 | 113 | 0.93 | 81 | 0.87 |

TABLE 37-continued

Patient Number 115

| | Treatment | | | | | | | |
|---|---|---|---|---|---|---|---|---|
| | Oral 150 U Insulin/ 200 mg 4-CNAB | | Oral 300 U Insulin/ 400 mg 4-CNAB | | SC 12 U Short-acting insulin | | Placebo | |
| Time (min) | Insulin (pmol/l) | C-Peptide (nmol/l) | Insulin (pmol/l) | C-Peptide (nmol/l) | Insulin (pmol/l) | C-Peptide (nmol/l) | Insulin (pmol/l) | C-Peptide (nmol/l) |
| 40 | | | 66 | 0.86 | 470 | 1.02 | 102 | 1.17 |
| 50 | | | 61 | 0.84 | 75 | 1.01 | 95 | 1.20 |
| 60 | | | 58 | 0.87 | 164 | 1.11 | 82 | 1.19 |
| 75 | | | 67 | 0.97 | 159 | 1.15 | 97 | 1.43 |
| 90 | | | 67 | 1.07 | 266 | 1.35 | 107 | 1.81 |
| 105 | | | 65 | 1.03 | 89 | 1.49 | 101 | 1.83 |
| 120 | | | 77 | 1.17 | 112 | 1.59 | 89 | 1.74 |
| 150 | | | 69 | 1.32 | 84 | 1.64 | 86 | 2.20 |
| 180 | | | 87 | 1.51 | 82 | 1.34 | 103 | 2.40 |
| 210 | | | 87 | 1.56 | 64 | 1.51 | 108 | 2.50 |
| 240 | | | 99 | 1.83 | 76 | 1.24 | 82 | 1.82 |
| 300 | | | 65 | 1.62 | 24 | 0.74 | 52 | 1.52 |
| 360 | | | 68 | 1.58 | 45 | 0.56 | 36* | 1.42* |

TABLE 38

Patient Number 116

| | Treatment | | | | | | | |
|---|---|---|---|---|---|---|---|---|
| | Oral 150 U Insulin/ 200 mg 4-CNAB | | Oral 300 U Insulin/ 400 mg 4-CNAB | | SC 12 U Short-acting insulin | | Placebo | |
| Time (min) | Insulin (pmol/l) | C-Peptide (nmol/l) | Insulin (pmol/l) | C-Peptide (nmol/l) | Insulin (pmol/l) | C-Peptide (nmol/l) | Insulin (pmol/l) | C-Peptide (nmol/l) |
| −60 | 36 | 0.66 | 30 | 0.49 | 41 | 0.55 | 31 | 0.48 |
| −30 | 39 | 0.65 | 27 | 0.49 | 34 | 0.58 | 27 | 0.48 |
| 0 | 45 | 0.68 | 538 | 0.34 | 30 | 0.53 | 26 | 0.46 |
| 10 | 54 | 0.62 | 66 | 0.26 | 46 | 0.64 | 19 | 0.52* |
| 20 | 45 | 0.67 | 52 | 0.31 | 88 | 0.69 | BLQ | BLQ |
| 30 | 122 | 0.93 | 96 | 0.52 | 161 | 1.05 | BLQ | BLQ |
| 40 | 206 | 1.26 | 115 | 0.70 | 245 | 1.52 | 129 | 0.94 |
| 50 | 249 | 1.76 | 137 | 0.86 | 271 | 1.68 | 247 | 1.40 |
| 60 | 310 | 2.00 | 161 | 1.21 | 342 | 2.10 | 287 | 1.78 |
| 75 | 473 | 2.90 | 219 | 1.55 | 366 | 2.30 | 358 | 2.80 |
| 90 | 602 | 3.70 | 206 | 1.86 | 388 | 2.80 | 410 | 2.80 |
| 105 | 643 | 4.60 | 270 | 2.30 | 418 | 2.70 | 403 | 4.20 |
| 120 | 746 | 4.20 | 291 | 2.70 | 409 | 2.80 | 423 | 5.50 |
| 150 | 632 | 4.30 | 357 | 3.10 | 343 | 2.80 | 441 | 4.10 |
| 180 | 386 | 3.50 | 162 | 2.50 | 122 | 1.74 | 315 | 3.20 |
| 210 | 140 | 2.20 | 111 | 1.61 | 42 | 0.97 | 70 | 1.89 |
| 240 | 76 | 1.51 | 39 | 0.90 | 50 | 0.89 | 42 | 1.26 |
| 300 | 46 | 0.97 | 37 | 0.72 | 24 | 0.56 | 38 | 0.81 |
| 360 | 36 | 0.72 | 25 | 0.51 | 23 | 0.41 | 34 | 0.62 |

TABLE 39

Patient Number 117

| | Treatment | | | | | | | |
|---|---|---|---|---|---|---|---|---|
| | Oral 150 U Insulin/ 200 mg 4-CNAB | | Oral 300 U Insulin/ 400 mg 4-CNAB | | SC 12 U Short-acting insulin | | Placebo | |
| Time (min) | Insulin (pmol/l) | C-Peptide (nmol/l) | Insulin (pmol/l) | C-Peptide (nmol/l) | Insulin (pmol/l) | C-Peptide (nmol/l) | Insulin (pmol/l) | C-Peptide (nmol/l) |
| −60 | | | 41 | 0.81 | 37 | 0.90 | 46 | 1.19 |
| −30 | | | 45 | 0.90 | 30 | 0.89 | 80 | 1.17 |
| 0 | | | 559 | 0.79 | 45 | 0.90 | 45 | 1.06 |
| 10 | | | 188 | 0.81 | 65 | 0.86 | 61 | 1.14 |
| 20 | | | 81 | 0.85 | 67 | 0.80 | 56 | 1.10 |
| 30 | | | 85 | 0.91 | 97 | 1.03 | 104 | 1.29 |
| 40 | | | 101 | 0.97 | 127 | 1.15 | 100 | 1.30 |

TABLE 39-continued

Patient Number 117

Treatment

| Time (min) | Oral 150 U Insulin/ 200 mg 4-CNAB | | Oral 300 U Insulin/ 400 mg 4-CNAB | | SC 12 U Short-acting insulin | | Placebo | |
|---|---|---|---|---|---|---|---|---|
| | Insulin (pmol/l) | C-Peptide (nmol/l) | Insulin (pmol/l) | C-Peptide (nmol/l) | Insulin (pmol/l) | C-Peptide (nmol/l) | Insulin (pmol/l) | C-Peptide (nmol/l) |
| 50 | | | 74 | 0.99 | 134 | 1.01 | 107 | 1.43 |
| 60 | | | 113 | 1.17 | 112 | 1.34 | 127 | 1.48 |
| 75 | | | 102 | 1.27 | 131 | 1.38 | 117 | 1.51 |
| 90 | | | 94 | 1.46 | 161 | 1.30 | 186 | 1.91 |
| 105 | | | 93 | 1.67 | 112 | 1.47 | 142 | 2.10 |
| 120 | | | 88 | 1.73 | 71 | 1.39 | 134 | 2.20 |
| 150 | | | 101 | 1.96 | 106 | 1.55 | 165 | 2.60 |
| 180 | | | 74 | 1.73 | 48 | 1.01 | 155 | 2.60 |
| 210 | | | 112 | 2.10 | 44 | 0.97 | 173 | 2.40 |
| 240 | | | 90 | 2.10 | 55 | 0.92 | 155 | 2.20 |
| 300 | | | 106 | 2.20 | 41 | 0.97 | 124 | 1.99 |
| 360 | | | 59 | 1.70 | 46 | 0.92 | 73 | 1.61 |

TABLE 40

Patient Number 118

Treatment

| Time (min) | Oral 150 U Insulin/ 200 mg 4-CNAB | | Oral 300 U Insulin/ 400 mg 4-CNAB | | SC 12 U Short-acting insulin | | Placebo | |
|---|---|---|---|---|---|---|---|---|
| | Insulin (pmol/l) | C-Peptide (nmol/l) | Insulin (pmol/l) | C-Peptide (nmol/l) | Insulin (pmol/l) | C-Peptide (nmol/l) | Insulin (pmol/l) | C-Peptide (nmol/l) |
| −60 | | | | | 23 | 0.53 | | |
| −30 | | | | | 29 | 0.47 | | |
| 0 | | | | | 32* | 0.58* | | |
| 10 | | | | | 41 | 0.64 | | |
| 20 | | | | | 45 | 0.65 | | |
| 30 | | | | | 40 | 0.77 | | |
| 40 | | | | | BLQ* | 0.82* | | |
| 50 | | | | | 67 | 0.90 | | |
| 60 | | | | | 72 | 0.82 | | |
| 75 | | | | | 66 | 0.96 | | |
| 90 | | | | | 65 | 0.94 | | |
| 105 | | | | | 52 | 0.96 | | |
| 120 | | | | | 43 | 0.92 | | |
| 150 | | | | | 68 | 0.92 | | |
| 180 | | | | | 64 | 0.75 | | |
| 210 | | | | | 56 | 0.82 | | |
| 240 | | | | | 57 | 0.66 | | |
| 300 | | | | | 46 | 0.59 | | |
| 360 | | | | | 46 | 0.55 | | |

*denotes samples that were hemolyzed

Table 41 below presents the mean time data (with standard deviation) of the plasma 4-CNAB concentrations for the two treatments involving 4-CNAB.

TABLE 41

Statistics on 4-CNAB Concentration (ng/mL) vs. Time

Treatment

| | Oral 150 U Insulin/200 mg 4-CNAB | | Oral 300 U Insulin/400 mg 4-CNAB | |
|---|---|---|---|---|
| Time | Mean | STD | Mean | STD |
| 10 min | 5031.01 | 1979.06 | 11005.11 | 4611.76 |
| 20 min | 3449.44 | 1612.48 | 7216.69 | 1858.48 |
| 30 min | 2528.54 | 986.25 | 5077.03 | 1401.94 |
| 40 min | 1587.28 | 561.28 | 3576.83 | 1001.72 |
| 60 min | 1198.71 | 858.55 | 2310.03 | 787.86 |
| 90 min | 604.81 | 395.73 | 1389.54 | 406.35 |
| 120 min | 348.73 | 178.14 | 963.92 | 273.23 |
| 240 min | 126.13 | 50.55 | 385.42 | 169.62 |
| 360 min | 111.86 | 44.91 | 281.18 | 151.58 |

Figure 2:
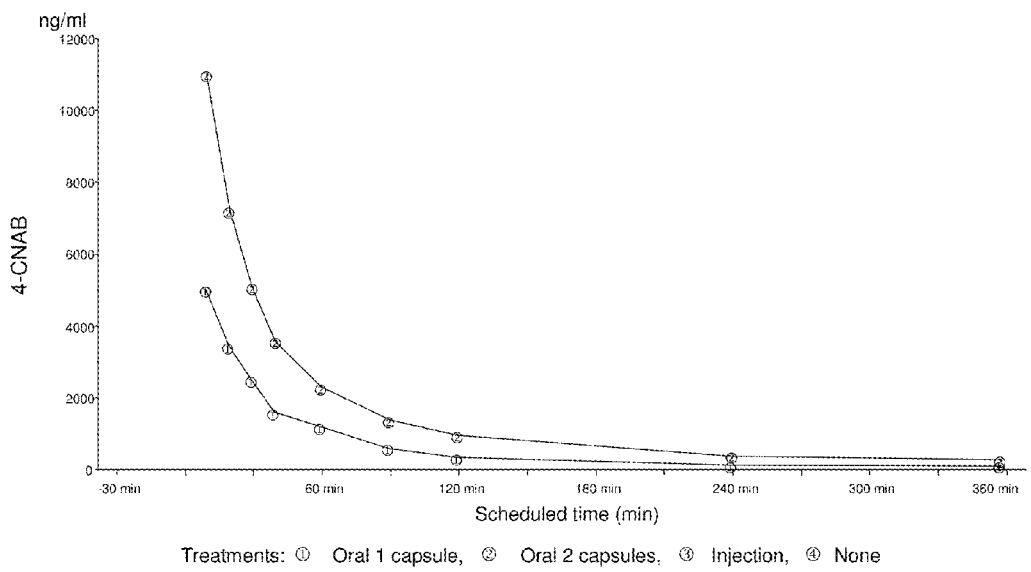
FIG. 2 shows a plot of 4-CNAB plasma concentrations (ng/mL) vs. time (arithmetic means).

FIG. 2 shows profiles of 4-CNAB plasma concentrations (ng/mL) vs. time (arithmetic means) for the two treatments involving 4-CNAB. As seen in FIG. 2, plasma 4-CNAB concentrations show a rapid decline within the first two hours after start of meal intake. After 2 hours, concentrations are less than 10% of the levels seen after 10 minutes. The results indicate that markedly higher concentrations might have been reached in the time between intake of the Insulin/4-CNAB capsules and the first measurement 10 minutes after start of meal intake. Concentrations after intake of 400 mg 4-CNAB are approximately twice as high as after intake of 200 mg.

Table 42 below presents the mean time data (with standard deviation) of the plasma insulin concentrations per treatment.

TABLE 42

Statistics on Insulin Concentration (pmol/L) vs. Time Profiles

| | Treatment | | | | | | | |
|---|---|---|---|---|---|---|---|---|
| | Oral 150 U Insulin/200 mg 4-CNAB | | Oral 300 U Insulin/400 mg 4-CNAB | | SC 12 U Short-acting insulin | | Placebo | |
| Time | Mean | STD | Mean | STD | Mean | STD | Mean | STD |
| −60 min | 67.67 | 35.07 | 44.25 | 17.21 | 53.67 | 35.86 | 58.53 | 37.49 |
| −30 min | 62.33 | 28.59 | 41.09 | 17.39 | 44.76 | 26.55 | 43.35 | 24.18 |
| 0 min | 88.83 | 74.69 | 389.58 | 476.10 | 58.17 | 38.02 | 53.76 | 27.05 |
| 10 min | 95.50 | 66.76 | 153.46 | 227.65 | 67.61 | 33.18 | 71.06 | 36.99 |
| 20 min | 124.83 | 92.52 | 94.69 | 84.76 | 103.88 | 66.49 | 124.81 | 107.93 |
| 30 min | 201.42 | 152.72 | 126.00 | 82.65 | 162.33 | 102.91 | 188.50 | 150.82 |
| 40 min | 222.50 | 112.69 | 161.08 | 85.98 | 236.82 | 113.90 | 205.82 | 143.56 |
| 50 min | 257.50 | 120.42 | 158.69 | 96.27 | 204.39 | 97.98 | 229.06 | 126.39 |
| 60 min | 273.92 | 136.46 | 157.62 | 82.77 | 238.06 | 131.97 | 235.65 | 114.90 |
| 75 min | 342.83 | 139.45 | 167.31 | 96.64 | 278.06 | 134.82 | 278.63 | 147.21 |
| 90 min | 347.25 | 160.66 | 202.62 | 131.93 | 271.18 | 139.21 | 312.47 | 132.36 |
| 105 min | 386.50 | 199.81 | 183.00 | 135.58 | 249.00 | 141.18 | 298.35 | 161.63 |
| 120 min | 392.83 | 192.71 | 210.23 | 113.84 | 219.56 | 133.35 | 336.76 | 179.17 |
| 150 min | 403.83 | 230.87 | 191.15 | 116.15 | 195.78 | 124.00 | 297.47 | 141.51 |
| 180 min | 330.25 | 145.58 | 183.85 | 90.79 | 133.28 | 83.95 | 235.35 | 125.05 |
| 210 min | 259.92 | 156.54 | 157.38 | 84.46 | 124.00 | 133.24 | 172.29 | 83.22 |
| 240 min | 214.17 | 124.78 | 129.00 | 63.79 | 81.94 | 56.35 | 137.94 | 86.82 |
| 300 min | 140.83 | 104.91 | 79.38 | 46.06 | 50.63 | 30.36 | 79.00 | 49.57 |
| 360 min | 84.25 | 65.03 | 60.23 | 40.69 | 45.33 | 22.59 | 53.13 | 26.81 |

Figure 5:
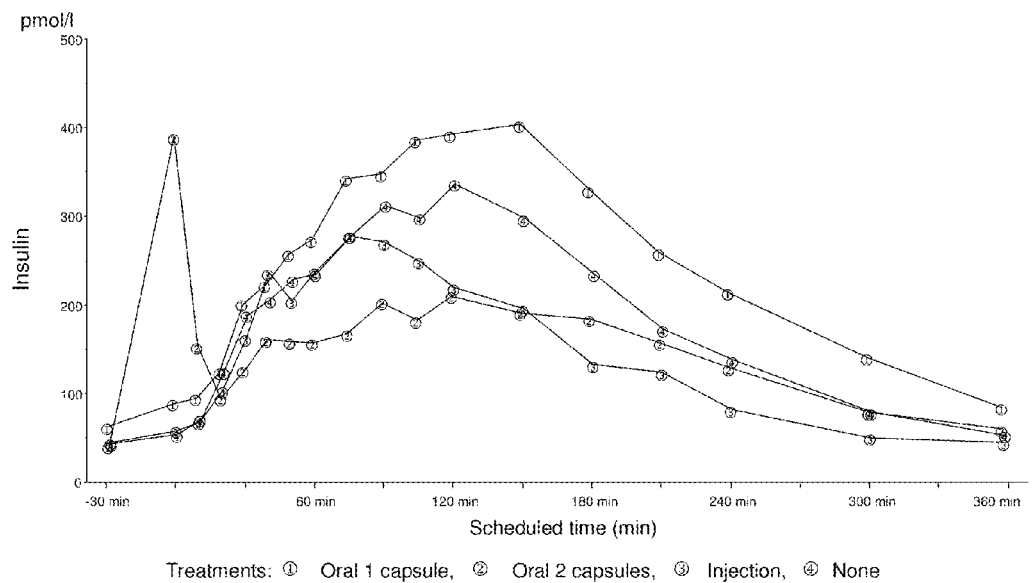
FIG. 5 shows a plot of insulin plasma concentrations (pmol/l) vs. time (arithmetic means).

FIG. 5 shows profiles of insulin plasma concentrations (pmol/l) vs. time (arithmetic means). As shown in FIG. 5 and in Table B above, highest mean insulin plasma concentrations are reached after the 150 U oral dose, followed by 300 U oral, placebo, and 12 U SC injection. The curve of oral 300 U Insulin/400 mg 4-CNAB shows two maxima, the first at 0 min and the second at 120 min. The peak at 0 min is due to one particular patient who contributed with a value of 1803 pmol/L the most to this marked shift of mean insulin concentration. Almost all patients showed a more or less marked isolated increase of insulin concentrations at time 0 but not to such an extent as that patient. In addition, the rise of insulin concentrations under placebo is explained by the patients' endogenous insulin production, induced by the meal intake.

Figure 7:
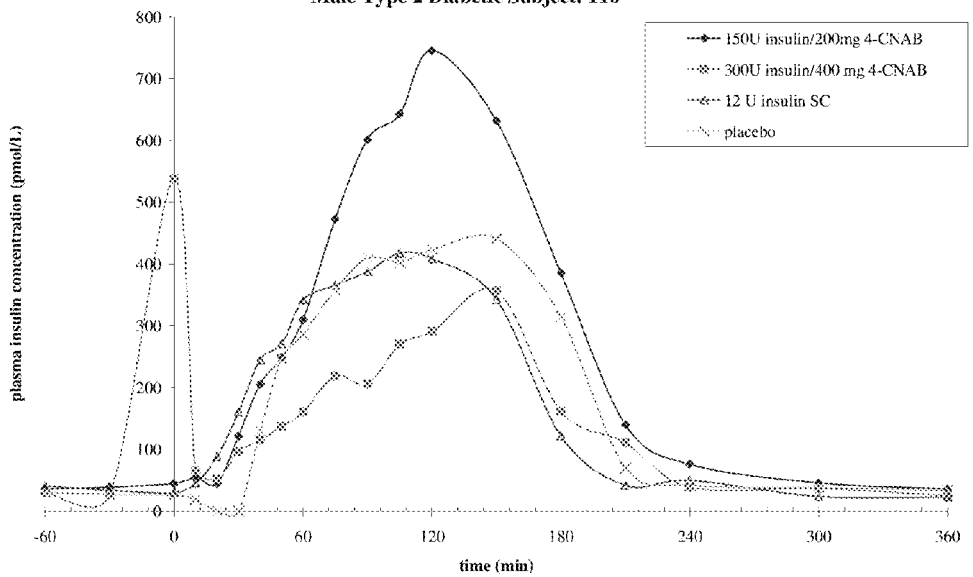
FIG. 7 shows a plot of insulin plasma concentration (pmol/l) vs. time for Type 2 Diabetic subject no. 116 after oral or subcutaneous administration of insulin or insulin/4-CNAB 30 minutes prior to a standard meal (meal at time=0).
Figure 8:
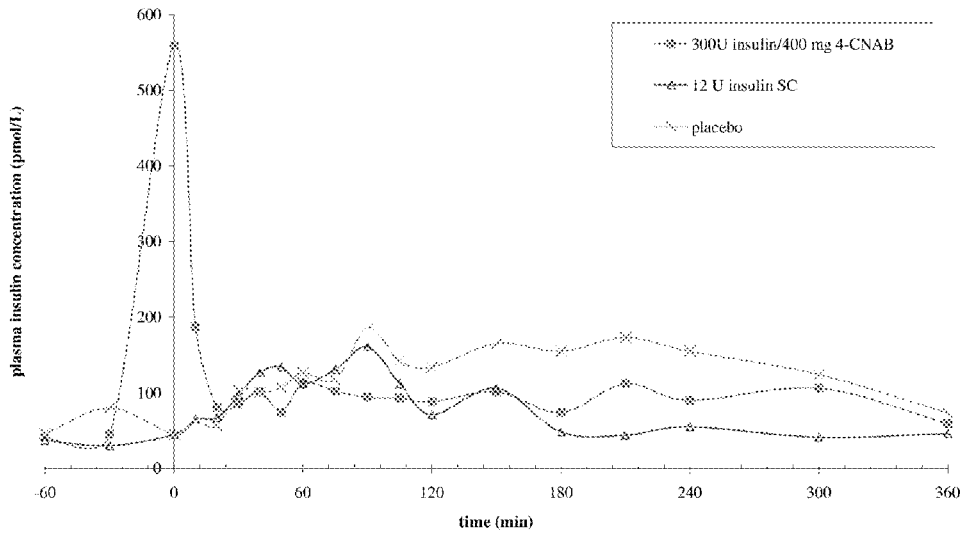
FIG. 8 shows a plot of insulin plasma concentration (pmol/l) vs. time for Type 2 Diabetic subject no. 117 after oral or subcutaneous administration of insulin or insulin/4-CNAB 30 minutes prior to a standard meal (meal at time=0).

FIGS. 7 and 8 show the insulin plasma concentration vs. time curves for subjects 116 and 117, respectively. For subject 116, who was an early stage Type II diabetic who produced his own insulin, the insulin plasma concentration vs. time curve shown in FIG. 7 mimicked that of healthy (normal) non-diabetic humans, i.e., it had the same biphasic secretion time curve shape, although the insulin peaks occurred slightly earlier than normal. For subject 117, who was an advanced stage Type II diabetic who produced very little endogenous insulin, the insulin plasma concentration vs. time curve shown in FIG. 8 shows levels of insulin after the initial peak that are lower that those for normal, non-diabetic humans and shows that no second peak of plasma insulin concentration occurred. This is an indication that this subject would also need to be administered basal long lasting insulin in order to maintain normal insulin plasma concentration and blood glucose levels.

Table 43 below presents the mean time data (with standard deviation) of the plasma C-peptide concentrations per treatment.

TABLE 43

Statistics on C-peptide Concentration (nmol/L) vs. Time

| | Treatment | | | | | | | |
|---|---|---|---|---|---|---|---|---|
| | Oral 150 U Insulin/200 mg 4-CNAB | | Oral 300 U Insulin/400 mg 4-CNAB | | SC 12 U Short-acting Insulin | | Placebo | |
| Time | Mean | STD | Mean | STD | Mean | STD | Mean | STD |
| −60 min | 0.96 | 0.38 | 0.76 | 0.26 | 0.82 | 0.35 | 0.80 | 0.24 |
| −30 min | 0.94 | 0.33 | 0.78 | 0.29 | 0.79 | 0.31 | 0.77 | 0.22 |
| 0 min | 0.92 | 0.29 | 0.76 | 0.27 | 0.83 | 0.33 | 0.78 | 0.20 |
| 10 min | 1.02 | 0.30 | 0.76 | 0.31 | 0.91 | 0.33 | 0.91 | 0.22 |
| 20 min | 1.18 | 0.41 | 0.79 | 0.29 | 0.97 | 0.34 | 1.09 | 0.38 |
| 30 min | 1.44 | 0.50 | 0.93 | 0.36 | 1.25 | 0.48 | 1.34 | 0.44 |
| 40 min | 1.59 | 0.45 | 1.15 | 0.48 | 1.43 | 0.62 | 1.47 | 0.38 |

TABLE 43-continued

Statistics on C-peptide Concentration (nmol/L) vs. Time

| | Treatment | | | | | | | |
|---|---|---|---|---|---|---|---|---|
| | Oral 150 U Insulin/200 mg 4-CNAB | | Oral 300 U Insulin/400 mg 4-CNAB | | SC 12 U Short-acting Insulin | | Placebo | |
| Time | Mean | STD | Mean | STD | Mean | STD | Mean | STD |
| 50 min | 1.82 | 0.39 | 1.22 | 0.49 | 1.48 | 0.51 | 1.63 | 0.44 |
| 60 min | 2.03 | 0.43 | 1.31 | 0.42 | 1.59 | 0.57 | 1.84 | 0.46 |
| 75 min | 2.38 | 0.57 | 1.52 | 0.54 | 1.82 | 0.76 | 2.11 | 0.51 |
| 90 min | 2.62 | 0.78 | 1.74 | 0.57 | 1.90 | 0.83 | 2.31 | 0.35 |
| 105 min | 2.92 | 0.91 | 1.84 | 0.60 | 1.93 | 0.72 | 2.57 | 0.59 |
| 120 min | 3.08 | 0.89 | 2.05 | 0.59 | 1.83 | 0.68 | 2.83 | 0.83 |
| 150 min | 3.31 | 1.03 | 2.20 | 0.58 | 2.00 | 0.98 | 2.77 | 0.63 |
| 180 min | 3.27 | 0.95 | 2.20 | 0.54 | 1.72 | 0.85 | 2.71 | 0.68 |
| 210 min | 2.84 | 0.82 | 2.26 | 0.64 | 1.47 | 0.74 | 2.45 | 0.48 |
| 240 min | 2.64 | 0.95 | 2.08 | 0.74 | 1.21 | 0.60 | 2.14 | 0.63 |
| 300 min | 2.08 | 0.92 | 1.58 | 0.80 | 0.94 | 0.51 | 1.50 | 0.59 |
| 360 min | 1.52 | 0.86 | 1.25 | 0.65 | 0.74 | 0.40 | 1.15 | 0.55 |

Figure 6:
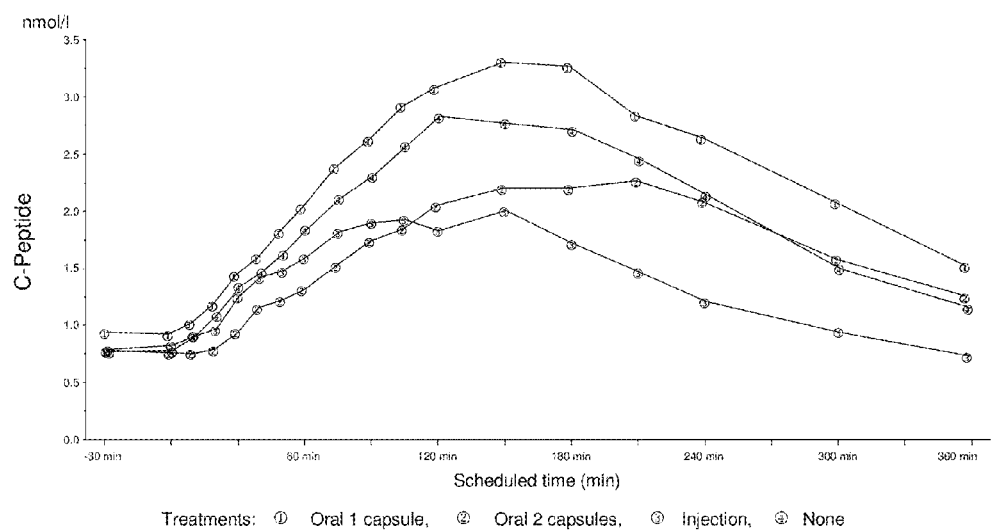
FIG. 6 shows a plot of C-peptide plasma concentrations (nmol/l) vs. time (arithmetic means).

FIG. 6 shows profiles of C-peptide plasma concentrations (nmol/l) vs. time (arithmetic means). Mean plasma concentrations of C-peptide, the indicator of endogenous insulin production, increased after all treatments. Decreasing, or more or less constant C-peptide concentrations, were seen only in a few patients and only after SC injection of short-acting insulin. This may reflect the fact that in most of the patients the ability to produce endogenous insulin was still maintained. As expected, the 150 U oral insulin dose and placebo show the most marked increase, whereas the increases after the 300 U oral dose and the 12 U SC injection are clearly lower.

Based on the insulin concentration vs. time profiles, the parameters $C_{max}$, $t_{max}$ and AUC from time 0 to the time when the baseline insulin level was reached again ($AUC_{0-t}*$) were calculated, as presented in Table 44 below.

TABLE 44

| Treatment | $AUC_{0-t}*$ (h*pmol/L) | | $C_{max}$ (pmol/L) | | $t_{max}$ (h) | | |
|---|---|---|---|---|---|---|---|
| | Mean | STD | Mean | STD | Median | MIN | MAX |
| Oral 150 U Insulin/ 200 mg 4-CNAB | 1469.42 | 684.92 | 461.50 | 219.29 | 2.00 | 0.50 | 3.00 |
| Oral 300 U Insulin/ 400 mg 4-CNAB | 866.45 | 372.85 | 439.23 | 437.80 | 1.50 | 0.00 | 3.50 |
| SC 12 U Short-acting insulin | 791.52 | 417.95 | 315.83 | 155.09 | 1.38 | 0.50 | 3.50 |
| Placebo | 1093.47 | 466.46 | 388.53 | 185.82 | 2.00 | 0.50 | 3.50 | t* denotes time when baseline insulin level is reached again, or last data point (360 min)

This data indicates that mean insulin plasma concentration vs. time profiles showed the highest AUC after 150 U oral insulin, followed by placebo, 300 U oral insulin, and 12 U SC injection. Highest mean $C_{max}$ was reached after 150 U oral insulin, followed by 300 U oral insulin, placebo, and 12 U SC injection. The median time until $C_{max}$ ($t_{max}$) was longest for 150 U oral insulin and placebo, followed by 300 U oral insulin and 12 U SC injection.

Conclusions

The primary objective of this study was to compare the effect of orally administered 300 U Insulin/400 mg 4-CNAB with that of 12 U subcutaneously injected short-acting insulin (Humalog®) on postprandial blood glucose excursions after a standardized breakfast. With respect to $AUC_{0-2h}$ as main parameter for pharmacodynamic evaluation, the highest effect on blood glucose excursions was found for 12 U SC short-acting insulin, followed by oral 300 U Insulin/400 mg 4-CNAB, oral 150 U Insulin/200 mg 4-CNAB and placebo, and the effects of the two latter appeared more or less equal. However, these results were not consistent for all calculated AUCs. During the first hour, 300 U oral insulin were superior to 12 U SC, and this order changed when the AUCs for more than 2 hours were compared: both oral treatments were no longer significantly different from no treatment (placebo), but the 12 U SC injection showed still a significant difference and clearly smaller AUCs.

After the 300 U oral insulin dose, mean blood glucose excursions turned (until −20.8 mg/dL at 15 minutes after start of meal intake) and returned to baseline at 30 minutes. This transient decline could be seen in most of the patients, but only in one particular with a baseline blood glucose below 80 mg/dL did it lead to a hypoglycemic episode. These findings may indicate a rapid onset of action of orally administered 300 U Insulin/400 mg 4-CNAB prior to considerable absorption of carbohydrates from the test meal. Therefore, a time span of 30 minutes between dose administration and start of meal intake might be too long.

Mean fasting blood glucose values at baseline (−1 minute) which served as reference for the calculation of excursions, were 124.38 mg/dL (99.10-172.00) for oral 150 U Insulin/ 200 mg 4-CNAB, 120.26 mg/dL (72.20-175.00) for oral 300 U Insulin/400 mg 4-CNAB, 143.11 mg/dL (104.00-190.00) for 12 U SC short-acting insulin, and 137.32 mg/dL (93.10-183.00) for placebo. With regard to these baseline values, the four treatments were split into two groups: the two oral treatments with values around 120 mg/dL, and the SC injection together with placebo showing values around 140 mg/dL. This finding may be explained by early action of the oral insulin formulations in the time between dose administration and start of meal intake, which is not covered by the profiles. However, the described non-homogeneity is not considered to impair the quality of the results.

The concentration vs. time profiles for 4-CNAB display only the elimination of the substance from plasma. The absorption phase and the maximum concentrations are missed. In the time between −30 and +10 minutes, a rapid rise followed by a rapid decline can be assumed, and the achieved maximum concentrations should be markedly higher than the values seen at 10 minutes after start of meal intake. Therefore, further investigations of 4-CNAB pharmacokinetics should include an appropriate number of samples from the first hour following dose administration.

The insulin profiles showed the highest AUC after 150 U oral insulin, followed by placebo, 300 U oral insulin, and 12 U SC short-acting insulin. The marked increase of mean plasma insulin concentrations after placebo indicates that the patients' ability of endogenous insulin production, induced by meal intake, was still maintained. Also the high AUC for 150 U oral insulin probably reflects mainly endogenous insulin production, and also the curves of the other treatments may account for a certain amount of endogenous insulin.

The C-peptide plasma concentration profiles confirm this view and also indicate the release of considerable amounts of endogenous insulin. The levels were highest after 150 U oral insulin, followed by placebo, 300 U oral insulin, and 12 U SC short-acting insulin. As expected, the 150 U oral dose and placebo led to the most marked increase, whereas the increase after the 300 U oral dose and the 12 U SC injection was clearly lower, and these findings correlate with the blood glucose lowering effect seen for the different treatments: the lower the effect of the external insulin dose, the higher were the amounts of C-peptide as indicator of endogenous insulin production.

The insulin concentration vs. time profiles seen for both oral doses in this study are considerably different from those obtained in Example 6 of International Publication No. WO 03057170, where mean insulin concentrations were back to baseline after approximately two hours and where maximum concentrations occurred after about half an hour. These differences might be due to the influence of the meal, stimulating endogenous insulin release and also possibly interfering with the resorption of the oral insulin preparations. In Example 6 of WO 03057170, patients fasted during the entire experiment, and endogenous insulin production was suppressed by a constant low-dose insulin infusion. Therefore, the concentration vs. time curves of Example 6 of WO 03057170 represent more the pure pharmacokinetics of the administered exogenous insulin, whereas in the present study the effects of exogenous and endogenous insulin are overlapping.

No adverse events were reported in this study. There were no treatment related findings of clinical laboratory safety parameters, vital signs, ECG or physical examination. The five hypoglycemic episodes that occurred in four patients remained symptomless due to immediate intervention with intravenous glucose infusion. Only one of the episodes was due to oral 300 U Insulin/400 mg 4-CNAB, and the majority (⅘) occurred after 12 U SC short-acting insulin injection. Accordingly, all study treatments were well tolerated.

Overall, the study results suggest (based on the primary endpoint $AUC_{0-2h}$) that orally administered 300 U Insulin/400 mg 4-CNAB are effective in lowering the postprandial rise of blood glucose in type 2 diabetic patients. However, the effect is smaller than after injection of 12 U SC short-acting insulin, which is significantly superior to both oral administrations. The oral dose of 150 U Insulin/200 mg 4-CNAB is similar effective as no treatment (placebo). At both doses, orally administered Insulin/4-CNAB seems to be well tolerated.

Example 2

In this example, as also set forth in International Patent Application No. PCT/US04/00273, oral insulin capsule(s) described herein were orally administered to twenty human subjects with diabetes at night before going to sleep.

An open-label, single-dose, crossover study was conducted in order to compare the safety of orally administered 4-CNAB/Insulin formulation with that of subcutaneously injected insulin in two groups of subjects with type 2 diabetes mellitus—one in the fasting state and one after a standard meal. The objectives were (1) to compare the safety, pharmacokinetics and pharmacodynamics of orally administered 4-CNAB/insulin with that of subcutaneously injected regular insulin in fasting type 2 diabetic subjects, and (2) to compare blood glucose, insulin and C-peptide levels after a standard meal with regular medication with blood glucose, insulin and C-peptide levels after a standard meal with 4-CNAB/insulin.

The focus of this study is the assessment of the safety of insulin/4-CNAB, administered orally at bedtime, to type 2 diabetic subjects. The purpose of the study was to determine if the administration of oral insulin at bedtime could exert effects on overnight-fasting glucose homeostatsis and insulin secretion. The postulated mode of action (e.g., suppressing the liver production of glucose, and thus preventing β-cell death or dysfunction of insulin producing) was the basis for the design of the study.

Twenty-four human subjects (patients) of age 35-70 years with elevated fasting blood glucose levels (type 2 diabetes), but in otherwise good general health on the basis of a medical history, physical examination, clinical laboratory studies, participated in the study and were studied in the overnight-fasted state on two occasions, separated by an interval of at least 7 days. The following treatment conditions were studied:

Group 1: twelve (12) type 2 diabetic subjects: (a) oral insulin/4-CNAB—fasted subjects, and (b) empty capsule—fasted subjects.

Group 2: twelve (12) type 2 diabetic subjects: (a) standard meal with regular medication, and (b) standard meal with oral human insulin/4-CNAB.

A total of twenty subjects participated in the second part of the study, relating to the safety of insulin/4-CNAB administered orally at bedtime, an additional four subjects not being included due to logistical considerations. These twenty subjects took an oral insulin capsule(s) at night before going to sleep. The trial took place at the home of the subject under the supervision of a bedside private duty nurse. The rationale to conduct the trial at the patient own environment was based on the fact that glucose homeostasis is best reflected when conducted in a familiar environment and changes significantly with hospitalization.

Fasting blood glucose, insulin and C-peptide levels were measured at 7:00 a.m. for three days to establish baseline levels. On two successive nights and mornings before taking the capsule, the subjects measured their glucose levels with a glucometer (supplied). If the subject's glucose levels were >120 mg/dL on the first two mornings (fasting), on the $3^{rd}$ night, the subject took the insulin capsule(s). If, on the first two successive mornings, the patient's fasting blood glucose was not greater than 120 mg/dL, then the patient was dismissed from the study and all final study procedures were performed as per the protocol. The subjects ate their regular dinner at home, as every evening, between the hours of 7:00 and 8:00 P.M. If the subjects usually took medication for the diabetes (metformin or acarbose) in the evening, they took their usual dose.

At 11:00 p.m. (at least two hours after dinner), the subjects took one oral insulin dose that contained the following ingredients: 300 mg 4-CNAB and insulin according to the dose (200-400 U) that the subject received during the first phase of the trial. If the subject had received 200 U insulin in the first phase of the trail and there was no drop in blood glucose level (<15% reduction), he now received 300 U of insulin. If the subject had received 300 U insulin in the first phase of the trail and there was no drop in blood glucose level (<15% reduction), he now received 400 U of insulin. None of the subjects received more than 400 U of insulin. The capsules were prepared by AAI and have shown stability.

A nurse was present at the home of the subjects when they took the oral insulin capsules and throughout the night. The nurse checked the blood glucose level with a glucometer before the subjects took the medication. In addition, blood was taken for further blood glucose levels, insulin and C-peptide. Orange juice was readily available for treatment in the unlikely event of hypoglycemia. During sleep the subjects wore a Glucowatch (which is a monitor of blood glucose and measures and records blood glucose levels at regular intervals). The Glucowatch is equipped with an alarm triggered when blood glucose levels reach predetermined blood glucose levels (hypoglycemic levels) determined by the investigator or patient. The bedside private duty nurse was also present during the night to monitor the patient. In the morning, when the subjects woke up (e.g., at 7:00 a.m.), the nurse checked their blood glucose level with the glucometer. Additional blood samples were taken for further blood glucose levels, insulin and C-peptide. The blood samples from the night before were stored in the refrigerator at home and in the morning the nurse brought the samples of blood (from the night and the morning) to the lab for analysis.

Figure 10:
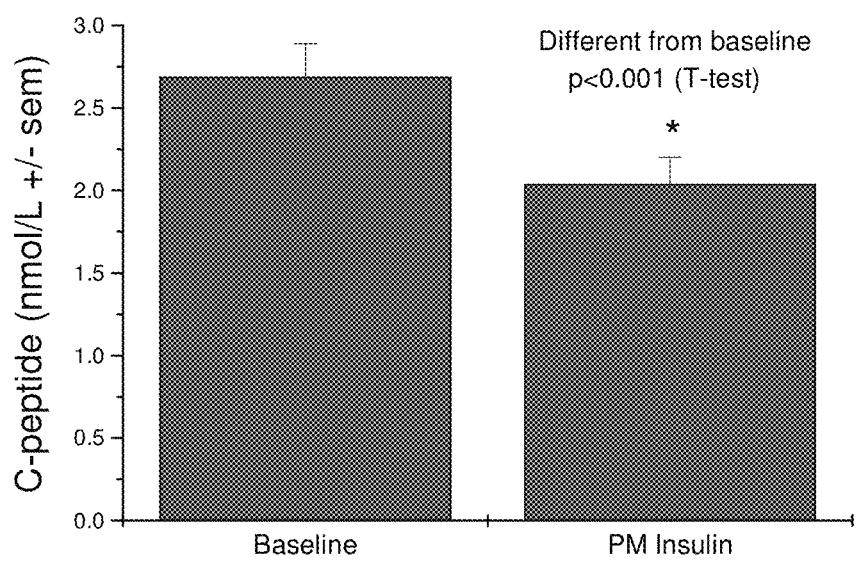
FIG. 10 is a bar graph showing the effect of nighttime dosing of insulin and 4-CNAB on blood C-peptide concentration.
Figure 11:
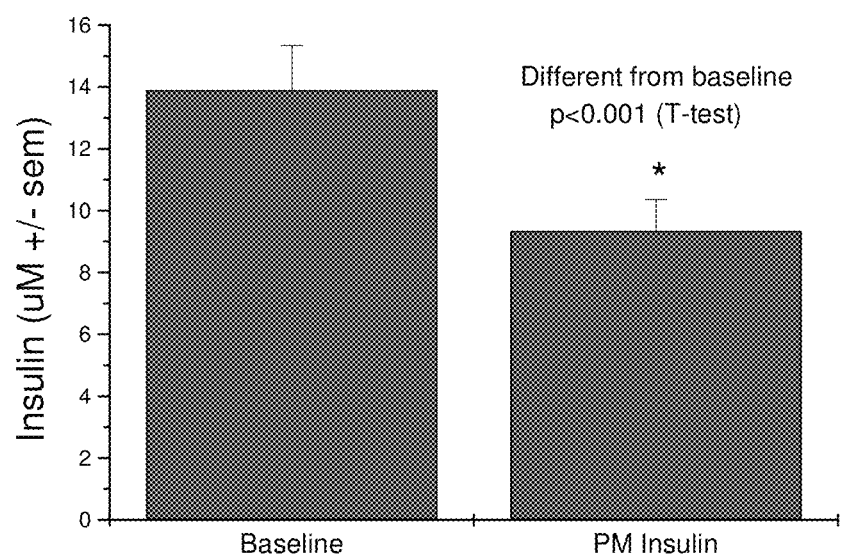
FIG. 11 is a bar graph showing the effect of nighttime dosing of insulin and 4-CNAB on blood insulin concentration.

There were no serious adverse effects in the course of the study. The results of the nighttime oral insulin study reported as the example herein (fasting blood glucose, insulin and C-peptide measured at approximately 7:00 a.m. and compared to the patient's own baseline levels) are set forth in FIGS. 9-12. The data (blood glucose, insulin and C-peptide) collected in the morning after nighttime dosing of insulin and 4-CNAB for each subject compared to that subject's own baseline levels is reported by patient in Table 45 (µUU/mL), and is graphically represented in FIGS. 9-11.

TABLE 45

| Subject # | C-peptide | | Insulin | | Glucose | |
|---|---|---|---|---|---|---|
| | Control | p.m. insulin | Control | p.m. insulin | control | p.m. insulin |
| 1 | 3.6 | 1.3 | 20.0 | 7.0 | 117 | 93 |
| 2 | 3.1 | 2.3 | 24.0 | 12.0 | 136 | 179 |
| 3 | 3.4 | 2.6 | 11.8 | 10.0 | 104 | 87 |
| 4 | 2.7 | 2.0 | 8.8 | 7.0 | 117 | 96 |
| 5 | 2.5 | 2.5 | 6.5 | 5.0 | 221 | 207 |
| 6 | 2.1 | 1.6 | 7.0 | 5.0 | 210 | 226 |
| 7 | 1.8 | 1.6 | 11.0 | 7.0 | 78 | 100 |
| 8 | 1.9 | 2.0 | 8.8 | 8.0 | 199 | 137 |
| 9 | 3.8 | 2.8 | 16.5 | 16.0 | 112 | 126 |
| 10 | 0.9 | 1.2 | 5.0 | 6.0 | | |

TABLE 45-continued

| Subject # | C-peptide | | Insulin | | Glucose | |
|---|---|---|---|---|---|---|
| | Control | p.m. insulin | Control | p.m. insulin | control | p.m. insulin |
| 11 | 2.7 | 2.2 | 17.0 | 12.0 | | |
| 12 | 3.0 | 1.4 | 13.0 | 7.0 | 125 | 107 |
| 13 | 2.9 | 2.3 | 18.0 | 10.0 | 124 | 103 |
| 14 | 1.4 | 1.3 | 9.3 | 5.0 | 123 | 104 |
| 15 | 2.6 | 1.3 | 17.0 | 5.0 | 93 | 78 |
| 16 | 4.9 | 3.3 | 29.0 | 23.0 | 156 | 173 |
| 17 | 2.6 | 2.0 | 19.8 | 12.0 | 144 | 125 |
| 18 | 2.3 | 1.3 | 16.0 | 8.0 | 142 | 121 |
| 19 | 2.6 | 1.9 | 14.0 | 8.0 | 84 | 84 |
| 20 | 2.9 | 3.8 | 5.5 | 14.0 | 123 | 118 |
| Average | 2.69 | 2.04 | 13.90 | 9.35 | 133.78 | 125.78 |
| Std Dev | 0.88 | 0.71 | 6.44 | 4.52 | 40.53 | 42.99 |
| Std Error Mean | 0.20 | 0.16 | 1.44 | 1.01 | 9.55 | 10.13 |
| $T_{test}$ | 0.00079 | | 0.00073 | | 0.16806 | |
| | 0.00039 | | 0.00036 | | 0.08403 | |

Figure 9:
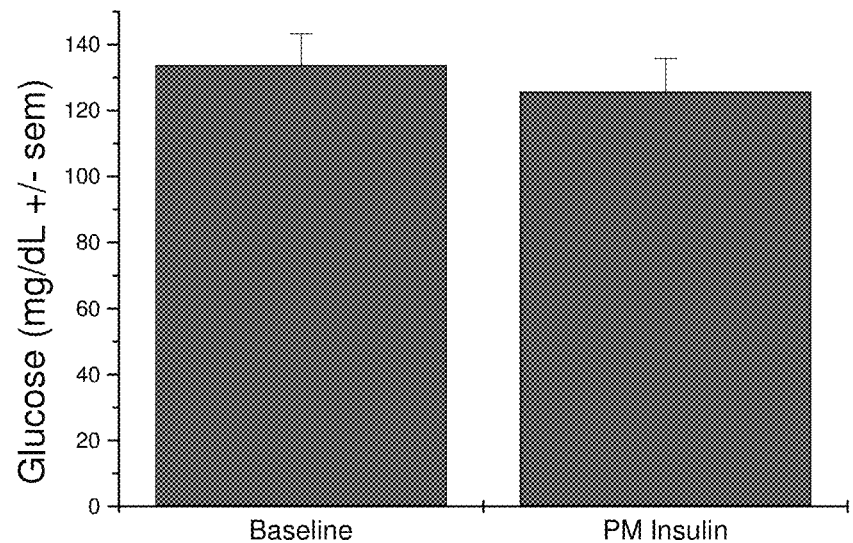
FIG. 9 is a bar graph showing the effect of nighttime dosing of insulin and 4-CNAB on blood glucose concentration.

The overnight study demonstrated that the metabolic effect of a single dose of oral insulin was still apparent in the morning, i.e., about eight hours after administration. As a result, there was a decrease in blood glucose output from the liver. As shown in FIG. 9 (effect on blood glucose), there was no statistically significant difference between the baseline blood glucose levels and the blood glucose levels in the patients after administration of the nighttime oral insulin capsules. Blood glucose measured the morning after administration decreased by 6% from baseline levels, i.e., from 133.78±40.53 mg/dL to 125.78±42.99 (p=0.017).

On the other hand, in all patients, a statistically significant reduction in C-peptide and insulin was detected in the morning (while the glucose levels were somewhat unchanged). A consistent compensatory decline in C-peptide levels from baseline by a mean of 24%, i.e., from 2.69±0.88 ng/mL to 2.04±0.71 (p<0.001) indicated that there was less activity in the β-cells that secrete endogenously produced insulin. Plasma insulin levels were reduced by a mean of 33%, i.e., from 13.90±6.44 µU/mL to 9.35±4.52 (p<0.001). These results are graphically depicted in FIGS. 3 and 4, respectively.

The interpretation of these results is that a "boost" of exogenous insulin at nighttime allows the patients' β-cells to rest and produce less insulin to achieve the same glycemic level. The suggested clinical implication is that, if such treatment were to be given (bedtime oral insulin) alone, it is likely to spare β-cell function as these cell become dysfunctional or die from exhaustion. This significance is supported by several reported studies which have shown that by intervening "aggressively" with insulin at early stages of the disease (such as IGT or "impaired glucose tolerance" stage), by giving insulin even for a short time such as two week duration, that this "rest" to the cells may provide for long term protection to develop overt diabetes.

It was further seen in this study that none of the patients had a clinically significant hypoglycemic episode, despite that the insulin was administered to the patients in the fasting state and with continued fasting. This result supports the conclusion that the administration of oral insulin formulations as described herein will be safe in terms of hypoglycemia.

Example 3

Preparation of Insulin/4-CNAB (75 U/100 mg) Tablets

This example describes the manufacturing procedure for Insulin/4-CNAB tablets. Each tablet contained about 75 units of insulin USP (equivalent to about 2.82 mg of recombinant human insulin with an as-is potency of about 26.6 U/mg) and about 100 mg of 4-CNAB monosodium salt.

Composition of Formulation (Theoretical, all Numbers are Approximate):

| Component | Weight (mg)/tablet |
|---|---|
| 4-CNAB, monosodium salt | 100 |
| Insulin | 2.82 |
| Povidone | 0.41 |
| Anhydrous Emcompress (extragranular) | 45.27 |
| Magnesium Stearate (extragranular) | 1.5 |
| Total | 150 |

4-CNAB and povidone (KOLLIDON® 90F (BASF Corporation, Mount Olive, N.J.)) were weighed. KOLLIDON® 90F was dissolved in 15% w/w water. Insulin (obtained from Diosynth, Inc.) was suspended in the KOLLIDON® solution, and then 4-CNAB was granulated using the insulin suspension as granulation media. Granulation was completed with additional water, as required. Granules were dried in a vacuum oven at about 50° C. Partly dried granules (about 0-10% w/w, preferably about 2-3% w/w moisture) were milled through about 0.02 inch screen using hammer mill Drying was continued to a final moisture content of less than about 0.6% w/w.

Dried granules were assayed for insulin and 4-CNAB. Based on the assay results, amounts of excipients (Anhydrous EMCOMPRESS® (dicalcium phosphate (JRS Pharma LP, Paterson, N.Y.) and magnesium-stearate) were calculated and weighed. Insulin/4-CNAB granules and anhydrous EMCOMPRESS® were blended in a V-blender for about 15 minutes. Samples were analyzed for blend uniformity. If samples passed blend uniformity specifications, magnesium stearate was blended for about 3 minutes. If samples did not pass blend uniformity specifications, then the mix was blended for an additional about 5 minutes, and the assay and analysis steps were repeated. Tablets were compressed on an EK-0 single station press with a hardness of about 7 KP.

The resulting tablet had a hardness of about 7.6 kP, a thickness of about 2.8 mm, a diameter of about 7.1 mm, a friability of 0.00% and a disintegration time of about 5 minutes. The dose for this preparation was about four tablets per patient, as described in Example 3 below.

Preparation of Insulin/4-CNAB (75 U/100 mg) Tablets

The resulting tablets were studied to determine whether they would remain within specification when stored under recommended storage conditions in order to provide evidence on how the product quality varies with time under the influence of temperature and humidity. The stability tests were conducted in compliance with the U.S. Federal Drug Administration current Good Manufacturing Practice Standards, 21 C.F.R. §210 and 211, and the International Conference on Harmonization (ICH) Guidance, ICH Q1A (R2), using qualified equipment, test methods and personnel.

Tablet samples were packaged in a number of closed containers that were then placed in controlled temperature and humidity chambers. For room temperature stability tests, the containers were stored at 25° C.±2° C./60%±5% Relative Humidity. Samples were then drawn from these chambers at specified time intervals and tested for conformance to the product stability specifications with regard to appearance (method No. AM001v2), insulin assay (method no. AM018), 4-CNAB assay (method no. AM018), moisture (method no. USP <921>), disintegration (method no. USP <701>) and, in some cases, microbial testing (method no. USP <1111>).

The following Table 46 shows the stability data for tablets of 75 U Insulin/100 mg 4-CNAB under 25° C.±2° C./60%±5% Relative Humidity conditions.

TABLE 46

| | | TIME (months) | | | | | |
|---|---|---|---|---|---|---|---|
| TEST METHODS | SPECIFICATIONS | Bulk Release (Jun. 20, 2003) | 0.5 (Jul. 7, 2003) | 1 (Jul. 21, 2003) | 2 (Aug. 20, 2003) | 3 (Sep. 22, 2003) | 6 (Dec. 19, 2003) |
| APPEARANCE (visual) | White, off-white or tan tablets | Conforms | Conforms | Conforms | Conforms | Conforms | Conforms |
| DISINTEGRATION (USP) | Report the time required for disintegration of six tablets | 5 min. | 5.25 min | 5 min | 5 min. | 5 min. | 5.5 min. |
| MOISTURE CONTENT | Report result | 1.2% | 2.8% | 2.6% | 3.6% | 1.7% | 1.1% |
| INSULIN ASSAY (HPLC) | 90.0-110.0% Label Claim | 100.1% | 96.4% | 96.7% | 92.0% | 87.5% | 83.3% |
| 4-CNAB ASSAY (HPLC) | 90.0-110.0% Label Claim | 96.9% | 97.1% | 96.8% | 98.6% | 97.2% | 98.6% |
| Total Bacterial Count | NMT 1000 CFU/g | <100 | N/A | N/A | N/A | N/A | N/A |
| Total Mold and Yeast | NMT 100 CFU/g | <100 | N/A | N/A | N/A | N/A | N/A |
| Staphylococcus aureus | Absent | Absent | N/A | N/A | N/A | N/A | N/A |
| Pseudomonas aeruginosa | Absent | Absent | | | | | |
| Salmonella | Absent | Absent | | | | | |
| Escherichia coli | Absent | Absent | | | | | |
| Enterobacteria | NMT 100/g | Absent | | | | | |

The insulin molecule appears to be stable (>90%) in the 75 U Insulin/100 mg 4-CNAB insulin tablet formulation when stored for two months at 25 degrees C. and 60% Relative Humidity ($^{25}/_{60}$).

Example 4

Preparation of Insulin/4-CNAB (150 U/80 mg) Tablets

This example describes the manufacturing procedure for Insulin/4-CNAB tablets. Each tablet contained about 150 units of insulin USP (equivalent to about 5.64 mg of recombinant human insulin with an as-is potency of about 26.6 U/mg) and about 80 mg of 4-CNAB monosodium salt. The insulin used in this study was obtained from Diosynth, Inc. and met the specifications for Human Insulin as described in the United States Pharmacopoeia.

Composition of Formulation (Theoretical, all Numbers are Approximate):

| Component | Weight (mg)/tablet |
|---|---|
| 4-CNAB, monosodium salt | 80 |
| Insulin | 5.64 |
| Povidone | 0.35 |
| Anhydrous EMCOMPRESS | 37.76 |
| Magnesium Stearate | 1.25 |
| Total | 125 |

4-CNAB and KOLLIDON® 90F were weighed. KOLLIDON® 90F was dissolved in water. The amount of water used in this step was about 1-50%, preferably about 15% w/w of the amount of material used in the granulation. Insulin (obtained from Diosynth, Inc.) and 4-CNAB were geometrically blended and charged to the 5 L bowl of a Key Instruments KG-5 high shear granulator. The insulin/4-CNAB blend was then granulated using the KOLLIDON® solution. The granulation was finished with additional water as required. Granules were dried in a vacuum oven at about 20-80° C., preferably about 50° C. Partly dried granules (about 0-10% w/w, preferably about 2-3% w/w moisture) were milled through about 0.02 inch screen using hammer mill Drying was continued to a final moisture content of less than about 0.6% w/w.

Dried granules were assayed for insulin and 4-CNAB. Based on the assay results, the amounts of excipients (Anhydrous EMCOMPRESS® and magnesium stearate) were calculated and weighed. Insulin/4-CNAB granules and anhydrous EMCOMPRESS® were blended in a V-blender for about 10-20 minutes, preferably about 15 minutes. Samples were analyzed for blend uniformity. If samples passed blend uniformity specifications, magnesium stearate was blended for about 1-5 minutes, preferably about 3 minutes. If samples did not pass blend uniformity specifications, then the mix was blended for an additional about 1-10 minutes, preferably about 5 minutes, and the assay and analysis steps were repeated. Tablets were compressed on an EK-0 single station press with a hardness of about 5 KP-10 KP, preferably about 7 KP. The resulting tablet had a hardness of about 7.8 kP, a thickness of about 2.8 mm, a diameter of about 6.5 mm, a friability of 0.02% and a disintegration time of about 6 minutes.

Preparation of Insulin/4-CNAB (150 U/80 mg) Tablets

The resulting tablets were studied to determine whether they would remain within specification when stored under recommended storage conditions in order to provide evidence on how the product quality varies with time under the influence of temperature and humidity. The stability tests were conducted in compliance with the U.S. Federal Drug Administration current Good Manufacturing Practice Standards, 21 C.F.R. §210 and 211, and the International Conference on Harmonization (ICH) Guidance, ICH Q1A (R2), using qualified equipment, test methods and personnel.

Tablet samples were packaged in a number of closed containers that were then placed in controlled temperature and humidity chambers. For room temperature stability tests, the containers were stored at 25° C.±2° C./60%±5% Relative Humidity. Samples were then drawn from these chambers at specified time intervals and tested for conformance to the product stability specifications with regard to appearance (method No. AM001v2), insulin assay (method no. AM018), 4-CNAB assay (method no. AM018), moisture (method no. USP<921>), disintegration (method no. USP <701>) and, in some cases, microbial testing (method no. USP <1111>).

The following Table 47 shows the stability data for tablets of 150 U Insulin/80 mg 4-CNAB under 25° C.±2° C./60%±5% Relative Humidity conditions.

| | | TIME (months) | | | | | |
|---|---|---|---|---|---|---|---|
| TEST METHODS | SPECIFICATIONS | Bulk Release (Jun. 20, 2003) | 0.5 (Jul. 7, 2003) | 1 (Jul. 21, 2003) | 2 (Aug. 20, 2003) | 3 (Sep. 22, 2003) | 6 (Dec. 19, 2003) |
| APPEARANCE (visual) | White, off-white or tan tablets | Conforms | Conforms | Conforms | Conforms | Conforms | Conforms |
| DISINTEGRATION (USP) | Report the time required for disintegration of six tablets | 5 min. | 4.5 min | 4.5 min | 4.5 min. | 4.5 min. | 5 min. |
| MOISTURE CONTENT | Report result | 1.2% | 4.2% | 3.5% | 4.3% | 3.3% | 2.2% |
| INSULIN ASSAY (HPLC) | 90.0-110.0% Label Claim | 100.1% | 104.5% | 106.4% | 103.3% | 102.0% | 99.1% |
| 4-CNAB ASSAY (HPLC) | 90.0-110.0% Label Claim | 96.9% | 104.7% | 101.9% | 104.0% | 103.0% | 104.2% |
| Total Bacterial Count | NMT 1000 CFU/g | <100 | N/A | N/A | N/A | N/A | N/A |
| Total Mold and Yeast | NMT 100 CFU/g | <100 | N/A | N/A | N/A | N/A | N/A |
| Staphylococcus aureus | Absent | Absent | N/A | N/A | N/A | N/A | N/A |
| Pseudomonas aeruginosa | Absent | Absent | | | | | |
| Salmonella | Absent | Absent | | | | | |
| Escherichia coli | Absent | Absent | | | | | |
| Enterobacteria | NMT 100/g | Absent | | | | | |

The insulin molecule appears to be stable (>90%) in the 150 U Insulin/80 mg 4-CNAB insulin tablet formulation when stored for six months at 25 degrees C. and 60% Relative Humidity (25/60). By comparison, a 150 Insulin/200 mg 4-CNAB capsule formulation yielded spurious HPLC data after two months, and a result below 90% after three months. The differences between the capsule and tablet formulations are that capsules allow higher surface area exposure to atmosphere, had a higher level of 4-CNAB, contained hydrous rather than anhydrous dicalcium phosphate, and contained sodium lauryl sulfate (a potential insulin denaturant).

Example 5

Preparation of 4-CNAB (100 mg) Tablets

This example describes the manufacturing procedure for 4-CNAB tablets. Each tablet contains about 100 mg of 4-CNAB monosodium salt.

Composition of Formulation (Theoretical, all Numbers are Approximate):

| Component | Weight (mg)/tablet |
|---|---|
| 4-CNAB, monosodium salt | 100 |
| Povidone | 0.4 |
| Anhydrous EMCOMPRESS ® | 48.1 |
| Magnesium Stearate | 1.5 |
| Total | 150 |

4-CNAB and povidone (KOLLIDON® 90F (BASF Corp., Mount Olive, N.J.)) were weighed. KOLLIDON 90F was dissolved in water. The amount of water used in this step should be about 1-50%, preferably about 15% w/w of the amount of material used in the granulation. 4-CNAB was granulated using the KOLLIDON® solution as granulation media. Granulation was completed with additional water, as required. Granules were dried in a vacuum oven at about 20-80° C., preferably about 50° C. Partly dried granules (about 0-10% w/w, preferably about 2-3% w/w moisture) were milled through about 0.02 inch screen using hammer mill Drying was continued to a final moisture content of less than about 1.0%, preferably less than about 0.6% w/w. Based on final moisture content, amounts of excipients (anhydrous EMCOMPRESS® (dicalcium phosphate (JRS Pharma PL, Patterson, N.Y.)) and magnesium stearate) were calculated, weighed and screened. 4-CNAB granules and anhydrous EMCOMPRESS® were blended in a V-blender for about 10-20 minutes, preferably about 15 minutes. Magnesium stearate was added and blended for about 1-5 minutes, preferably about 3 minutes. Tablets were compressed on an EK-0 single station press with a hardness of about 5 KP-10KP, preferably about 7 KP.

Example 6

In this example, a single-blind, crossover study was done in order to assess the safety, tolerability, pharmacokinetics and pharmacodynamics of oral Insulin/4-CNAB tablets in fasted and pre-prandial type 2 diabetic patients. A crossover design was selected for this study so as to reduce the inter-subject variability and to allow maximum use of the limited sample size, and a blinded study design was selected in order to reduce the bias from the patient side.

Eight (8) male subjects, aged 30 to 65 inclusive and having a body mass index <32 kg/m$^2$, with clinically documented diet-controlled type 2 diabetes and a fasting blood glucose level of <150 mg/dL, were chosen for this study. These patients were generally in good health, evidenced by lack of significant findings in medical history, physical examination, clinical laboratory tests, vital signs and ECG, and liver and kidney laboratory evaluations within normal limits. These patients had neither current nor past use of insulin to control their diabetes, and no clinically significant disease or abnormal condition of the liver, kidneys, or gastrointestinal system.

The subjects fasted for at least 8 hours overnight prior to administration of each dosage, and each study drug was administered with exactly 150 mL of water and followed by a 72 hour wash-out period in order to eliminate pharmacological treatment interactions. An indwelling catheter was inserted for pharmacokinetic, pharmacodynamic and clinical blood sample collection.

The study drug regimen was as follows:

Period 1: Subjects were administered four 4 tablets of 75 U Insulin/100 mg 4-CNAB (total dose 300 U Insulin/400 mg 4-CNAB) in the morning and remained in a fasted state for 4.5 hours.

Period 2: Subjects were administered four tablets of 75 U Insulin/100 mg 4-CNAB (total dose 300 U Insulin/400 mg 4-CNAB) exactly 10 minutes before receiving a standard ADA breakfast.

Period 3: Subjects were administered two tablets of 150 U Insulin/80 mg 4-CNAB (total dose 300 U Insulin/160 mg 4-CNAB) in the morning and remained in a fasted state for 4.5 hours.

Period 4: Subjects were administered two tablets of 150 U Insulin/80 mg 4-CNAB (total dose 300 U Insulin/160 mg 4-CNAB) exactly 10 minutes before receiving a standard ADA breakfast.

Period 5: All the subjects were administered 300 U Insulin with 160 mg of 4-CNAB (2 tablets).

Three patients were administered one tablet containing 150 U Insulin/80 mg 4-CNAB exactly 10 minutes before breakfast and one tablet containing 150 U Insulin/80 mg 4-CNAB exactly 0 minutes before breakfast. Five patients were administered two tablets containing a total of 300 U Insulin/160 mg 4-CNAB exactly 0 minutes before breakfast (N=5)

Period 6: Subjects were administered two tablets of 100 mg 4-CNAB (total dose 200 mg 4 CNAB) exactly 10 minutes before receiving a standard ADA breakfast.

The dose levels for this study were selected based upon previous human experience in both healthy and diabetic subjects, wherein up to 450 U Insulin/600 mg 4-CNAB has been safely tolerated in Diabetes Type 1 and Type 2 patients. The formulation and dose ratio of insulin to 4-CNAB were chosen to investigate a drug/carrier ratio-response relationship for formulation optimization. The 75 U Insulin/100 mg 4-CNAB tablets and the 150 U Insulin/80 mg 4-CNAB tablets were manufactured as described in Examples 1 and 2 above, respectively.

Blood samples for pharmacokinetic analysis of 4-CNAB, insulin and C-peptide and for pharmacodynamic analysis of insulin and glucose were collected at each period at the following times (except that 4-CNAB was not measured after the sixth period):

4-CNAB (12 samples): 5 minutes pre-study dose; and 5, 10, 15, 20, 25, 30, 40, 50 and 60 minutes, and 2 and 4 hours post-study dose.

Insulin (13 samples): 15 and 5 minutes pre-study dose; and 5, 10, 15, 20, 25, 30, 40, 50 and 60 minutes, and 2 and 4 hours post-study dose.

C-peptide (9 samples): 15 and 5 minutes pre-study dose; and 10, 20, 30, 40 and 60 minutes, and 2 and 4 hours post study dose.

Plasma or blood glucose (13 samples): 15 and 5 minutes pre-study dose; and 5, 10, 15, 20, 25, 30, 40, 50 and 60 minutes, and 2 and 4 hours post-study dose (blood glucose used the SuperGL equipment; plasma used an Elisa assay).

The pharmacokinetic parameters determined or calculated from the plasma concentration time data for 4-CNAB were $C_{max}$, $t_{max}$, $t_{1/2}$, $AUC_{0-last}$, $AUC_{inf}$, $AUC_{0-t}$, and CL/F. The pharmacokinetic parameters determined or calculated from the plasma concentration time data for insulin and C-peptide were $C_{max}$, $t_{max}$, $AUC_{0-t}$ (for t=1, 2), $AUC_{0-last}$ and $AUC_{0-inf}$.

The pharmacodynamic parameters computed from the plasma concentration-time data of glucose were percent decrease from baseline, absolute blood glucose concentration, $E_{max}$, $t_{emax}$ and $EAUC_{last}$.

Pharmacokinetic/Pharmacodynamic Evaluation

Data collected following administration of oral Insulin/4-CNAB tablets, namely, the concentrations of 4-CNAB, insulin, C-peptide and glucose, in fasted and pre-prandial type 2 diabetic patients will now be presented.

Table 48 below sets forth the data for mean blood glucose change vs. time:

TABLE 48

Mean Percent Change from Baseline Blood Glucose vs. Time

| time (min) | 300 U/400 mg fasted (N = 8) | 300 U/400 mg 10 min meal (N = 8) | 300 U/160 mg fasted (N = 8) | 300 U/160 mg 10 min meal (N = 8) | 150 U/80 mg -10 min + 150 U/80 mg @ 0 min w/meal (N = 3) | 300 U/160 mg 0 min meal (N = 5) | 4-CNAB alone 10 min meal (N = 7) |
|---|---|---|---|---|---|---|---|
| | | | | Mean (%) | | | |
| 0 | 0.0% | 0.0% | 0.0% | 0.0% | 0.0% | 0.0% | 0.0% |
| 5 | −1.6% | 3.2% | −0.3% | −1.0% | −1.0% | −0.4% | −0.6% |
| 10 | −3.5% | 0.8% | −2.1% | −2.2% | −2.7% | 0.5% | −1.9% |
| 15 | −3.7% | −1.3% | −2.8% | −2.6% | −3.9% | 4.6% | −0.6% |
| 20 | −4.7% | −4.1% | −4.8% | −4.5% | −7.0% | 7.7% | 0.4% |
| 25 | −7.4% | −0.1% | −6.5% | −1.5% | −0.1% | 13.1% | 6.4% |
| 30 | −9.3% | 5.4% | −9.4% | 3.5% | 4.9% | 19.1% | 18.6% |
| 40 | −13.1% | 18.3% | −14.9% | 10.4% | 16.8% | 30.3% | 33.3% |
| 50 | −17.0% | 26.9% | −16.9% | 15.9% | 45.7% | 35.9% | 47.4% |
| 60 | −16.0% | 32.7% | −16.9% | 21.1% | 49.1% | 35.8% | 49.5% |
| 90 | −13.0% | 37.4% | −11.8% | 23.0% | 57.8% | 33.3% | 49.5% |
| 120 | −7.7% | 28.3% | −6.5% | 22.0% | 50.8% | 27.5% | 44.9% |
| 150 | −11.7% | 15.2% | −5.8% | 13.4% | 26.4% | 14.3% | 28.9% |
| 180 | −8.3% | 4.3% | −3.1% | 8.2% | 6.2% | 4.8% | 20.1% |
| 210 | −9.4% | −4.0% | −4.5% | −1.0% | −4.4% | −5.7% | 11.1% |
| 240 | −9.2% | −4.7% | −5.4% | −3.5% | −9.4% | −11.3% | 2.0% |
| | | | | Standard Deviation (SD) | | | |
| 0 | 0.00% | 0.00% | 0.00% | 0.00% | 0.00% | 0.00% | 0.00% |
| 5 | 4.78% | 8.87% | 2.85% | 2.95% | 1.89% | 3.26% | 3.05% |
| 10 | 3.77% | 6.64% | 2.59% | 3.08% | 4.86% | 3.84% | 4.87% |
| 15 | 6.19% | 5.84% | 2.05% | 2.90% | 2.20% | 7.96% | 5.23% |
| 20 | 5.53% | 7.98% | 2.87% | 3.87% | 1.57% | 10.28% | 7.28% |
| 25 | 5.49% | 7.54% | 4.33% | 4.65% | 6.82% | 4.95% | 11.65% |
| 30 | 5.63% | 12.11% | 6.87% | 3.87% | 14.96% | 4.93% | 14.10% |
| 40 | 8.12% | 14.58% | 10.52% | 5.52% | 18.98% | 3.71% | 18.58% |
| 50 | 11.59% | 17.06% | 12.63% | 5.42% | 20.84% | 1.75% | 23.62% |
| 60 | 13.54% | 18.72% | 13.48% | 5.41% | 22.51% | 6.84% | 20.86% |
| 90 | 13.06% | 18.69% | 6.71% | 6.73% | 17.22% | 12.49% | 16.85% |
| 120 | 10.53% | 23.90% | 6.11% | 5.39% | 26.58% | 16.76% | 13.15% |
| 150 | 13.68% | 22.17% | 5.80% | 6.10% | 12.97% | 17.34% | 10.48% |
| 180 | 9.31% | 20.37% | 6.38% | 9.01% | 11.04% | 14.88% | 13.00% |
| 210 | 11.74% | 19.78% | 5.20% | 9.30% | 8.55% | 14.22% | 10.21% |
| 240 | 8.89% | 14.05% | 5.17% | 10.12% | 6.82% | 10.41% | 8.62% |

Figure 12:
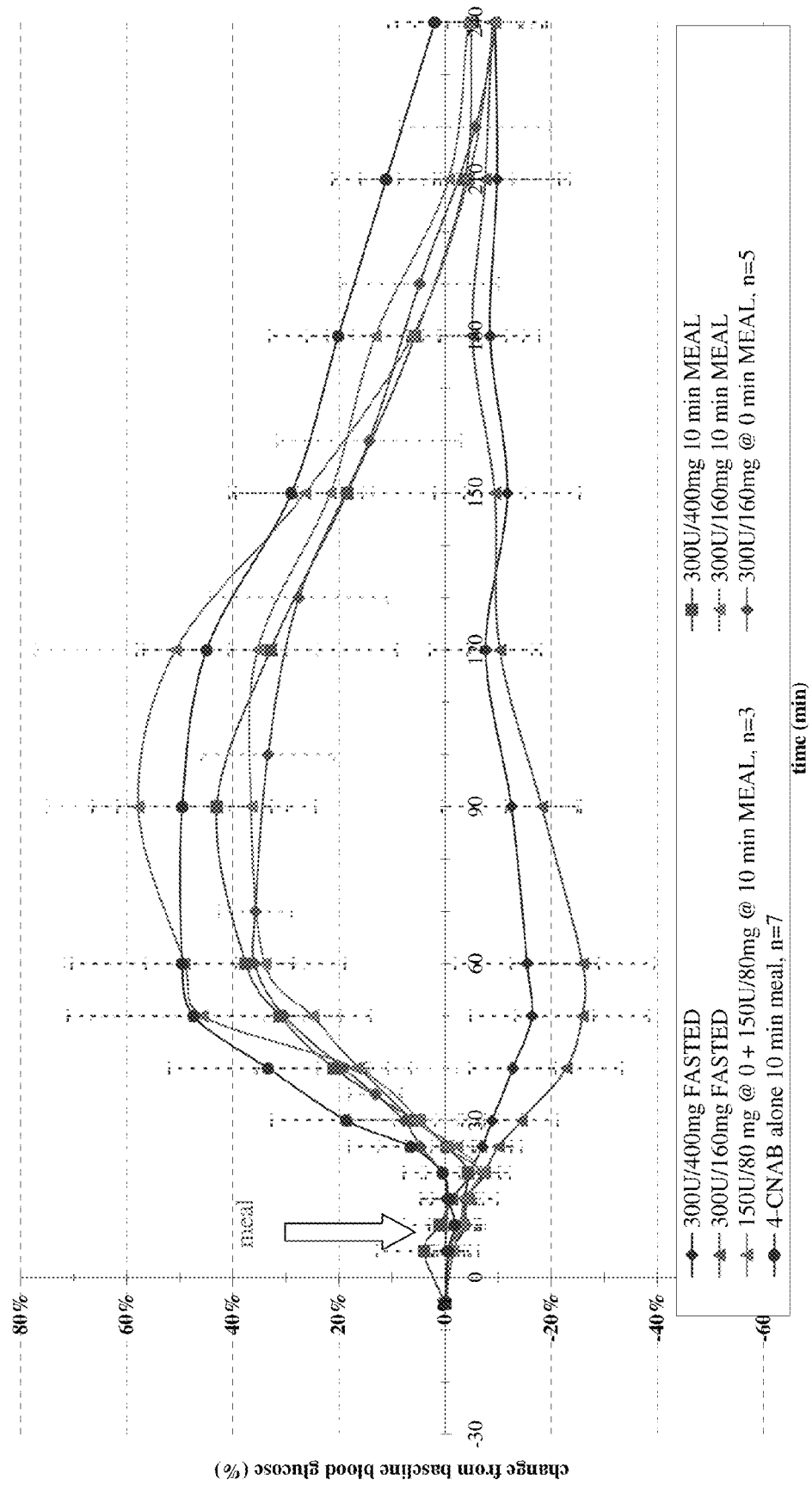
FIG. 12 is a plot of Preliminary Mean+/−SD % Change in Baseline Blood Glucose (SuperGL) Following Oral Administration of Insulin/4-CNAB Tablets to Fed of Fasted Type 2 Diabetic Patients.

FIG. 12 shows graphs of mean (for all eight subjects) percent change in blood glucose concentration from baseline levels following oral administration of the various Insulin/4-CNAB tablet combinations and control described above to Type 2 diabetic patients, both with and without a meal. The mean FIG. 12 is based upon FIGS. 15-22, which show percent change in blood glucose concentrations from baseline levels for subjects 101-108 following oral administration of the various Insulin/4-CNAB tablet combinations described above. The oral insulin/4-CNAB tablets appeared to be well-tolerated in Type 2 diabetes patients.

These figures show that the oral insulin tablets exhibited a fast on-set of action and produced significant reduction in glucose excursion in Type 2 diabetes patients when compared to the control (4-CNAB alone). This is shown clearly in FIG. 2, which shows a comparison of graphs of the mean percent change in blood glucose concentration following oral administration of Insulin/4-CNAB tablet combinations vs. control, all taken with a meal. It can be seen that all Insulin/4-CNAB tablet formulations provided a significant (p<0.0005) reduction in post-prandial glucose excursions when compared to the formulation without insulin (control, 4-CNAB alone). (There was no significant difference in fasting glucose excursion reduction between the formulations.)

Figure 13:
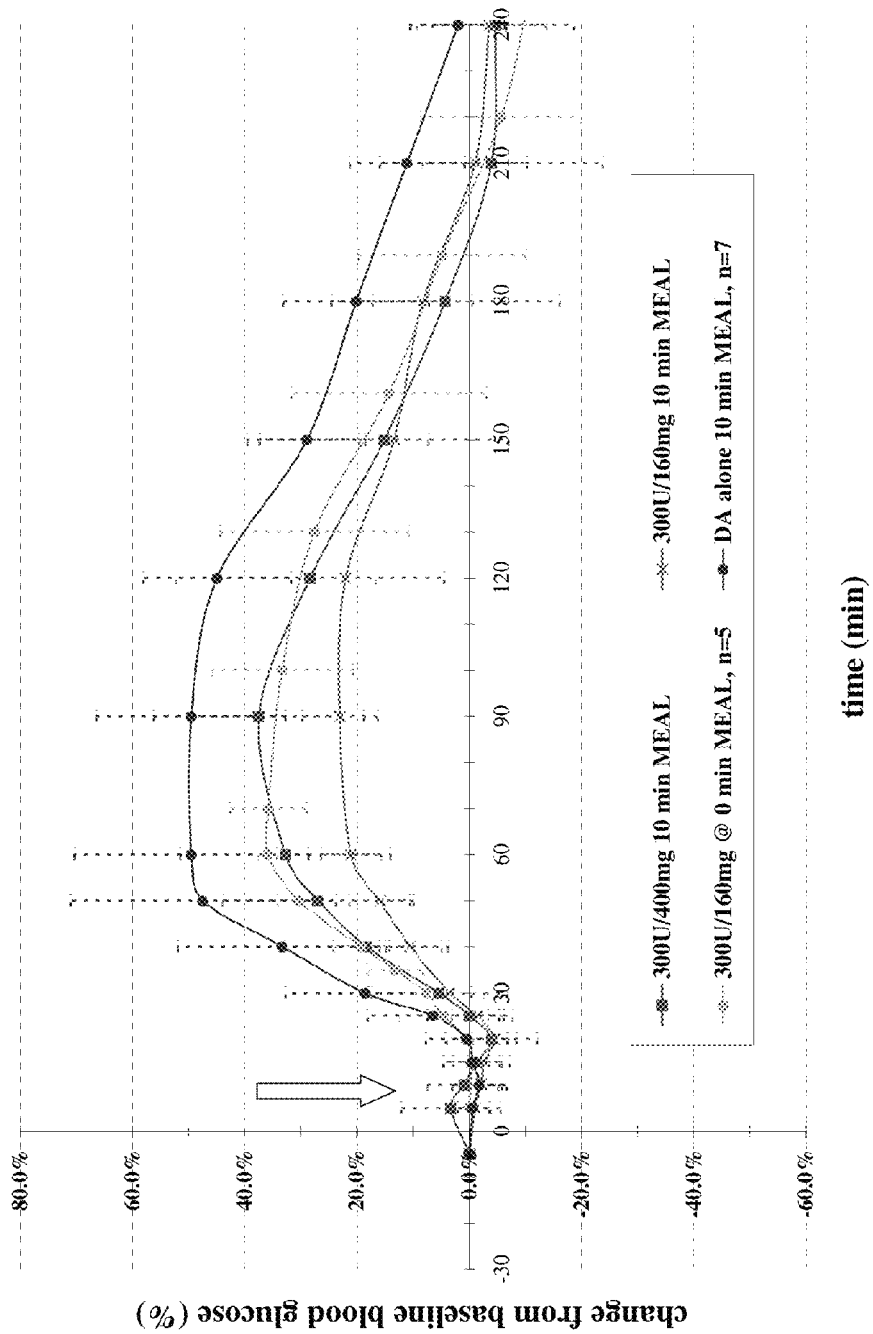
FIG. 13 is a plot of Preliminary Mean+/−SD % Change in Blood Glucose (SuperGL) Following Oral Administration of Insulin/4-CNAB Tablets to Type 2 Diabetic Patients with a Standard Meal.

FIG. 13 also shows that the 300 U insulin/160 mg 4-CNAB ratio appeared to have been more effective at delivering insulin than was the 300 U insulin/400 mg 4-CNAB ratio, because the 300 U insulin/160 mg 4-CNAB ratio produced a slightly greater decrease in blood glucose when administered 10 minutes prior to a meal than did the 300 U insulin/400 mg 4-CNAB ratio. Therefore, at controlling post-prandial glucose excursion, the 300 U insulin/160 mg 4-CNAB ratio appeared to be at least as effective as, if not more effective than, the 300 U insulin/400 mg 4-CNAB ratio.

FIG. 13 also indicated that the 300 U insulin/160 mg 4-CNAB ratio, when administered 0 minutes prior to a meal (N=5), showed a lower blood glucose excursion profile than did the control (4-CNAB alone) when administered 10 minutes prior to a meal. This shows that the 300 U insulin/160 mg 4-CNAB tablet dose was t absorbed and produced a desired effect when administered at mealtime.

For the 300 U Insulin/160 mg 4-CNAB tablets, whose ratio appears in this study to perform best at lowering glucose excursions, FIG. 3 shows a comparison of the mean (for all eight subjects) percent change in blood glucose concentration following oral administration at 10 minutes before a meal and fasting (compared to the control at 10 minutes before a meal n=7).

Figure 14:
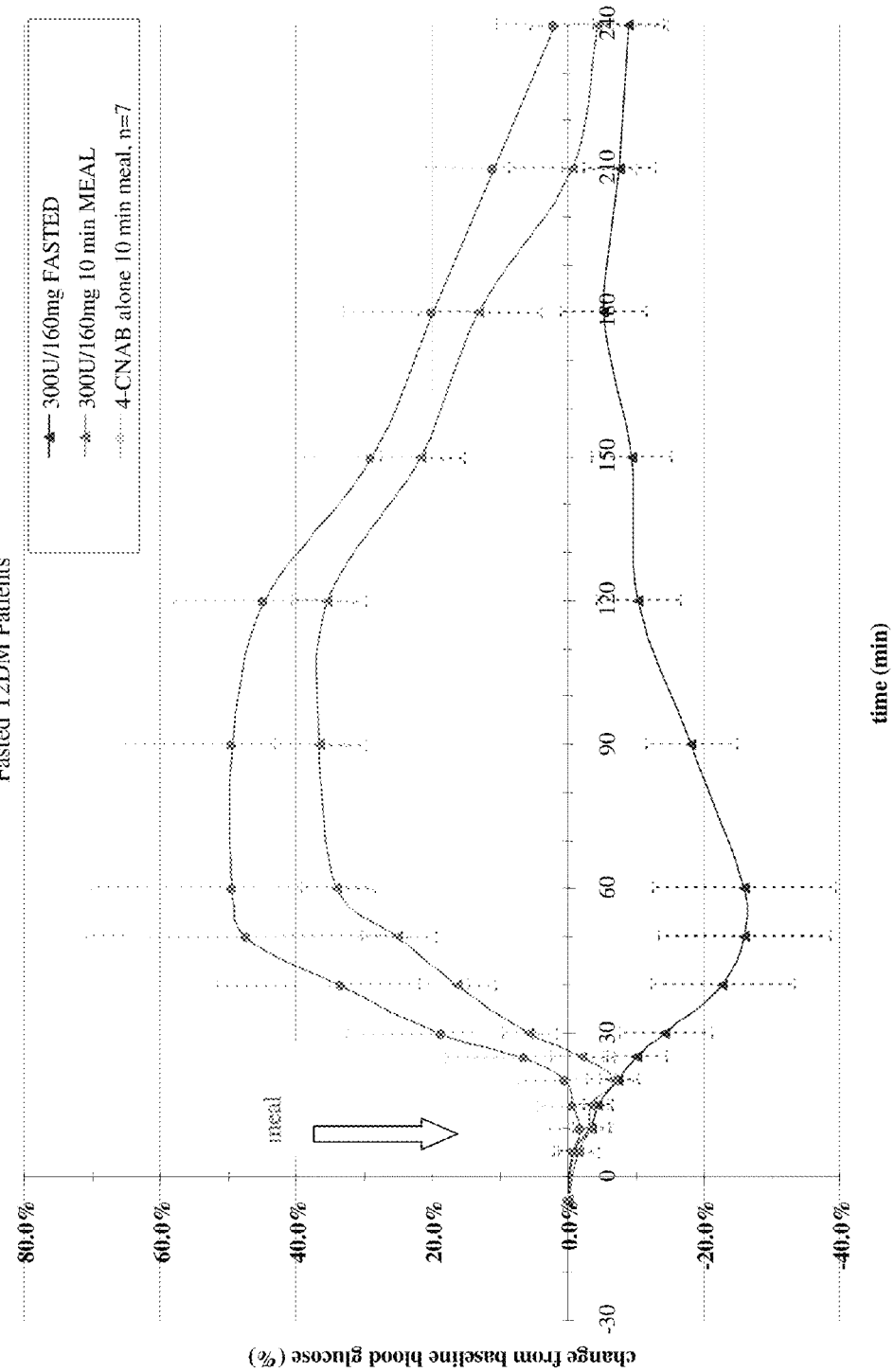
FIG. 14 is a plot of Preliminary Mean+/−SD % Change in Blood Glucose (SuperGL) Following Oral Administration of Insulin/4-CNAB Tablets to Type 2 Diabetic Patients with or without a Meal.
Figure 15:
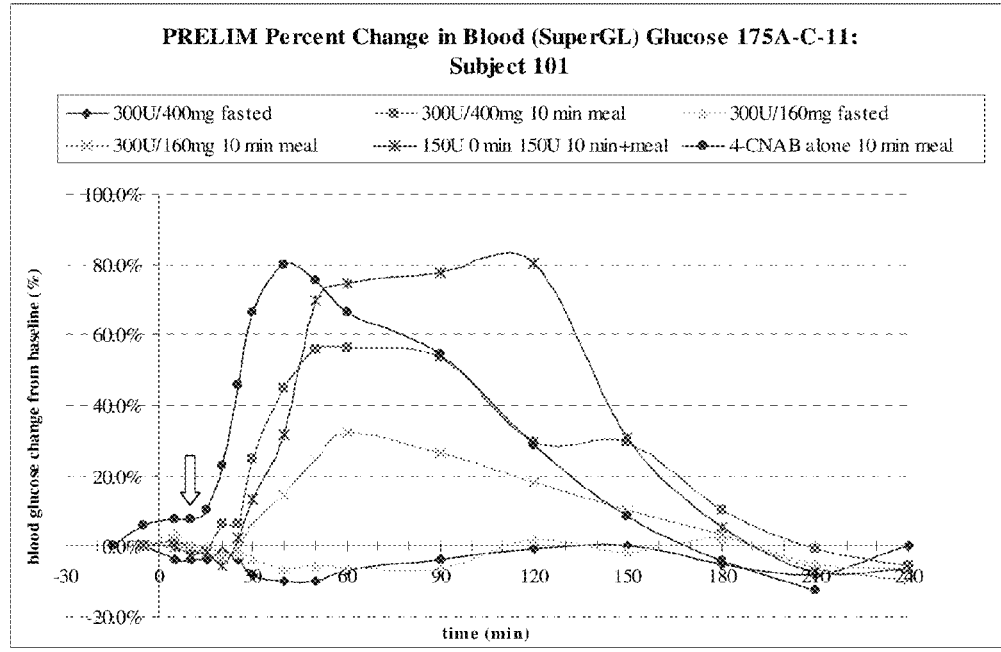
FIGS. 15-22 are plots of Preliminary Percent Change in Blood (SuperGL) Glucose for Subjects 101-108, respectively.
Figure 16:
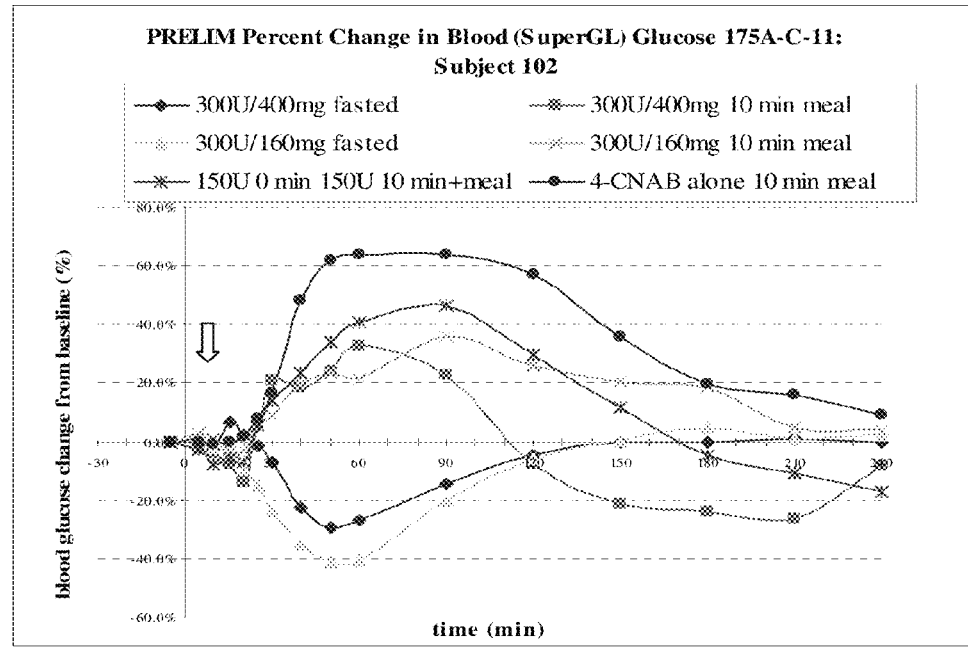
Figure 17:
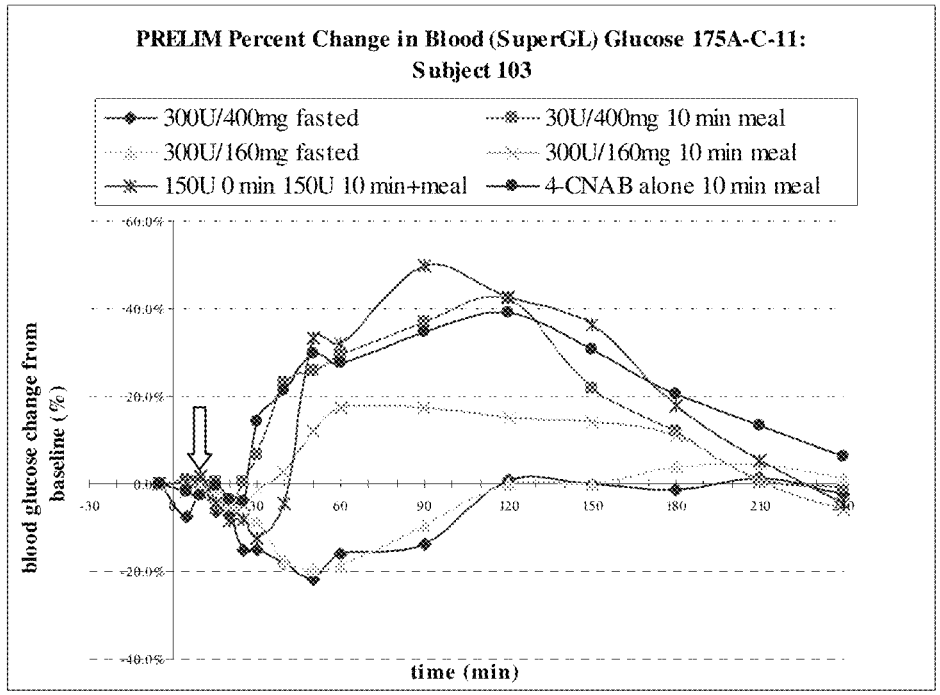
Figure 18:
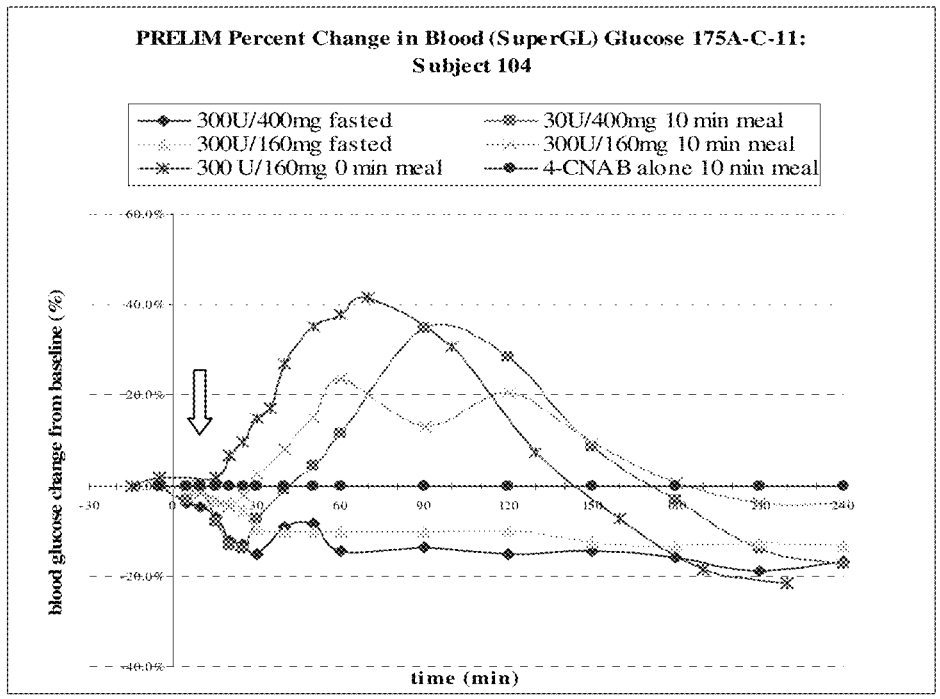
Figure 19:
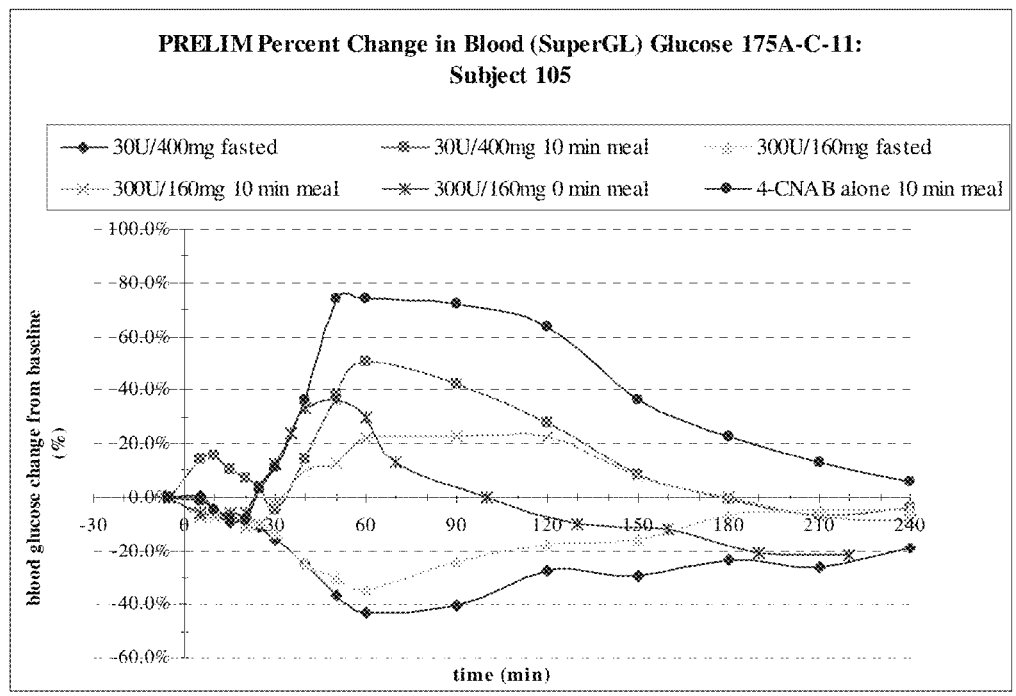
Figure 20:
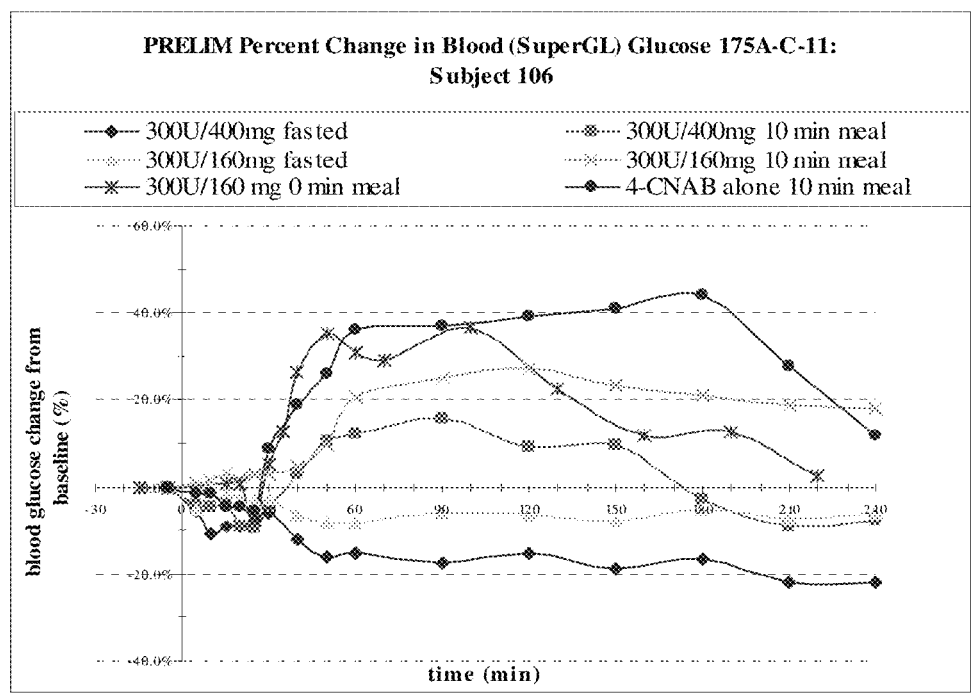
Figure 21:
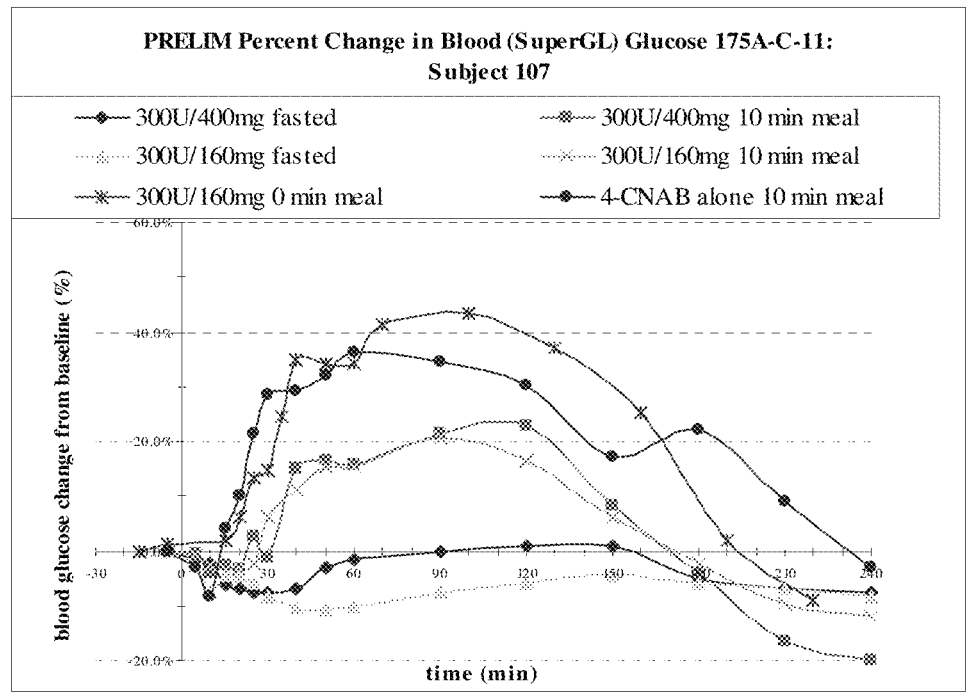
Figure 22:
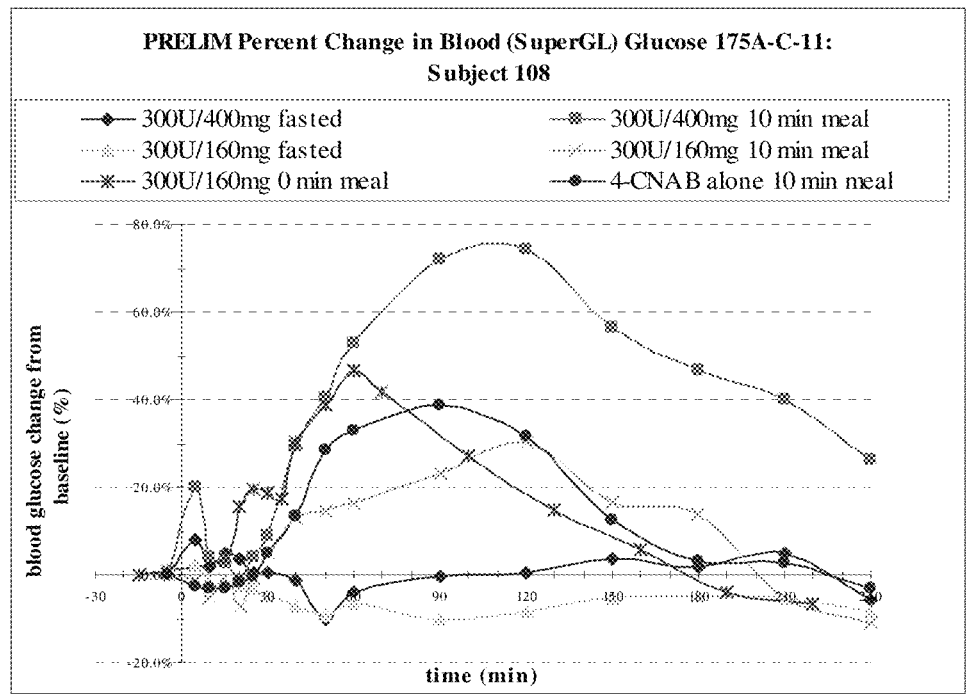
Figure 23:
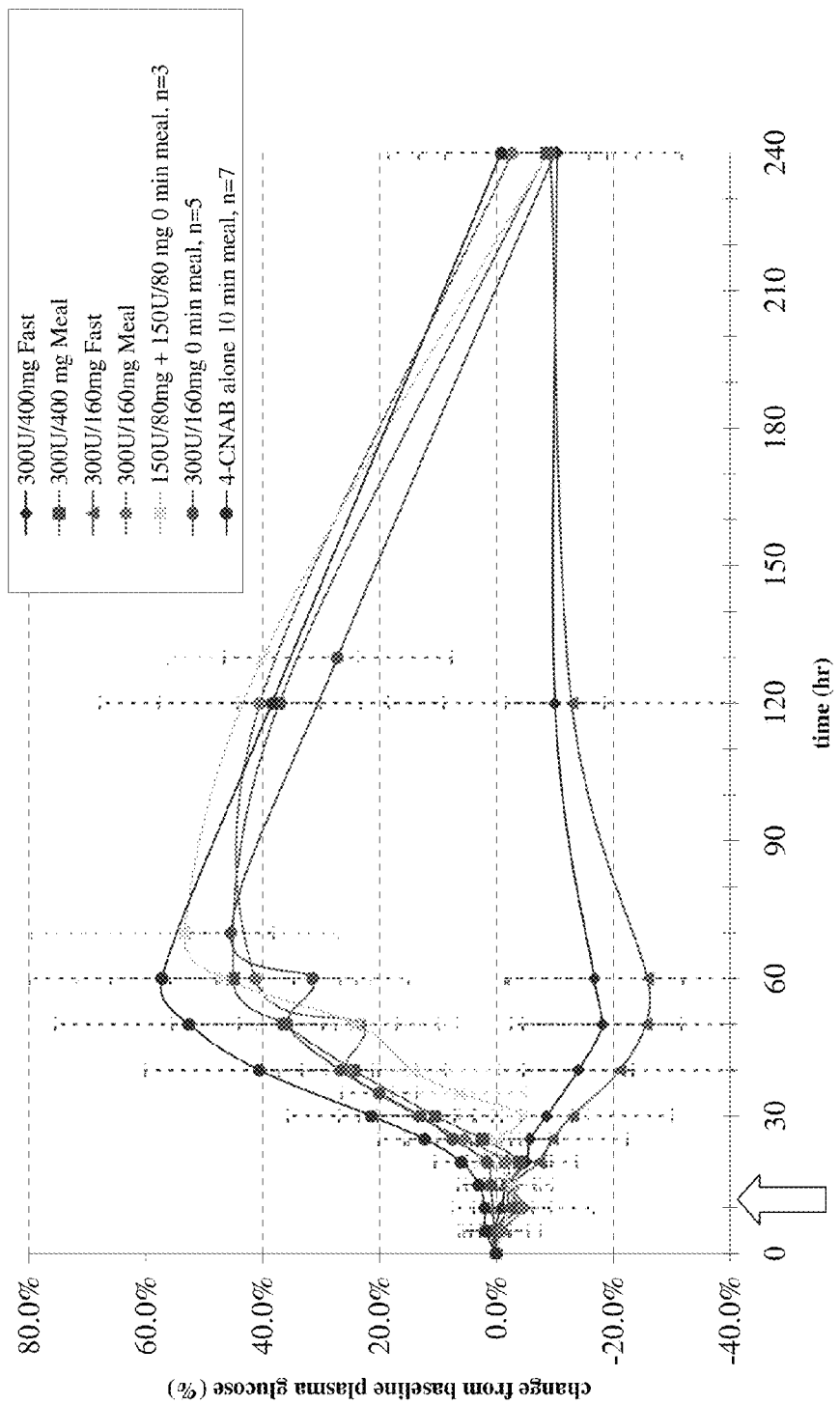
FIG. 23 is a plot of Preliminary Mean+/−SD Plasma Glucose Change (%) Following Oral Tablet Administration of Insulin/4-CNAB to Type 2 Diabetic Patients with or without a Meal.
Figure 24:
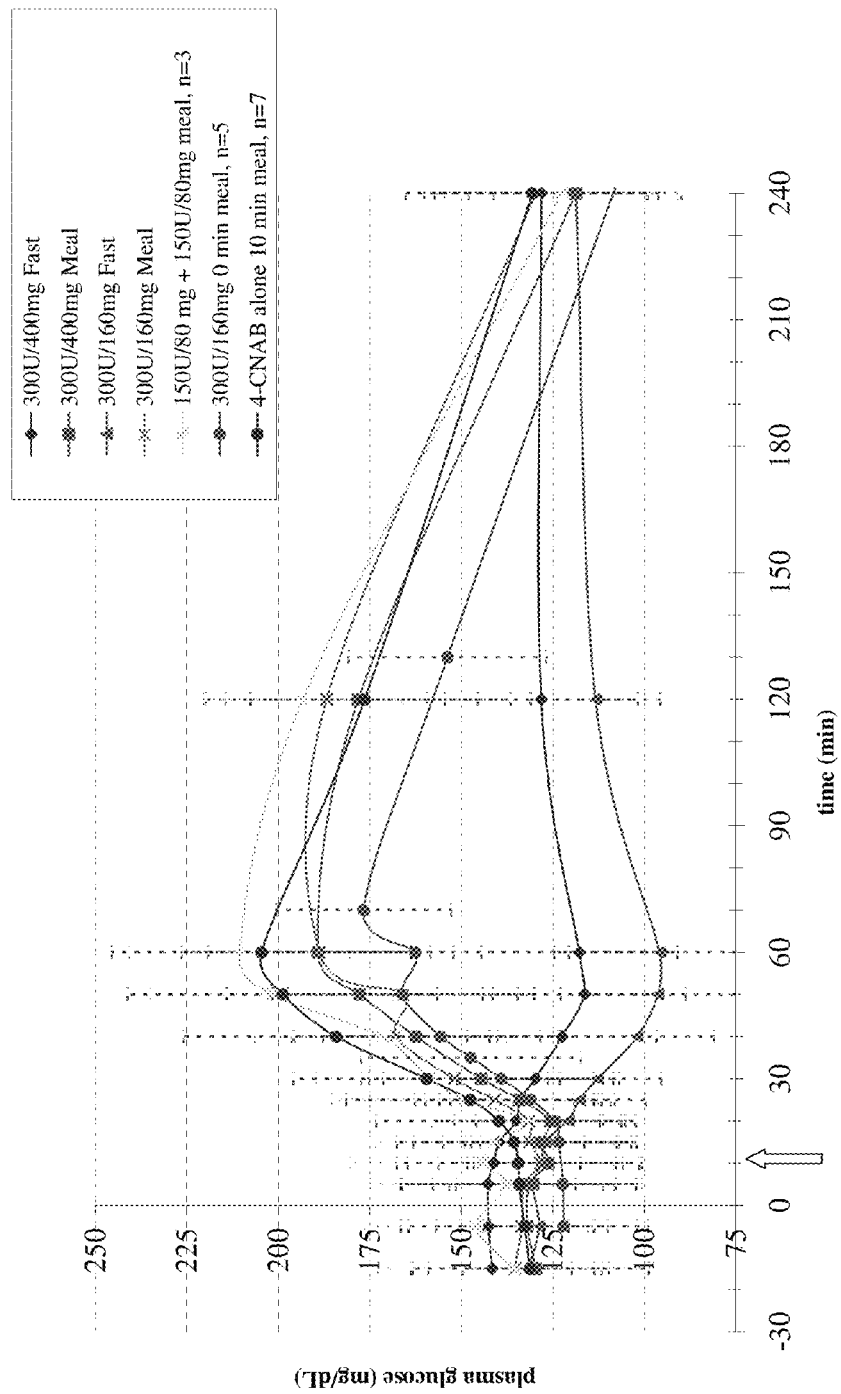
FIG. 24 is a plot of Preliminary Mean+/−SD Plasma Glucose concentration Following Oral Administration of Insulin/4-CNAB Tablets to Type 2 Diabetic Patients with or without a Meal.

FIG. 23 shows graphs of mean (for all eight subjects) percent change in plasma glucose concentration from baseline levels following oral administration of the various Insulin/4-CNAB tablet combinations described above to type 2 diabetic patients, both with and without a meal. FIG. 24 shows a comparison of the mean (for all eight subjects) percent change in plasma glucose concentration for only the 300 U Insulin/160 mg 4-CNAB tablets and the 4-CNAB alone tablets, in both cases 10 minutes before a meal. These figures are similar to FIGS. 12 and 14, except that plasma glucose concentration, instead of blood glucose concentration, was measured.

Table 49 below sets forth the data for mean absolute blood glucose concentration vs. time:

TABLE 49

Mean Blood Glucose Concentration vs. Time

| time (min) | 300 U/400 mg fasted (N = 8) | 300 U/400 mg 10 min meal (N = 8) | 300 U/160 mg fasted (N = 8) | 300 U/160 mg 10 min meal (N = 8) | 150 U/80 mg -10 min + 150 U/80 mg @ 0 min w/meal (N = 3) | 300 U/160 mg 0 min meal (N = 5) | 4-CNAB alone 10 min meal (N = 7) |
|---|---|---|---|---|---|---|---|
| Mean (mg/dL) | | | | | | | |
| -15 | 134 | 128 | 128 | 130 | 134 | 127 | 133 |
| -5 | 135 | 130 | 129 | 129 | 135 | 127 | 133 |
| 5 | 132 | 134 | 128 | 127 | 133 | 126 | 132 |
| 10 | 130 | 130 | 124 | 125 | 131 | 127 | 131 |
| 15 | 130 | 127 | 123 | 124 | 129 | 132 | 132 |
| 20 | 128 | 123 | 119 | 120 | 125 | 137 | 133 |
| 25 | 125 | 129 | 115 | 126 | 134 | 144 | 141 |
| 30 | 122 | 137 | 109 | 136 | 140 | 152 | 157 |
| 40 | 117 | 156 | 98 | 150 | 155 | 166 | 176 |
| 50 | 112 | 168 | 94 | 161 | 192 | 172 | 195 |
| 60 | 113 | 176 | 94 | 172 | 197 | 172 | 197 |
| 90 | 117 | 183 | 105 | 175 | 209 | 169 | 198 |
| 120 | 124 | 170 | 115 | 173 | 198 | 162 | 192 |
| 150 | 115 | 151 | 117 | 156 | 170 | 145 | 171 |
| 180 | 124 | 135 | 122 | 146 | 143 | 133 | 158 |
| 210 | 123 | 123 | 119 | 127 | 129 | 119 | 147 |
| 240 | 121 | 122 | 117 | 122 | 122 | 112 | 136 |
| Standard Deviation (SD) | | | | | | | |
| -15 | 21.0 | 18.5 | 13.0 | 23.9 | 28.1 | 16.9 | 29.2 |
| -5 | 21.6 | 15.5 | 17.6 | 26.6 | 27.8 | 16.9 | 29.3 |
| 5 | 21.2 | 18.1 | 18.5 | 25.1 | 27.6 | 16.0 | 28.1 |
| 10 | 24.2 | 18.7 | 15.9 | 24.4 | 28.5 | 15.1 | 28.7 |
| 15 | 22.6 | 16.6 | 15.3 | 21.3 | 24.4 | 14.4 | 29.4 |
| 20 | 21.7 | 16.1 | 14.3 | 22.1 | 24.3 | 21.2 | 27.7 |
| 25 | 18.2 | 20.8 | 13.9 | 25.0 | 26.2 | 19.8 | 26.4 |
| 30 | 18.0 | 27.8 | 16.5 | 24.8 | 27.0 | 25.1 | 32.3 |
| 40 | 20.4 | 27.4 | 20.0 | 28.9 | 25.1 | 25.1 | 36.3 |
| 50 | 21.1 | 28.3 | 23.8 | 28.7 | 16.1 | 21.4 | 41.4 |
| 60 | 23.4 | 31.0 | 25.9 | 24.4 | 15.7 | 18.6 | 37.5 |
| 90 | 23.4 | 30.4 | 16.2 | 29.9 | 24.4 | 24.1 | 40.3 |
| 120 | 25.4 | 36.1 | 19.6 | 25.8 | 17.4 | 29.1 | 40.6 |
| 150 | 22.1 | 30.1 | 20.8 | 28.2 | 37.6 | 30.3 | 36.4 |
| 180 | 25.7 | 29.2 | 22.3 | 32.6 | 36.0 | 26.9 | 30.7 |
| 210 | 29.0 | 28.4 | 22.8 | 27.7 | 33.1 | 19.4 | 32.5 |
| 240 | 26.5 | 24.3 | 21.3 | 27.3 | 25.0 | 13.5 | 32.9 |

Figure 25:
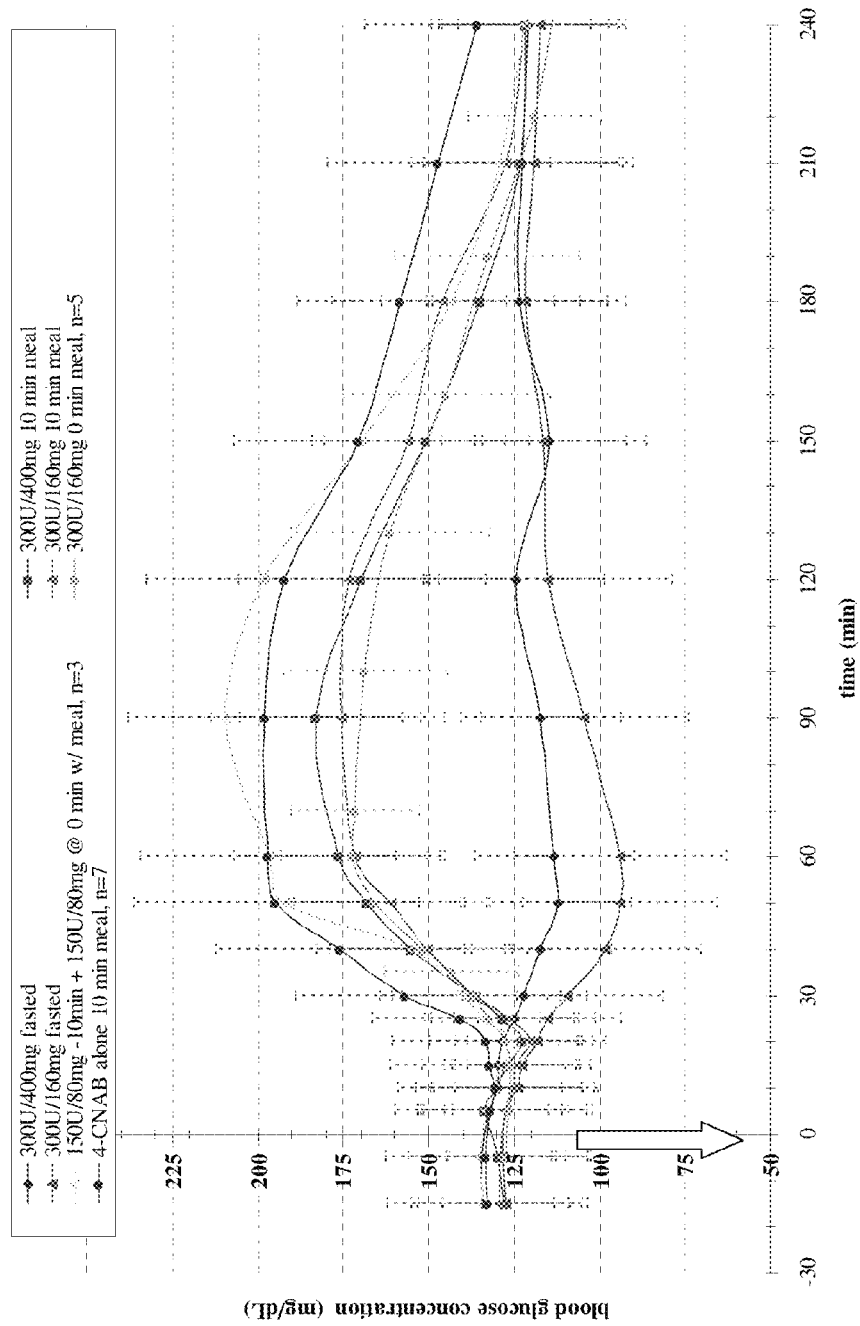
FIG. 25 is a plot of Preliminary Mean+/−SD Blood (SuperGL) Glucose concentration Following Oral Administration of Insulin/4-CNAB Tablets to type 2 diabetic patients with or without a Meal.
Figure 26:
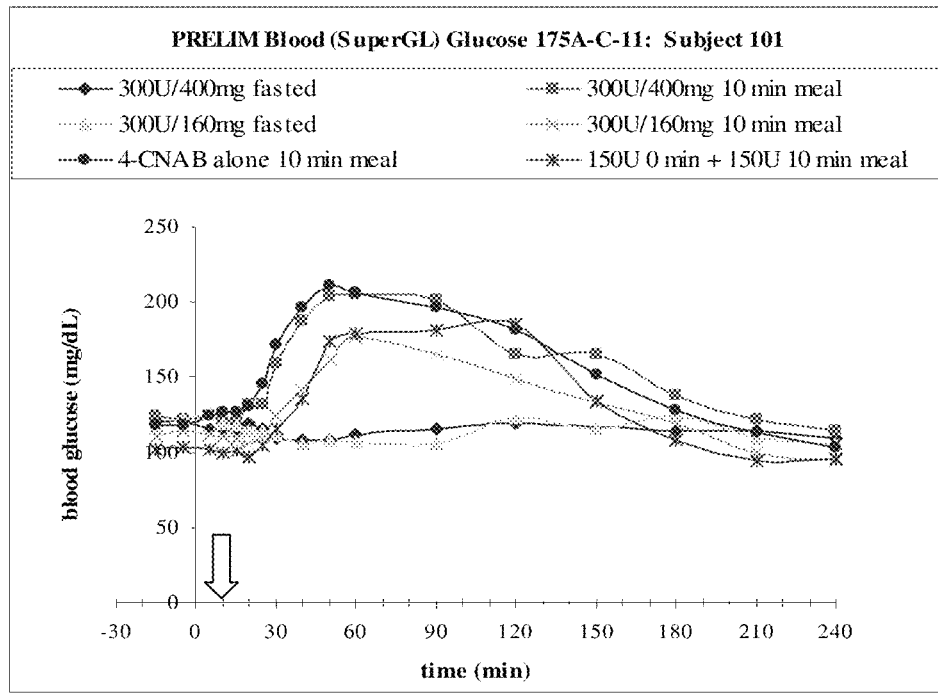
FIGS. 26-33 are plots of Preliminary Blood (SuperGL) Glucose concentrations for Subjects 101-108, respectively.
Figure 27:
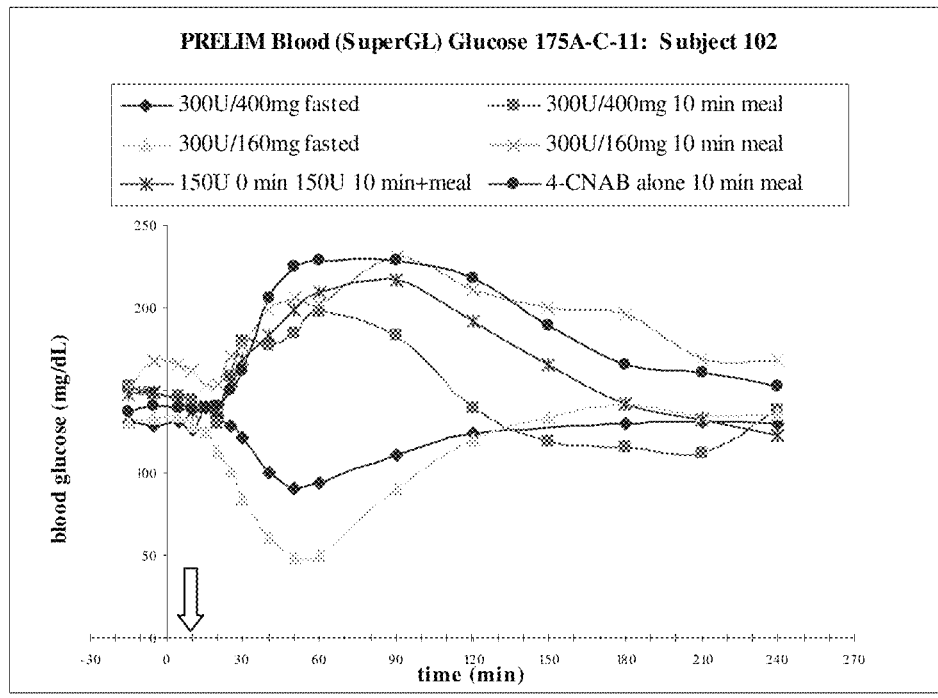
Figure 28:
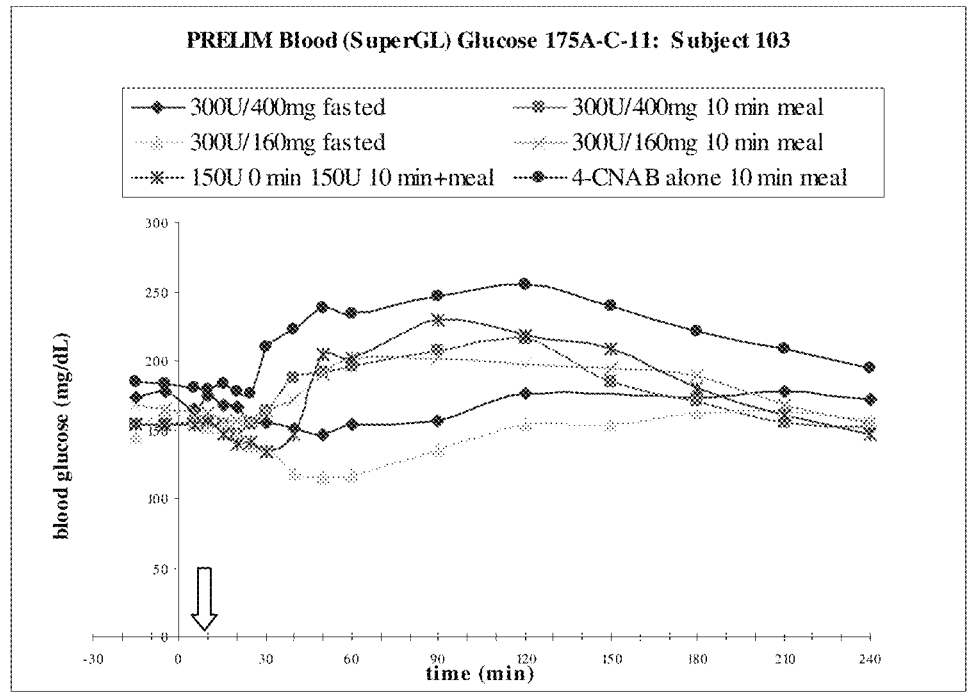
Figure 29:
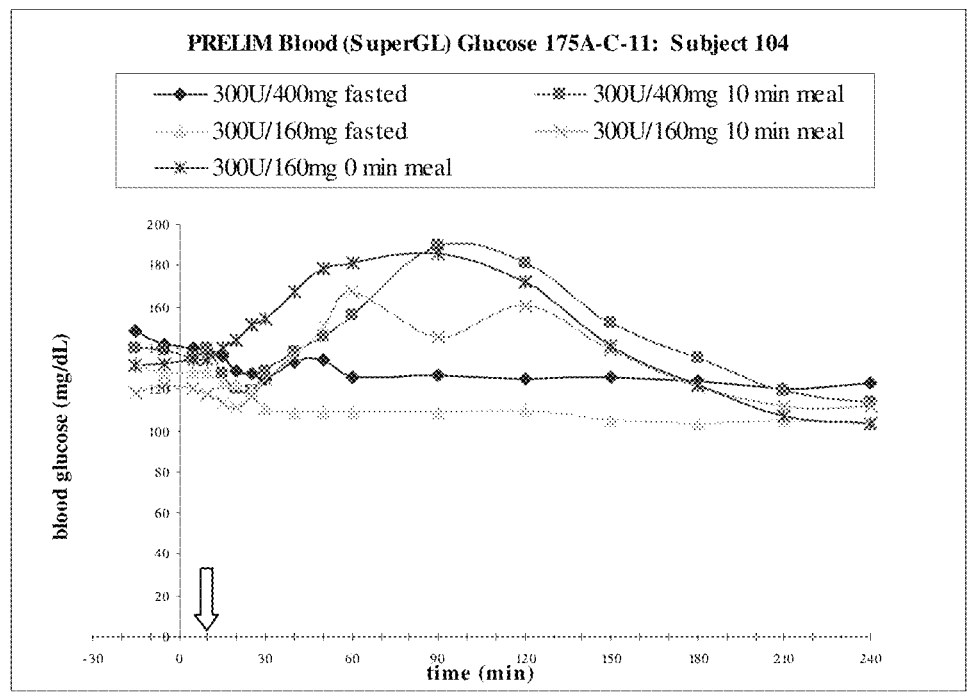
Figure 30:
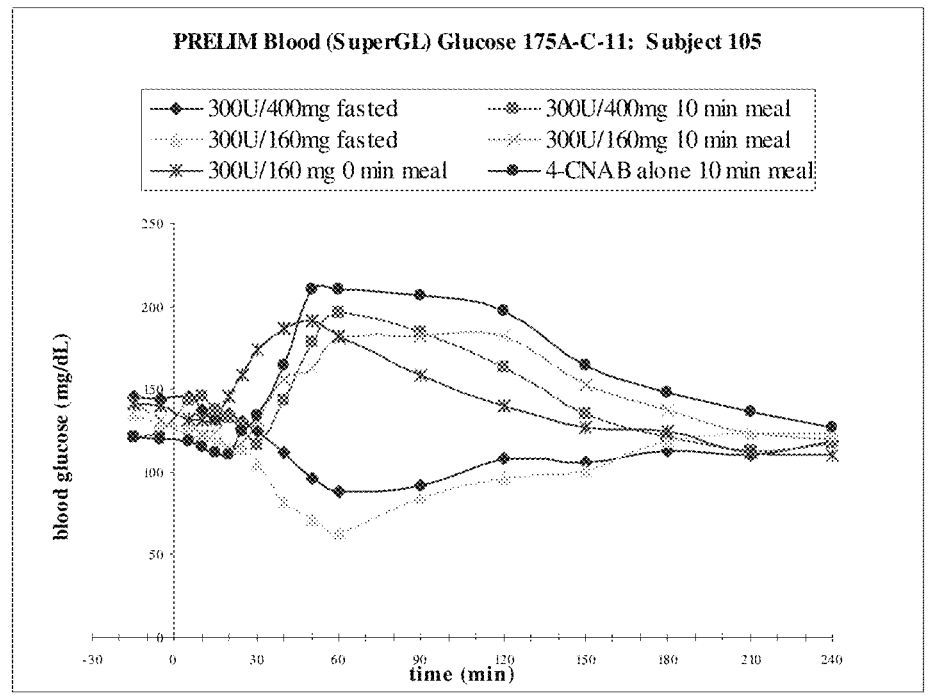
Figure 31:
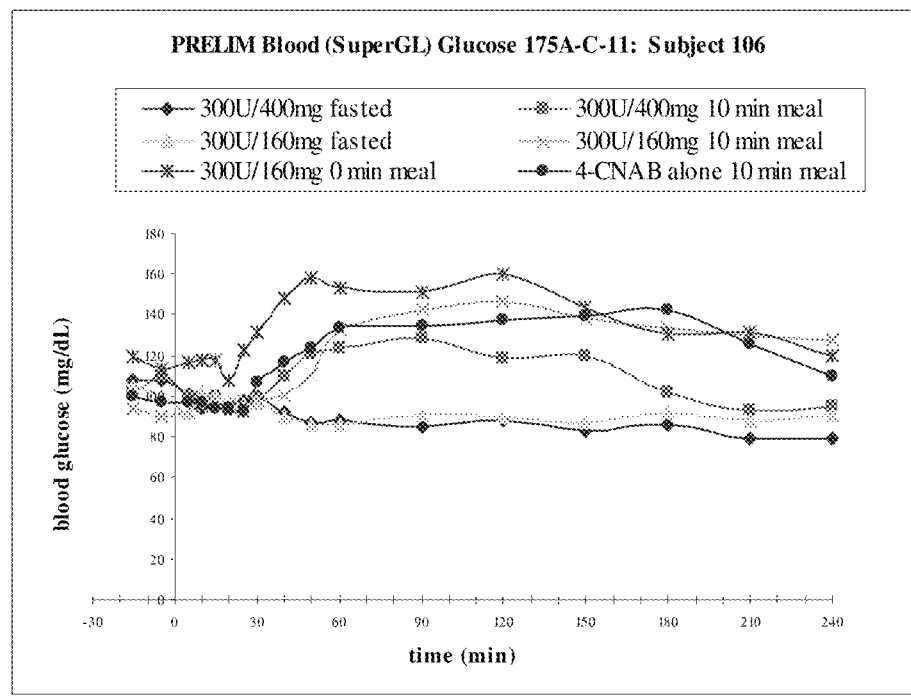
Figure 32:
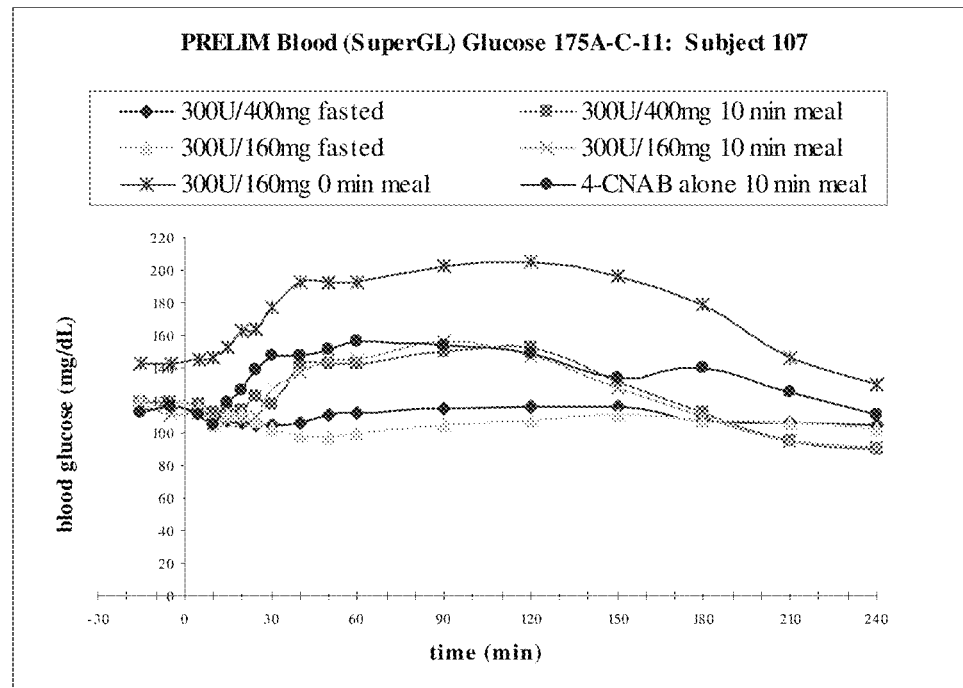

FIG. 25 shows graphs of mean (for all eight subjects) blood glucose concentration following oral administration of the various Insulin/4-CNAB tablet combinations described above to type 2 diabetic patients, both with and without a meal. The mean FIG. 25 is based upon FIGS. 26-33, which show blood glucose concentration vs. time curves for subjects 101-108 following oral administration of the various Insulin/4-CNAB tablet combinations described above.

Table 50 below sets forth the data for mean serum insulin concentration vs. time:

TABLE 50

Mean Serum Insulin Concentration vs. Time

| time (min) | 300 U/400 mg fasted (N = 8) | 300 U/400 mg 10 min meal (N = 8) | 300 U/160 mg fasted (N = 8) | 300 U/160 mg 10 min meal (N = 8) | 150 U/80 mg -10 min + 150 U/80 mg @ 0 min w/meal (N = 3) | 300 U/160 mg 0 min meal (N = 5) | 4-CNAB alone 10 min meal (N = 7) |
|---|---|---|---|---|---|---|---|
| Mean (ng/mL) | | | | | | | |
| -15 | 18.9 | 23.2 | 22.2 | 21.6 | 22.7 | 17.0 | 19.7 |
| -5 | 19.6 | 21.7 | 18.6 | 20.1 | 17.1 | 20.3 | 18.7 |
| 5 | 22.1 | 24.9 | 25.8 | 31.3 | 16.8 | 26.7 | 15.3 |
| 10 | 42.2 | 56.3 | 100.4 | 62.4 | 40.5 | 42.7 | 17.9 |
| 15 | 81.7 | 78.5 | 168.0 | 65.9 | 63.2 | 47.4 | 24.8 |
| 20 | 90.1 | 61.6 | 147.9 | 53.0 | 72.3 | 50.7 | 28.7 |
| 25 | 66.3 | 50.3 | 119.7 | 51.7 | 81.4 | 51.9 | 33.0 |
| 30 | 49.9 | 54.3 | 84.8 | 52.1 | 95.0 | 55.3 | 45.2 |
| 40 | 29.2 | 57.4 | 42.7 | 56.0 | 98.5 | 66.4 | 58.6 |
| 50 | 20.5 | 61.6 | 25.4 | 66.4 | 106.1 | 74.4 | 66.0 |

TABLE 50-continued

Mean Serum Insulin Concentration vs. Time

| time (min) | 300 U/400 mg fasted (N = 8) | 300 U/400 mg 10 min meal (N = 8) | 300 U/160 mg fasted (N = 8) | 300 U/160 mg 10 min meal (N = 8) | 150 U/80 mg -10 min + 150 U/80 mg @ 0 min w/meal (N = 3) | 300 U/160 mg 0 min meal (N = 5) | 4-CNAB alone 10 min meal (N = 7) |
|---|---|---|---|---|---|---|---|
| 60 | 29.4 | 73.9 | 20.5 | 73.1 | 113.4 | 83.3 | 78.7 |
| 120 | 17.3 | 71.6 | 12.1 | 83.6 | 104.9 | 93.4 | 83.9 |
| 240 | 15.9 | 25.2 | 15.0 | 47.9 | 18.2 | 69.1 | 24.9 |
| Standard Deviation (SD) | | | | | | | |
| −15 | 11.04 | 19.45 | 16.74 | 19.31 | 8.21 | 14.09 | 15.78 |
| −5 | 9.63 | 11.65 | 8.50 | 16.51 | 5.39 | 12.01 | 14.51 |
| 5 | 10.60 | 14.30 | 15.27 | 20.42 | 5.77 | 12.07 | 7.80 |
| 10 | 31.64 | 23.07 | 64.02 | 29.82 | 6.13 | 24.88 | 13.74 |
| 15 | 58.49 | 37.67 | 117.46 | 26.96 | 22.93 | 21.72 | 11.95 |
| 20 | 75.06 | 26.64 | 94.77 | 30.10 | 33.52 | 18.23 | 14.36 |
| 25 | 45.23 | 18.65 | 94.68 | 30.23 | 42.76 | 17.23 | 21.17 |
| 30 | 33.72 | 30.31 | 61.13 | 36.87 | 65.55 | 22.10 | 27.94 |
| 40 | 19.17 | 40.97 | 27.22 | 37.80 | 78.31 | 45.79 | 43.33 |
| 50 | 9.20 | 51.21 | 13.22 | 50.09 | 59.32 | 56.60 | 46.39 |
| 60 | 30.81 | 59.88 | 9.31 | 54.07 | 58.83 | 71.24 | 57.68 |
| 120 | 9.12 | 32.46 | 5.64 | 89.48 | 32.72 | 63.82 | 47.49 |
| 240 | 6.95 | 21.15 | 6.37 | 84.60 | 8.25 | 91.69 | 18.01 |

Figure 34:
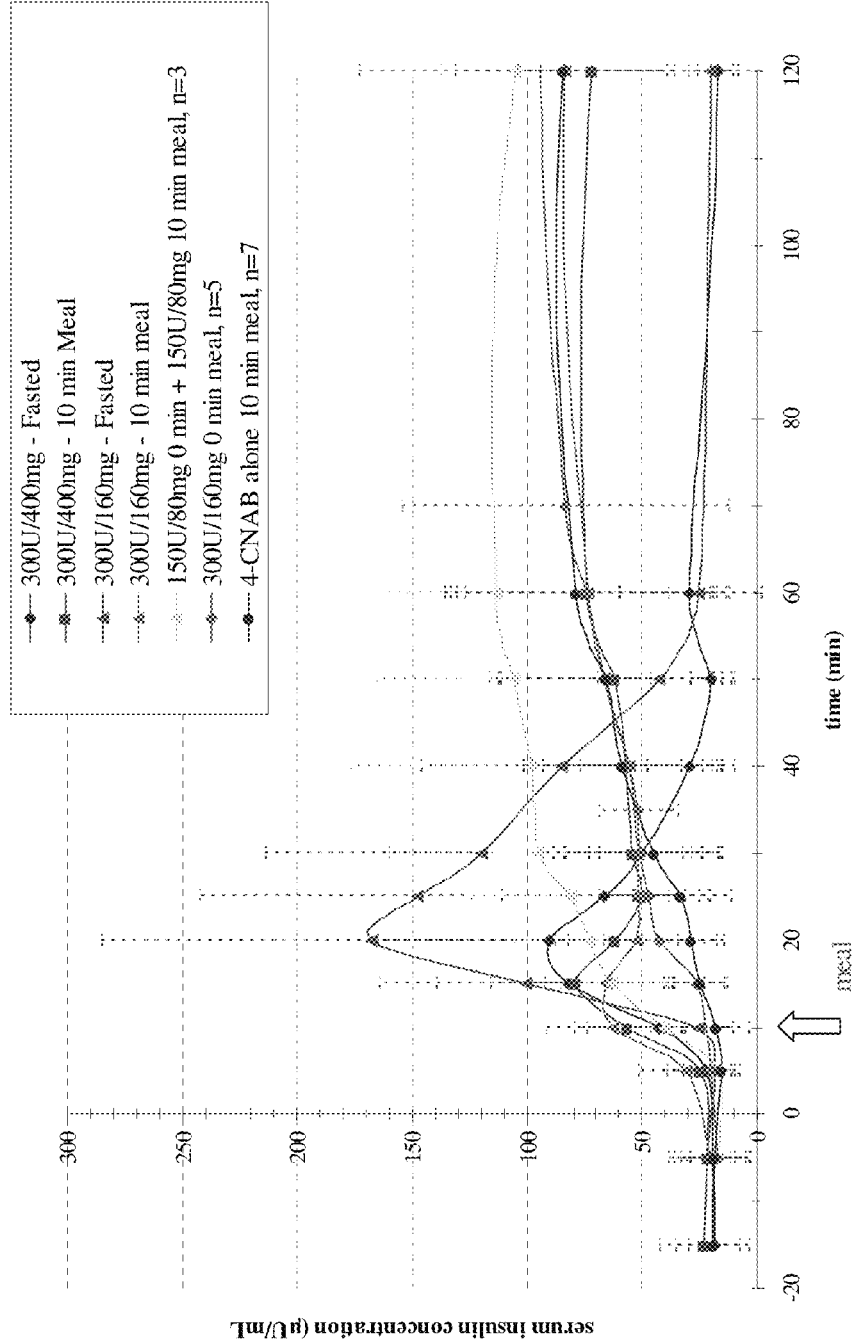
FIG. 34 is a plot of Mean+/−SD Serum Insulin Concentration Following a Single Oral Administration of Insulin/4-CNAB Tablets to Fasted or Fed Type 2 Diabetic Patients.

FIG. 34 shows curves of mean (for all eight subjects) serum insulin concentration following oral administration of the various Insulin/4-CNAB tablet combinations described above to type 2 diabetic patients, both with and without a meal. The mean FIG. 34 is based upon FIGS. 36-43, which show graphs of serum insulin concentration vs. time following oral administration of the various Insulin/4-CNAB tablet combinations described above for subjects 101-108, both with and without a meal.

Figure 35:
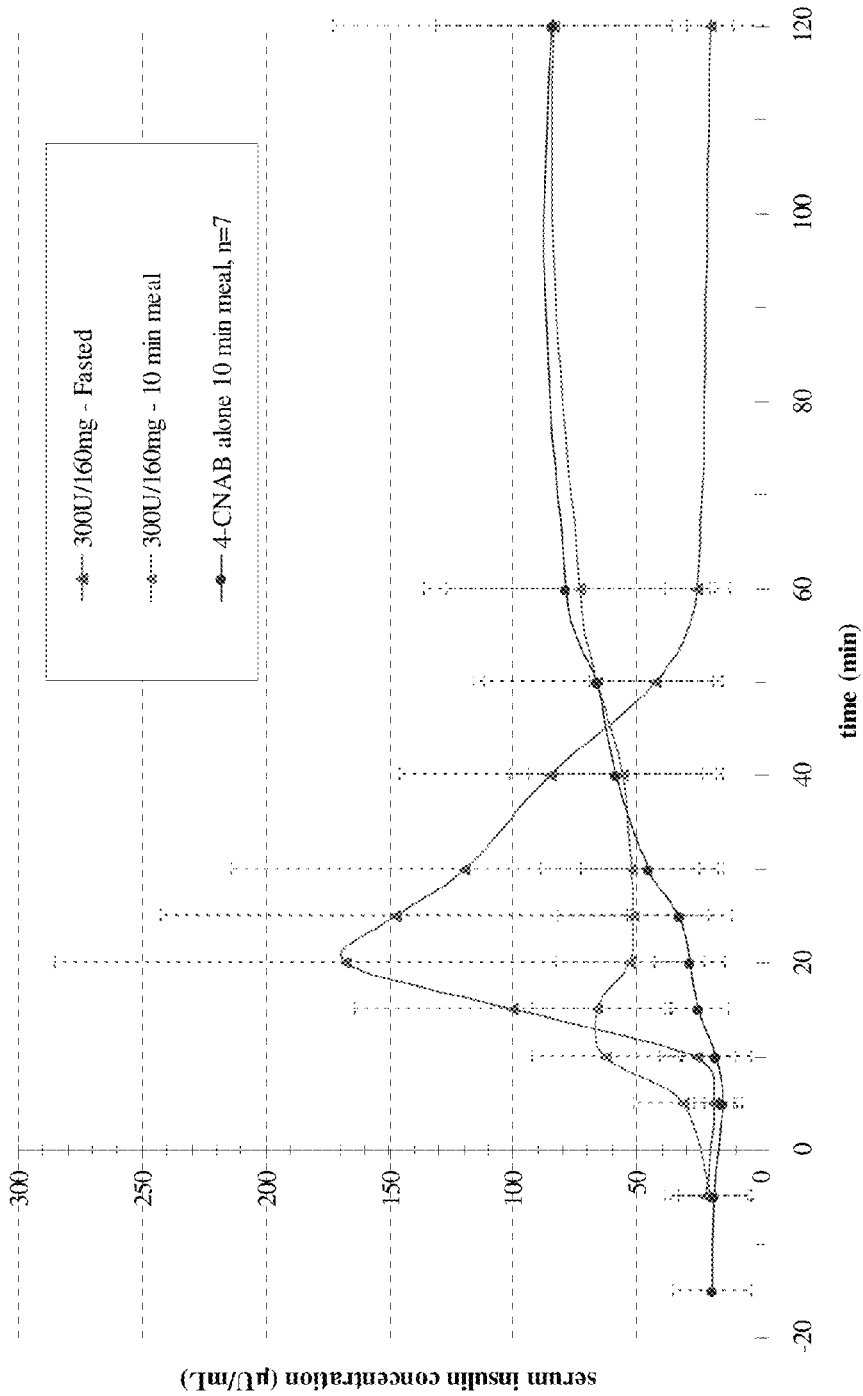
FIG. 35 is a plot of Mean+/−SD Serum Insulin Concentration Following a Single Oral Administration of Insulin/4-CNAB Tablets to Fasted or Fed Type 2 Diabetic Patients.
Figure 36:
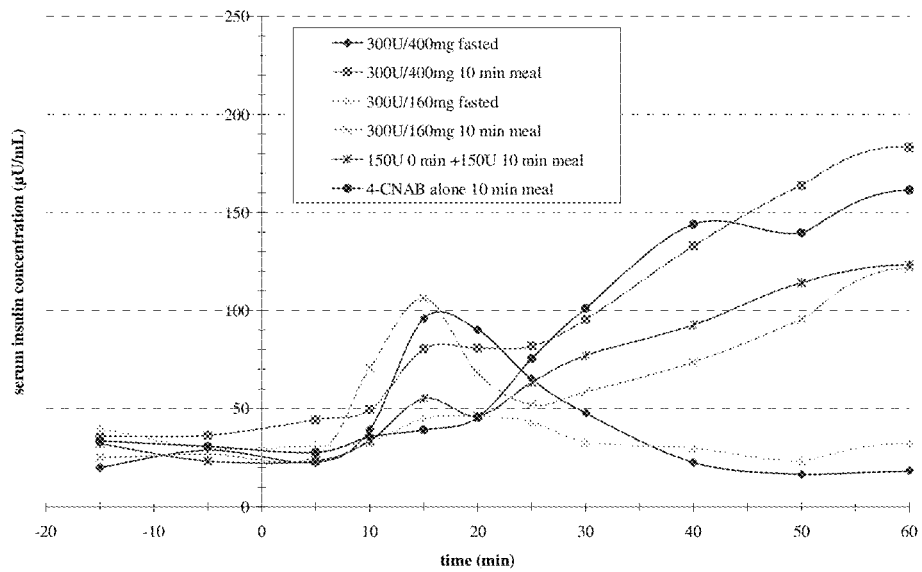
FIGS. 36-43 are plots of Serum Insulin Concentration Following a Single Oral Administration of Insulin/4-CNAB Tablets to Fasted Type 2 Diabetic Patients Subjects 101-108, respectively.
Figure 37:
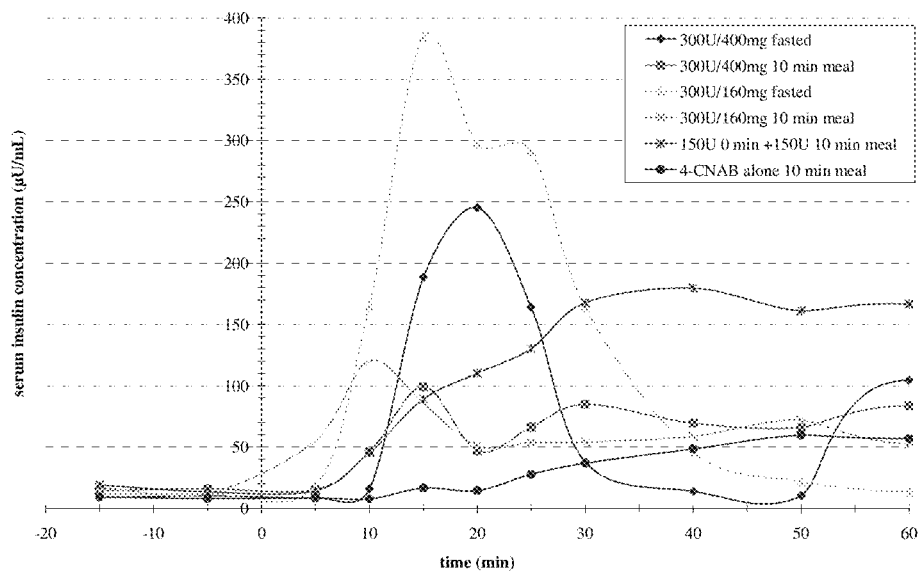
Figure 38:
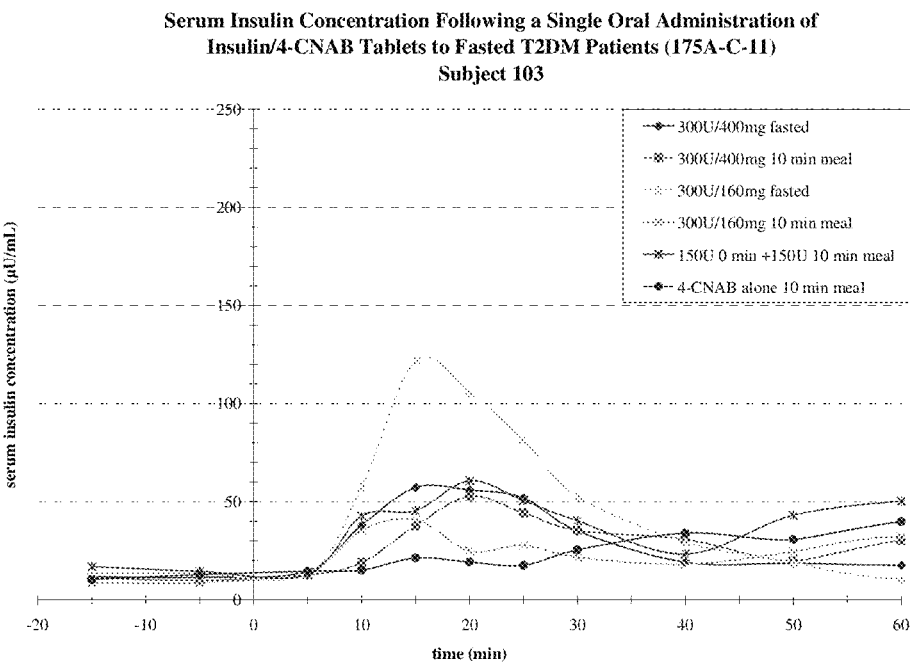
Figure 39:
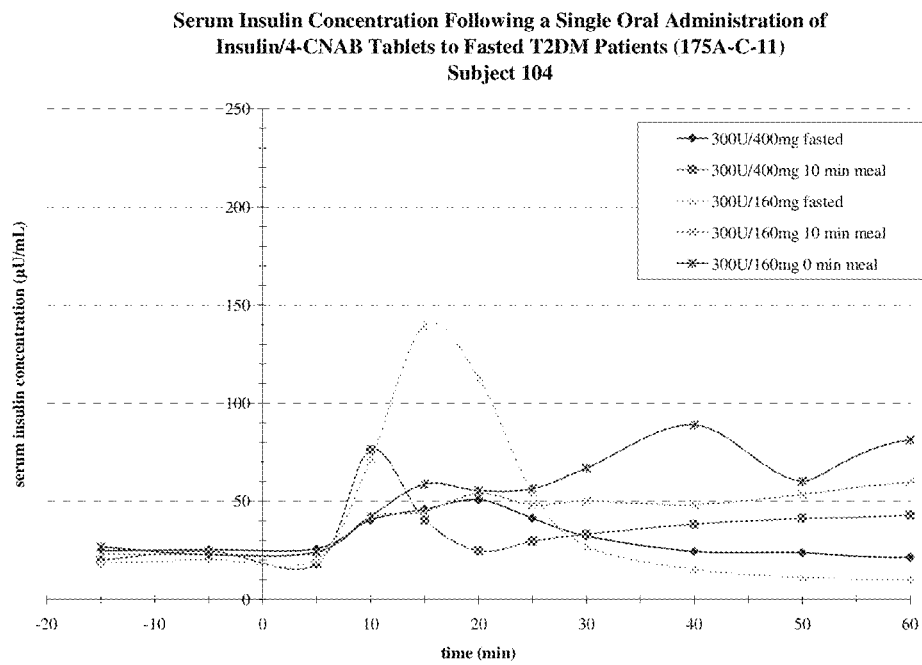
Figure 40:
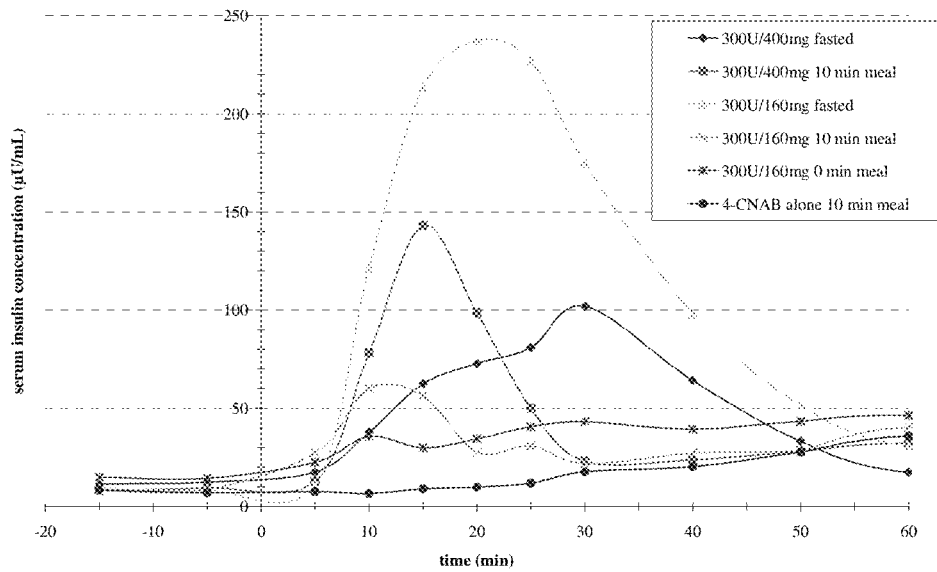
Figure 41:
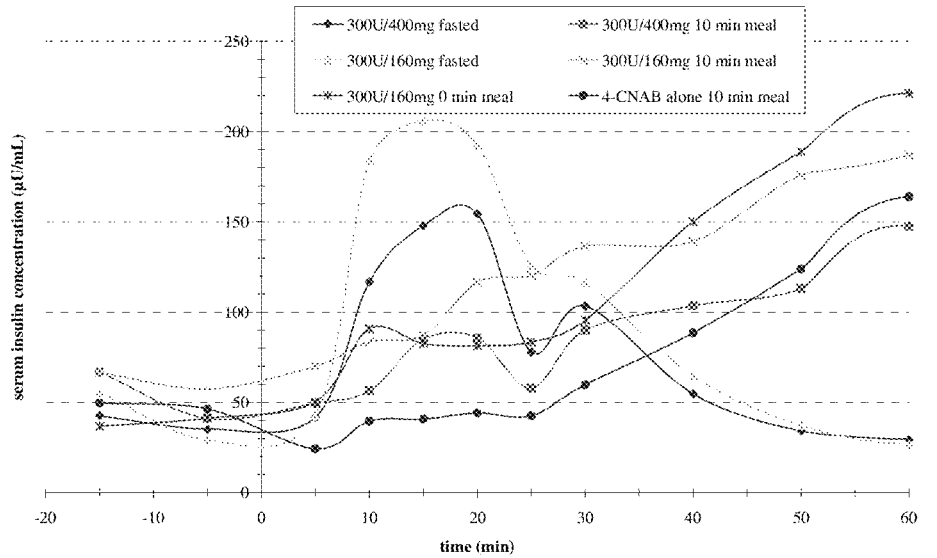
Figure 42:
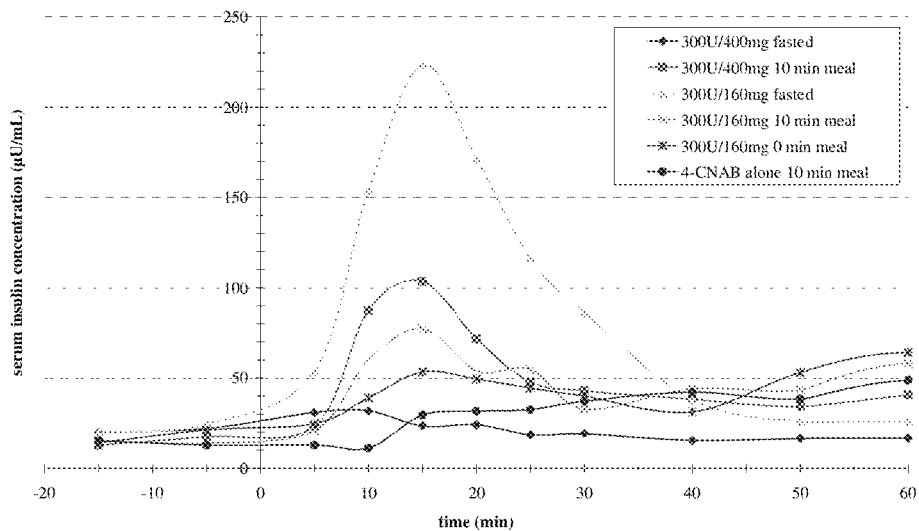
Figure 43:
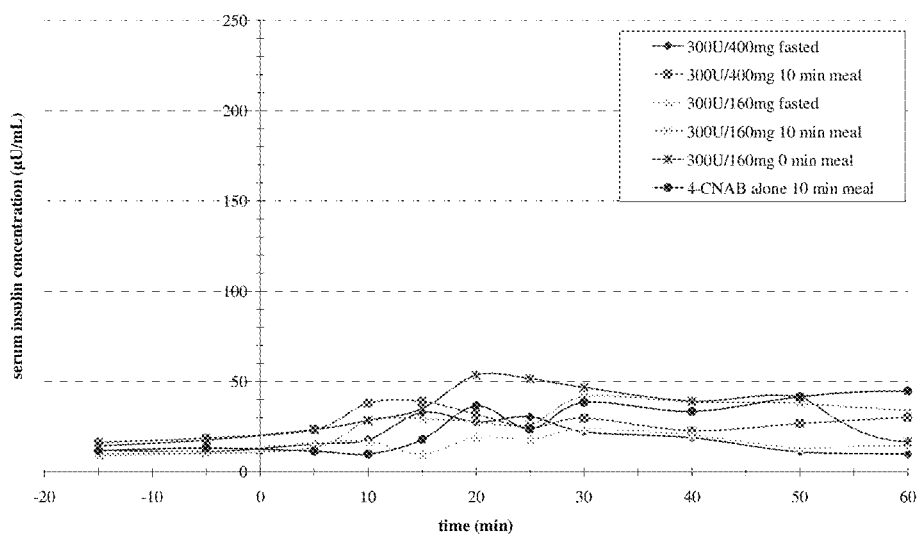
Figure 44:
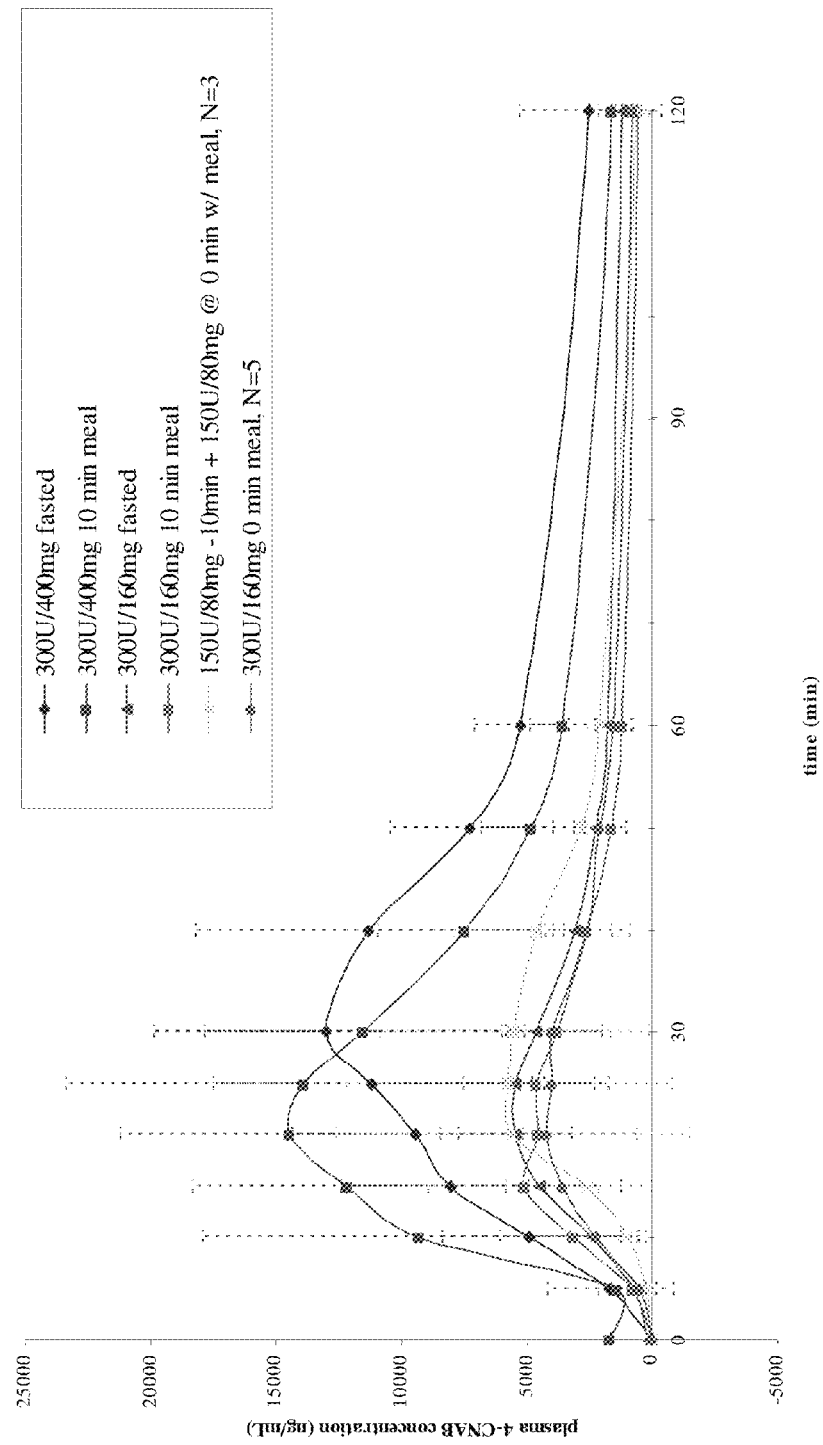
FIG. 44 is a plot of Mean+/−SD Plasma 4-CNAB Concentration Following a Single Oral Tablet Administration of Insulin/4-CNAB to Fed or Fasted Type 2 Diabetic Patients.

FIG. 35 shows a comparison of graphs of mean (for all eight subjects) serum insulin concentration vs. time for only the 300 U Insulin/160 mg 4-CNAB tablets (both fasted afterwards and at 10 minutes before a meal) and the control (4-CNAB alone) 10 minutes before a meal.

The $C_{max}$ was somewhat higher, and the $t_{max}$ was somewhat later, for the fasted state than it was for the prandial state (administration 0 or 10 minutes prior to a meal) in both the 300 U insulin/160 mg 4-CNAB ratio group and the 300 U insulin/400 mg 4-CNAB ratio group. For example, for the 300 U insulin/160 mg 4-CNAB ratio tablet, mean fasted $C_{max}$ was about 170 μU/mL and mean fasted $t_{max}$ was at about 20 minutes post administration, and mean $C_{max}$ was about 65 μU/mL and mean $t_{max}$ was at about 15 minutes post administration when administered 10 minutes prior to a meal. Similarly, for the 300 U insulin/400 mg 4-CNAB ratio tablet, mean fasted $C_{max}$ was about 90 μU/mL and mean fasted $t_{max}$ was at about 20 minutes post administration, and mean $C_{max}$ was about 75 μU/mL and mean $t_{max}$ was at about 15 minutes post administration when administered 10 minutes prior to a meal.

Table 51 below sets forth the data for mean plasma 4-CNAB concentration vs. time:

TABLE 51

Mean Plasma 4-CNAB Concentration vs. Time

| time (min) | 300 U/400 mg fasted (N = 8) | 300 U/400 mg 10 min meal (N = 8) | 300 U/160 mg fasted (N = 8) | 300 U/160 mg 10 min meal (N = 8) | 150 U/80 mg 10 min meal + 150 U/80 mg 0 min meal (N = 3) | 300 U/160 mg 0 min meal (N = 5) |
|---|---|---|---|---|---|---|
| Mean (ng/mL) | | | | | | |
| 0 | 0 | 1,680 | 177 | 0 | 0 | 0 |
| 5 | 1,703 | 1,445 | 716 | 772 | 223 | 488 |
| 10 | 4,903 | 9,274 | 2,416 | 3,181 | 990 | 2283 |
| 15 | 8,081 | 12,134 | 4,459 | 5,109 | 2,622 | 3,590 |
| 20 | 9,468 | 14,489 | 5,461 | 4,564 | 5,593 | 4,230 |
| 25 | 11,184 | 13,875 | 5,460 | 4,650 | 5,743 | 4,010 |
| 30 | 12,969 | 11,519 | 4,624 | 3,808 | 5,550 | 4,014 |
| 40 | 11,340 | 7,469 | 3,098 | 2,607 | 4,647 | 2,598 |
| 50 | 7,270 | 4,815 | 2,273 | 1,641 | 2,810 | 2,106 |
| 60 | 5,245 | 3,598 | 1,789 | 1,197 | 2,147 | 1,539 |
| 120 | 2,513 | 1,653 | 1,199 | 607 | 662 | 820 |
| 240 | 344 | 732 | 145 | 303 | 224 | 243 |
| Standard Deviation (SD) | | | | | | |
| 0 | 0.0 | 0.0 | 0.0 | 0.0 | 0.0 | 0.0 |
| 5 | 2,494.0 | 749.2 | 572.8 | 856.2 | 210.0 | 290.8 |
| 10 | 3,523.6 | 8,713.2 | 1,495.1 | 2,684.1 | 1,010.5 | 361.0 |
| 15 | 4,394.9 | 6,250.0 | 3,881.1 | 3,846.0 | 1,421.3 | 2,544.2 |
| 20 | 4,930.2 | 6,734.3 | 4,492.7 | 3,890.2 | 987.6 | 7,035.0 |
| 25 | 6,337.2 | 9,503.9 | 3,787.1 | 2,899.7 | 1,682.0 | 6,457.8 |

TABLE 51-continued

Mean Plasma 4-CNAB Concentration vs. Time

| time (min) | 300 U/400 mg fasted (N = 8) | 300 U/400 mg 10 min meal (N = 8) | 300 U/160 mg fasted (N = 8) | 300 U/160 mg 10 min meal (N = 8) | 150 U/80 mg 10 min meal + 150 U/80 mg 0 min meal (N = 3) | 300 U/160 mg 0 min meal (N = 5) |
|---|---|---|---|---|---|---|
| 30 | 6,952.6 | 6,393.7 | 2,270.2 | 2,095.7 | 1,980.6 | 5,359.2 |
| 40 | 6,877.7 | 3,483.1 | 1,227.4 | 1,007.7 | 1,657.5 | 3,256.2 |
| 50 | 3,250.3 | 2,041.4 | 613.5 | 572.0 | 1,061.3 | 155.2 |
| 60 | 1,870.0 | 1,289.1 | 604.3 | 408.1 | 684.1 | 484.0 |
| 120 | 2,823.8 | 523.9 | 1,071.5 | 256.1 | 667.9 | 261.2 |
| 240 | 134.7 | 722.1 | 72.6 | 253.2 | 197.6 | 160.0 |

Figure 33:
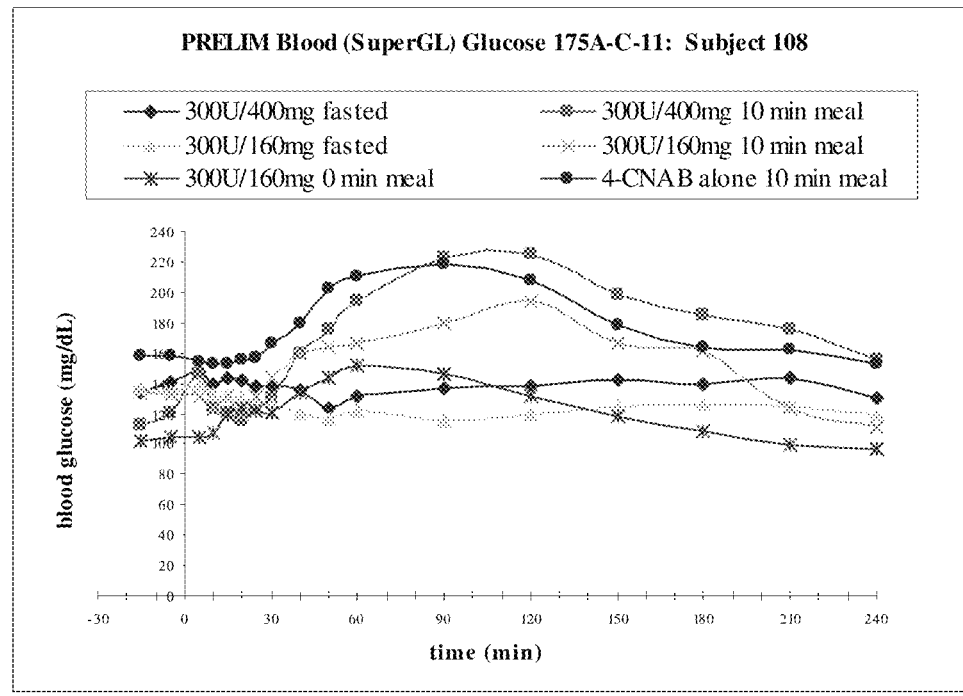

FIG. 33 shows graphs of mean (for all eight subjects) plasma 4-CNAB concentration vs. time following oral administration of the various Insulin/4-CNAB tablet combinations described above to type 2 diabetic patients, both with and without a meal.

For the 300 U insulin/160 mg 4-CNAB ratio tablet, mean fasted $t_{max}$ was at about 20-25 minutes post administration, and mean $t_{max}$ was at about 15 minutes post administration when administered 10 minutes prior to a meal. For the 300 U insulin/400 mg 4-CNAB ratio tablet, mean fasted $t_{max}$ was at about 30 minutes post administration, and mean $t_{max}$ was at about 20 minutes post administration when administered 10 minutes prior to a meal.

Figure 46:
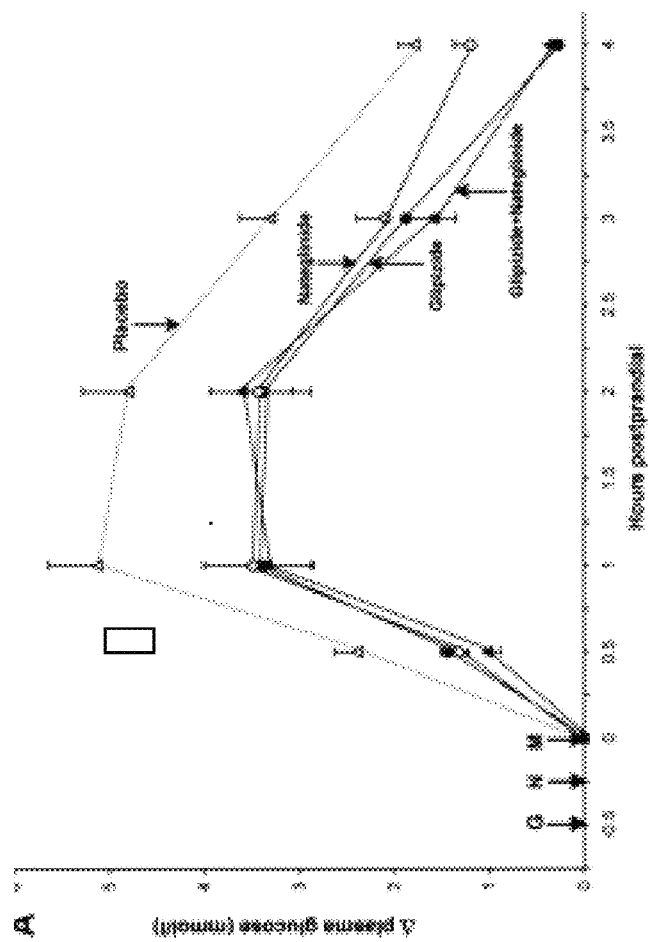
FIG. 46 is a prior art graph showing mean change in plasma glucose concentration from baseline for administration of placebo, glipizide, nateglinide, and glipizide plus nateglinide.

Table 52 below sets forth the data for mean plasma C-peptide concentration vs. time:

meal as observed with the secretagogues. This can be seen by comparing glucose excursion profiles shown in FIGS. 14 and 46. In FIG. 3, the change in blood glucose concentration from baseline of 300 U insulin/160 mg 4-CNAB administered 10 minutes before a meal is compared with that for 4-CNAB alone administered 10 minutes before a meal (control). Here, the oral insulin dose resulted in about a 30% reduction in the post-prandial glucose excursion for about 60 minutes. In FIG. 46, which is taken from M.F. Carrot et al., *Control of Post-prandial Hyperglycemia*, Diabetes Care, Volume 25, page 2152 (2002), the change in plasma glucose concentration from baseline is shown for placebo, for glipizide, for nateglinide, and for glipizide plus nateglinide. Here, the secretagogues resulted in about a 30% reduction sustained for about 60 minutes. Thus, the reduction in glucose excursion (about

TABLE 52

Mean Plasma C-Peptide Concentration vs. Time

| time (min) | 300 U/400 mg fasted (N = 8) | 300 U/400 mg 10 min meal (N = 8) | 300 U/160 mg fasted (N = 8) | 300 U/160 mg 10 min meal (N = 8) | 150 U/80 mg -10 min + 150 U/80 mg @ 0 min w/meal (N = 3) | 300 U/160 mg 0 min meal (N = 5) | 4-CNAB alone 10 min meal (N = 7) |
|---|---|---|---|---|---|---|---|
| Mean (ng/mL) | | | | | | | |
| −15 | 2.61 | 4.62 | 3.45 | 3.50 | 4.27 | 4.32 | 2.96 |
| −5 | 2.65 | 4.46 | 3.53 | 3.54 | 4.16 | 4.20 | 2.88 |
| 10 | 2.58 | 4.32 | 3.56 | 4.06 | 4.12 | 4.73 | 2.79 |
| 20 | 2.57 | 4.48 | 3.33 | 3.98 | 4.43 | 5.04 | 3.33 |
| 30 | 2.42 | 5.19 | 3.06 | 4.65 | 5.64 | 5.50 | 3.88 |
| 40 | 2.20 | 6.02 | 2.80 | 5.04 | 6.40 | 6.57 | 4.31 |
| 60 | 2.24 | 6.83 | 2.72 | 5.96 | 8.16 | 8.85 | 5.16 |
| 120 | 2.27 | 9.47 | 2.65 | 7.62 | 10.60 | 9.53 | 6.85 |
| 240 | 2.31 | 5.34 | 2.72 | 5.91 | 4.71 | 6.39 | 4.42 |
| Standard Deviation (SD) | | | | | | | |
| −15 | 1.045 | 1.781 | 1.694 | 2.101 | 1.426 | 0.700 | 2.424 |
| −5 | 1.028 | 1.776 | 1.420 | 2.127 | 1.393 | 0.821 | 2.227 |
| 10 | 1.259 | 1.762 | 1.378 | 2.546 | 1.369 | 0.501 | 2.163 |
| 20 | 1.068 | 1.667 | 1.121 | 2.295 | 1.472 | 0.318 | 2.195 |
| 30 | 1.071 | 2.210 | 1.269 | 1.860 | 1.731 | 1.020 | 2.556 |
| 40 | 0.904 | 2.942 | 1.354 | 2.556 | 3.602 | 1.640 | 2.881 |
| 60 | 0.981 | 3.320 | 1.531 | 2.616 | 3.706 | 2.903 | 3.390 |
| 120 | 1.121 | 2.848 | 1.569 | 4.361 | 5.088 | 3.584 | 4.031 |
| 240 | 0.835 | 2.702 | 1.110 | 4.804 | 4.059 | 1.724 | 3.390 |

Figure 45:
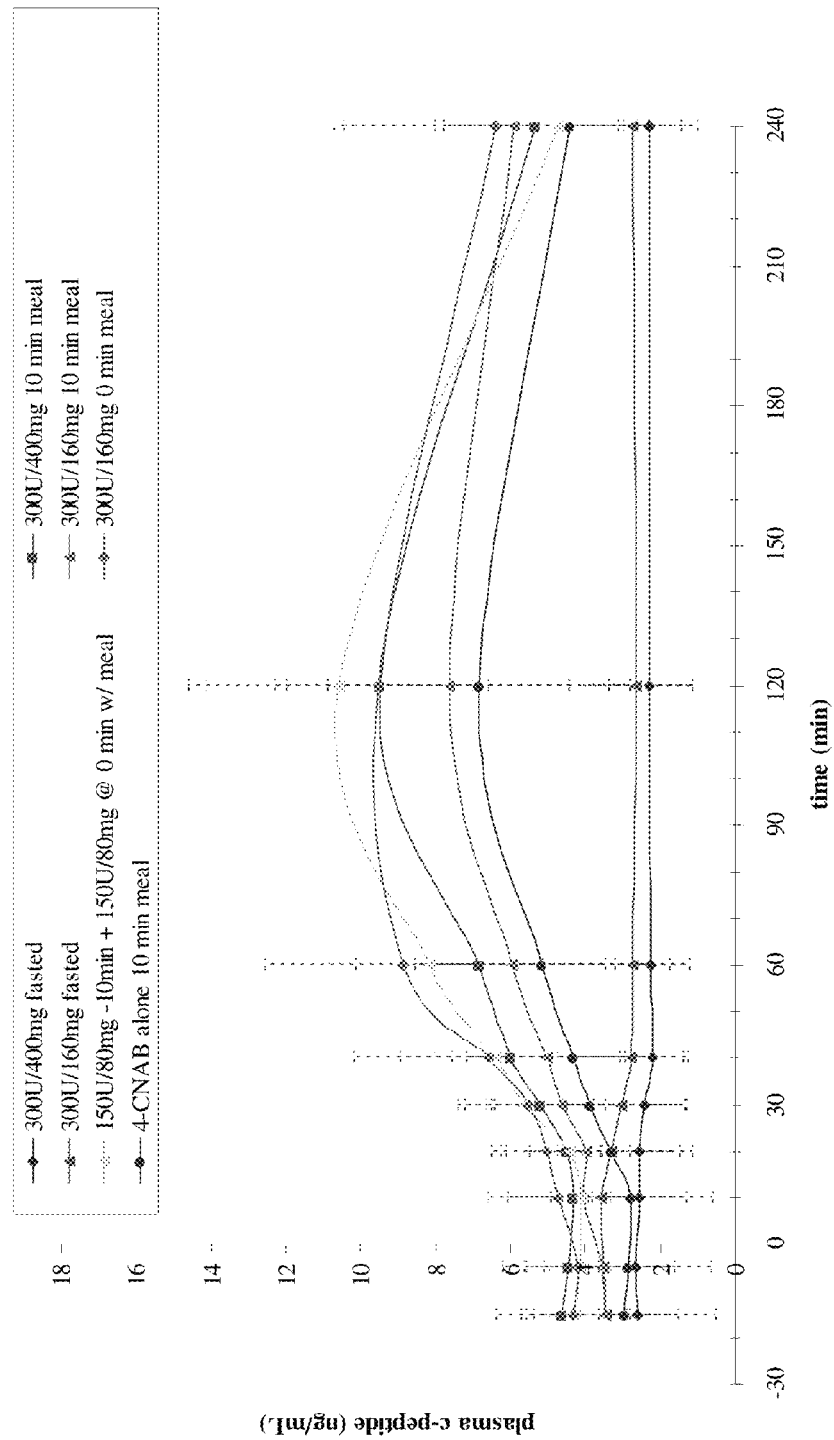
FIG. 45 is a plot of Mean+/−SD Plasma C-Peptide Concentration Following a Single Oral Administration of Insulin/4-CNAB Tablets to Fed or Fasted Type 2 Diabetic Patients.

FIG. 45 shows graphs of mean (for all eight subjects) plasma C-Peptide concentration vs. time following oral administration of the various Insulin/4-CNAB tablet combinations described above to type 2 diabetic patients, both with and without a meal.

In addition, when compared to drugs that enhance insulin secretion from the pancreatic beta cells, also called insulin secretagogues, the oral insulin formulation disclosed herein has the same effect on glucose suppression after a standard 25% to 30%) and the duration of action (sustained for about 60 minutes) was similar in both the oral insulin formulation and the secretagogues, evidence that secretagogues have same magnitude and duration of action as does oral insulin.

These results demonstrated a substantial enhancement of key attributes that were shown previously with an oral insulin capsule formulation. The tablet formulations disclosed herein, therefore, are suitable for oral administration at or shortly prior to mealtime in order to treat diabetes and other insulin-related dependencies. The current oral insulin tablet formulation represents the prospect of a convenient and effective oral insulin product that could be dosed very close to, i.e., within 10 minutes of, mealtime or immediately prior to mealtime.

Example 7

The aim of this study was to evaluate the safety, tolerability and pharmacokinetics of oral Insulin/4-CNAB following two weeks of preprandial and bedtime administration and to investigate the effect on glycemic control, insulin secretion capacity, insulin sensitivity and glucose tolerance in diet-treated type 2 diabetic subjects in good to moderate metabolic control. This was a single center, double-blind, randomized, controlled, parallel-group study in diet-controlled type 2 diabetic patients to determine whether repeated dosing of oral insulin can exert a sustained therapeutic effect in patients with type 2 diabetes.

More particularly, this study was to evaluate whether repeated dosing of oral insulin multiple times daily can exert a sustained therapeutic effect in patients with type 2 diabetes. The information gained in this study is to provide further insight into the beneficial effects of a preprandial treatment with oral insulin/4-CNAB in early phase type 2 diabetic patients.

Thirteen male and female patients, aged 30 to 75 years, with a Body Mass Index <32 kg/m$^2$ and HbA$_1$c between 6.1% and 7.8%, completed the study (out of the original fourteen patients who were enrolled). All the patients were diagnosed with type 2 diabetes for more than one year as defined by the American Diabetes Association and controlled their diabetes with diet only, not with any oral antidiabetic agents and/or insulin. These patients were generally in good health, evidenced by lack of significant findings in medical history, physical examination, clinical laboratory tests, vital signs and ECG, and had liver and kidney laboratory evaluations within normal limits.

During the screening phase of this study, patients were evaluated for study eligibility. An oral glucose tolerance test (OGTT) was also performed, wherein patients drank 300 mL of a glucose solution (75 g Glucose, Dextro® O.G-T. Saft, Hoffmann La Roche, Grenzach-Wyhlen, Germany) within a 10 minute period. Ten blood samples, consisting of fasting glucose, C-peptide, insulin and pro-insulin, were taken during this four-hour test.

On the evening prior to the first day of the treatment phase of the study, the patients had their last food intake no later than 10 p.m. and arrived at the investigational site in a fasting state in the morning. Blood samples for the determination of blood glucose concentrations, insulin, pro-insulin, and C-peptide were drawn at regular intervals over the next 24 hours, first at 30 minutes before a standard breakfast is served, and later throughout lunch, dinner, at bedtime, and the following morning. In addition, a fasting blood sample for fructosamine was taken, and a 24-hour urine collection for the determination of C-peptide was obtained.

Patients were randomized to one of two treatment groups to receive an active dose of Insulin/4-CNAB or a control dose of 4-CNAB alone for a two-week period four times daily, 10 minutes before breakfast, lunch and dinner and at bedtime). The seven patients in the active group were to be treated with two tablets totaling 300 U insulin/160 mg 4-CNAB, and the six patients in the control group were treated with two tablets totaling 200 mg 4-CNAB. Those chosen for active treatment had HbA$_1$c between 6.1% and 7.7%, with a mean HbA$_1$c of 6.5%, meaning that they were early stage type 2 diabetics. Those chosen for active treatment also had a body weight between 71.3 kg and 101.4 kg, with a median of 96.9 kg and a mean of 92.4 kg.

During the first three days of the treatment phase, patients remained at the research site and were administered study medication before breakfast, lunch, and dinner and at bedtime. Thereafter, patients were given study medication to be taken on an out-patient basis for the remainder of the treatment phase. The doses of study medication were administered 10 minutes before every meal and before bedtime with 150 mL of water. Glucose readings were obtained from the patients at mid-night and at 3 a.m. Blood samples for the determination of blood glucose concentrations, insulin, pro-insulin, C-peptide and 4-CNAB were drawn at regular intervals over the first 24 hours beginning before the first dose of study dose, i.e., immediately before breakfast is served, and throughout lunch and dinner, at bedtime, and the following morning.

Patients were instructed to self-monitor blood glucose while on out-patient medication and to record their data in a diary. Thereafter, when dosing occurred at home, the patients self-monitored their blood glucose concentrations and visited the investigational site on three of the days for measurement of blood glucose, insulin, pro-insulin, C-peptide and 4-CNAB concentrations.

On the evening prior to the final day, the patients had their last food intake no later than 10 p.m. and arrived at the investigational site in a fasting state in the morning. Blood samples for determination of blood glucose concentrations, insulin, pro-insulin, C-peptide, and 4-CNAB were drawn at the same specified interval time points as in the first treatment day 1 over a 24 hour period, while patients continued to take their study medication 10 minutes prior to each meal and at bedtime. In addition, urine was collected over 24 hours for the determination of C-peptide. At the end of the 24-hour blood sampling period, a fasting blood sample was drawn for the evaluation of fructosamine, and an oral glucose tolerance test was performed as discussed above with ten blood samples being drawn over a 4 hour period for fasting glucose, C-peptide, insulin and pro-insulin.

At each follow-up visit, vital signs (heart rate, blood pressure, temperature) were measured, and a fasting blood samples were drawn for blood glucose, insulin, C-peptide and pro-insulin concentrations. In addition, patients will be asked about potential adverse events, and a follow up of any adverse events previously reported will be performed.

All blood samples were collected via a venous cannula. For insulin assays, 1.5 mL of blood was drawn and collected in sodium-heparin tubes, from which the resulting plasma samples were kept at −70° C. Plasma concentrations of insulin were determined from approximately 0.5 ml of plasma at Huntingdon Life Sciences by means of a GLP validated RIA assay. Blood glucose concentrations were measured immediately after sample collection using a laboratory method (Super GL Ambulance glucose analyzer, Ruhrtal Labortechnik, Delecke-Mohnesee, Germany) based on the glucooxidase-reaction.

Plasma C-peptide was measured from 0.5 ml serum, obtained from a 3 ml blood sample, which was kept at −70° C. An evaluated RIA-Assay with double determinations was used for the measurements. Urinary C-peptide was measured by liquid chromatography-tandem mass spectrometry with a stable isotopically-labeled internal standard. Plasma proinsulin was measured from 1 ml serum obtained from the same sample as C-peptide, and an evaluated RIA-Assay with double determinations was used for the measurements.

Serum fructosamine was measured from 0.5 mL serum obtained from a 1 mL blood sample collection, which was kept at −70° C. until assayed. Plasma 4-CNAB was measured from 0.5 mL plasma obtained from a 1 mL blood sample collected into a sodium heparin tube and stored frozen at −70° C. until shipment to Huntingdon Life Science Laboratories for analysis by a validated LC/MS/MS assay.

Data Analysis

In order to assess and compare the biological effect of the treatment formulations, several characteristics were derived from the preliminary and unaudited pharmacokinetic and pharmacodynamic data, and were calculated for each patient and evaluated with standard numeric and descriptive statistical procedures.

The pharmacokinetic values of insulin and 4-CNAB and the pharmacodynamic values of glucose were compared at Study Day 1 and Day 14. The following PK/PD parameters were evaluated for 4-CNAB: $C_{max}$, $t_{max}$, $AUC_{last}$, $AUC_{inf}$, $t_{1/2}$, $CL/f$ and $V_d$. The following PK/PD parameters were evaluated for insulin and C-Peptide: $C_{max}$, $t_{max}$, $AUC_{(0-1)}$, $AUC_{(0-2)}$, $AUC_{(0-3)}$, $AUC_{(0-last)}$ and $AUC_{(0-inf)}$.

Figure 49B:
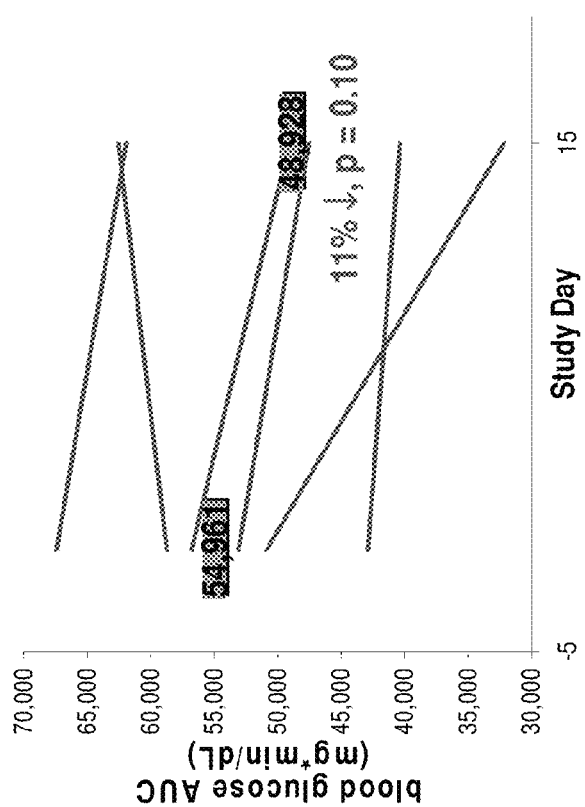
FIGS. 49A and 49B are curves showing preliminary Mean and Individual Blood Glucose AUC0-240 min Following Oral Glucose Tolerance Test At Screening and on Day 15 Following 14 Days of Daily QID Administration of 300 U Insulin/160 mg 4-CNAB to Type 2 Diabetic Subjects (49A) and 200 mg 4-CNAB Alone to Type 2 Diabetic Subjects (49B).
Figure 49A:
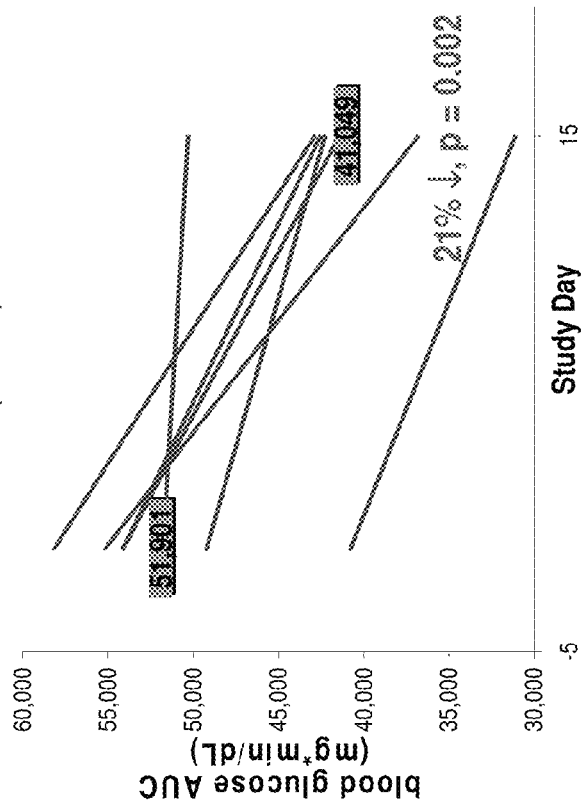

Areas under the curve (AUC) were calculated for the glucose concentrations after ingestion of the oral glucose solution ($AUC_{BG}$) for the time intervals 0-60 min, 0-120 min, 0-180 min, 0-240 min, 0-300 min and 0-360 min ($AUC_{BG\,0-60}$, $AUC_{BG\,0-120}$, etc.) and were compared between the two treatment groups (see FIGS. 49A and 49B). Likewise, AUCs were calculated for insulin ($AUC_{INS}$), proinsulin ($AUC_{PRO}$), and C-peptide ($AUC_{CP}$) but only for the first two hours, six hours and the total duration of the experiments ($AUC_{0-120}$, $AUC_{0-360}$, and $AUC_{0-1440}$) (see FIGS. 52A and 52B for insulin AUC). All AUCs were calculated as incremental AUCs, i.e., area under the curve of the absolute values minus the baseline values, with the trapezoidal rule. In case of many negative incremental AUCs (which occur when baseline values are higher than subsequent values), absolute AUCs were calculated additionally. All AUCs were compared between the treatment arms.

In addition, mean concentrations for each timepoint and maximal concentrations were calculated for glucose ($C_{BG\,max}$), insulin ($C_{Ins\,max}$), proinsulin ($C_{Pro\,max}$) and C-peptide ($C_{CP\,max}$). The time point of maximal concentration ($t_{max}$) was also calculated for all these parameters.

Insulin sensitivity was assessed on previously described parameters derived from insulin and blood glucose values during the oral glucose tolerance tests. The following indices for insulin sensitivity (IS) were calculated:

$$AUC\text{-Ratio: } IS = \frac{AUC(BG)}{AUC(Ins)}$$

$$\text{Belfiore: } IS = \frac{2}{(AUC(Ins) \cdot AUC(BG) + 1}$$

$$\text{Composite Index: } IS = \frac{10{,}000}{\sqrt{[Ins(0) \cdot BG(0)] \cdot [Ins(OGTT) \cdot BG(OGTT)]}}$$

$$\text{Stumvoll: } IS = 0.226 - 0.0032 \cdot BMI - 0.0000645 \cdot INS(120) - 0.0037 \cdot BG(90)$$

$$\text{HOMA: } IS = \frac{22.5 \cdot e^{-Ln(BG(0))}}{Ins(0)}$$

$$FIRI^{-1}: IS = \frac{25}{BG(0) \cdot Ins(0)}$$

wherein

AUC(BG)/AUC(Ins): area under the blood glucose (BG) or insulin (INS) concentration curve.

BG/Ins(0): blood glucose (BG) or insulin (INS) concentration at time point 0, i.e., immediately before ingestion of the oral glucose load.

BG/Ins(OGTT): mean blood glucose (BG) or insulin (INS) concentrations during the oral glucose tolerance test.

INS(120): insulin concentration 120 minutes after ingestion of the oral glucose load.

BG(90): blood glucose concentration 90 minutes after ingestion of the oral glucose load.

The following indices for insulin secretion capacity (ISC) were calculated:

$$\text{HOMA: } ISC = 20 \cdot \frac{Ins(0)}{BG(0) - 3.5}$$

$$\text{Stumvoll } 1^{st} \text{ phase: } ISC = 1283 + 1.829 \cdot Ins(30) - 138.7 \cdot BG(90) + 3.772 \cdot Ins(0)$$

$$\text{Stumvoll } 2^{nd} \text{ phase: } ISC = 287 + 0.4164 \cdot Ins(30) - 26.07 \cdot BG(30) + 0.9226 \cdot Ins(0)$$

$$\text{Insulinogenic}(30): ISC = \frac{Ins(30) - Ins(0)}{BG(30) - BG(0)}$$

$$\text{Insulinogenic}(120): ISC = \frac{\Delta AUC(Ins)}{\Delta AUC(BG)}$$

The following index for insulin resistance (IR) was calculated:

$$\text{HOMA: } IR = \frac{BG \cdot Ins}{22.5}$$

The HOMA and the FIRI indices will be calculated not only from the OGTT experiments, but also from the fasting samples drawn at the ambulatory and the follow-up visits.

The primary efficacy parameters assess the effect of a two week treatment with an oral insulin/4-CNAB tablet formulation on insulin secretion capacity, insulin sensitivity, and glucose tolerance in diet-treated patients with type 2 diabetes. As the main parameter, the Stumvoll indices of insulin secretion and first phase insulin secretion were determined.

The secondary efficacy parameters assess the effect of a two week treatment with an oral insulin formulation on glycemic control in diet-treated patients with type 2 diabetes. Glycemic control was assessed by the measurement of fructosamine and 24-hour blood glucose profiles. To assess glycemic control, the absolute concentrations at the scheduled time-points as well as the maximal concentrations, time of maximal concentrations, and the area under the curves for various time-intervals were determined. All other parameters of insulin sensitivity and insulin secretion, and the AUCs and maximal concentrations of insulin, C-peptide and proinsulin are regarded as secondary outcome parameters.

The safety parameters to be assessed are: physical examination, electrocardiograms, vital signs, clinical labs (chemistry, hematology, urinalysis), and continuous glucose monitoring. At the end of the study, those chosen for active treatment had a body weight between 70.3 kg and 99.2 kg, with a median of 94.3 kg, down from a median of 96.9 prior to the study.

Conclusions

As a result, the following conclusions may be drawn. In general, patients receiving oral insulin tablets for two weeks showed improvements versus baseline on key parameters, including:

reduced fasting blood glucose;

reduced average blood glucose, as evidenced by a decrease in the AUC (area under the curve) following an oral glucose tolerance test (OGTT) at Day 15;

decreased two-hour, post-load blood glucose following an OGTT at Day 15;

reduced serum fructosamine levels (an indicator of average glycemic control over approximately the previous two weeks); and improved insulin secretion capacity and sensitivity based on at least two widely used indices (the Stumvoll first-phase insulin secretion capacity index and the Homeostasis Model Assessment, or HOMA, index).

Tables 53 below set forth some of the data that was obtained:

TABLE 53A

Preliminary (Unaudited) Data

| | Mean Changes (±SD) | | % Change | |
|---|---|---|---|---|
| | Oral Insulin | Control | Oral Insulin | Control |
| BG-AUC$_{0-1\,h}$ (OGTT) [mg * h/dL] | −57 ± 44 | −16 ± 33 | −22 | −8 |
| BG-AUC$_{total}$ (standardized diet) [mg * h/dL] | −335 ± 250 | −184 ± 206 | −19 | −11 |
| INS-AUC$_{0-1\,h}$ (OGTT) [μU * h/mL] | −9.9 ± 21.0 | 0.8 ± 10.2 | −17 | 2 |
| INS-AUC$_{total}$ (standardized diet) [μU * h/mL] | −55 ± 126 | −23 ± 119 | −8 | −7 |
| Insulin resistance (HOMA-IR) | −52 ± 57 | −14 ± 42 | −37 | −16 |

End of treatment vs. baseline. Total AUCs: sum of the 3-hour postprandial AUCs after each meal during the in-house days.

TABLE 53B

Further Audited Data

| | Mean Changes | | % Changes | |
|---|---|---|---|---|
| | Oral Insulin | Control | Oral Insulin | Control |
| Triple Meal Test | | | | |
| BG-AUC$_{total}$ [mg · h/dl]$^+$ | −335 ± 250* | −185 ± 206 | −19 ± 13 | −11 ± 12 |
| BG-AUC$_{0-2\,h,\,breakfast}$ [mg · h/dl] | −53 ± 54 | −30 ± 52 | −12 ± 12 | −8 ± 13 |
| BG-AUC$_{0-2\,h,\,lunch}$ [mg · h/dl] | −27 ± 35 | −20 ± 59 | −7 ± 9 | −5 ± 15 |
| BG-AUC$_{0-2\,h,\,dinner}$ [mg · h/dl] | −39 ± 60 | −19 ± 52 | −9 ± 13 | −4 ± 14 |
| BG-C$_{max}$ [mg/dl] | −33 ± 26* | −22 ± 38 | −13 ± 10 | −9 ± 15 |
| Insulin-AUC$_{total}$ [μU · h/ml]$^+$ | −55 ± 126 | −23 ± 119 | −8 ± 24 | −7 ± 32 |
| Insulin-AUC$_{0-2\,h,\,breakfast}$ [μU · h/ml] | +1 ± 26 | −6 ± 30 | 8 ± 29 | −8 ± 34 |
| Insulin-AUC$_{0-2\,h,\,lunch}$ [μU · h/ml] | −11 ± 27 | −2 ± 28 | −12 ± 20 | −7 ± 34 |
| Insulin-AUC$_{0-2\,h,\,dinner}$ [μU · h/ml] | −19 ± 55$^\#$ | +2 ± 23 | −6 ± 36 | −3 ± 29 |
| Insulin-C$_{max}$ [μU/ml] | −26 ± 41 | +3 ± 35 | −16 ± 30 | +1 ± 40 |
| OGTT | | | | |
| Fasting BG [mg/dl] | −27 ± 29$^\#$ | −21 ± 20 | −16 ± 17 | −13 ± 11 |
| BG-AUC$_{0-2\,h}$ [mg · h/dl] | −115 ± 81* | −48 ± 68 | −20 ± 13 | −10 ± 14 |
| BG-AUC$_{0-4\,h}$ [mg · h/dl] | −219 ± 115* | −118 ± 109 | −22 ± 11 | −12 ± 11 |
| BG-C$_{max}$ [mg/dl] | −57 ± 46* | −33 ± 37 | −17 ± 14 | −11 ± 14 |
| Insulin-AUC$_{0-2\,h}$ [μU · h/ml] | −5 ± 49 | −5 ± 34 | −1 ± 55 | 0 ± 38 |
| Insulin-AUC$_{0-4\,h}$ [μU · h/ml] | 0 ± 68 | −23 ± 48 | +2 ± 49 | −10 ± 26 |
| Insulin-C$_{max}$ [μU/ml] | 9 ± 46 | −7 ± 30 | 22 ± 93 | 0 ± 47 |
| Additional Assessments | | | | |
| Fructosamine [μmol/l] | −22 ± 7 | −18 ± 30 | −9 ± 2 | −6 ± 10 |
| Insulin resistance (HOMA-IR) | −52 ± 57$^\#$ | −14 ± 42 | −37 ± 41 | −16 ± 43 |

End of treatment values were determined at the last day of treatment for the triple meal test, but at the first day after treatment for OGTT and additional assessments

*p < 0.05, $^\#$p < 0.1 (end of treatment vs. baseline);

$^+$Total AUCs: sum of the 3-hour postprandial AUCs after each meal

Figure 47:
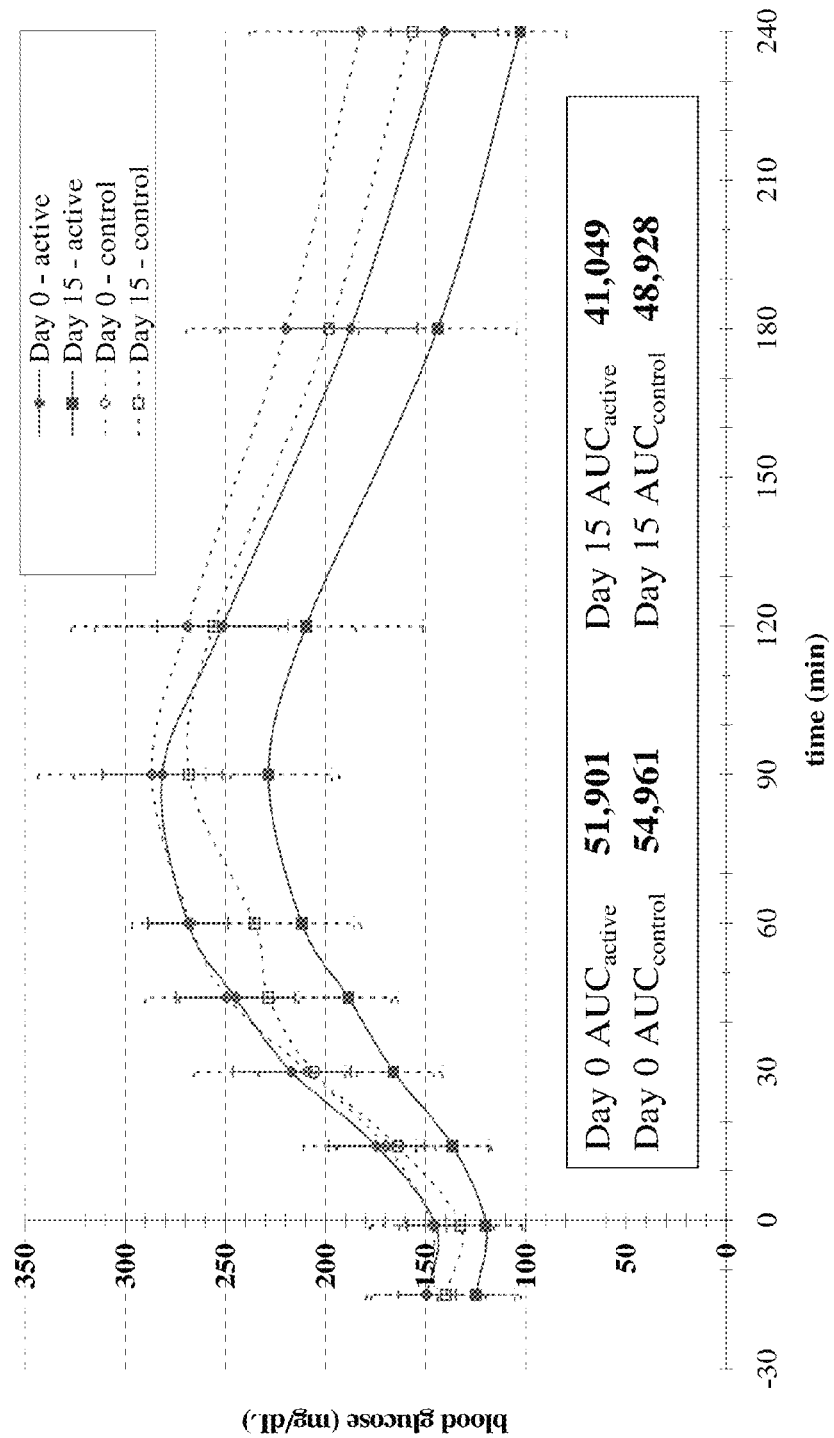
FIG. 47 is a curve showing preliminary Mean (n=6 or 7, SD) Blood (SuperGL) Glucose Following Oral Glucose Tolerance Test on Day 0 and Day 15 Following 14 Days of Daily QID Administration of 300 U Insulin/160 mg 4-CNAB OR 200 mg 4-CNAB alone.
Figure 48B:
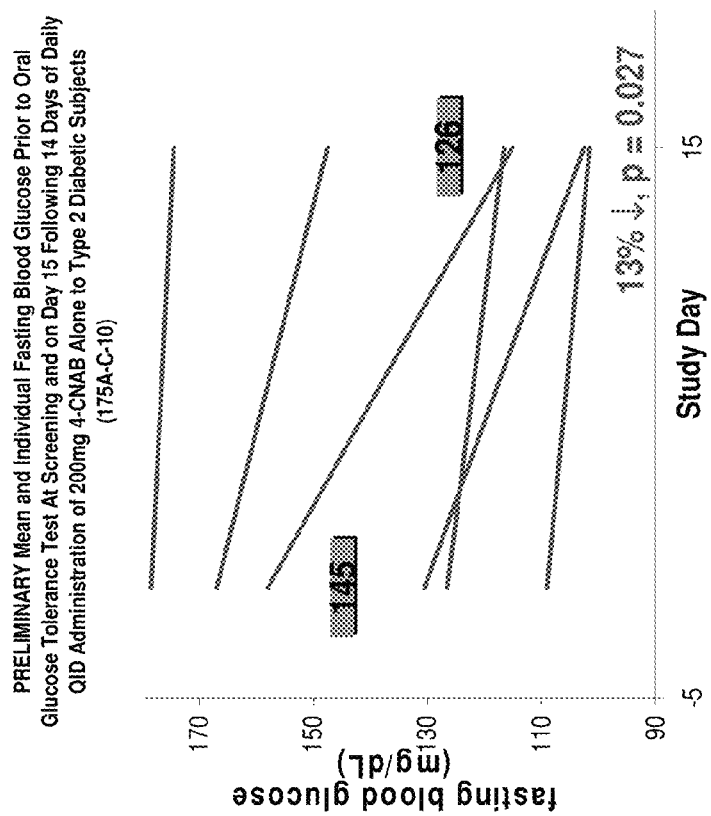
FIGS. 48A and 48B are curves showing preliminary Mean and Individual Fasting Blood Glucose Prior to Oral Glucose Tolerance Test at Screening and on Day 15 Following 14 Days of Daily QID Administration of 300 U Insulin/160 mg 4-CNAB to Type 2 Diabetic Subjects (48A) and 200 mg 4-CNAB Alone to Type 2 Diabetic Subjects (48B).
Figure 48A:
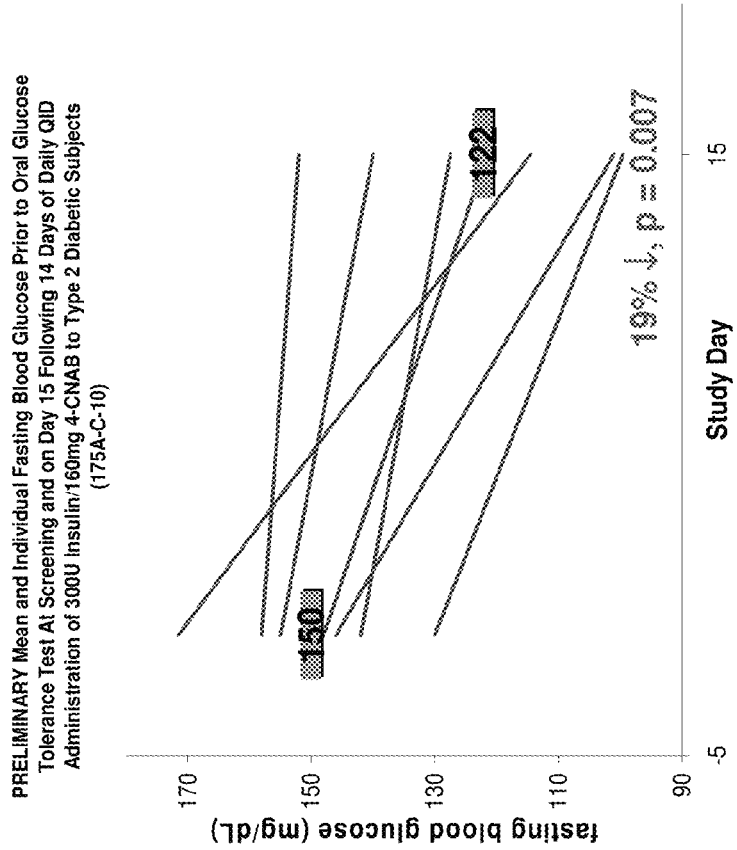

As shown in FIG. 47, patients receiving oral insulin tablets for two weeks showed clear improvements versus baseline levels on reduced fasting blood glucose by lowered levels of glucose excursion after an oral glucose tolerance test. As shown in FIG. 48A, there were clinically relevant decreases in fasting blood glucose concentrations versus baseline levels after an oral glucose tolerance test at Day 15 (mean 19%). Thus, after two weeks of treatment, the patients achieved improved glycemic control compared with baseline levels prior to treatment.

Using the triple meal test, the two-week treatment with oral insulin reduced postprandial blood glucose concentrations after each meal (total area under the blood glucose concentrations, curves ($AUC_{total}$) decreased by 19%, and maximal blood glucose ($C_{max}$) by 13%, p<0.05 vs. baseline, respectively.

Figure 50A:
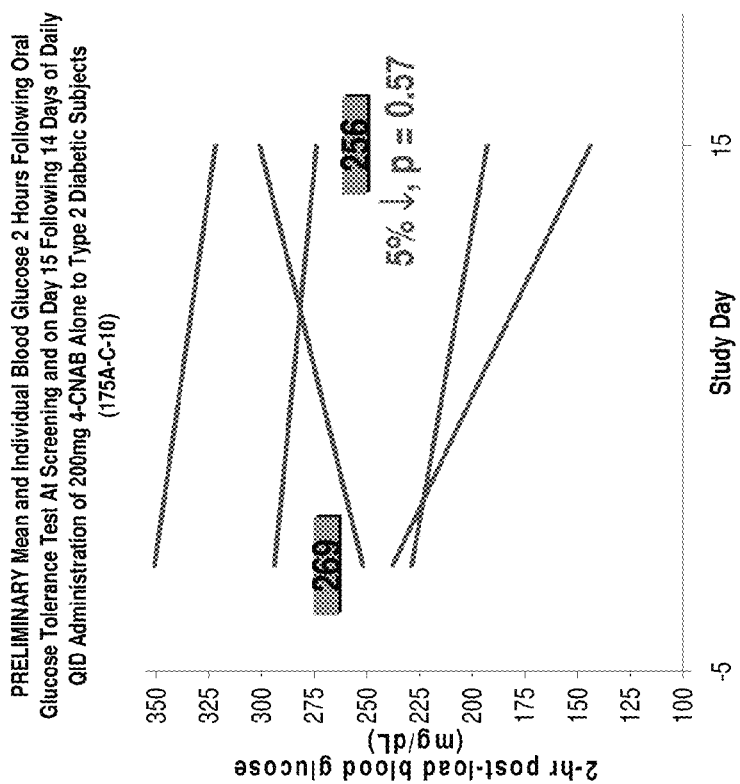
FIGS. 50A and 50B are curves showing preliminary Mean and Individual Blood Glucose 2 Hours Following Oral Glucose Tolerance Test at Screening and on Day 15 Following 14 Days of Daily QID Administration of 300 U Insulin/160 mg 4-CNAB to Type 2 Diabetic Subjects (50A) and 200 mg 4-CNAB Alone to Type 2 Diabetic Subjects (50B).
Figure 50B:
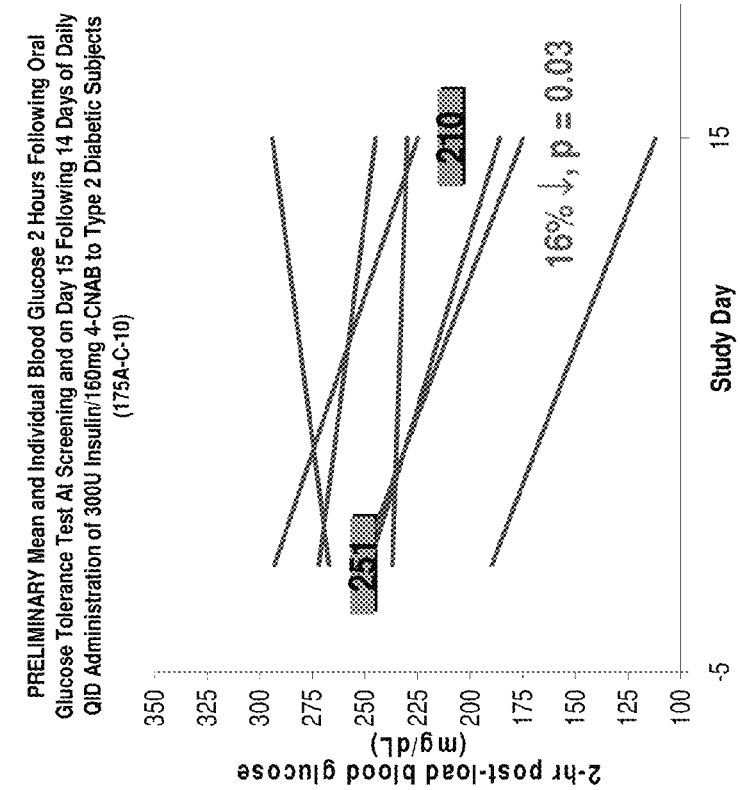

In addition, as shown in FIG. 49A, which shows blood glucose AUC of FIG. 48A after an oral glucose tolerance test, patients receiving oral insulin tablets for two weeks showed significantly lower exposure to glucose versus baseline levels based upon reduced average blood glucose concentration, as evidenced by a decrease in the AUC (mean 21%) following an oral glucose tolerance test at Day 15. Furthermore, as shown in FIG. 50A, patients receiving oral insulin tablets for two weeks showed decreased two-hour, post-load blood glucose concentration versus baseline levels (mean 16%) following an oral glucose tolerance test at Day 15. As shown in Table 53, blood glucose excursions were significantly reduced after two-week treatment with oral insulin (indicated by significantly lower values for $BG\text{-}AUC_{0\text{-}2h}$, $BG\text{-}AUC_{0\text{-}4h}$, and $BG\text{-}C_{max}$). Thus, after two weeks of treatment, the patients achieved improved glucose tolerance and a better capacity to handle a sugar load compared with baseline levels prior to treatment. In addition, because a patient's two-hour post-load glucose is a standard clinical marker for assessing a patient's diabetic disease state, lowering of this marker, especially by a mean of 16%, is perhaps an indication of a reversal of the patients' diabetic disease states.

Figure 51:
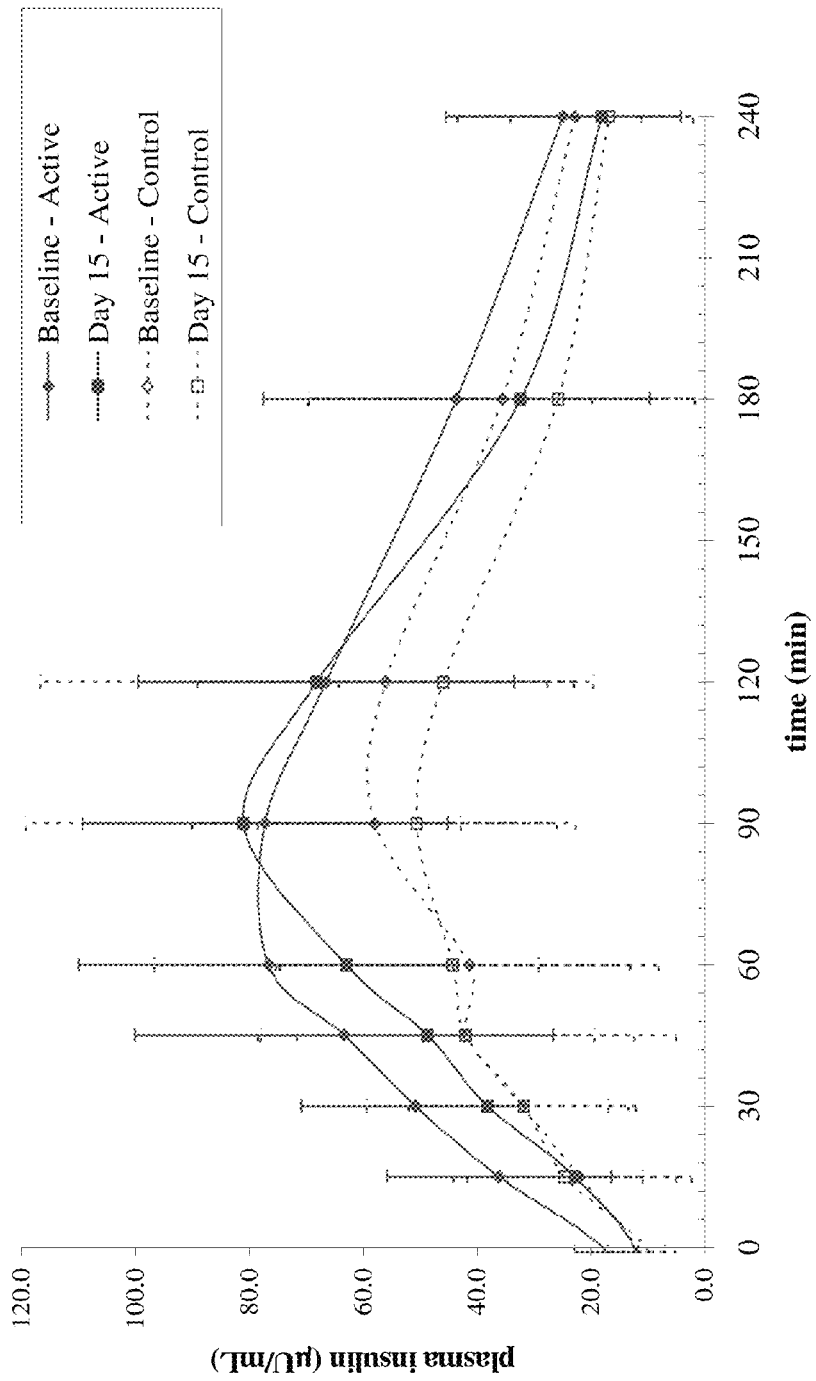
FIG. 51 is a curve showing preliminary Mean (SD, n=6 or 7) Plasma Insulin Concentration Following OGTT at Baseline and on Day 15 Following 14 Days of Daily QID Oral Doses of 300 U Insulin/160 mg 4-CNAB OR 200 mg 4-CNAB alone.
Figure 52A:
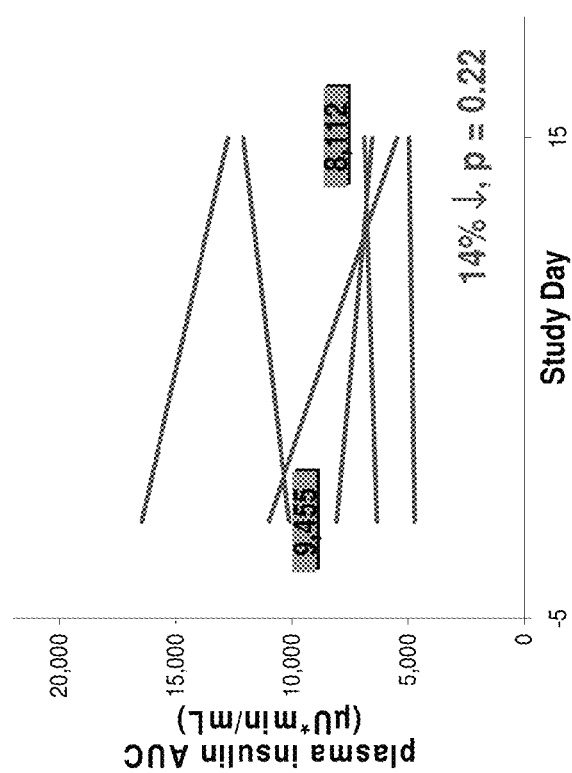
FIGS. 52A and 52B are curves showing preliminary Mean and Individual Plasma Insulin $AUC_{0-240min}$ Following Oral Glucose Tolerance Test At Screening and on Day 15 Following 14 Days of Daily QID Administration of 300 U Insulin/160 mg 4-CNAB to Type 2 Diabetic Subjects (52A) and 200 mg 4-CNAB Alone to Type 2 Diabetic Subjects (52B).
Figure 52B:
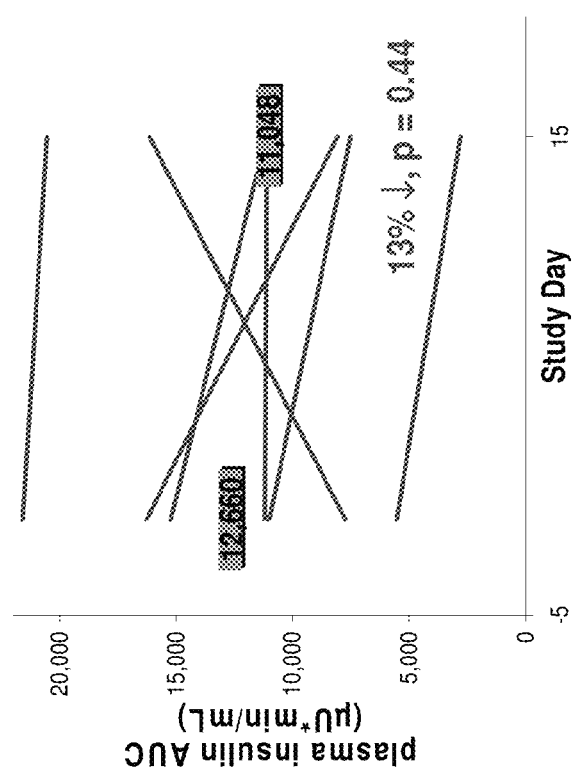
Figure 58:
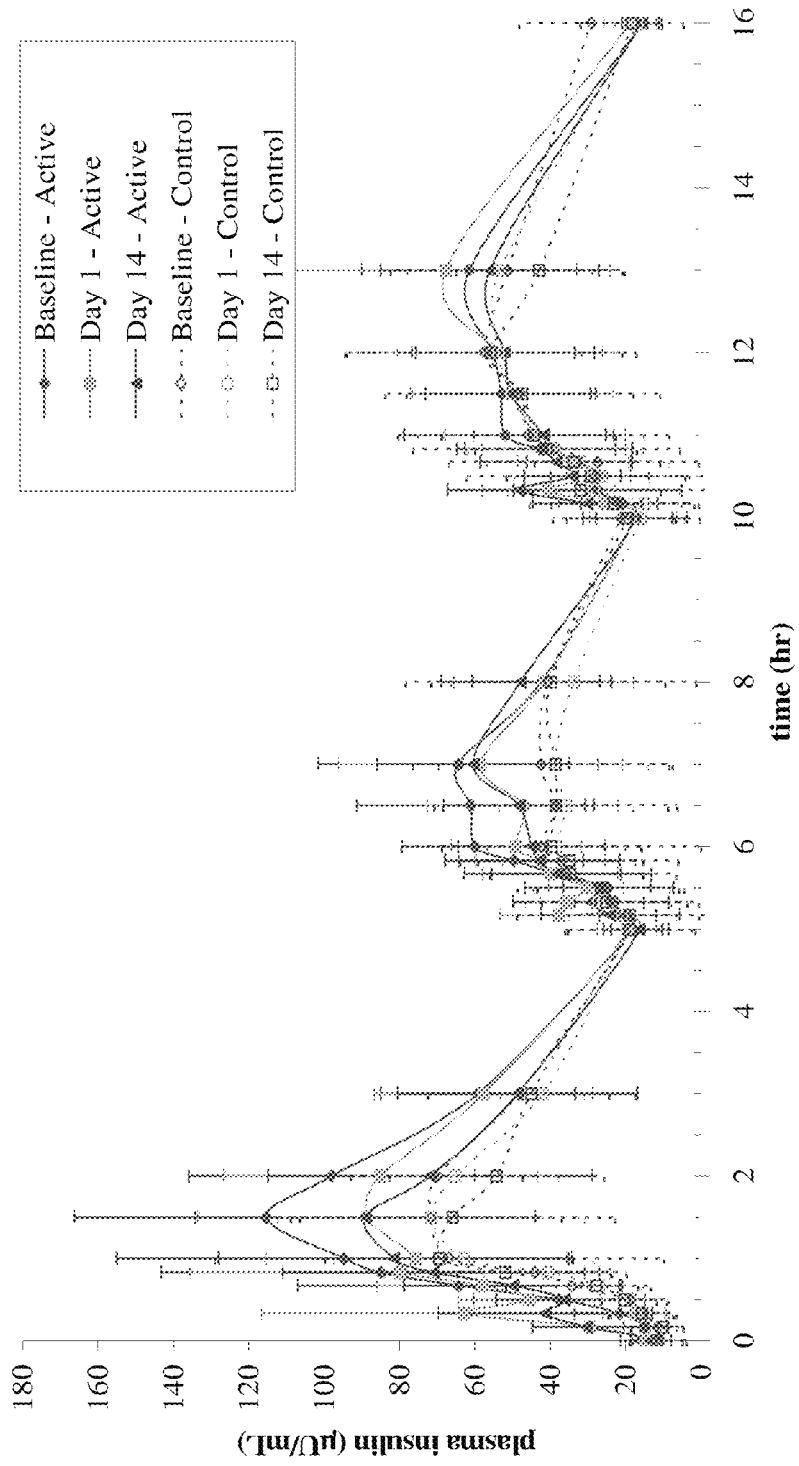
FIG. 58 is a curve showing preliminary Mean (n=6 or 7, SD) Plasma Insulin Concentration on Days 0 (baseline), 1 and 14 Following Daily QID Doses of Oral 300 U Insulin/160 mg 4-CNAB OR 200 mg 4-CNAB alone.

Oral insulin absorption was evident, by the clear insulin peaks that were observed at 15-20 minutes post-dose, as shown in FIG. 58. In addition, the oral insulin was safe and well-tolerated, as there was no hypoglycemia in diet-controlled subjects and there were no serious adverse effects. As seen in FIGS. 51 and 52A, patients receiving oral insulin tablets for two weeks showed no increase in systemic plasma insulin exposure versus baseline levels, as well as no increase in average blood glucose concentration versus baseline levels, following an oral glucose tolerance test at Day 15. Similarly, the data showed that there were no significant differences in fasting or post-load plasma insulin concentration in the active group. These results show that, even in a diabetic population with $HbA_1c\sim6.5$ (range of $HbA_1c$ 6.1 to 7.5), which is generally considered to be impaired glucose tolerance to with early to moderate stage diabetes, who do not suffer from an inability to produce endogenous insulin, oral administration of additional insulin by the formulations disclosed herein does not result in hyperinsulinemia.

Figure 53B:
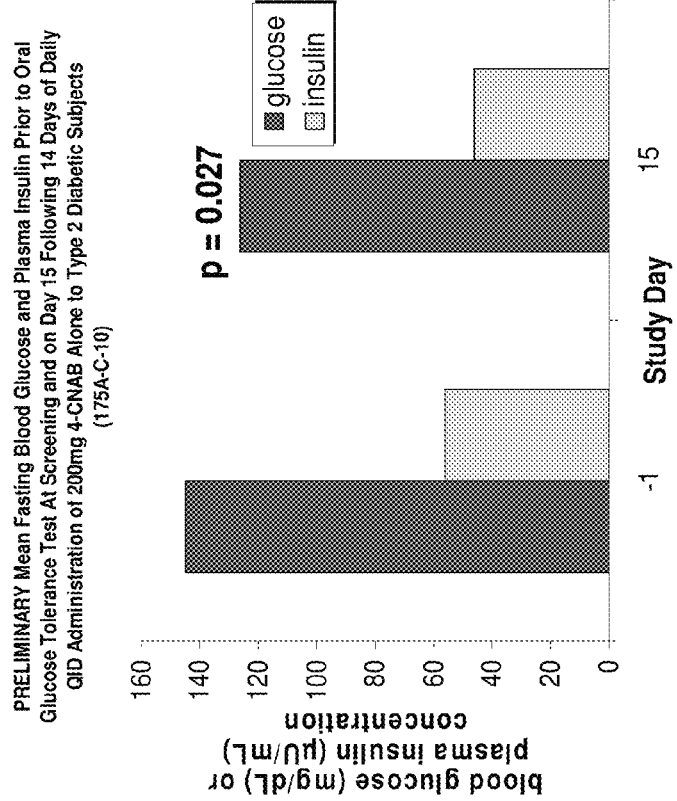
FIGS. 53A and 53B are bar graphs showing preliminary Mean and Fasting Blood Glucose and Plasma Insulin Prior to Oral Glucose Tolerance Test At Screening and on Day 15 Following 14 Days of Daily QID Administration of 300 U Insulin/160 mg 4-CNAB to Type 2 Diabetic Subjects (53) and 200 mg 4-CNAB Alone to Type 2 Diabetic Subjects (53B).
Figure 53A:
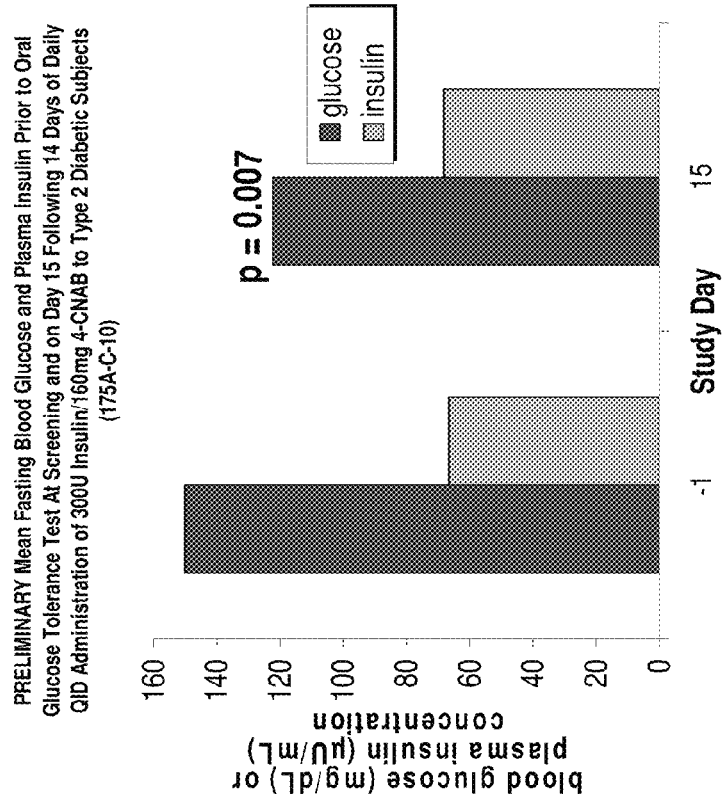
Figure 54A:
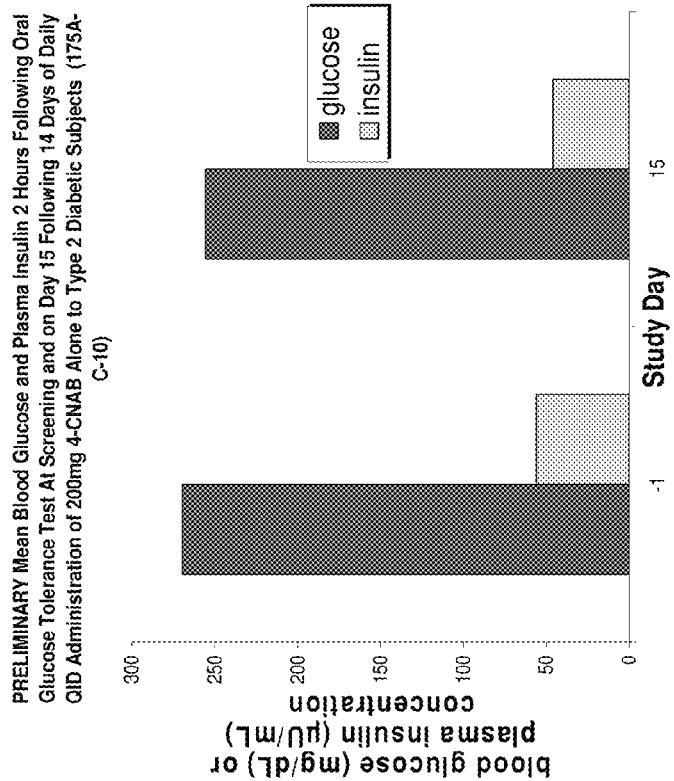
FIGS. 54A and 54B are bar graphs showing preliminary Mean Blood Glucose and Plasma Insulin 2 Hours Following Oral Glucose Tolerance Test at Screening and on Day 15 Following 14 Days of Daily QID Administration of 300 U Insulin/160 mg 4-CNAB to Type 2 Diabetic Subjects (54A) and 200 mg 4-CNAB Alone to Type 2 Diabetic Subjects (54B).
Figure 54B:
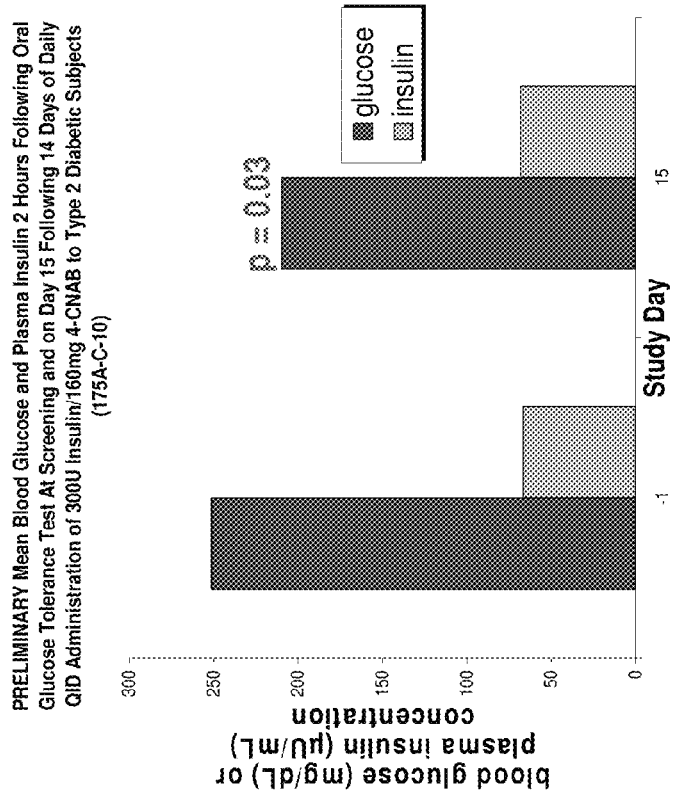

These results are especially remarkable given the amount of insulin that was administered over the two-week period and the marked improvement in glucose control. As graphically shown in FIG. 53A, patients receiving oral insulin tablets for two weeks showed reduced fasting blood glucose concentrations versus baseline levels after an oral glucose tolerance test at Day 15 but without any increase in plasma insulin concentration. Similarly, as graphically shown in FIG. 54A, patients receiving oral insulin tablets for two weeks showed decreased two-hour, post-load blood glucose concentration versus baseline levels after an oral glucose tolerance test at Day 15 but without any increase in plasma insulin concentration. Accordingly, this study showed improved sensitivity of the patients' livers to insulin or the improved ability of the patients' pancreas to produce insulin and to thereby control overnight glucose concentrations, as seen from the significant decrease in fasting and two-hour, post-load blood glucose concentration versus baseline levels.

The improved insulin secretion capacity and insulin sensitivity based on at least two widely used indices (the Stumvoll first-phase insulin secretion capacity index and the Homeostasis Model Assessment, or HOMA, indices). Using the HOMA index as a benchmark for insulin sensitivity, it was determined that patients receiving oral insulin tablets for two weeks showed a significant increase in insulin sensitivity from baseline (mean 0.010) to day 14 (mean 0.018) of the treatment. Using the Strumvoll first phase index as a benchmark for insulin secretion capacity, it was again determined that patients receiving oral insulin tablets for two weeks showed a significant increase in insulin secretion capacity from baseline (mean −37594) to day 14 (mean −30264). (The HOMA index as a benchmark for insulin secretion capacity, however, showed a slight decrease in insulin secretion capacity from baseline (mean 2.328) to day 14 (mean 2.134).) Similarly, using the HOMA index as a benchmark for insulin resistance showed a significant decrease (see Table 53B).

Figure 55:
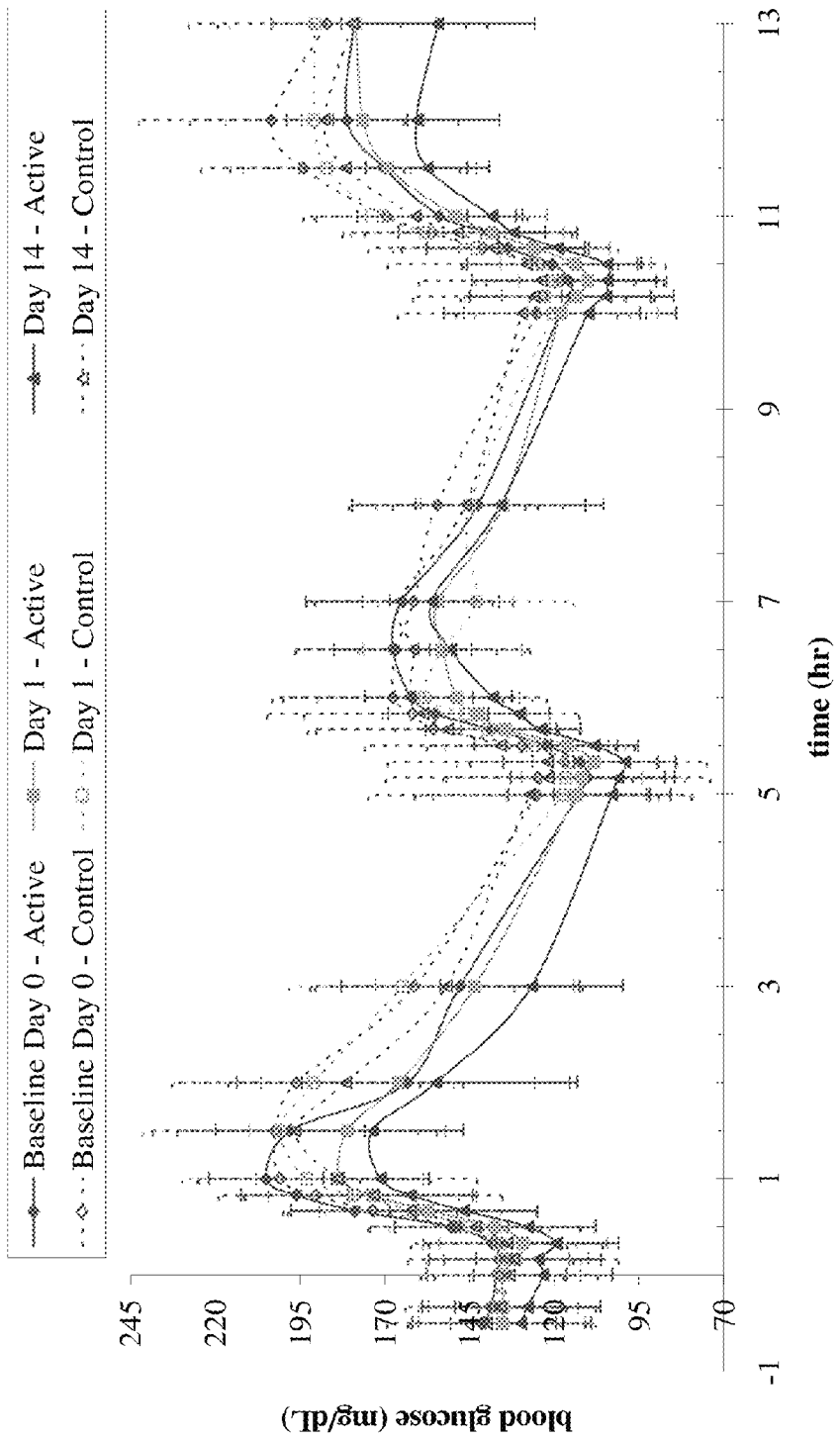
FIG. 55 is a curve showing preliminary Mean (N=6 or 7, SD) Blood Glucose Concentration Following Daily Mealtime Doses of Oral 300 U Insulin/160 mg 4-CNAB OR 200 mg 4-CNAB Alone to Type 2 Diabetic Subjects.
Figure 56:
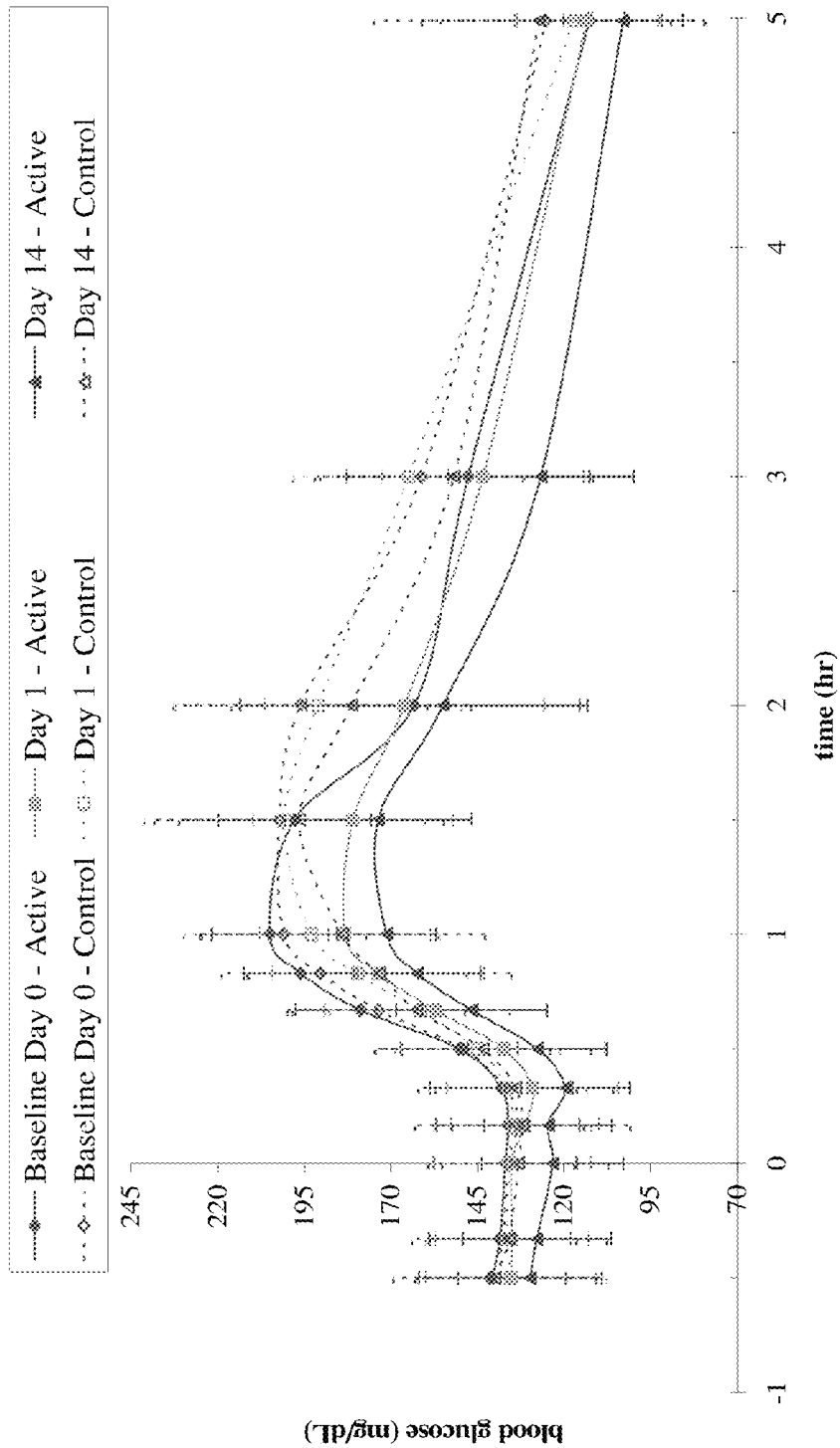
FIG. 56 is a curve showing preliminary Mean (N=6 or 7, SD) Blood Glucose Concentration Following Daily Mealtime Doses of Oral 300 U Insulin/160 mg 4-CNAB OR 200 mg 4-CNAB Alone to Type 2 Diabetic Subjects.
Figure 57:
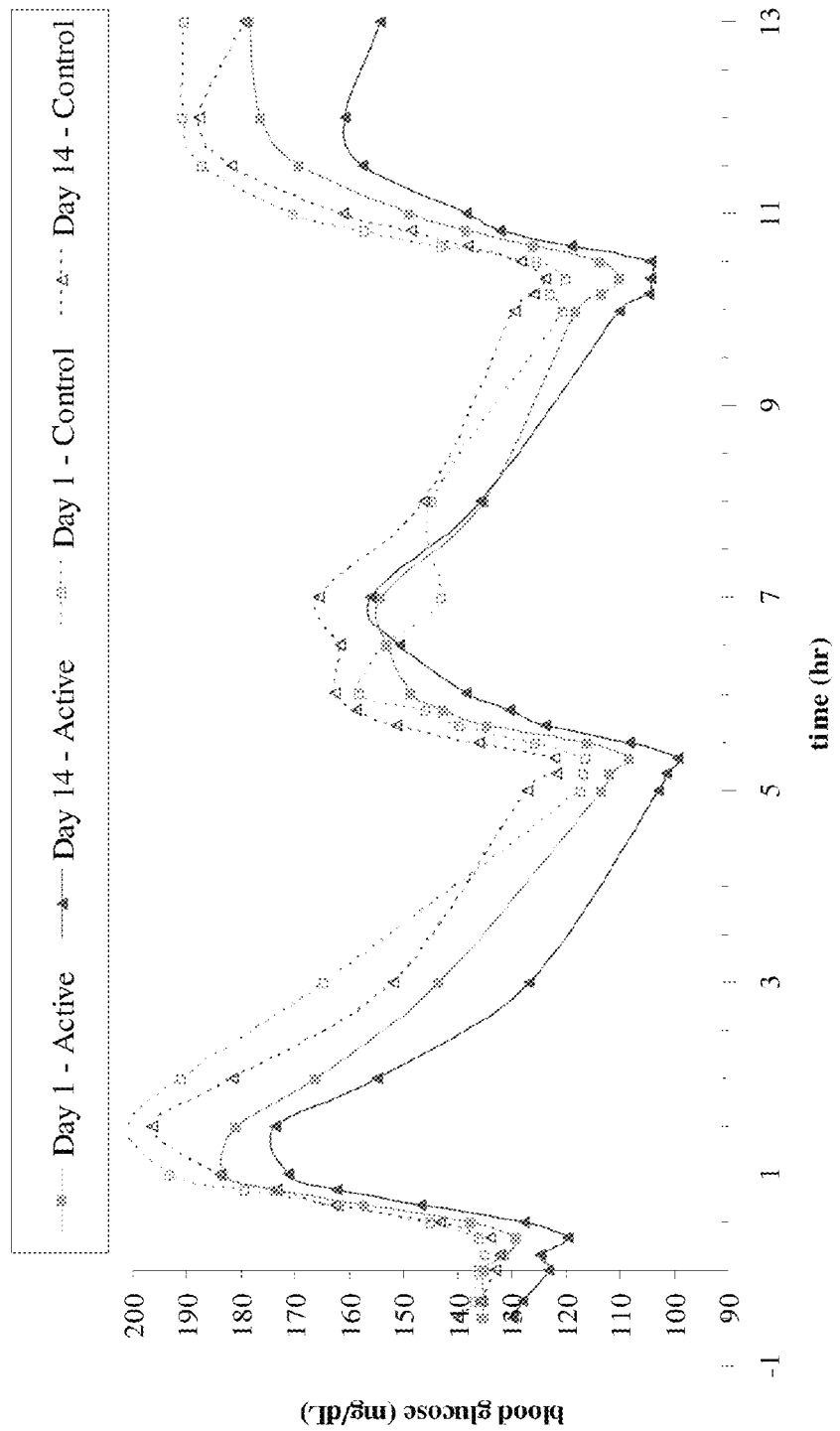
FIG. 57 is a curve showing preliminary Mean (N=6 or 7, SD) Blood Glucose Concentration Following Daily Mealtime Doses of Oral 300 U Insulin/160 mg 4-CNAB OR 200 mg 4-CNAB Alone to Type 2 Diabetic Subjects.

With regard to post-prandial effect, oral insulin efficacy was observed in the "real-life" outpatient dosing design. As shown in FIGS. 55 and 56, patients receiving oral insulin tablets for two weeks showed a significant decrease in post-prandial glucose excursion from baseline to day 1 of the treatment to day 14 of the treatment. Likewise, post-prandial (breakfast) glucose $C_{max}$ declined from a baseline level of 209 mg/dL to 194 after one day of treatment and further declined to 186 mg/dL after two weeks of treatment. FIG. 57 shows a comparison post-prandial glucose excursion from day 1 of the treatment to day 14 of the treatment, in order to demonstrate the continuing and cumulative impact of the two-week treatment on post-prandial glucose excursion, i.e., that the lowered post-prandial glucose excursion on day 14 was not due to that day's dosage but rather was even lower than the post-prandial glucose excursion of day 1, evidencing a cumulative effect of the two-week treatment on lowering post-prandial glucose excursions.

As shown in FIG. 58, post-prandial insulin absorption did not reach higher levels than baseline levels, indicating that no hyperinsulinemia resulted from the two-week treatment. In fact, post-prandial insulin absorption was lower, as evidenced by the decline in post-prandial (breakfast) insulin $C_{max}$ from a baseline level of 129.1 µU/mL to 123.7 µU/mL after one day of treatment and a further decline to 105.4 µU/mL after two weeks of treatment. Accordingly, this study showed that administering to patients oral insulin tablets for two weeks provided them with improved post-prandial glycemic control, as seen from the significant decrease in post-prandial glucose excursion and the fact that there was no hyperinsulinemia associated with the improved glycemic control.

Accordingly, the two weeks of oral insulin resulted in improved post-prandial glycemic control, evidenced by significantly lower $C_{max}$ values on Day 14 as compared to baseline values (an 11% decrease in mean maximum blood glucose), as well as significantly lower glucose AUC values on Day 14 as compared to baseline (12% decrease in mean glucose AUC). In addition, the two 6weeks of oral insulin resulted in no hyperinsulinemia, as evidenced by no significant differences in insulin $C_{max}$ and no significant differences in insulin AUC (there was, in fact, slightly lower mean AUC values from Day 0 to Day 14). Furthermore, none of the patients receiving oral insulin tablets for two weeks had episodes of hypoglycemia, and no subject required rescue throughout the study.

Thus, even in a diabetic population with $HbA_1c$~6.5 (range of $HbA_1c$ 6.1 to 7.5), which is generally considered to be impaired glucose tolerance to with early to moderate stage diabetes, oral administration of additional insulin by the formulations disclosed herein provided improved post-prandial glycemic control without any hypoglycemia. Significantly, even at day 14, when the patients' $HbA_1c$ was at their lowest, no hypoglycemic events occurred. As a result, this insulin therapy may be administered to patients with impaired glucose tolerance or with early or late stage diabetes without the need for frequent monitoring of the patients' blood glucose concentrations and $HbA_1c$ levels.

Figure 59A:
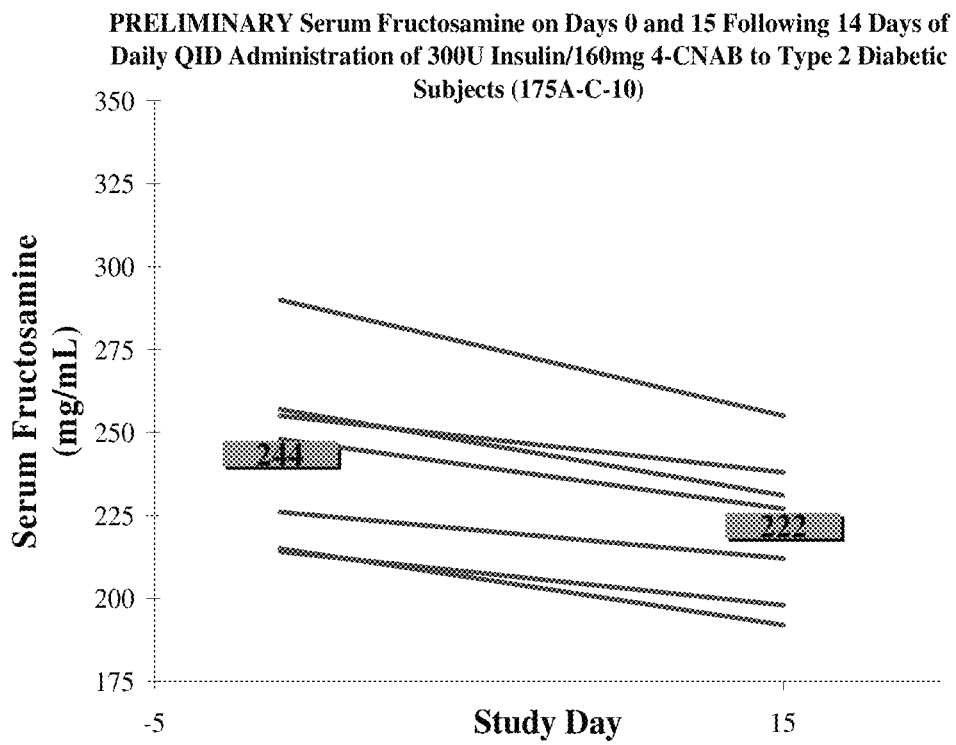
FIGS. 59A and 59B are curves showing preliminary Serum Fructosamine on Days 0 and 15 Following 14 Days of Daily QID Administration of 300 U Insulin/160 mg 4-CNAB to Type 2 Diabetic Subjects (59A) and 200 mg 4-CNAB alone (control) to Type 2 Diabetic Subjects (59B).
Figure 59B:
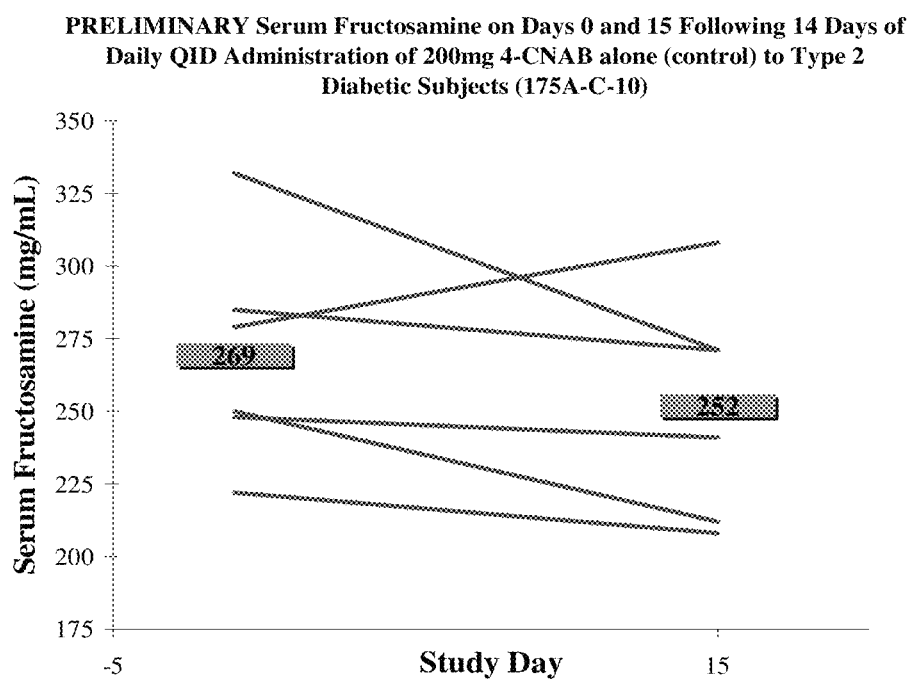

The treatment also provided the patients with demonstrably improved glycemic control over the previous period of two weeks, as evidenced by serum fructosamine levels. As shown in FIG. 59, based upon fructosamine assay, patients receiving oral insulin tablets for two weeks (mean baseline $HbA_1c$ of 6.5%) showed a mean 8.8% decrease in fructosamine levels versus baseline levels, meaning that the patients had a better average glycemic control over approximately the two week study period. Thus, by lowering the patients' fructosamine levels, there was approximately a 9% decrease in fructosamine levels in the diabetic population with $HbA_1c$~6.5 (range of $HbA_1c$ 6.1 to 7.5), suggesting that the oral insulin therapy discussed herein may be effective to actually reduce, or even reverse, diabetic and pre-diabetic conditions.

At the end of the study, those chosen for active treatment had a body weight between 70.3 kg and 99.2 kg, with a median of 94.3 kg, down from a median of 96.9 prior to the study. Thus, patients receiving oral insulin tablets for two weeks did not show any weight increase, as usually accompanies conventional diabetes therapy. Accordingly, this study showed that administering patients oral insulin tablets for two weeks provided them with improved post-prandial glycemic control, without the weight gain normally associated with insulin therapy.

Thus, in patients with type 2 diabetes, more particularly those with impaired glucose tolerance or with early or late stage diabetes, treatment for two weeks with oral insulin/4-CNAB before meals and at bedtime briefly augments systemic insulin concentrations shortly after each dose (~20 min) but lowers fasting blood glucose and improves 24-hour glycemic control, without systemic hyperinsulinemia, hypoglycemia and weight gain. This treatment also improves oral glucose tolerance after the treatment has been stopped It should also be noted that the control group also experienced some improvements in certain key parameters. For example, patients receiving tablets containing only delivery agent showed somewhat lowered levels of glucose excursion, decreased fasting blood glucose concentrations versus baseline levels (mean 13%), lower exposure to glucose to glucose (AUC) versus baseline levels (mean 11%) and decreased two-hour post-load glucose concentrations versus baseline levels (mean 5%) following a glucose tolerance test at Day 15, as well as reduced postprandial blood glucose concentrations after each meal ($AUC_{total}$, mean 11%) and maximal blood glucose ($C_{max}$, mean 9%) vs. baseline using triple meal test. In addition, patients receiving tablets containing only delivery agent showed somewhat improved insulin sensitivity and insulin secretion capacity based on statistically significant increase in the HOMA index for insulin sensitivity (0.015 to 0.021), in the Strumvoll first phase index benchmark for insulin secretion capacity (−38371 to −35815) and in the HOMA index for insulin resistance. However, most improvements were not considered overall to be statistically significant compared with baseline levels, and certainly were less pronounced that the active group. These changes were instead attributed to the fact that patients in this group likely better regulated their diet and made other lifestyle modifications based on their glucose monitoring results and mandatory diary keeping practices, such that improvement in this group was to be expected as is typically observed within the first two weeks of studies in diabetics. By contrast, in the active group, it was observed that, for all key parameters for which a change was desired, the marked improvements from baseline were consistent and statistically significant (p<0.05 using a paired parametric T-test), and in all cases were of greater magnitude than in the control group. However, the study was not powered to demonstrate statistical significance between the active and control groups. A larger sample size would be required to evaluate statistically significant differences between the active and the control groups.

The oral insulin tablets proved to be safe and tolerable to the patients receiving them, based upon no hypoglycemic events even in patients with tight glycemic control (HbA1c~6.5%), as well as no serious adverse events and a low incidence of mild to moderate adverse events (of which two were deemed potentially related to the study drug).

It is contemplated that the invention may be characterized by any aspect of any of the in-vivo clinical (human) data set forth herein, as well as any combination thereof. Thus, for example, the invention is deemed to encompass (i) patentable aspects of the efficacy values, onset and duration obtained for the tested formulations with respect to direct measurements of insulin levels, glucose levels and C-peptide levels (including but not limited to $t_{max}$, $C_{max}$, shape of the plasma concentration curve (e.g., plasma insulin levels); (ii) any combination of the various direct measurements of the treatment efficacy characteristics set forth in the above specification and/or as demonstrated by the appended examples; (iii) any combination of any of the above-mentioned characteristics of the invention together with aspects of the contemplated formulations themselves, including but not limited to the method of manufacture of the formulation, the drug load, the delivery agent load, the drug and form of the drug used (e.g., unmodified insulin), the delivery agent used, the ratio of drug to the total weight of the formulation, the ratio of drug to delivery agent, the actual amounts of drug with or without optional delivery agent used; etc.

While certain preferred and alternative embodiments of the invention have been set forth for purposes of disclosing the invention, modifications to the disclosed embodiments may occur to those who are skilled in the art. Accordingly, the appended claims are intended to cover all embodiments of the invention and modifications thereof that do not depart from the spirit and scope of the invention.

What is claimed is:

1. A method for treating a human patient who is pre-diabetic or who is suffering from type 2 diabetes comprising orally administering to the patient on a chronic basis a pharmaceutical formulation comprising a therapeutically effective dose of insulin and a delivery agent selected from 4-[(4-chloro,2-hydroxybenzoyl)amino]butanoic acid, 8-[(2-hydroxybenzoyl)amino]octanoic acid and pharmaceutically acceptable salts thereof that facilitates absorption of insulin from the gastrointestinal tract.

2. The method of claim 1, wherein said patient is pre-diabetic.

3. The method of claim 1, wherein said patient is at the early stage of type 2 diabetes along said continuum of development of diabetes.

4. The method of claim 1, wherein said patient is at the late stage of type 2 diabetes along said continuum of development of diabetes.

5. The method of claim 1, wherein said patient is at the late stage type 2 diabetes stage along said continuum of development of diabetes.

6. The method of claim 1, wherein said administration results in a reduced risk of hyperinsulinemia to the patient.

7. The method of claim 1, wherein administration to the patient is at bedtime and preprandial all meals at from about 30 minutes prior to ingestion of a meal to concurrently with ingestion of the meal.

8. The method of claim 1, further comprising administering to the patient on a chronic basis a therapeutically effective dose of a second pharmaceutical formulation comprising an intermediate-acting insulin or a long-acting insulin or both.

9. The method of claim 8, wherein the second pharmaceutical formulation is administered at least once a day orally.

10. The method of claim 8, wherein the second pharmaceutical formulation is administered at least once a day subcutaneously.

11. The method of claim 1, wherein the delivery agent is sodium 8-[(2-hydroxy benzoyl)amino]octanoate.

12. A method for treating impaired glucose tolerance in a human patient comprising orally administering to the patient on a chronic basis a pharmaceutical formulation comprising a therapeutically effective dose of insulin and a delivery agent selected from 4-[(4-chloro,2-hydroxybenzoyl)amino]butanoic acid, 8-[(2-hydroxybenzoyl)amino]octanoic acid and pharmaceutically acceptable salts thereof that facilitates absorption of insulin from the gastrointestinal tract.

13. The method of claim 12, wherein said patient is suffering from type 2 diabetes.

14. The method of claim 12, wherein said patient is pre-diabetic.

15. The method of claim 12, wherein said patient is at the early stage of type 2 diabetes along said continuum of development of diabetes.

16. The method of claim 12, wherein said patient is at the late stage of type 2 diabetes along said continuum of development of diabetes.

17. The method of claim 12, wherein said administration results in a reduced risk of hyperinsulinemia to the patient.

18. The method of claim 12, wherein administration to the patient is at bedtime and preprandial all meals at from about 30 minutes prior to ingestion of a meal to concurrently with ingestion of the meal.

19. The method of claim 12, further comprising administering to the patient on a chronic basis a therapeutically effective dose of a second pharmaceutical formulation comprising an intermediate-acting insulin or a long-acting insulin or both.

20. The method of claim 19, wherein the second pharmaceutical formulation is administered at least once a day orally.

21. The method of claim 19, wherein the second pharmaceutical formulation is administered at least once a day subcutaneously.

22. The method of claim 12, wherein the delivery agent is sodium 8-[(2-hydroxy benzoyl)amino]octanoate.

* * * * *